(12) United States Patent
Bruenker et al.

(10) Patent No.: US 10,087,250 B2
(45) Date of Patent: Oct. 2, 2018

(54) FC-FREE ANTIBODIES COMPRISING TWO FAB-FRAGMENTS AND METHODS OF USE

(71) Applicant: Roche Glycart AG, Schlieren (CH)

(72) Inventors: Peter Bruenker, Hittnau (CH); Tanja Fauti, Zurich (CH); Christiane Neumann, Niederweningen (CH); Christian Klein, Weilheim (DE); Pablo Umaña, Wollerau (CH)

(73) Assignee: Roche Glycart AG, Schlieren (CH)

( * ) Notice: Subject to any disclaimer, the term of this patent is extended or adjusted under 35 U.S.C. 154(b) by 0 days.

(21) Appl. No.: 14/434,168

(22) PCT Filed: Oct. 3, 2013

(86) PCT No.: PCT/EP2013/070607
§ 371 (c)(1),
(2) Date: Apr. 8, 2015

(87) PCT Pub. No.: WO2014/056783
PCT Pub. Date: Apr. 17, 2014

(65) Prior Publication Data
US 2016/0130347 A1 May 12, 2016

(30) Foreign Application Priority Data
Oct. 8, 2012 (EP) .................................. 12187647

(51) Int. Cl.
A61K 39/00 (2006.01)
C07K 16/28 (2006.01)
C07K 16/30 (2006.01)
C07K 16/46 (2006.01)
C07K 16/18 (2006.01)
A61K 39/395 (2006.01)

(52) U.S. Cl.
CPC .......... C07K 16/2809 (2013.01); C07K 16/18 (2013.01); C07K 16/30 (2013.01); C07K 16/3053 (2013.01); C07K 16/468 (2013.01); A61K 39/39541 (2013.01); A61K 39/39558 (2013.01); A61K 2039/505 (2013.01); C07K 2317/31 (2013.01); C07K 2317/33 (2013.01); C07K 2317/52 (2013.01); C07K 2317/54 (2013.01); C07K 2317/55 (2013.01); C07K 2317/66 (2013.01); C07K 2317/75 (2013.01); C07K 2317/92 (2013.01); C07K 2317/94 (2013.01); C07K 2319/00 (2013.01)

(58) Field of Classification Search
CPC ........ A61K 39/39558; A61K 2039/505; A61K 39/39541
See application file for complete search history.

(56) References Cited

U.S. PATENT DOCUMENTS

| 5,571,894 | A | 11/1996 | Wels et al. |
| 5,587,458 | A | 12/1996 | King et al. |
| 5,591,828 | A | 1/1997 | Bosslet et al. |
| 5,731,168 | A | 3/1998 | Carter et al. |
| 5,821,337 | A | 10/1998 | Carter et al. |
| 5,869,046 | A | 2/1999 | Presta et al. |
| 6,248,516 | B1 | 6/2001 | Winter et al. |
| 6,737,056 | B1 | 5/2004 | Presta |
| 6,809,185 | B1* | 10/2004 | Schoonjans ............ C07K 16/00 530/387.1 |
| 7,332,581 | B2 | 2/2008 | Presta |
| 7,695,936 | B2 | 4/2010 | Carter et al. |
| 8,227,577 | B2* | 7/2012 | Klein .................. C07K 16/468 424/133.1 |
| 8,242,247 | B2* | 8/2012 | Klein .................... C07K 16/22 424/133.1 |
| 8,703,132 | B2 | 4/2014 | Imhof-Jung et al. |
| 8,709,421 | B2 | 4/2014 | Heiss et al. |
| 8,796,424 | B2 | 8/2014 | Croasdale et al. |
| 8,969,526 | B2 | 3/2015 | Baehner et al. |
| 9,068,008 | B2 | 6/2015 | Mossner et al. |
| 9,266,938 | B2 | 2/2016 | Ast et al. |
| 9,266,967 | B2 | 2/2016 | Klein et al. |
| 9,382,323 | B2 | 7/2016 | Brinkmann et al. |
| 9,447,159 | B2 | 9/2016 | Ast et al. |
| 9,526,797 | B2 | 12/2016 | Gerdes et al. |
| 2002/0004587 | A1* | 1/2002 | Miller .................... C07K 16/00 530/388.8 |
| 2006/0160184 | A1* | 7/2006 | Mattheus Hoogenboom et al. ..... C07K 16/005 435/69.1 |
| 2007/0111281 | A1 | 5/2007 | Sondermann et al. |
| 2007/0274985 | A1 | 11/2007 | Dubel et al. |
| 2008/0241152 | A1 | 10/2008 | Alitalo et al. |
| 2009/0162360 | A1* | 6/2009 | Klein .................... C07K 16/22 424/136.1 |
| 2009/0252683 | A1 | 10/2009 | Kischel et al. |
| 2010/0015133 | A1 | 1/2010 | Igawa et al. |
| 2010/0150918 | A1 | 6/2010 | Kufer et al. |
| 2010/0316645 | A1 | 12/2010 | Imhof-Jung et al. |
| 2011/0293613 | A1 | 12/2011 | Brinkmann et al. |

(Continued)

FOREIGN PATENT DOCUMENTS

EP 0404097 B1 9/1996
EP 1870459 A1 12/2007
(Continued)

OTHER PUBLICATIONS

Schaefer et al. (Proc. Natl. Acad. Sci. USA. Jul. 5, 2011; 108 (27): 11187-92).*

(Continued)

Primary Examiner — Stephen L Rawlings
(74) Attorney, Agent, or Firm — Clark & Elbing LLP; Karen L. Elbing

(57) ABSTRACT

The present invention relates to bispecific antibodies comprising at least two Fab fragments, wherein the first Fab fragment comprises at least one antigen binding site specific for a first antigen; and the second Fab fragment comprises at least one antigen binding site specific for a second antigen, wherein either the variable regions or the constant regions of the second Fab heavy and light chain are exchanged and the two Fab fragments are connected to each other by two peptide linkers; and wherein the bispecific antibody is devoid of a Fc domain; methods for their production, pharmaceutical compositions containing said antibodies, and uses thereof.

12 Claims, 28 Drawing Sheets
Specification includes a Sequence Listing.

(56) References Cited

U.S. PATENT DOCUMENTS

| | | |
|---|---|---|
| 2012/0225071 A1 | 9/2012 | Klein et al. |
| 2012/0276125 A1 | 11/2012 | Ast et al. |
| 2012/0321626 A1* | 12/2012 | Zhou ............ C07K 14/705 424/136.1 |
| 2013/0022601 A1 | 1/2013 | Brinkmann et al. |
| 2013/0078249 A1 | 3/2013 | Ast et al. |
| 2013/0058936 A1 | 7/2013 | Bruenker et al. |
| 2013/0058937 A1 | 7/2013 | Auer et al. |
| 2013/0060011 A1 | 7/2013 | Bruenker et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0170148 A1* | 6/2014 | De Goeij ........ A61K 47/48676 424/136.1 |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0056206 A1* | 2/2015 | Zhou ............ C07K 14/705 424/136.1 |
| 2015/0166654 A1* | 6/2015 | Igawa ............ C07K 16/005 530/387.3 |
| 2015/0166661 A1 | 6/2015 | Chen et al. |
| 2015/0010567 A1 | 8/2015 | Bourquin et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | |
|---|---|---|
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| WO | WO 91/03493 * | 3/1991 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | 2011/023787 A1 | 3/2001 |
| WO | 01/077342 A1 | 10/2001 |
| WO | WO-02/09573 A2 | 2/2002 |
| WO | WO-2005/044859 A2 | 5/2005 |
| WO | 2006/082515 A2 | 8/2006 |
| WO | WO-2007/024715 A2 | 3/2007 |
| WO | WO-2007/042261 A2 | 4/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | 2009/080254 A1 | 7/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/089004 A1 | 7/2009 |
| WO | 2010/033229 A2 | 3/2010 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | 2012/020006 A2 | 2/2012 |
| WO | WO-2012/058768 A1 | 5/2012 |
| WO | WO-2012/058768 A8 | 6/2012 |
| WO | WO-2012/073985 A1 | 6/2012 |
| WO | WO-2012/130831 A1 | 10/2012 |
| WO | WO-2012/158818 A2 | 11/2012 |
| WO | WO-2012/162067 A2 | 11/2012 |
| WO | 2013026839 A1 | 2/2013 |
| WO | WO-2013/026831 A1 | 2/2013 |
| WO | WO-2013/026833 A1 | 2/2013 |
| WO | WO-2013/026837 A1 | 2/2013 |
| WO | WO-2013/096291 A2 | 6/2013 |
| WO | WO-2013/157953 A1 | 10/2013 |
| WO | WO-2013/157954 A1 | 10/2013 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/081955 A1 | 5/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/141152 A2 | 9/2014 |
| WO | WO-2014/153002 A1 | 9/2014 |
| WO | WO-2014/122251 A3 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2014/191113 A8 | 2/2015 |
| WO | WO-2015/150447 A1 | 10/2015 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/179003 A1 | 11/2016 |
| WO | WO-2017/021450 A1 | 2/2017 |

OTHER PUBLICATIONS

Bluemel e al. (Cancer Immunol. Immunother. Aug. 2010; 59 (8): 1197-209).*

Klein et al. (MAbs. Nov.-Dec. 2012; 4 (6): 653-63).*

Chan et al. (Mol. Immunol. Jul. 2004; 41 (5): 527-38).*

(56) References Cited

OTHER PUBLICATIONS

Simon et al. (EMBO J. Apr. 1990; 9 (4): 1051-6).*
Bosch et al., "MCSP/CD3-bispecific single-chain antibody construct engages CD4+ and CD*+ T cells for lysis of MCSP-expressing human uveal melanoma cells" AACR 101st Annual Meeting 2010, Abstract No. 5621 (2010), ( Apr. 21, 2010).
Hollander et al., "Bispecific antibodies for cancer therapy" Immunotherapy 1(2):211-222 ( 2009).
Klein, C. et al., "Progress in overcoming the chain association issue in bispecific heterodimeric IgG antibodies" mAbs 4(6):653-663 ( 2012).
Schaefer et al., "Immunoglobulin domain crossover as a generic approach for the production of bispecific IgG antibodies" Proceedings of the National Academy of Sciences :108(27):11187-11192 (Jul. 5, 2011).
Coloma and Morrison, "Design and production of novel tetravalent bispecific antibodies" Nat Biotechnol 15(2):159-163 (Feb. 1997).
Fischer and Leger, "Bispecific antibodies: Molecules that enable novel therapeutic strategies" Pathobiology 74:3-14 ( 2007).
Holliger et al., "Engineered Antibody Fragments and the Rise of Single Domains" Nature Biotechnol 23(9):1126-1136 ( 2005).
Holliger et al., "Specific killing of lymphoma cells by cytotoxic T-cells mediated by a bispecifc diabody" Protein Engineering 9(3):299-305 ( 1996).
Kipriyanov et al., "Bispecific Tandem Diabody for Tumor Therapy with Improved Antigen Binding and Pharmacokinetics" J. Mol. Biol. 293:41-56 ( 1999).
Moore et al., "Application of dual affinity retargeting molecules to achieve optimal redirected T-cell killing of B-cell lymphoma" Blood 117(17):4542-51 ( 2011).
Morrison, S., "Two Heads are Better Than One—A new Design for Bispecific Antibodies Enables Effcient Production of Stable Molecules with Good Pharmacodynamic Properties." Nat Biotechnol 25(11):1233-1234 ( 2007).
Nagorsen et al., "Immunomodulatory therapy of cancer with T cell-engaging BiTE antibody" Exp Cell Res. 317(9):1255-60 ( 2011).
Seimetz et al., "Development and approval of the trifunctional antibody catumaxomab (anti-EpCAM x anti-CD3) as a target cancer immunotherapy" Cancer Treatment Reviews 36:458-467 ( 2010).
Shen et al., "Single variable domain antibody as a versatile building block for the construction of IgG-like bispecific antibodies" J Immunol Methods 318:65-74 ( 2007).
Wu et al., "Simultaneous targeting of multiple disease mediators by a dual-variable-domain Immunoglobulin" Nature Biotechnol 25(11):1290-1297 ( 2007).
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Carter, "Bispecific human IgG by design," J Immunol Methods. 248(1-2):7-15 (2001).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kontermann, "Dual targeting strategies with bispecific antibodies," MAbs. 4(2):182-97 (2012).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Oshimi et al., "Increased lysis of patient CD10-positive leukemic cells by T cells coated with anti-CD3 Fab' antibody cross-linked to anti-CD10 Fab' antibody," Blood. 77(5)1044-9 (1991).
Pessano et al., "The T3/T cell receptor complex: antigenic distinction between the two 20-kd T3 (T3-delta and T3-epsilon) subunits," EMBO J. 4(2):337-44 (1985).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wolf et al., "BiTEs: bispecific antibody constructs with unique anti-tumor activity," Drug Discov Today. 10(18):1237-44 (2005).
Zhu et al., "Identification of heavy chain residues in a humanized anti-CD3 antibody important for efficient antigen binding and T cell activation," J Immunol. 155(4):1903-10 (1995).
Le Gall et al., "Effect of linker sequences between the antibody variable domains on the formation, stability and biological activity of a bispecific tandem diabody," Protein Eng Des Sel. 17(4):357-66 (2004).
Stamova et al., "Cancer immunotherapy by retargeting of immune effector cells via recombinant bispecific antibody constructs," Antibodies. 1(2):172-98. (2012).

* cited by examiner

FC-FREE ANTIBODIES COMPRISING TWO FAB-FRAGMENTS AND METHODS OF USE

SEQUENCE LISTING

The instant application contains a Sequence Listing which has been submitted electronically in ASCII format and is hereby incorporated by reference in its entirety. Said ASCII copy, created on Sep. 9, 2015, is named P31270-US_SL.txt and is 205,458 bytes in size.

FIELD OF THE INVENTION

The present invention relates to bispecific antibodies comprising at least two Fab fragments, wherein the first Fab fragment comprises at least one antigen binding site specific for a first antigen; and the second Fab fragment comprises at least one antigen binding site specific for a second antigen, wherein either the variable regions or the constant regions of the second Fab heavy and light chain are exchanged and the two Fab fragments are connected to each other by two peptide linkers; and wherein the bispecific antibody is devoid of a Fc domain; methods for their production, pharmaceutical compositions containing said antibodies, and uses thereof.

The present invention further relates to bispecific antibodies that specifically bind a T-cell activating antigen and a Tumor Antigen (TA), comprising a first Fab fragment and a second Fab fragment, wherein either the variable regions or the constant regions of the second Fab heavy and light chain are exchanged and the two Fab fragments are connected to each other by two peptide linkers; and wherein the bispecific antibody does not comprise a Fc domain; methods for their production, pharmaceutical compositions containing said antibodies, and uses thereof.

BACKGROUND

Monoclonal antibodies (mAbs) are an increasingly important class of therapeutic agents. Apart from mAb products composed of the full-size form of IgG, a wide variety of multispecific recombinant antibody formats have been developed, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Léger, O., Pathobiology 74 (2007) 3-14). Tandem scFVs are two scFv fragments linked by an extra peptide linker and are also referred to as (scFv)2. By reducing the length of the peptide linker between the variable domains, Diabodies are generated. Adding an extra peptide linker between the two polypeptides yields so called single chain diabodies. US 2007/0274985 relates to antibodies comprising single chain Fab (scFab) fragments.

Antibody fragments have both pros and cons as therapeutics compared with full-size monoclonal antibodies: One advantage is that they are smaller and penetrate tissues and tumors more rapidly. In addition, the small size of fragments has been suggested to permit binding to epitopes not accessible to full-sized monoclonal antibodies. On the downside, fragments demonstrate short circulating half-lives in humans, likely due to kidney clearance. The shorter half-life may prevent sufficient accumulation of therapy at the targeted site. Production of antibody fragments is not trivial, as fragments are likely to form aggregates and can be less stable than full-size monoclonal antibodies. In addition, unwanted pairing of noncongnate heavy and light chains results in formation of inactive antigen-binding sites and/or other non-functional undesired side-products, which is a major problem in clinical-scale production and therapeutic application of antibody fragments. In particular Tandem-Fab constructs where two or more Fabs are fused with each other via one connector are not feasible due to the random association of the two light chains resulting in inactive, undesired side products. These drawbacks have now been overcome with the new antibody format of the invention. Provided therein is a new bispecific antibody format that can be easily produced with an increased yield due to a decreased amount of mispaired side-products, which show less aggregation than bispecific antibody fragments known in the art. Using the crossover approach correct LC association can be enforced without the need for the generation of a common light chain. Common light chan approach is not possible for existing antibodies. Further, the new bispecific antibody format is stable and does not aggregate at higher temperatures than existing bispecific formats, which allows better producability and developability. In addition, the new bispecific antibody format has a higher molecular weight compared to many conventional bispecific antibody fragments, thus preventing excessive kidney clearance and leading to an improved half-life in vivo. The new bispecific antibody format is fully functional and has comparable or improved binding and activity as corresponding conventional bispecific antibodies.

The selective destruction of an individual cell or a specific cell type is often desirable in a variety of clinical settings. For example, it is a primary goal of cancer therapy to specifically destroy tumor cells, while leaving healthy cells and tissues undamaged. One approach is to selectively induce an immune response against the tumor, which triggers the attack and subsequent destruction of tumor cells by immune effector cells such as natural killer (NK) cells or cytotoxic T lymphocytes (CTLs). CTLs constitute the most potent effector cells of the immune system, however they cannot be activated by the effector mechanism mediated by the Fc domain of conventional therapeutic antibodies. In this regard, bispecific antibodies which are able to bind to a surface antigen on cancer cells and to an activating invariant component of the cell receptor (TCR) complex have become of interest in recent years. The simultaneous binding of the bispecific antibody to both of its targets forces a temporary interaction between cancer cell and T cell, causing activation of cytotoxic T cells and subsequent lysis of the tumor cell.

Several bispecific antibody formats have been developed and their suitability for T cell mediated cancer immunotherapy investigated. Out of these, the so-called BiTE (bispecific T cell engager) molecules have been very well characterized and already shown some promising results in the clinic (reviewed in Nagorsen and Baiuerle, Exp Cell Res 317, 1255-1260 (2011)). BiTEs are tandem scFv molecules wherein two scFv molecules are fused by a flexible linker.

Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). A more recent development are the so-called DART (dual affinity retargeting) molecules, which are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

However, the bispecific antibodies developed for T cell mediated cancer immunotherapy known so far have major drawbacks relating to their efficacy, toxicity and applicability. Small constructs such as, for example, BiTE molecules—while being able to efficiently crosslink effector and target cells—have a very short serum half life requiring them to be administered to patients by continuous infusion. IgG-like formats on the other hand—while having the great benefit of a long half life—suffer from toxicity associated with the native effector functions inherent to IgG molecules. This immunogenic potential constitutes another unfavorable feature of IgG-like bispecific antibodies, for successful therapeutic development. Finally, a major challenge in the general development of bispecific antibodies remains the production of bispecific antibody constructs at a clinically sufficient quantity and purity. The mispairing of antibody heavy and light chains of different specificities upon co-expression, decreases the yield of the correctly assembled construct and results in a number of non-functional side products.

Given the difficulties and disadvantages associated with currently available bispecific antibodies for T cell mediated cancer immunotherapy, there remains a need for novel, improved formats of such molecules. These drawbacks have now been overcome with the new bispecific antibodies of the invention. The new bispecific antibodies can be easily produced, with an increased yield due to a decreased amount of mispaired side-products, which show less aggregation than bispecific antibody fragments known in the art. In addition, the new bispecific antibodies are stable at increased temperatures compared to bispecific antibody formats known in the art. Using the crossover approach correct chain association can be enforced without the need for the generation of a common light chain. In addition, the new the new bispecific antibodies has a higher molecular weight compared to many conventional bispecific antibody fragments, thus preventing excessive kidney clearance and leading to an improved half-life in vivo. Further, only two plasmids are needed to produce the new bispecific antibodies. The new bispecific antibodies are fully functional and have comparable or improved binding and activity as corresponding conventional bispecific antibodies.

The present invention provides bispecific antigen binding molecules designed for T cell activation and re-direction that combine good efficacy and produceability with low toxicity and favorable pharmacokinetic properties.

SUMMARY

The present invention relates to bispecific antibodies comprising at least two Fab fragments, wherein the first Fab fragment comprises at least one antigen binding site specific for a first antigen; and the second Fab fragment comprises at least one antigen binding site specific for a second antigen wherein either the variable regions or the constant regions of the second Fab heavy and light chain are exchanged and the two Fab fragments are connected to each other by two peptide linkers; and wherein the bispecific antibody is devoid of a Fc domain. Preferably said peptide linker is a (G4S)2 linker (SEQ ID NO: 28).

In one embodiment said antibody additionally comprises a third Fab fragment. In another embodiment said third Fab fragment comprises at least one antigen binding site specific for the first or second antigen, preferably for the first antigen.

In one embodiment the third Fab fragment is connected to the light chain or the heavy chain of the first Fab fragment. In another embodiment the third Fab fragment is connected to N or C-terminus of the light chain or the heavy chain of the second Fab fragment. In one embodiment the third Fab fragment is connected to the first or second Fab fragment via one or more peptide linker(s). Preferably said peptide linker is a (G4S)2 linker (SEQ ID NO: 28).

The bispecific antibodies according to the invention are at least bivalent and can be trivalent or multivalent e.g. tetravalent. In one embodiment said bispecific antibodies are bivalent (1+1 format) with one binding site each targeting a first antigen and a second antigen, respectively. In another embodiment said bispecific antibodies are trivalent (2+1 format) with two binding sites each targeting a first antigen and one binding site targeting a second antigen, as detailed in the following section.

The present invention relates to bispecific antibodies that specifically bind a T-cell activating antigen and a Tumor Antigen (TA), comprising a first Fab fragment and a second Fab fragment, wherein either the variable regions or the constant regions of the second Fab heavy and light chain are exchanged and the two Fab fragments are connected to each other by two peptide linkers and wherein the bispecific antibody does not comprise a Fc domain.

The antibodies of the invention specifically bind to a Tumor Antigen on the surface of a tumor cell and at the same time bind to T-cell activating antigen. By that the bispecific antibody is capable to elecit an immune response specifically at the site of the tumor, subsequently resulting in apoptosis of the target cell.

In one aspect, a bispecific antibody that specifically binds a T-cell activating antigen and a Tumor Antigen (TA) is provided, comprising at least twoFab fragments which are connected to each other by two peptide linkers, wherein the first Fab fragment comprises at least one antigen binding site specific for a Tumor Antigen (TA); and the second Fab fragment comprises at least one antigen binding site specific for a T-cell activating antigen, wherein either the variable regions or the constant regions of the second Fab heavy and light chain are exchanged; and wherein the bispecific antibody is devoid of a Fc domain.

In particular, the present invention relates to bispecific antibodies wherein the T-cell activating antigen is a CD3 T-Cell Co-Receptor (CD3) targeting antigen. In one embodiment the Tumor Antigen is selected from the group of Melanoma-associated Chondroitin Sulfate Proteoglycan (MCSP), Epidermal Growth Factor Receptor (EGFR), Carcinoembryonic Antigen (CEA), Fibroblast Activation Protein (FAP) and CD33. In one preferred embodiment the Tumor Antigen is MCSP.

In one aspect, a bispecific antibody that specifically binds CD3 T-Cell Co-Receptor (CD3) antigen and a Tumor Antigen (TA) is provided, comprising at least two Fab fragments which are connected to each other by two peptide linkers, wherein the first Fab fragment comprises at least one antigen binding site specific for a Tumor Antigen (TA); and the second Fab fragment comprises at least one antigen binding site specific for a CD3 T-Cell Co-Receptor (CD3) wherein either the variable regions or the constant regions of the second Fab heavy and light chain are exchanged; and wherein the bispecific antibody is devoid of a Fc domain- Preferably said peptide linker is a (G4S)2 linker (SEQ ID NO: 28).

In one embodiment said antibody additionally comprises a third Fab fragment, which is connected to the first or second fragment by one or two peptide linkers. In another embodiment said third Fab fragment comprises at least one antigen binding site specific for a Tumor Antigen. In one embodiment the third Fab fragment is connected to the N or C-terminus of the light chain or the heavy chain of the first Fab fragment. In another embodiment the third Fab fragment is connected to the N or C-terminus of the light chain or the heavy chain of the second Fab fragment. In one embodiment the third Fab fragment is connected to the first or second Fab fragment by one or two peptide linkers. Preferably said peptide linker is a (G4S)2 linker (SEQ ID NO: 28)

The bispecific antibodies according to the invention are at least bivalent and can be trivalent or multivalent e.g. tetravalent or hexavalent. In one embodiment said bispecific antibodies are bivalent (1+1 format) with one binding site each targeting a Tumor Antigen (TA) and a T-cell activating antigen, respectively. In another embodiment said bispecific antibodies are trivalent (2+1 format) with two binding sites each targeting a Tumor Antigen (TA) and one binding site targeting a T-cell activating antigen, as detailed in the following section. In a preferred embodiment said a T-cell activating antigen is CD3.

In a second object the present invention relates to a pharmaceutical composition comprising a bispecific antibody of the present invention.

In a third object the present invention relates to a bispecific antibody of the present invention for the treatment of cancer. In another embodiment, use of the bispecific antibody as a medicament is provided. Preferably said use is for the treatment of cancer.

In further objects the present invention relates to a nucleic acid sequence comprising a sequence encoding a heavy chain of a bispecific antibody of the present invention, a nucleic acid sequence comprising a sequence encoding a light chain of a bispecific antibody of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

In a further embodiment an immunoconjugate comprising the bispecific antibody of the invention and a cytotoxic agent is provided.

There was no significant secretion of Th2 cytokines (IL-10 and IL-4) upon activation of T cells by the bispecific constructs in the presence (or absence) of target cells. In this assay there was also a weak secretion of IFNgamma, induced by the "(Fab)2-Crossfab" construct in the absence of target cells.

Figure 16:
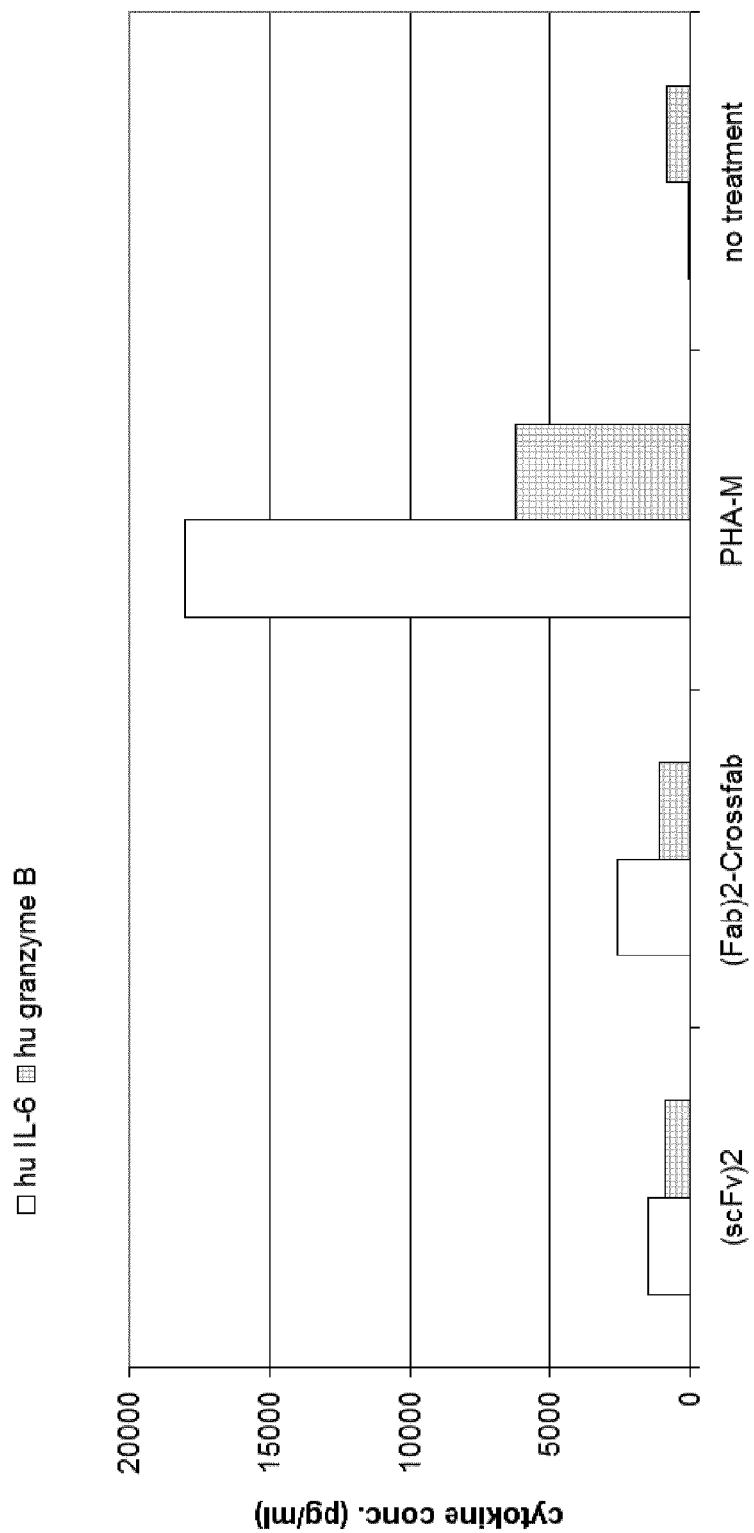

FIG. 16: Surface expression level of the late activation marker CD25 on murine pan T cells, isolated from splenocytes. Murine pan T cells were incubated with 50 nM of the murine Crossfab(CD3)-Fab(MCSP)-Fab(MCSP) construct (=(Fab)2-CrossFab) bispecific construct (targeting murine CD3, as well as human MCSP), in the presence or absence of B16/F10-huMCSP Fluc2 clone 48 tumor target cells, as indicated (E:T ratio is 10:1). Depicted is the expression level of the late activation marker CD25 on CD8+ T cells after 70 hours. Up-egulation of CD25 on CD8+ T cells with the (Fab)2-CrossFab construct occurs only in the presence of target cells. The reference IgGs, used adjusted to the same molarity, were not able to up-regulate CD25.

FIGS. 17A-B: Analysis of Fab(CD33)-CrossFab (CD3) production and purification. SDS-Page: A 3-8% Tris/Acetate (NuPage [invitrogen]; coomassie stained): B 1—HiMark (invitrogen), 2—Fab(CD33)-CrossFab (CD3) non reduced; b) 4-12% Bis/Tris (NuPage [invitrogen]: 1—Mark 12 (invitrogen), 2—Fab(CD33)-CrossFab (CD3) reduced.

Figure 18:
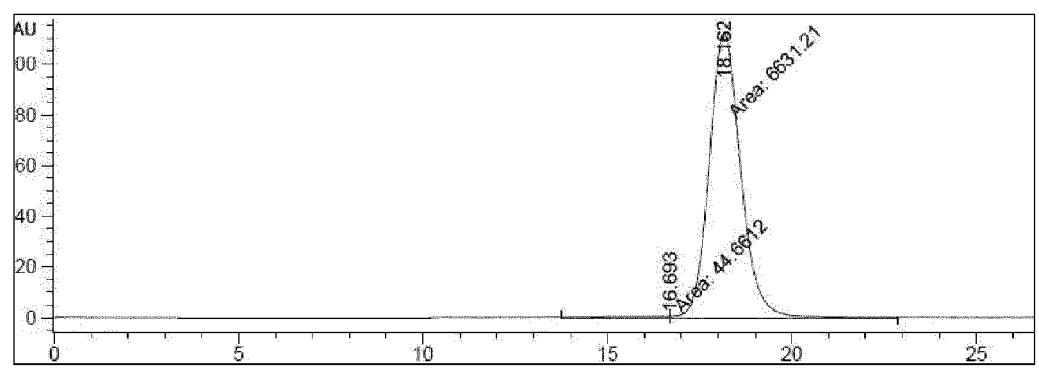

FIG. 18: Analysis of Fab(CD33)-CrossFab (CD3) production and purification. Analytical size exclusion chromatography, Chromatogram A280 (Superdex 200 10/300 GL [GE Healthcare]; 2 mM MOPS pH 7.3, 150 mM NaCl, 0.02% (w/v) NaCl; 50 µg sample were injected).

Figure 19:
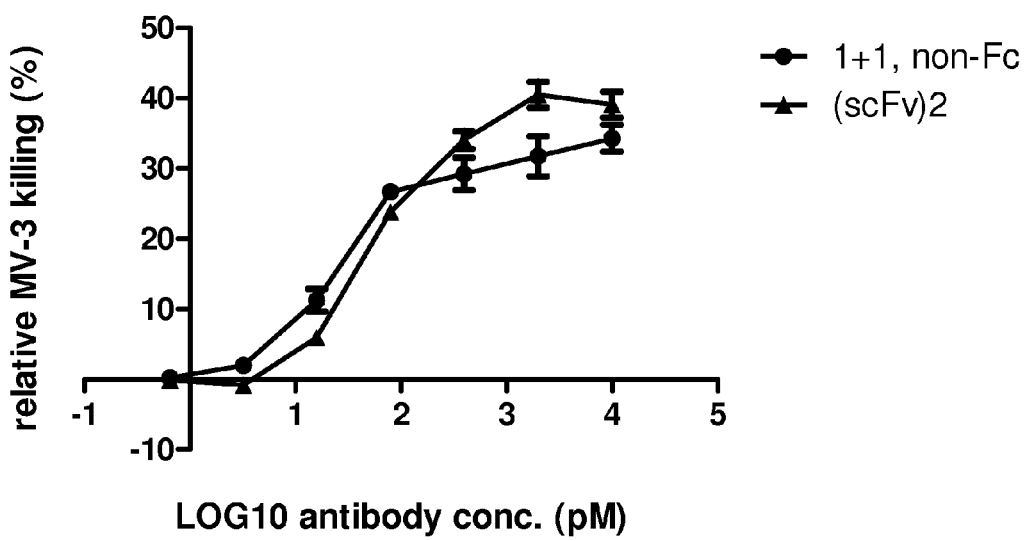

FIG. 19: Killing (as measured by LDH release) of MV-3 tumor cells upon co-culture with human PBMCs (E:T ratio=10:1) and activation for 24 hours by different concentrations of CD3-MCSP bispecific constructs (hu Fab (MCSP)-Crossfab(CD3); designated as "1+1 non-Fc", and the (scFv)2 (antiMCSP/anti huCD3e) (="(scFv)2") reference molecule). The "1+1 non-Fc" construct induces apoptosis in MV-3 target cells with a calculated EC50 of 25.4 µM, whereas the calculated EC50 for the "(scFv)2" reference molecule is 57 µM, showing a slight better potency of the "1+1 non-Fc" molecule in terms of EC50.

FIGS. 20a-b: Activation of CD4+ or CD8+ T cells, as measured by up-regulation of CD69 (a), respective increase of CD69-positive cells (b) in the presence of huMCSP-positive MV-3 tumor cells upon co-culture with human PBMCs (E:T ratio=10:1), treated with the CD3-MCSP bispecific constructs (hu Fab(MCSP)-Crossfab(CD3); designated as "1+1 non-Fc", and the (scFv)2 (antiMCSP/anti huCD3e) (="(scFv)2") reference molecule, respectively) for ~24 hours. In general, the CD69 median values are higher on CD8+ T cells compared to CD4+T cells. There is a clear concentration-dependent increase in both, CD69 median values, as well percentage of CD69 positive cells for both constructs.

Figure 21:
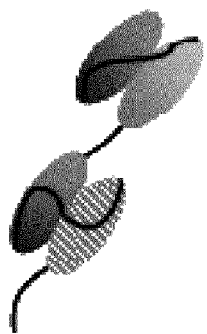

FIG. 21: Illustration of (scFv)2 reference molecule.

Figure 22:
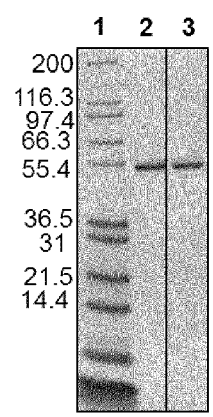

FIG. 22: Analysis of (scFv)2 (antiMCSP/anti huCD3e) production and purification. SDS-Page: 4-12% Bis/Tris (NuPage [invitrogen]; coomassie stained): 1—Mark 12 (invitrogen), 2—(scFv)2 (antiMCSP/anti huCD3e) reduced; 3—(scFv)2 (antiMCSP/anti huCD3e) non reduced FIG. 23: Analysis of (scFv)2 (antiMCSP/anti huCD3e) production and purification Analytical size exclusion chromatography, Chromatogram A280 (Superdex 75 10/300 GL [GE Healthcare]; 2 mM MOPS pH 7.3, 150 mM NaCl, 0.02% (w/v) NaCl; 50 µg sample ((scFv)2 (antiMCSP/anti huCD3e)) were injected).

FIGS. 24a-e: Schematic illustration of exemplary bispecific antibody formats wherein the two Fab fragments are connected to each other by two linkers a) Fab=Crossfab molecule C-terminal, b) Fab=Crossfab molecule N-terminal c) Fab-Fab=Crossfab molecule and Fab=Fab=Crossfab molecule C-terminal d) Fab-Fab=Crossfab molecule and Fab=Fab=Crossfab molecule N-terminal e) Fab-Crossfab=Fab and Fab=Crossfab=Fab molecule.

Figure 25:
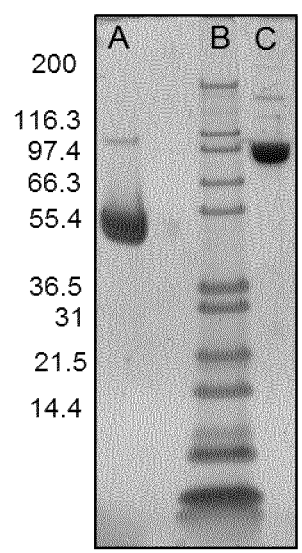
Figure 26:
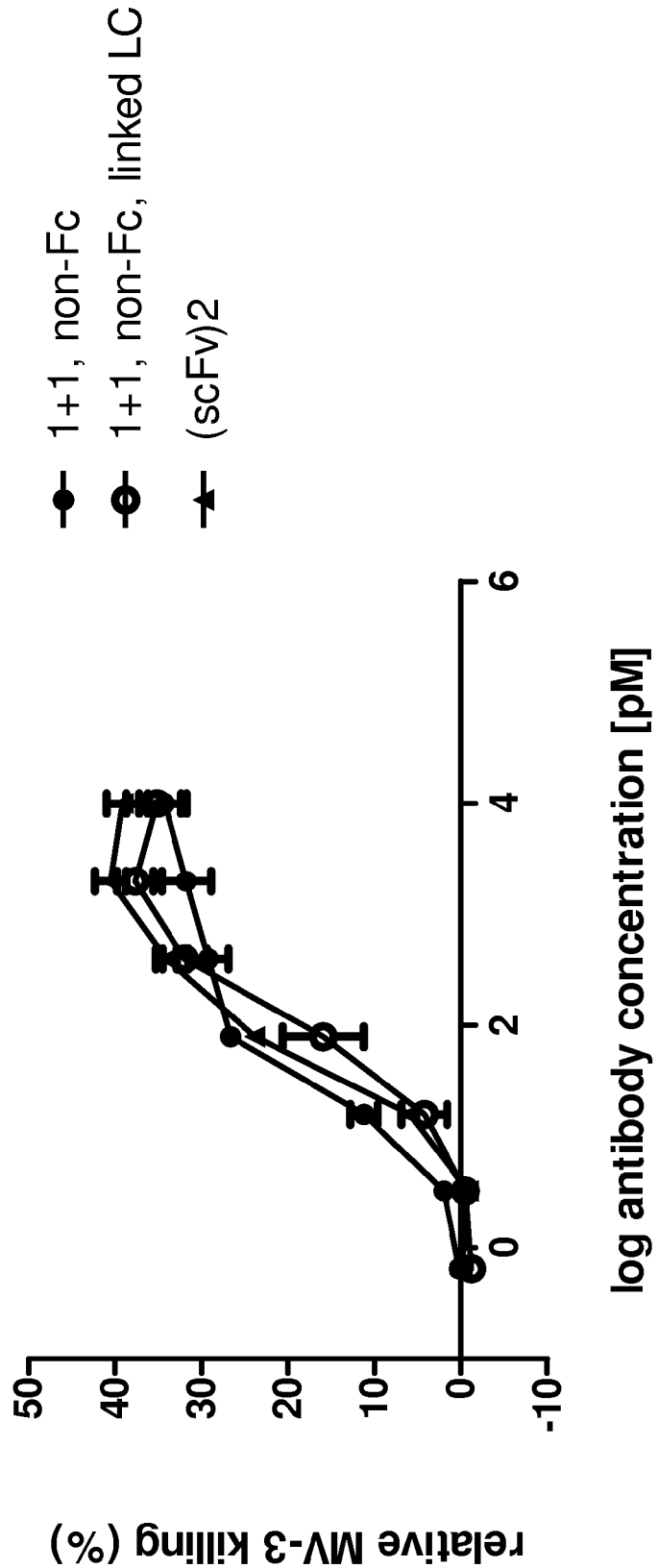

FIG. 25: Analysis of hu Fab(MCSP)=Crossfab(CD3) production and purification: SDS-Page: 4-12% Bis/Tris (NuPage [invitrogen]; coomassie stained): A) hu Fab(MCSP)=Crossfab(CD3) reduced; B) Mark 12 (invitrogen), C) hu Fab(MCSP)=Crossfab(CD3) non reduced;

FIG. 26: Killing (as measured by LDH release) of MCSP-positive MV-3 human melanoma cells upon co-culture with human PBMCs (E:T ratio=10:1), treated with different CD3-MCSP bispecific constructs (hu Fab(MCSP)=Crossfab (CD3), designated as "1+1 non-Fc, linked LC"; hu Fab (MCSP)-Crossfab(CD3), designated as "1+1 non-Fc"; and the (scFv)2 (antiMCSP/anti huCD3e) (="(scFv)2") reference molecule, respectively) for ~24 hours. Human PBMCs were isolated from fresh blood of healthy volunteers. EC50 values were determined using Graph Pad Prism software.

FIGS. 27a-b: Surface expression level of the early activation marker CD69 on human CD4and CD8 T cells after 24 hours incubation with 10 nM, 80 pM or 16 pM of the non-Fc T cell bispecific constructs targeting human CD3 and human MCSP (hu Fab(MCSP)=Crossfab(CD3), designated as "1+1 non-Fc, linked LC"; hu Fab(MCSP)-Crossfab(CD3), designated as "1+1 non-Fc"; and the (scFv)2(antiMCSP/anti huCD3e) (="(scFv)2") reference molecule, respectively)) in the presence of human MCSP-expressing MV-3 melanoma target cells (E:T ratio=10:1).

(a) Shows the median expression values of CD69, (b) depicts the percentage of CD69 positive T cells.

Figure 28:
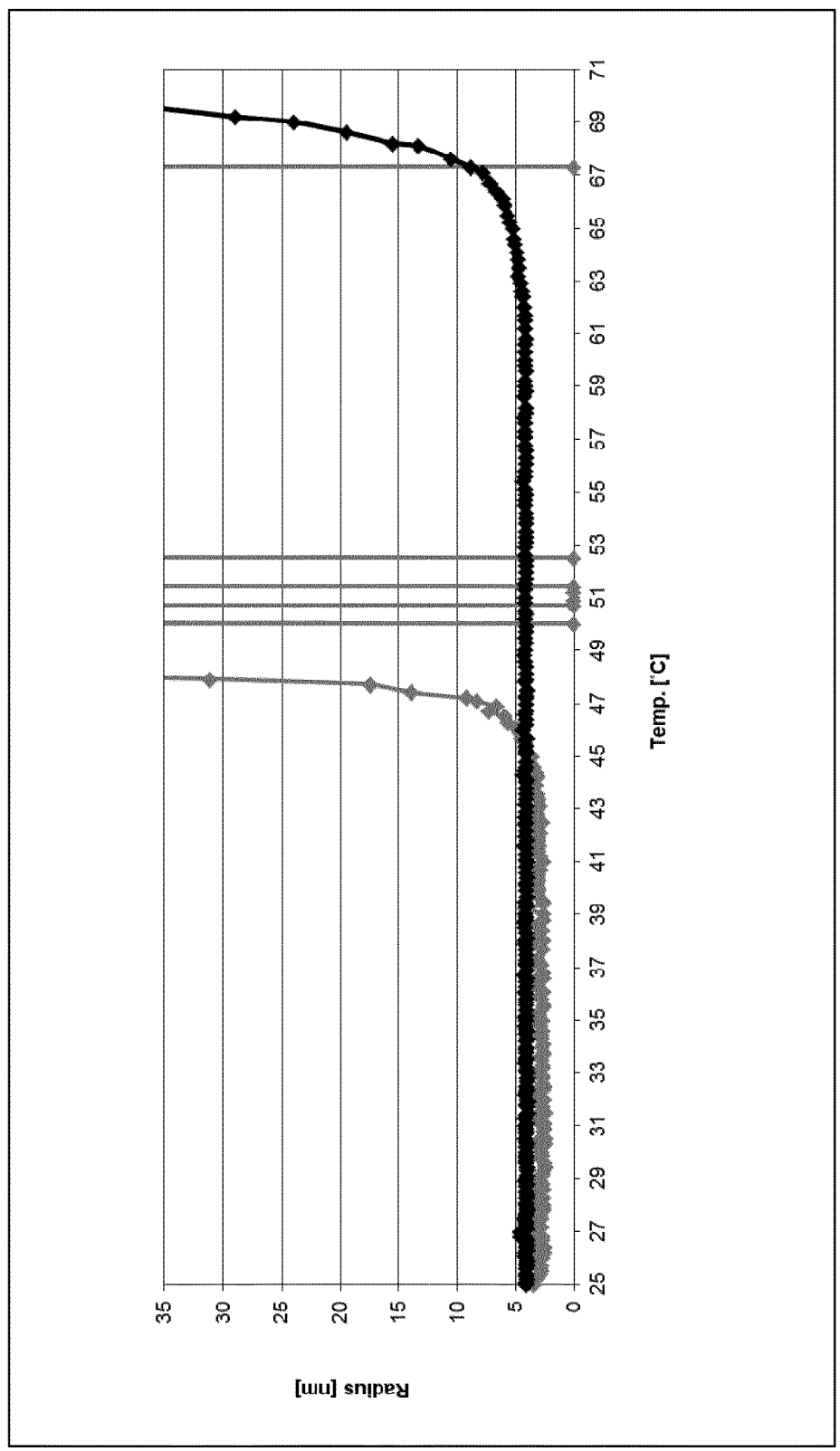

FIG. 28: Thermal stability of Fab-Crossfab molecule with two linkers (antiMCSP/anti huCD3) in comparison to the "(scFv)2" reference molecule (antiMCSP/anti huCD3). Dynamic Light Scattering. measured in a temperature ramp from 25-75° C. at 0.05° C./min. Fab-Crossfab molecule with two linkers is shown in black and the "(scFv)2" reference molecule is shown in grey.

DETAILED DESCRIPTION OF EMBODIMENTS OF THE INVENTION

I. Definitions

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) The terms hypervariable regions (HVRs) and complementarity determining regions (CDRs), are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In particular the term "antibody" also includes the bispecific antibodies of the invention comprising at least two Fab fragments connected to each other by two linkers and which are devoid of a Fc domain.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "antibody fragment" refers to a molecule other than an intact antibody that comprises a portion of an intact antibody that binds the antigen to which the intact antibody binds. Examples of antibody fragments include but are not limited to Fv, Fab', Fab'-SH, F(ab')$_2$; diabodies; linear antibodies; single-chain antibody molecules (e.g. scFv); and multispecific antibodies formed from antibody fragments. scFv antibodies are, e.g. described in Houston, J.S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CH1) of a heavy chain. The bispecific antibodies of the invention comprise at least two Fab fragments, wherein either the variable regions or the constant regions of the heavy and light chain of the second Fab fragment are exchanged. Due to the exchange of either the variable regions or the constant regions, said second Fab fragment is also referred to as "cross-Fab fragment" or "xFab fragment" or "crossover Fab fragment". Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

The Fab fragments are connected to each other by at least two peptide linkers, as outlined below.

If not otherwise defined, "connected" means that the Fab fragments are linked by peptide bonds, either directly or via one or more peptide linker The term "peptide linker" as used within the invention denotes a peptide with amino acid sequences, which is preferably of synthetic origin. These peptide linkers according to invention are used to connect one of the Fab fragments to the C-or N-terminus of the other Fab fragment to form a multispecific antibody according to the invention. Preferably said peptide linkers are peptides with an amino acid sequence with a length of at least 5 amino acids, preferably with a length of 5 to 100, more preferably of 10 to 50 amino acids. In one embodiment said peptide linker is (GxS)n or (GxS)nGm with G =glycine, S=serine, and (x=3, n=3, 4, 5 or 6, and m=0, 1, 2 or 3) or (x=4,n=2, 3, 4 or 5 and m=0, 1, 2 or 3) (SEQ ID NOS 204, 206, 205 and 207, respectively, in order of appearance), preferably x=4 and n=2 or 3, more preferably with x=4, n=2. Additionally, linkers may comprise (a portion of) an immunoglobulin hinge region. In one embodiment said peptide linker is (G$_4$S)$_2$ (SEQ ID: NO 28). Other peptide linkers suitable for connecting the Fab fragments, for example, (G$_4$S)$_6$-GG (SEQ ID NO: 147) or (SG$_3$)$_2$-(SEG$_3$)$_4$-(SG$_3$)-SG (SEQ ID NO: 148), or EPKSC(D)-(G$_4$S)$_2$ (SEQ ID NOs 145 and 146).

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The term "Fc domain" herein is used to define a C-terminal region of an immunoglobulin heavy chain that contains at least a portion of the constant region. For example in natural antibodies, the Fc domain is composed of two identical protein fragments, derived from the second and third constant domains of the antibody's two heavy chains in IgG, IgA and IgD isotypes; IgM and IgE Fc domains contain three heavy chain constant domains (C$_H$ domains 2-4) in each polypeptide chain. The bispecific antibodies of the invention are devoid of the Fc domain. "Devoid of the Fc domain" as used herein means that the bispecific antibodies of the invention do not comprise a CH2, CH3 or CH4 domain; i.e. the constant heavy chain consists solely of one or more CH1 domains.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Specific illustrative and exemplary embodiments for measuring binding affinity are described in the following.

As used herein, the term "binding" or "specifically binding" means that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIACORE® instrument (GE Healthcare, Marlborough, Mass) (Liljeblad et al., Glyco J 17, 323-329 (2000)), and traditional binding assays (Heeley, Endocr Res 28, 217-229 (2002). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant (K$_D$) of <1 µM, ≤100 nM, ≤10 nM, ≤1 nM, ≤0.1 nM, ≤0.01 nM, or ≤0.001 nM (e.g. 10$^{-8}$ M or less, e.g. from 10$^{-8}$ M to 10$^{-13}$ M, e.g., from 10$^{-9}$ M to 10$^{-13}$ M).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

In one embodiment, the extent of binding of a bispecific antibody that specifically binds a first antigen and a second antigen to an unrelated, protein is less than about 10% of the binding of the antibody to the first or second antigen as measured, e.g., by a radioimmunoassay (RIA) or flow cytometry (FACS). In certain embodiments, a bispecific antibody that specifically binds a first antigen and a second antigen has a dissociation constant (KD) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, a bispecific antibody that specifically binds a first antigen and a second antigen binds to an epitope of the first antigen or the second antigen that is conserved among the first or second antigen from different species.

In one embodiment, the extent of binding of a bispecific antibody that specifically binds to a T-cell activating antigen and a Tumor Antigen (TA) to an unrelated protein is less than about 10% of the binding of the antibody to a T-cell activating antigen or a Tumor Antigen (TA) as measured, e.g., by a radioimmunoassay (RIA) or flow cytometry (FACS). In certain embodiments, a bispecific antibody that specifically binds T-cell activating antigen and a Tumor Antigen (TA) has a dissociation constant (KD) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, a bispecific antibody that specifically binds a T-cell activating antigen and a Tumor Antigen (TA) binds to an epitope of a T-cell activating antigen or a Tumor Antigen (TA) that is conserved among a T-cell activating antigen or a Tumor Antigen (TA) from different species.

The terms "A bispecific antibody that specifically binds a T cell activating antigen and a Tumor Antigen (TA)" refers to a bispecific antibody that is capable of binding a T cell activating antigen and a Tumor Antigen with sufficient affinity such that the antibody is useful in mediating a T-cell mediated immune response in or near cells expressing a Tumor Antigen. In a particular embodiment the T cell activating antigen is the CD3 T-Cell Co-Receptor (CD3) antigen, particularly human or cynomolgus CD3, most particularly human CD3. In some embodiments, the T cell activating antigen is the epsilon subunit of CD3. In other embodiments, the T cell activating antigen is the alpha or beta subunit of CD3.

In one embodiment, the bispecific antibody that specifically binds a T cell activating antigen and a Tumor Antigen (TA) can compete with monoclonal antibody H2C (described in PCT publication no. WO2008/119567) for binding an epitope of CD3. In another embodiment, the bispecific antibody that specifically binds a T cell activating antigen and a Tumor Antigen (TA) can compete with monoclonal antibody V9 (described in Rodrigues et al., Int J Cancer Suppl 7, 45-50 (1992) and U.S. Pat. No. 6,054,297) for binding an epitope of CD3. In yet another embodiment, the bispecific antibody that specifically binds a T cell activating antigen and a Tumor Antigen (TA) can compete with monoclonal antibody FN18 (described in Nooij et al., Eur J Immunol 19, 981-984 (1986)) for binding an epitope of CD3. In one embodiment the bispecific antibody comprises an antigen binding moiety that can compete with monoclonal antibody CH2527 (Sequence ID 157 and 158) or an affinity matured variant thereof for binding to an epitope of CD3.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

The term "CD3 T-Cell Co-Receptor (CD3)", as used herein, refers to a protein complex and is composed of four distinct chains. In mammals, the complex contains a CD3γ chain, a CD3δ chain, and two CD3∈ chains. These chains associate with a molecule known as the T cell receptor (TCR) and the ζ-chain to generate an activation signal in T lymphocytes. The term "CD3 T-Cell Co-Receptor (CD3)" includes any native CD3 from any vertebrate source, including mammals such as primates (e.g. humans) and rodents (e.g., mice and rats), unless otherwise indicated, preferably from a human source. The term encompasses "full-length," unprocessed CD3 as well as any form of CD3 that results from processing in the cell. The term also encompasses naturally occurring variants of CD3, e.g., splice variants or allelic variants. In a preferred embodiment, the term CD3 T-Cell Co-Receptor refers to human or cynomolgus CD3, particularly human CD3. In some embodiments, the T cell activating antigen is the epsilon subunit of CD3. In other embodiments, the T cell activating antigen is the alpha or beta subunit of CD3. An exemplary sequence of human CD3 is given in SEQ ID NO.: 103.

The term "Tumor Antigen (TA)", as used herein, refers to tumor-associated antigens as well as tumor-specific antigens, i.e. any immunogenic epitope (e.g., protein) expressed by a tumor cell. The protein may be expressed by non tumor cells but be immunogenic only when expressed by a tumor cell. Alternatively, the protein may be expressed by tumor cells, but not normal cells. Preferably, an anti-TA antibody of the invention binds to the extracellular domain of TA. In one preferred embodiment said Tumor Antigen is a human Tumor Antigen. Exemplary Tumor Antigens include but are not limited to Melanoma-associated Chondroitin Sulfate Proteoglycan (MCSPB, UniProt Q6UVK1, NCBI Accession NP_001888), Fibroblast Activation Protein (FAP, Uni Prot Q12884, Q86Z29, Q99998; NCBI Accession NP_004451), Epidermal Growth Factor Receptor (EGFR, also known as ErbB1 and Her1, UniProt P00533; NCBI Accession NP_958439, NP_958440), Carcinoembryonic Antigen (CEA, also known as Carcinoembryonic antigen-related cell adhesion molecule 5 or CD66e; UniProt P06731, NCBI Accession NP_004354) and CD33 (also known as gp76 or Sialic acid-binding Ig-like lectin 3 (Siglec-3), UniProt P20138, NCBI Accession NP_001076087, NP_001171079).

In one embodiment the bispecific antibody of the invention comprises at least one antigen binding site that is specific for Melanoma-associated Chondroitin Sulfate Proteoglycan (MCSP).

Antibody specificity refers to selective recognition of the antibody for a particular epitope of an antigen. Natural antibodies, for example, are monospecific. "Bispecific antibodies" according to the invention are antibodies which have two different antigen-binding specificities. Antibodies of the present invention are specific for two different antigens, i.e. for a first antigen and a second antigen. Provided herein is a bispecific antibody, with binding specificities for a Tumor Antigen (TA) and a T-cell activating antigen. In certain embodiments, bispecific antibodies may bind to two different epitopes of TA. Bispecific antibodies may also be used to localize cytotoxic agents to cells which express TA.

The term "monospecific" antibody as used herein denotes an antibody that has one or more binding sites each of which bind to the same epitope of the same antigen.

The term "bispecific" antibody as used herein denotes an antibody that has at least two binding sites each of which bind to different epitopes of the same antigen or a different antigen.

The antibody provided herein is a multispecific antibody, e.g. a bispecific antibody. Multispecific antibodies are monoclonal antibodies that have binding specificities for at least two different sites. Provided herein is a bispecific antibody, with binding specificities for a first antigen and a second antigen. In certain embodiments, bispecific antibodies may bind to two different epitopes of a first antigen or a second antigen.

Bispecific antibodies may also be used to localize cytotoxic agents to cells which express a first antigen or a second antigen.

In one embodiment, the extent of binding of a bispecific antibody that specifically binds to a T-cell activating antigen and a Tumor Antigen (TA) to an unrelated protein is less than about 10% of the binding of the antibody to a T-cell activating antigen or a Tumor Antigen (TA) as measured, e.g., by a radioimmunoassay (RIA) or flow cytometry (FACS). In certain embodiments, a bispecific antibody that specifically binds T-cell activating antigen and a Tumor Antigen (TA) has a dissociation constant (KD) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, a bispecific antibody that specifically binds a T-cell activating antigen and a Tumor Antigen (TA) binds to an epitope of a T-cell activating antigen or a Tumor Antigen (TA) that is conserved among a T-cell activating antigen or a Tumor Antigen (TA) from different species.

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount selected from the group consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antibody of the invention" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Isolated nucleic acid encoding a bispecific antibody that specifically binds a T-Cell activating antigen and a Tumor Antigen (TA)" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "naked antibody" refers to an antibody that is not conjugated to a heterologous moiety (e.g., a cytotoxic moiety) or radiolabel. The naked antibody may be present in a pharmaceutical formulation.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "N-terminus" denotes the last amino acid of the N-terminus, the term "C-terminus" denotes the last amino acid of the C-terminus.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "effective amount" of an agent, e.g., a pharmaceutical formulation, refers to an amount effective, at dosages and for periods of time necessary, to achieve the desired therapeutic or prophylactic result.

The term "cancer" as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "package insert" is used to refer to instructions customarily included in commercial packages of therapeutic products, that contain information about the indications, usage, dosage, administration, combination therapy, contraindications and/or warnings concerning the use of such therapeutic products.

II. Compositions and Methods

A. Exemplary Bispecific Antibodies

The present invention relates to bispecific antibodies comprising at least two Fab fragments, wherein the first Fab fragment comprises at least one antigen binding site specific for a first antigen; and the second Fab fragment comprises at least one antigen binding site specific for a second antigen, wherein either the variable regions or the constant regions of the heavy and light chain of the second Fab fragment are exchanged; and wherein the two Fab fragments are connected to each other by two peptide linkers; and wherein the bispecific antibody is devoid of a Fc domain. Preferably said peptide linker is a peptide with an amino acid sequence with a length of at least 5 amino acids, preferably with a length of 5 to 100, more preferably of 10 to 50 amino acids. In one embodiment said peptide linker is (GxS)n or (GxS)nGm with G =glycine, S=serine, and (x=3, n=3, 4, 5 or 6, and m=0, 1, 2 or 3) or (x=4, n=2, 3, 4 or 5 and m=0, 1, 2 or 3) (SEQ ID NOS 204, 206, 205 and 207, respectively, in order of appearance), preferably x=4 and n=2 or 3, more preferably with x=4, n=2. In one embodiment said peptide linker is $(G_4S)_2$ (SEQ ID NO: 28). The peptide linkers are used to connect the first and the second Fab fragment.

In one embodiment the first Fab fragment is connected to the N-terminus of the second Fab fragment by two peptide linkers. Depending on whether the variable or the constant domains of the heavy and the light chains of the second Fab fragment are exchanged, different bispecific antibody molecules are possible when the first Fab fragment is connected to the N-terminus of the second Fab fragment by two peptide linkers.

In one embodiment the variable domains of the second Fab fragment are exchanged (i.e. the second Fab fragment is a CrossFab$_{(VHVL)}$), and the C-terminus of the heavy chain of the first Fab fragment is connected to the N-terminus of the VLCH1 chain of the second Fab fragment by a peptide linker, and the C-terminus of the light chain of the first Fab fragment is connected to the N-terminus of the VHCL chain of the second Fab fragment by a peptide linker. Thus, in one embodiment the bispecific antibody comprises two chains: a light chain (VLCL) of the first Fab fragment connected to the VHCL chain of the second Fab fragment via a peptide linker (VLCL-linker-VHCL) and the heavy chain (VHCH1) of the first Fab fragment connected to the VLCH1 chain of the second Fab fragment via a peptide linker (VHCH1-linker-VLCH1).

In another embodiment the constant domains of the second Fab fragment are exchanged (i.e the second Fab fragment is a CrossFab$_{(CLCH1)}$) and the C-terminus of the heavy chain of the first Fab fragment is connected to the N-terminus of the VHCL chain of the second Fab fragment by a peptide linker, and the light chain of the first Fab fragment is connected to the N-terminus of the VLCH1 chain by a peptide linker. Thus, in one embodiment the bispecific antibody comprises two chains: a light chain (VLCL) of the first Fab fragment connected to the VLCH1 chain of the second Fab fragment via a peptide linker (VLCL-linker-VLCH1), and the heavy chain (VHCH1) of the first Fab fragment connected to the VHCL chain of the second Fab fragment via a peptide linker (VHCH1-linker-VHCL).

In one embodiment the first Fab fragment is connected to the C-terminus of the second Fab fragment by two peptide linkers. Depending on whether the variable or the constant domains of the heavy and the light chains of the second Fab fragment are exchanged different bispecific antibody molecules are possible when the first Fab fragment is connected to the C-terminus of the second Fab fragment by two peptide linkers.

In one embodiment the variable domains of the second Fab fragment are exchanged (i.e. the second Fab fragment is a CrossFab$_{(VHVL)}$), and the N-terminus of the heavy chain of the first Fab fragment is connected to the C-terminus of the VLCH1 chain of the second Fab fragment by a peptide linker, and the N-terminus of the light chain of the first Fab fragment is connected to the C-terminus of the VHCL chain of the second Fab fragment by a peptide linker. Thus, in one embodiment the bispecific antibody comprises two chains: the VHCL chain of the second Fab fragment connected to a light chain (VLCL) of the first Fab fragment via a peptide linker (VHCL-linker-VLCL) and the VLCH1 chain of the second Fab fragment connected to the heavy chain (VHCH1) of the first Fab fragment via a peptide linker (VLCH1-linker-VHCH1).

In another embodiment the constant domains of the second Fab fragment are exchanged (i.e the second Fab fragment is a CrossFab (CLCH1)) and the N-terminus of the heavy chain of the first Fab fragment is connected to the C-terminus of the VHCL chain of the second Fab fragment by a peptide linker, and the N-terminus of the light chain of the first Fab fragment is connected to the C-terminus of the VLCH1 chain by a peptide linker. Thus, in one embodiment the bispecific antibody comprises two chains: the VLCH1 chain of the second Fab fragment connected to a light chain (VLCL) of the first Fab fragment via a peptide linker (VLCH1-linker-VLCL), and the VHCL chain of the second Fab fragment connected to the heavy chain (VHCH1) of the first Fab fragment via a peptide linker (VHCL-linker-VHCH1). The bispecific antibodies according to the invention are at least bivalent and can be trivalent or multivalent e.g. tetravalent. In one embodiment said bispecific antibodies are bivalent (1+1 format) with one binding site each targeting a first antigen and a second antigen, respectively. In another embodiment said bispecific antibodies are trivalent (2+1 format) with two binding sites each targeting a first antigen and one binding site targeting a second antigen, as detailed in the following section.

In one embodiment said antibody additionally comprises a third Fab fragment. In another embodiment said third Fab fragment comprises at least one antigen binding site specific for the first or second antigen, preferably for the first antigen.

In one embodiment the third Fab fragment is connected to the N or C-terminus of the first Fab fragment. In one embodiment the third Fab fragment is connected to the first Fab fragment via at least one peptide linker. Preferably said peptide linker is a (G4S)2 linker (SEQ ID NO: 28).

In one embodiment the third Fab fragment is connected to the N or C-terminus of the light chain or the heavy chain of the first Fab fragment. Depending on which terminus of the first Fab fragment is connected to the second Fab fragment (as detailed above), the third Fab fragment is connected on the opposite (free) terminus of the first fragment. The third Fab fragment can be connected by either one or two linkers.

In one embodiment, the bispecific antibody of the invention comprises three Fab fragments wherein said Fab fragments and said linkers are connected in the following order from N-terminal to C-terminal direction: Fab fragment 3- (1 or 2 linkers)-Fab fragment 1- (2 linkers)-Fab fragment 2, wherein either the variable regions or the constant regions of the heavy and light chain of the second Fab fragment are exchanged. In this embodiment the C-terminus of the third Fab fragment is connected to the N-terminus of the first Fab fragment. As detailed above, the Fab fragments can be connected to each other via the heavy or the light chains. In one embodiment the C-terminus of the heavy chain of the third Fab fragment is connected to the N-terminus of the heavy chain of the first Fab fragment via a peptide linker; and the first Fab fragment is connected to the second Fab fragment by two linkers, wherein either the variable regions or the constant regions of the heavy and light chain of the second Fab fragment are exchanged. Depending on whether the variable or the constant domains of the heavy and the light chains of the second Fab fragment are exchanged different bispecific antibody molecules are possible.

In one embodiment the variable domains of the second Fab fragment are exchanged (i.e. the second Fab fragment is a CrossFab$_{(VHVL)}$), and the chains of the three Fab fragments are connected in the following order from N-terminal to C-terminal direction: VHCH1-linker-VHCH1-linker-VLCH1. In one embodiment the bispecific antibody comprises three chains: a light chain (VLCL) of the third Fab fragment, a light chain (VLCL) of the first Fab fragment connected to the VHCL chain of the second Fab fragment by a peptide linker (VLCL-linker-VHCL), and the heavy chain of the third fragment connected to the heavy chain of the first Fab fragment which itself is connected to the VLCH1 chain of the second Fab fragment via a peptide linker (VHCH1-linker-VHCH1-linker-VLCH1). In another embodiment said third Fab fragment is connected to the first Fab fragment by two linkers, and the bispecific antibody comprises two chains: the light chain (VLCL) of the third Fab fragment connected by linker to a light chain (VLCL) of the first Fab fragment which is in turn connected to the VHCL chain of the second Fab fragment by a peptide linker (VLCL-linker-VLCL-linker-VHCL), and the heavy chain of the third fragment connected to the heavy chain of the first Fab fragment which itself is connected to the VLCH1 chain of the second Fab fragment via a peptide linker (VHCH1-linker-VHCH1-linker-VLCH1).

In one embodiment the constant domains of the second Fab fragment are exchanged (i.e. the second Fab fragment is a CrossFab$_{(CLCH1)}$), and the chains of the three Fab fragments are connected in the following order from N-terminal to C-terminal direction: VHCH1-linker-VHCH1-linker-VHCL. In one embodiment the bispecific antibody comprises three chains: a light chain (VLCL) of the third Fab fragment, a light chain (VLCL) of the first Fab fragment to the VLCH1 chain of the second Fab fragment by a peptide linker (VLCL-linker-VLCH1), and the heavy chain of the third fragment connected to the heavy chain of the first Fab fragment which itself is connected to the VHCL chain of the second Fab fragment via a peptide linker (VHCH1-linker-VHCH1-linker-VHCL). In another embodiment said third Fab fragment is connected to the first Fab fragment by two linkers, and the bispecific antibody comprises two chains: a light chain (VLCL) of the third Fab fragment connected to a light chain (VLCL) of the first Fab fragment which is in turn connected to the VLCH1 chain of the second Fab fragment by a peptide linker (VLCL-linker-VLCL-linker-VLCH1), and the heavy chain of the third fragment connected to the heavy chain of the first Fab fragment which itself is connected to the VHCL chain of the second Fab fragment via a peptide linker (VHCH1-linker-VHCH1-linker-VHCL)

In one embodiment the bispecific antibody of the invention comprises three Fab fragments wherein said Fab fragments and said linker are connected in the following order from N-terminal to C-terminal direction: Fab fragment 2- (2 linkers)-Fab fragment 1- (1 or 2 linkers)-Fab fragment 3, wherein either the variable regions or the constant regions of the heavy and light chain of the second Fab fragment are exchanged. In this embodiment the N-terminus of the third Fab fragment is connected to the C-terminus of the first Fab fragment. As detailed above, the Fab fragments can be connected to each other via the heavy or the light chains. In one embodiment the N-terminus of the heavy chain of the third Fab fragment is connected to the C-terminus of the heavy chain of the first Fab fragment via a peptide linker; and the first Fab fragment is connected to the second Fab fragment by two linkers, wherein either the variable regions or the constant regions of the heavy and light chain of the second Fab fragment are exchanged. Depending on whether the variable or the constant domains of the heavy and the light chains of the second Fab fragment are exchanged different bispecific antibody molecules are possible.

In one embodiment the variable domains of the second Fab fragment are exchanged (i.e. the second Fab fragment is a CrossFab$_{(VHVL)}$), and the chains of the three Fab fragments are connected in the following order from N-terminal to C-terminal direction: VLCH1-linker-VHCH1-linker-VHCH1. In one embodiment the bispecific antibody comprises three chains: a light chain (VLCL) of the third Fab fragment, a VHCL chain of the second Fab fragment connected to a light chain (VLCL) of the first Fab fragment by a peptide linker (VHCL-linker-VLCL), and the VLCH1 chain of the second Fab fragment connected to the heavy chain of the first fragment which itself is connected to the heavy chain of the first Fab fragment via a peptide linker (VLCH1-linker-VHCH1-linker-VHCH1). In another embodiment said third Fab fragment is connected to the first Fab fragment by two linkers, and the bispecific antibody comprises two chains: a VHCL chain of the second Fab fragment connected to a light chain (VLCL) of the first Fab fragment by a peptide linker, which is in turn connected to a light chain (VLCL) of the third Fab fragment by a peptide linker (VHCL-linker-VLCL-linker-VLCL), and the VLCH1 chain of the second Fab fragment connected to the heavy chain of the first fragment which itself is connected to the heavy chain of the first Fab fragment via a peptide linker (VLCH1-linker-VHCH1-linker-VHCH1).

In one embodiment the constant domains of the second Fab fragment are exchanged (i.e. the second Fab fragment is a CrossFab$_{(CLCH1)}$), and the chains of the three Fab fragments are connected in the following order from N-terminal to C-terminal direction: VHCL-linker-VHCH1-linker-VHCH1. In one embodiment the bispecific antibody comprises three chains: a light chain (VLCL) of the third Fab fragment, and a VLCH1 chain of the second Fab fragment connected to a light chain (VLCL) of the first Fab fragment (VLCH1-linker-VLCL), and the VHCL chain of the second Fab fragment connected to the heavy chain of the first fragment which itself is connected to the heavy chain of the first Fab fragment via a peptide linker (VHCL-linker-VHCH1-linker-VHCH1). In another embodiment said third Fab fragment is connected to the first Fab fragment by two linkers, and the bispecific antibody comprises two chains: a VLCH1 chain of the second Fab fragment connected to a light chain (VLCL) of the first Fab fragment, which is in turn connected to a light chain of the third fragment (VLCH1-linker-VLCL-linker-VLCL) and the VHCL chain of the second Fab fragment connected to the heavy chain of the first fragment which itself is connected to the heavy chain of the first Fab fragment via a peptide linker (VHCL-linker-VHCH1-linker-VHCH1).

In another embodiment the third Fab fragment is connected to N or C-terminus of the light chain or the heavy chain of the second Fab fragment. In one embodiment the third Fab fragment is connected to the second Fab fragment via a peptide linker. Preferably said peptide linker is a (G4S)2 linker (SEQ ID NO: 28). As detailed above, the Fab fragments can be connected to each other via the heavy or the light chains.

In one embodiment the bispecific antibody of the invention comprises three Fab fragments wherein said Fab fragments and said linker are connected in the following order from N-terminal to C-terminal direction: Fab fragment 1- (2 linkers)-Fab fragment 2- (1 or 2 linkers)-Fab fragment 3, wherein either the variable regions or the constant regions of the heavy and light chain of the second Fab fragment are exchanged. In one embodiment the N-terminus of the third Fab fragment is connected to the C-terminus of the second Fab fragment.

In another embodiment the C-terminus of the heavy chain of the third Fab fragment is connected to the N-terminus of the second Fab fragment via a peptide linker; and the first Fab fragment is connected to the second Fab fragment by two linkers, wherein either the variable regions or the constant regions of the heavy and light chain of the second Fab fragment are exchanged.

Depending on whether the variable or the constant domains of the heavy and the light chains of the second Fab fragment are exchanged different bispecific antibody molecules are possible.

In one embodiment the variable domains of the second Fab fragment are exchanged (i.e. the second Fab fragment is a CrossFab$_{(VHVL)}$), and the chains of the three Fab fragments are connected in the following order from N-terminal to C-terminal direction:VHCH1-linker-VLCH1-linker-VHCH1. In one embodiment the bispecific antibody comprises three chains: a light chain (VLCL) of the third Fab fragment, a light chain (VLCL) of the first Fab fragment connected to a VHCL chain of the second Fab fragment by a linker (VLCL-linker-VHCL), and the heavy chain of the third fragment connected to the N-terminus of the VLCH1 chain of the second Fab fragment, and the C-terminus of said VLCH1 chain connected to the N-terminus of the heavy chain of the first Fab fragment via a peptide linker (VHCH1-linker-VLCH1-linker-VHCH1). In another embodiment said third Fab fragment is connected to the second Fab fragment by two linkers, and the bispecific antibody comprises two chains: a light chain (VLCL) of the first Fab fragment connected to a VHCL chain of the second Fab fragment by a linker, which is in turn connected to the light chain of the third Fab fragment (VLCL-linker-VHCL-linker-VLCL), and the heavy chain of the third fragment connected to the N-terminus of the VLCH1 chain of the second Fab fragment, and the C-terminus of said VLCH1 chain connected to the N-terminus of the heavy chain of the first Fab fragment via a peptide linker (VHCH1-linker-VLCH1-linker-VHCH1).

In one embodiment the constant domains of the second Fab fragment are exchanged (i.e. the second Fab fragment is a CrossFab$_{(CLCH1)}$), and the chains of the three Fab fragments are connected in the following order from N-terminal to C-terminal direction:VHCH1-linker-VHCL-linker-VHCH1. In one embodiment the bispecific antibody comprises three chains: a light chain (VLCL) of the third Fab fragment, a light chain (VLCL) of the first Fab fragment connected to a VLCH1 chain of the second Fab fragment by a peptide linker (VLCL-linker-VHCH1), and the heavy chain of the third fragment connected to the N-terminus of the VHCL chain of the second Fab fragment, and the C-terminus of said VHCL chain connected to the N-terminus of the heavy chain of the first Fab fragment via a peptide linker (VHCH1-linker-VHCL-linker-VHCH1). In another embodiment said third Fab fragment is connected to the second Fab fragment by two linkers, and the bispecific antibody comprises two chains: a light chain (VLCL) of the first Fab fragment connected to a VLCH1 chain of the second Fab fragment by a peptide linker, which is in turn connected to the light chain of the third Fab fragment (VLCL-linker-VHCH1-linker-VLCL), and the heavy chain of the third fragment connected to the N-terminus of the VHCL chain of the second Fab fragment, and the C-terminus of said VHCL chain connected to the N-terminus of the heavy chain of the first Fab fragment via a peptide linker (VHCH1-linker-VHCL-linker-VHCH1).

B. Exemplary Bispecific Antibodies that Bind to a T-cell Activating Antigen and a Tumor Antigen (TA)

The present invention relates to bispecific antibodies combining a T-cell activating antigen binding site with a second antigen binding site that targets a Tumor Antigen (TA). The antibodies of the invention specifically bind to a Tumor Antigen on the surface of a tumor cell and at the same time bind to an antigen on the surface of cytotoxic T lymphocytes. Preferably said antigen is a CD3 T-Cell Co-Receptor (CD3) antigen. The bispecific antibody is capable to elicit an immune response specifically at the site of the tumor, subsequently resulting in apoptosis of the target cell. It is understood that the sequences exemplified in this section can be arranged in any antibody format exemplified in the embodiments in section A above.

In a particular embodiment according to the invention, the T cell activating bispecific antibody is capable of simultaneous binding to a tumor cell antigen, and an activating T cell antigen. In one embodiment, the T cell activating bispecific antibody is capable of crosslinking a cell and a tumor cell by simultaneous binding to a tumor cell antigen and an activating T cell antigen. In an even more particular embodiment, such simultaneous binding results in lysis of the tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antibody to the activating T cell antigen without simultaneous binding to the target cell antigen does not result in cell activation.

In one embodiment, the T cell activating bispecific antibody is capable of re-directing cytotoxic activity of a T cell to a target cell. In a particular embodiment, said re-direction is independent of MHC-mediated peptide antigen presentation by the target cell and/or specificity of the T cell. Particularly, a T cell according to any of the embodiments of the invention is a cytotoxic T cell. In some embodiments the T cell is a CD4$^+$ or a CD8$^+$ T cell, particularly a CD8$^+$ T cell.

In one embodiment bispecific antibodies are provided that specifically bind a T-cell activating antigen and a Tumor Antigen (TA), comprising a first Fab fragment and a second Fab fragment, wherein either the variable regions or the constant regions of the second Fab heavy and light chain are exchanged and the two Fab fragments are connected to each other by two peptide linkers and wherein the bispecific antibody does not comprise a Fc domain, as detailed in section A above.

In one aspect, a bispecific antibody that specifically binds a T-cell activating antigen and a Tumor Antigen (TA) is provided, comprising at least two Fab fragments connected by two peptide linkers, wherein the first Fab fragment comprises at least one antigen binding site specific for a Tumor Antigen (TA); and the second Fab fragment comprises at least one antigen binding site specific for a T-cell activating antigen, wherein either the variable regions or the constant regions of the second Fab heavy and light chain are exchanged; and wherein the bispecific antibody is devoid of a Fc domain.

In a particular embodiment the T cell activating antigen is the CD3 T-Cell Co-Receptor (CD3) antigen, particularly human or cynomolgus CD3, most particularly human CD3. In some embodiments, the T cell activating antigen is the epsilon subunit of CD3. In other embodiments, the T cell activating antigen is the alpha or beta subunit of CD3.

In one aspect, a bispecific antibody that specifically binds CD3 T-Cell Co-Receptor (CD3) antigen and a Tumor Antigen (TA) is provided, comprising at least two Fab fragments which are connected by two peptide linkers, wherein the first Fab fragment comprises at least one antigen binding site specific for a Tumor Antigen (TA); and the second Fab fragment comprises at least one antigen binding site specific for a CD3 T-Cell Co-Receptor (CD3) wherein either the variable regions or the constant regions of the second Fab heavy and light chain are exchanged; and wherein the bispecific antibody is devoid of a Fc domain.

The bispecific antibodies according to the invention are at least bivalent and can be trivalent or multivalent e.g. tetravalent or hexavalent. In one embodiment said bispecific antibodies are bivalent (1+1 format) with one binding site each targeting a Tumor Antigen (TA) and a T-cell activating antigen, respectively. In another embodiment said bispecific antibodies are trivalent (2+1 format) with two binding sites each targeting a Tumor Antigen (TA) and one binding site targeting a T-cell activating antigen, as detailed in the following section.

In one embodiment said antibody additionally comprises a third Fab fragment, as detailed in section A above. In one embodiment said third Fab fragment comprises at least one antigen binding site specific for a Tumor Antigen. In one embodiment the antigen binding site of said third Fab fragment is specific for the same Tumor Antigen as the antigen binding site of the first Fab fragment.

In one embodiment, the antigen binding site of said third Fab fragment is specific for the same Tumor Antigen as the antigen binding site of the first Fab fragment, and the bispecific antibody of the invention comprises three Fab fragments connected by peptide linkers in the following order (either from N-terminal to C-terminal direction or from C-terminal to N-terminal direction): Fab$_{(TA)}$-(1 or 2 linkers)-Fab$_{(TA)}$-(2 linkers)-xFab$_{(T\text{-}cell\ activating\ antigen)}$, wherein Fab$_{(TA)}$ denotes a Fab fragment with antigen binding site specific for a Tumor Antigen and xFab$_{(T\text{-}cell\ activating\ antigen)}$ denotes a Fab fragment with antigen binding site specific for a T-cell activating antigen, wherein either the variable regions or the constant regions of the heavy and light chain are exchanged.

In one embodiment, the antigen binding site of said third Fab fragment is specific for the same Tumor Antigen as the antigen binding site of the first Fab fragment, and the bispecific antibody of the invention comprises three Fab fragments connected by peptide linkers in the following order (either from N-terminal to C-terminal direction or from C-terminal to N-terminal direction): Fab$_{(TA)}$-(2 linkers)-xFab$_{(T\text{-}cell\ activating\ antigen)}$-(1 or 2 linkers)-Fab$_{(TA)}$, wherein Fab$_{(TA)}$ denotes a Fab fragment with antigen binding site specific for a Tumor Antigen and xFab$_{(T\text{-}cell\ activating\ antigen)}$ denotes a Fab fragment with antigen binding site specific for a T-cell activating antigen, wherein either the variable regions or the constant regions of the heavy and light chain are exchanged.

In one embodiment the bispecific antibody comprises an antigen binding moiety that can compete with monoclonal antibody V9 for binding to an epitope of CD3. See for example Rodigues et al., Int J Cancer Suppl 7 (1992), 45-50; U.S. Pat. No. 6,054,297, incorporated herein by reference in its entirety.

In one embodiment the bispecific antibody comprises an antigen binding moiety that can compete with monoclonal antibody FN18 for binding to an epitope of CD3. See Nooij et al., Eur J Immunol 19 (1986), 981-984, incorporated herein by reference in its entirety.

In one embodiment the bispecific antibody comprises an antigen binding moiety that can compete with monoclonal antibody CH2527 (Sequence ID 157 and 158 and humanized variants) or an affinity matured variant thereof for binding to an epitope of CD3.

In one embodiment the bispecific antibody comprises a second Fab fragment specifically binding to CD3, wherein the heavy chain variable region comprises a CDR1 of SEQ ID. NO. 10 or SEQ ID. NO. 32, a CDR2 of SEQ ID. NO. 11 or SEQ ID. NO. 33, and a CDR3 of SEQ ID. NO. 12 or SEQ ID. NO. 34; and wherein the light chain variable region comprises a CDR1 of SEQ ID. NO. 7 or SEQ ID. NO. 29, a CDR2 of SEQ ID. NO. 8 or SEQ ID. NO. 30, and a CDR3 of SEQ ID. NO. 9 or SEQ ID. NO.31.

In one embodiment the bispecific antibody comprises a second Fab fragment specifically binding to CD3, wherein the heavy chain variable region comprises a CDR1 of SEQ ID. NO. 10, a CDR2 of SEQ ID. NO. 11, and a CDR3 of SEQ ID. NO. 12; and wherein the light chain variable region comprises a CDR1 of SEQ ID. NO. 7, a CDR2 of SEQ ID. NO. 8 and a CDR3 of SEQ ID. NO. 9.

In one embodiment the bispecific antibody comprises a second Fab fragment specifically binding to CD3, wherein the heavy chain variable region comprises a CDR1 of SEQ ID. NO. 32, a CDR2 SEQ ID. NO. 33, and a CDR3 of SEQ ID. NO. 34; and wherein the light chain variable region comprises a CDR1 of SEQ ID. NO. 29, a CDR2 of SEQ ID. NO. 30, and a CDR3 of SEQ ID. NO.31.

In one embodiment the bispecific antibody comprises a second Fab fragment specifically binding to CD3, wherein the heavy chain variable region comprises a CDR1 of SEQ ID. NO. 170, a CDR2 of SEQ ID. NO. 171, and a CDR3 of SEQ ID. NO. 172; and wherein the light chain variable region comprises a CDR1 of SEQ ID. NO. 174, a CDR2 of SEQ ID. NO. 175 and a CDR3 of SEQ ID. NO. 176.

In one embodiment the bispecific antibody comprises a light chain and a heavy chain of a second Fab fragment specifically binding to CD3, wherein the heavy chain variable region sequence is at least about 80%, 85%, 90%, 95%, 96%, 97%, 98%, 99% or 100% identical to SEQ ID. NO. 20 or SEQ ID. NO. 36; wherein the light chain variable region sequence is at least about 80%, 85%, 90%, 95%, 96%, 97%, 98%, 99% or 100% identical to SEQ ID. NO. 19. or SEQ ID. NO 35, or variants thereof that retain functionality. In one embodiment the bispecific antibody comprises a light chain and a heavy chain of a second Fab fragment specifically binding to CD3, wherein the heavy chain variable region comprises an amino acid sequence of SEQ ID. NO. 20; and a light chain variable region comprising an amino acid sequence of SEQ ID. NO. 19 or variants thereof that retain functionality.

In one embodiment the bispecific antibody comprises a light chain and a heavy chain of a second Fab fragment specifically binding to CD3, wherein the heavy chain variable region comprises an amino acid sequence of SEQ ID. NO. 36; and a light chain variable region comprising an amino acid sequence of SEQ ID. NO. 35 or variants thereof that retain functionality.

In one embodiment the bispecific antibody comprises a light chain and a heavy chain of a second Fab fragment specifically binding to CD3, wherein the heavy chain variable region comprises an amino acid sequence of SEQ ID. NO. 158; and a light chain variable region comprising an amino acid sequence of SEQ ID. NO. 157 or variants thereof that retain functionality. In one embodiment the bispecific antibody comprises a light chain and a heavy chain of a second Fab fragment specifically binding to CD3, wherein the heavy chain variable region sequence is at least about 80%, 85%, 90%, 95%, 96%, 97%, 98%, 99% or 100% identical to SEQ ID. NO. 158; wherein the light chain variable region sequence is at least about 80%, 85%, 90%, 95%, 96%, 97%, 98%, 99% or 100% identical to SEQ ID. NO. 157, or variants thereof that retain functionality. In one embodiment the bispecific antibody comprises a light chain and a heavy chain of a second Fab fragment specifically binding to CD3, wherein the heavy chain variable region sequence is an affinity matured variant of SEQ ID. NO. 158 and wherein the light chain variable region sequence is an affinity matured variant of SEQ ID. NO. 157. Affinity matured variants in this embodiment means that independently 1, 2, 3 or 4 amino acids of SEQ ID. NO. 158 and/or SEQ ID. NO. 157 are exchanged.

In one embodiment the bispecific antibody comprises a light chain and a heavy chain of a second Fab fragment specifically binding to CD3, wherein the heavy chain variable region comprises an amino acid sequence of SEQ ID. NO. 169; and a light chain variable region comprising an amino acid sequence of SEQ ID. NO. 173.

In one embodiment, the bispecific antibody comprises a light chain and a heavy chain of second Fab fragment specifically binding to CD3, wherein said heavy chain comprises a constant region comprising the amino acid sequence of SEQ ID NO: 22 or SEQ ID. NO. 38 or variants thereof that retain functionality. In one embodiment, the bispecific antibody comprises a light chain and a heavy chain of a second Fab fragment specifically binding to CD3, wherein said heavy chain comprises a constant region comprising the amino acid sequence of SEQ ID NO: 22 or SEQ ID. NO 38, and a light chain and a heavy chain of first Fab fragment specific for a Tumor Antigen (TA) comprising one or more amino acid sequences as defined in any of the embodiments described herein.

In one embodiment, the bispecific antibody comprises a light chain and a heavy chain of 15 second Fab fragment specifically binding to CD3, wherein said heavy chain comprises a constant region comprising the amino acid sequence of SEQ ID NO: 22. In one embodiment, the bispecific antibody comprises a light chain and a heavy chain of a second Fab fragment specifically binding to CD3, wherein said heavy chain comprises a constant region comprising the amino acid sequence of SEQ ID NO: 22, and a light chain and a heavy chain of first Fab fragment specific for a Tumor Antigen (TA) comprising one or more amino acid sequences as defined in any of the embodiments described herein.

In one embodiment, the bispecific antibody comprises a light chain and a heavy chain of a second Fab fragment specifically binding to CD3, wherein said light chain comprises a constant region comprising the amino acid sequence of SEQ ID NO: 21 or SEQ ID. NO. 37. In one embodiment, the bispecific antibody comprises a light chain and a heavy chain of a second Fab fragment specifically binding to CD3, wherein said light chain comprises a constant region comprising the amino acid sequence of SEQ ID NO: 21 or SEQ ID. NO. 37, and a light chain and a heavy chain of a first Fab fragment specific for a Tumor Antigen (TA) comprising one or more amino acid sequences as defined in any of the embodiments described herein.

In one embodiment, the bispecific antibody comprises a light chain and a heavy chain of a second Fab fragment specifically binding to CD3, wherein said light chain comprises a constant region comprising the amino acid sequence of SEQ ID NO: 21. In one embodiment, the bispecific antibody comprises a light chain and a heavy chain of a second Fab fragment specifically binding to CD3, wherein said light chain comprises a constant region comprising the amino acid sequence of SEQ ID NO: 21, and a light chain and a heavy chain of a first Fab fragment specific for a Tumor Antigen (TA) comprising one or more amino acid sequences as defined in any of the embodiments described herein.

In yet another specific embodiment, a bispecific antibody of the invention comprises a light chain and a heavy chain of a second Fab fragment specifically binding to CD3, said heavy chain comprising a heavy chain constant region comprising the amino acid sequence of SEQ ID NO: 22 or SEQ ID. NO. 38; and said light chain comprising a light chain constant region comprising the amino acid sequence of SEQ ID NO: 21 or SEQ ID. NO. 37.

In yet another specific embodiment, a bispecific antibody of the invention comprises a light chain and a heavy chain of a second Fab fragment specifically binding to CD3, said heavy chain comprising a heavy chain constant region comprising the amino acid sequence of SEQ ID NO: 22; and said light chain comprising a light chain constant region comprising the amino acid sequence of SEQ ID NO: 21.

In yet another specific embodiment, a bispecific antibody of the invention comprises a light chain and a heavy chain of a second Fab fragment specifically binding to CD3, said heavy chain comprising a heavy chain constant region comprising the amino acid sequence of SEQ ID NO: 22; and said light chain comprising a light chain constant region comprising the amino acid sequence of SEQ ID NO: 21, and a light chain and a heavy chain of a first Fab fragment specific for a Tumor Antigen (TA) comprising one or more amino acid sequences as defined in any of the embodiments described herein.

In one embodiment the bispecific antibody of the invention comprises a light chain and a heavy chain of a second Fab fragment specifically binding to CD3, comprising a variable light chain of SEQ ID NO: 19 and a variable heavy chain of SEQ ID NO: 20, and a heavy chain constant region comprising the amino acid sequence of SEQ ID NO: 22, and a light chain constant region comprising the amino acid sequence of SEQ ID NO: 21.

In one embodiment the bispecific antibody of the invention comprises a light chain and a heavy chain of a second Fab fragment specifically binding to CD3, comprising a variable light chain of SEQ ID NO: 19 and a variable heavy chain of SEQ ID NO: 20, and a heavy chain constant region comprising the amino acid sequence of SEQ ID NO: 22, and a light chain constant region comprising the amino acid sequence of SEQ ID NO: 21, and a light chain and a heavy chain of a first Fab fragment specific for a Tumor Antigen (TA) comprising one or more amino acid sequences as defined in any of the embodiments described herein.

In one embodiment the bispecific antibody of the invention comprises a light chain and a heavy chain of a second Fab fragment specifically binding to CD3, comprising a variable light chain of SEQ ID NO: 35 and a variable heavy chain of SEQ ID NO: 36, and a heavy chain constant region comprising the amino acid sequence of SEQ ID NO: 38, and a light chain constant region comprising the amino acid sequence of SEQ ID NO: 37.

In one embodiment the bispecific antibody of the invention comprises a light chain and a heavy chain of a second Fab fragment specifically binding to CD3, comprising a variable light chain of SEQ ID NO: 35 and a variable heavy chain of SEQ ID NO: 36, and a heavy chain constant region comprising the amino acid sequence of SEQ ID NO: 38, and a light chain constant region comprising the amino acid sequence of SEQ ID NO: 37., and a light chain and a heavy chain of a first Fab fragment specific for a Tumor Antigen (TA) comprising one or more amino acid sequences as defined in any of the embodiments described herein.

In one embodiment the bispecific antibody of the invention comprises a light chain and a heavy chain of a second Fab fragment specifically binding to CD3, comprising a variable light chain of SEQ ID NO: 173 and a variable heavy chain of SEQ ID NO: 169, and a heavy chain constant region comprising the amino acid sequence of SEQ ID NO: 38, and a light chain constant region comprising the amino acid sequence of SEQ ID NO: 37.

In one embodiment the bispecific antibody of the invention comprises a light chain and a heavy chain of a second Fab fragment specifically binding to CD3, comprising a variable light chain of SEQ ID NO: 173 and a variable heavy chain of SEQ ID NO: 169, and a heavy chain constant region comprising the amino acid sequence of SEQ ID NO: 38, and a light chain constant region comprising the amino acid sequence of SEQ ID NO: 37., and a light chain and a heavy chain of a first Fab fragment specific for a Tumor Antigen (TA) comprising one or more amino acid sequences as defined in any of the embodiments described herein.

In one embodiment the bispecific antibody of the invention comprises a light chain and a heavy chain of a second Fab fragment specifically binding to CD3, comprising a variable light chain of SEQ ID NO: 157 and a variable heavy chain of SEQ ID NO: 158, and a heavy chain constant region comprising the amino acid sequence of SEQ ID NO: 22, and a light chain constant region comprising the amino acid sequence of SEQ ID NO: 21.

In one embodiment the bispecific antibody of the invention comprises a light chain and a heavy chain of a second Fab fragment specifically binding to CD3, comprising a variable light chain of SEQ ID NO: 157 or an affinity matured variant thereof and a variable heavy chain of SEQ ID NO: 158 or an affinity matured variant thereof, and a heavy chain constant region comprising the amino acid sequence of SEQ ID NO: 22, and a light chain constant region comprising the amino acid sequence of SEQ ID NO: 21. Affinity matured variants in this embodiment means that independently 1, 2, 3 or 4 amino acids of SEQ ID. NO. 158 and/or SEQ ID. NO. 157 are exchanged.

In one embodiment the bispecific antibody of the invention comprises a light chain and a heavy chain of a second Fab fragment specifically binding to CD3, comprising a variable light chain of SEQ ID NO: 157 and a variable heavy chain of SEQ ID NO: 158, and a heavy chain constant region comprising the amino acid sequence of SEQ ID NO: 22, and a light chain constant region comprising the amino acid sequence of SEQ ID NO: 21, and a light chain and a heavy chain of a first Fab fragment specific for a Tumor Antigen (TA) comprising one or more amino acid sequences as defined in any of the embodiments described herein.

In one embodiment the bispecific antibody of the invention comprises a light chain and a heavy chain of a second Fab fragment specifically binding to CD3, comprising a variable light chain of SEQ ID NO: 157 or an affinity matured variant thereof and a variable heavy chain of SEQ ID NO: 158 or an affinity matured variant thereof, and a heavy chain constant region comprising the amino acid sequence of SEQ ID NO: 22, and a light chain constant region comprising the amino acid sequence of SEQ ID NO: 21 and a heavy chain of a first Fab fragment specific for a Tumor Antigen (TA) comprising one or more amino acid sequences as defined in any of the embodiments described herein. Affinity matured variants in this embodiment means that independently 1, 2, 3 or 4 amino acids of SEQ ID. NO. 158 and/or SEQ ID. NO. 157 are exchanged.

In one embodiment the Tumor Antigen is selected from the group of Melanoma-associated Chondroitin Sulfate Proteoglycan (MCSP), Epidermal Growth Factor Receptor (EGFR), Carcinoembryonic Antigen (CEA), Fibroblast Activation Protein (FAP) and CD33. In one preferred embodiment the Tumor Antigen is MCSP.

In one embodiment the T cell activating bispecific antibody comprises at least one antigen binding site that is specific for Melanoma-associated Chondroitin Sulfate Proteoglycan (MCSP). In another embodiment the T cell activating bispecific antibody comprises at least one, typically two or more antigen binding moieties that can compete with monoclonal antibody M4-3 ML2 (Sequence ID 161 and 162) or an affinity matured variant thereof for binding to an epitope of MCSP.

In one embodiment the bispecific antibody comprises a light chain and a heavy chain of a first Fab fragment specifically binding to MCSP, wherein the variable heavy chain comprises a CDR1 of SEQ ID. NO. 4, a CDR2 of SEQ ID. NO. 5, a CDR3 of SEQ ID. NO. 6; and the variable light chain comprises a CDR1 of SEQ ID. NO. 1, a CDR2 of SEQ ID. NO.2, and a CDR3 of SEQ ID. NO. 3.

In one embodiment the bispecific antibody comprises a light chain and a heavy chain of a first Fab fragment specifically binding to MCSP, wherein the variable heavy chain comprises a CDR1 of SEQ ID. NO. 180, a CDR2 of SEQ ID. NO. 181, a CDR3 of SEQ ID. NO. 6; and the variable light chain comprises a CDR1 of SEQ ID. NO. 183, a CDR2 of SEQ ID. NO.2, and a CDR3 of SEQ ID. NO. 184.

In one embodiment the bispecific antibody comprises a light chain and a heavy chain of a first Fab fragment specifically binding to MCSP, wherein the heavy chain variable region sequence that is at least about 80%, 85%, 90%, 95%, 96%, 97%, 98%, 99% or 100% identical to SEQ ID. NO. 14; and a light chain variable region is at least about 80%, 85%, 90%, 95%, 96%, 97%, 98%, 99% or 100% identical to SEQ ID. NO. 13.

In one embodiment the bispecific antibody comprises a light chain and a heavy chain of a first Fab fragment specifically binding to MCSP, wherein the heavy chain variable region sequence that is at least about 80%, 85%, 90%, 95%, 96%, 97%, 98%, 99% or 100% identical to SEQ ID. NO. 161; and a light chain variable region is at least about 80%, 85%, 90%, 95%, 96%, 97%, 98%, 99% or 100% identical to SEQ ID. NO. 162.

In one embodiment the bispecific antibody comprises a light chain and a heavy chain of a first Fab fragment specifically binding to MCSP, wherein the heavy chain variable region sequence is an affinity matured variant of SEQ ID. NO. 161 and wherein the light chain variable region sequence is an affinity matured variant of SEQ ID. NO. 162. Affinity matured variants in this embodiment means that independently 1, 2, 3 or 4 amino acids of SEQ ID. NO. 161 and/or SEQ ID. NO. 162 are exchanged.

In one embodiment said affinity matured variant comprises a variable heavy chain comprising a CDR1 of SEQ ID. NO. 180, a CDR2 of SEQ ID. NO. 181, a CDR3 of SEQ ID. NO. 6; and a variable light chain comprising a CDR1 of SEQ ID. NO. 183, a CDR2 of SEQ ID. NO.2, and a CDR3 of SEQ ID. NO. 184. In another embodiment said affinity matured variant comprises a heavy chain variable region sequence of SEQ ID. NO. 179 and wherein the light chain variable region sequence is an affinity matured variant of SEQ ID. NO. 182.

In one embodiment, the bispecific antibody comprises a light chain and a heavy chain of a first Fab fragment specifically binding to MCSP, wherein said heavy chain comprises a constant region comprising the amino acid sequence of SEQ ID NO: 16. In one embodiment, the bispecific antibody comprises a light chain and a heavy chain of a first Fab fragment specifically binding to MCSP, wherein said heavy chain comprises a constant region comprising the amino acid sequence of SEQ ID NO: 16, and a light chain and a heavy chain of a second Fab fragment specific for CD3 comprising one or more amino acid sequences as defined in any of the embodiments described herein.

In one embodiment, the bispecific antibody comprises a light chain and a heavy chain of a first Fab fragment specifically binding to MCSP, wherein said light chain comprises a constant region comprising the amino acid sequence of SEQ ID NO: 15. In one embodiment, the bispecific antibody comprises a light chain and a heavy chain of a second antibody specifically binding to MCSP, wherein said light chain comprises a constant region comprising the amino acid sequence of SEQ ID NO: 15, and a light chain and a heavy chain of a second Fab fragment specific for CD3 comprising one or more amino acid sequences as defined in any of the embodiments described herein.

In one embodiment the bispecific antibody comprises a light chain and a heavy chain of a first Fab fragment specifically binding to MCSP, wherein the heavy chain constant region comprises an amino acid sequence of SEQ ID NO: 16; and a light chain constant region comprising an amino acid sequence of SEQ ID NO: 15.

In one embodiment the bispecific antibody comprises a light chain and a heavy chain of a first Fab fragment specifically binding to MCSP, wherein the heavy chain variable region comprises an amino acid sequence of SEQ ID NO: 14; and a light chain variable region comprising an amino acid sequence of SEQ ID NO: 13, and wherein the heavy chain constant region comprises an amino acid sequence of SEQ ID NO: 16; and a light chain constant region comprising an amino acid sequence of SEQ ID NO: 15.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 13 and a variable heavy chain of SEQ ID NO: 14.

In one embodiment the bispecific antibody comprises a light chain and a heavy chain of a first Fab fragment specifically binding to MCSP, wherein the heavy chain variable region comprises an amino acid sequence of SEQ ID NO: 161; and a light chain variable region comprising an amino acid sequence of SEQ ID NO: 162, and wherein the heavy chain constant region comprises an amino acid sequence of SEQ ID NO: 16; and a light chain constant region comprising an amino acid sequence of SEQ ID NO: 15.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 161 and a variable heavy chain of SEQ ID NO: 162.

In one embodiment the bispecific antibody comprises a light chain and a heavy chain of a first Fab fragment specifically binding to MCSP, wherein the heavy chain variable region comprises an amino acid sequence of SEQ ID NO: 161 or an affinity matured variant thereof; and a light chain variable region comprising an amino acid sequence of SEQ ID NO: 162 or an affinity matured variant thereof, and wherein the heavy chain constant region comprises an amino acid sequence of SEQ ID NO: 16; and a light chain constant region comprising an amino acid sequence of SEQ ID NO: 15. Affinity matured variants in this embodiment means that independently 1, 2, 3 or 4 amino acids of SEQ ID. NO. 161 and/or SEQ ID. NO. 162 are exchanged.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 161 or an affinity matured variant thereof and a variable heavy chain of SEQ ID NO: 162 or an affinity matured variant thereof. Affinity matured variants in this embodiment means that independently 1, 2, 3 or 4 amino acids of SEQ ID. NO. 161 and/or SEQ ID. NO. 162 are exchanged.

In a further embodiment, the bispecific antibody of the invention comprises a light chain and a heavy chain of a second Fab fragment specifically binding to CD3, comprising a variable light chain of SEQ ID NO: 158 and a variable heavy chain of SEQ ID NO: 157; and a light chain and a heavy chain of a first Fab fragment specific for MCSP, comprising a variable light chain of SEQ ID NO: 161 and a variable heavy chain of SEQ ID NO: 162.

In a further embodiment, the bispecific antibody of the invention comprises a light chain and a heavy chain of a second Fab fragment specifically binding to CD3, comprising a variable light chain of SEQ ID NO: 158 or an affinity matured variant thereof and a variable heavy chain of SEQ ID NO: 157 or an affinity matured variant thereof; and a light chain and a heavy chain of a first Fab fragment specific for MCSP, comprising a variable light chain of SEQ ID NO: 161 or an affinity matured variant thereof and a variable heavy chain of SEQ ID NO: 162 or an affinity matured variant thereof. Affinity matured variants in this embodiment means that independently 1, 2, 3 or 4 amino acids of one or more of SEQ ID. NO. 157, SEQ ID. NO. 158, SEQ ID. NO. 161 and/or SEQ ID. NO. 162 are exchanged.

In one embodiment the bispecific antibody comprises a third Fab fragment, comprising a light chain and a heavy chain specifically binding to MCSP, wherein the variable heavy chain comprises a CDR1 of SEQ ID. NO. 4, a CDR2 of SEQ ID. NO. 5, a CDR3 of SEQ ID. NO. 6; and the variable light chain comprises a CDR1 of SEQ ID. NO. 1, a CDR2 of SEQ ID. NO.2, and a CDR3 of SEQ ID. NO. 3.

In one embodiment the bispecific antibody comprises a third Fab fragment, comprising a a light chain and a heavy chain specifically binding to MCSP, wherein the heavy chain variable region sequence that is at least about 80%, 85%, 90%, 95%, 96%, 97%, 98%, 99% or 100% identical to SEQ ID. NO. 14; and a light chain variable region is at least about 80%, 85%, 90%, 95%, 96%, 97%, 98%, 99% or 100% identical to SEQ ID. NO. 13.

In one embodiment the bispecific antibody comprises a third Fab fragment, comprising a a light chain and a heavy chain specifically binding to MCSP, wherein the heavy chain variable region sequence that is at least about 80%, 85%, 90%, 95%, 96%, 97%, 98%, 99% or 100% identical to SEQ ID. NO. 161; and a light chain variable region is at least about 80%, 85%, 90%, 95%, 96%, 97%, 98%, 99% or 100% identical to SEQ ID. NO. 162.

In one embodiment the bispecific antibody comprises a third Fab fragment, comprising a a light chain and a heavy chain specifically binding to MCSP, wherein the heavy chain variable region sequence is an affinity matured variant of SEQ ID. NO. 161 and wherein the light chain variable region sequence is an affinity matured variant of SEQ ID. NO. 162. Affinity matured variants in this embodiment means that independently 1, 2, 3 or 4 amino acids of SEQ ID. NO. 161 and/or SEQ ID. NO. 162 are exchanged.

In one embodiment the bispecific antibody comprises a third Fab fragment, comprising a light chain and a heavy chain specifically binding to MCSP, wherein said heavy chain comprises a constant region comprising the amino acid sequence of SEQ ID NO: 16. In one embodiment the bispecific antibody comprises a third Fab fragment, comprising a light chain and a heavy chain specifically binding to MCSP, wherein said heavy chain comprises a constant region comprising the amino acid sequence of SEQ ID NO: 16, and a light chain and a heavy chain of a second Fab fragment specific for CD3 comprising one or more amino acid sequences as defined in any of the embodiments described herein, and a a light chain and a heavy chain of a first Fab fragment specific for MCSP comprising one or more amino acid sequences as defined in any of the embodiments described herein.

In one embodiment the bispecific antibody comprises a third Fab fragment, comprising a light chain and a heavy chain specifically binding to MCSP, wherein said light chain comprises a constant region comprising the amino acid sequence of SEQ ID NO: 15. In one embodiment, the bispecific antibody comprises a light chain and a heavy chain of a second antibody specifically binding to MCSP, wherein said light chain comprises a constant region comprising the amino acid sequence of SEQ ID NO: 15, and a light chain and a heavy chain of a second Fab fragment specific for CD3, and a light chain and a heavy chain of a first Fab fragment specific for MCSP comprising one or more amino acid sequences as defined in any of the embodiments described herein.

In one embodiment the bispecific antibody comprises a third Fab fragment, comprising a light chain and a heavy chain specifically binding to MCSP, wherein the heavy chain constant region comprises an amino acid sequence of SEQ ID NO: 16; and a light chain constant region comprising an amino acid sequence of SEQ ID NO: 15.

In one embodiment the bispecific antibody comprises a third Fab fragment, comprising a light chain and a heavy chain specifically binding to MCSP, wherein the heavy chain variable region comprises an amino acid sequence of SEQ ID NO: 14; and a light chain variable region comprising an amino acid sequence of SEQ ID NO: 13, and wherein the heavy chain constant region comprises an amino acid sequence of SEQ ID NO: 16; and a light chain constant region comprising an amino acid sequence of SEQ ID NO: 15.

In one embodiment the bispecific antibody comprises a third Fab fragment, comprising a light chain and a heavy chain specifically binding to MCSP, wherein the heavy chain variable region comprises an amino acid sequence of SEQ ID NO: 161; and a light chain variable region comprising an amino acid sequence of SEQ ID NO: 162, and wherein the heavy chain constant region comprises an amino acid sequence of SEQ ID NO: 16; and a light chain constant region comprising an amino acid sequence of SEQ ID NO: 15.

In one embodiment the bispecific antibody comprises a third Fab fragment, comprising a light chain and a heavy chain specifically binding to MCSP, wherein the heavy chain variable region sequence is an affinity matured variant of SEQ ID. NO. 161 and wherein the light chain variable region sequence is an affinity matured variant of SEQ ID. NO. 162, and wherein the heavy chain constant region comprises an amino acid sequence of SEQ ID NO: 16; and a light chain constant region comprising an amino acid sequence of SEQ ID NO: 15. Affinity matured variants in this embodiment means that independently 1, 2, 3 or 4 amino acids of SEQ ID. NO. 161 and/or SEQ ID. NO. 162 are exchanged.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 13 and a variable heavy chain of SEQ ID NO: 14, and a light chain and a heavy chain of a third Fab fragment specific for MCSP, comprising a variable light chain of SEQ ID NO: 13 and a variable heavy chain of SEQ ID NO: 14.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 162 and a variable heavy chain of SEQ ID NO: 161, and a light chain and a heavy chain of a third Fab fragment specific for MCSP, comprising a variable light chain of SEQ ID NO: 162 and a variable heavy chain of SEQ ID NO: 161.

In a further embodiment, the bispecific antibody of the invention comprises a light chain and a heavy chain of a second Fab fragment specifically binding to CD3, comprising a variable light chain of SEQ ID NO: 19 and a variable heavy chain of SEQ ID NO: 20; and a light chain and a heavy chain of a first Fab fragment specific for MCSP, comprising a variable light chain of SEQ ID NO: 162 or an affinity matured variant thereof and a variable heavy chain of SEQ ID NO: 161 or an affinity matured variant thereof, and a light chain and a heavy chain of a third Fab fragment specific for MCSP, comprising a variable light chain of SEQ ID NO: 162 or an affinity matured variant thereof and a variable heavy chain of SEQ ID NO: 161 or an affinity matured variant thereof. Affinity matured variants in this embodiment means that independently 1, 2, 3 or 4 amino acids of SEQ ID. NO. 161 and/or SEQ ID. NO. 162 are exchanged.

In a further embodiment, the bispecific antibody of the invention comprises a light chain and a heavy chain of a second Fab fragment specifically binding to CD3, comprising a variable light chain of SEQ ID NO: 157 and a variable heavy chain of SEQ ID NO: 158; and a light chain and a heavy chain of a first Fab fragment specific for MCSP, comprising a variable light chain of SEQ ID NO: 162 and a variable heavy chain of SEQ ID NO: 161, and a light chain and a heavy chain of a third Fab fragment specific for MCSP, comprising a variable light chain of SEQ ID NO: 162 and a variable heavy chain of SEQ ID NO: 161.

In a further embodiment, the bispecific antibody of the invention comprises a light chain and a heavy chain of a second Fab fragment specifically binding to CD3, comprising a variable light chain of SEQ ID NO: 157 and a variable heavy chain of SEQ ID NO: 158; and a light chain and a heavy chain of a first Fab fragment specific for MCSP, comprising a variable light chain of SEQ ID NO: 162 or an affinity matured variant thereof and a variable heavy chain of SEQ ID NO: 161 or an affinity matured variant thereof, and a light chain and a heavy chain of a third Fab fragment specific for MCSP, comprising a variable light chain of SEQ ID NO: 162 or an affinity matured variant thereofand a variable heavy chain of SEQ ID NO: 161 or an affinity matured variant thereof. Affinity matured variants in this embodiment means that independently 1, 2, 3 or 4 amino acids of SEQ ID. NO. 161 and/or SEQ ID. NO. 162 are exchanged.

In yet another embodiment said bispecific antibody comprises one or more amino acid sequences selected from the group of SEQ ID NO: 25, SEQ ID NO: 26, SEQ ID NO: 27, SEQ ID NO. 41 and SEQ ID NO. 43.

In one embodiment said bispecific antibody comprises SEQ ID NO: 23, SEQ ID NO: 25, SEQ ID NO: 26, SEQ ID NO: 27.

In one preferred embodiment said bispecific antibody comprises SEQ ID NO: 163 and, SEQ ID NO: 164.

In one embodiment the T cell activating bispecific antibody comprises at least one antigen binding site that is specific for Epidermal Growth Factor Receptor (EGFR). In another embodiment the T cell activating bispecific antibody comprises at least one, typically two or more antigen binding moieties that can compete with monoclonal antibody GA201 for binding to an epitope of EGFR. See PCT publication WO 2006/082515, incorporated herein by reference in its entirety. In one embodiment, the antigen binding site that is specific for EGFR comprises the heavy chain CDR1 of SEQ ID NO: 68, the heavy chain CDR2 of SEQ ID NO: 69, the heavy chain CDR3 of SEQ ID NO: 70, the light chain CDR1 of SEQ ID NO: 71, the light chain CDR2 of SEQ ID NO: 72, and the light chain CDR3 of SEQ ID NO: 73. In a further embodiment, the antigen binding site that is specific for EGFR comprises a heavy chain variable region sequence that is at least about 80%, 85%, 90%, 95%, 96%, 97%, 98%, 99% or 100% identical to SEQ ID NO: 74 and a light chain variable region sequence that is at least about 80%, 85%, 90%, 95%, 96%, 97%, 98%, 99% or 100% identical to SEQ ID NO: 75, or variants thereof that retain functionality.

In a further embodiment, the bispecific antibody comprises a first Fab fragment comprising an antigen binding site that is specific for EGFR comprising a heavy chain variable region sequence that is at least about 80%, 85%, 90%, 95%, 96%, 97%, 98%, 99% or 100% identical to SEQ ID NO: 74 and a light chain variable region sequence that is at least about 80%, 85%, 90%, 95%, 96%, 97%, 98%, 99% or 100% identical to SEQ ID NO: 75, or variants thereof that retain functionality, and a light chain and a heavy chain of a second Fab fragment specific for CD3 comprising one or more amino acid sequences as defined in any of the embodiments described herein.

In a further embodiment, the bispecific antibody comprises a first and a third Fab fragment comprising an antigen binding site that is specific for EGFR comprising a heavy chain variable region sequence that is at least about 80%, 85%, 90%, 95%, 96%, 97%, 98%, 99% or 100% identical to SEQ ID NO: 74 and a light chain variable region sequence that is at least about 80%, 85%, 90%, 95%, 96%, 97%, 98%, 99% or 100% identical to SEQ ID NO: 75, or variants thereof that retain functionality, and a light chain and a heavy chain of a second Fab fragment specific for CD3 comprising one or more amino acid sequences as defined in any of the embodiments described herein.

In one embodiment the T cell activating bispecific antibody comprises at least one antigen binding site that is specific for Fibroblast Activation Protein (FAP). In another embodiment the T cell activating bispecific antibody comprises at least one, typically two or more antigen binding moieties that can compete with monoclonal antibody 3F2 for binding to an epitope of FAP. See European patent application no. EP10172842.6, incorporated herein by reference in its entirety. In one embodiment, the antigen binding site that is specific for FAP comprises the heavy chain CDR1 of SEQ ID NO: 76, the heavy chain CDR2 of SEQ ID NO: 77, the heavy chain CDR3 of SEQ ID NO: 78, the light chain CDR1 of SEQ ID NO: 79, the light chain CDR2 of SEQ ID NO: 80, and the light chain CDR3 of SEQ ID NO: 81. In a further embodiment, the antigen binding site that is specific for FAP comprises a heavy chain variable region sequence that is at least about 80%, 85%, 90%, 95%, 96%, 97%, 98%, 99% or 100% identical to SEQ ID NO: 82 and a light chain variable region sequence that is at least about 80%, 85%, 90%, 95%, 96%, 97%, 98%, 99% or 100% identical to SEQ ID NO: 83, or variants thereof that retain functionality.

In a further embodiment, the bispecific antibody comprises a first Fab fragment comprising an antigen binding site that is specific for FAP comprising a heavy chain variable region sequence that is at least about 80%, 85%, 90%, 95%, 96%, 97%, 98%, 99% or 100% identical to SEQ ID NO: 82 and a light chain variable region sequence that is at least about 80%, 85%, 90%, 95%, 96%, 97%, 98%, 99% or 100% identical to SEQ ID NO: 83, or variants thereof that retain functionality, and a light chain and a heavy chain of a second Fab fragment specific for CD3 comprising one or more amino acid sequences as defined in any of the embodiments described herein.

In a further embodiment, the bispecific antibody comprises a first and a third Fab fragment comprising an antigen binding site that is specific for FAP comprising a heavy chain variable region sequence that is at least about 80%, 85%, 90%, 95%, 96%, 97%, 98%, 99% or 100% identical to SEQ ID NO: 82 and a light chain variable region sequence that is at least about 80%, 85%, 90%, 95%, 96%, 97%, 98%, 99% or 100% identical to SEQ ID NO: 83, or variants thereof that retain functionality, and a light chain and a heavy chain of a second Fab fragment specific for CD3 comprising one or more amino acid sequences as defined in any of the embodiments described herein.

In one embodiment the T cell activating bispecific antibody comprises at least one antigen binding site that is specific for Carcinoembryonic Antigen (CEA). In another embodiment the T cell activating bispecific antibody comprises at least one, typically two or more antigen binding moieties that can compete with monoclonal antibody CH1A1A for binding to an epitope of CEA. In one embodiment the T cell activating bispecific antibody comprises at least one, typically two or more antigen binding moieties that can compete with monoclonal antibody CH1A1A clone 98/99 (CH1A1$_{(98/99)}$) for binding to an epitope of CEA. See PCT patent application number PCT/EP2010/062527, incorporated herein by reference in its entirety. In one embodiment, the antigen binding site that is specific for CEA comprises the heavy chain CDR1 of SEQ ID NO: 84, the heavy chain CDR2 of SEQ ID NO: 85, the heavy chain CDR3 of SEQ ID NO: 86, the light chain CDR1 of SEQ ID NO: 87, the light chain CDR2 of SEQ ID NO: 88, and the light chain CDR3 of SEQ ID NO: 89. In a further embodiment, the antigen binding site that is specific for CEA comprises a heavy chain variable region sequence that is at least about 80%, 85%, 90%, 95%, 96%, 97%, 98%, 99% or 100% identical to SEQ ID NO: 90 or SEQ ID NO: 159 and a light chain variable region sequence that is at least about 80%, 85%, 90%, 95%, 96%, 97%, 98%, 99% or 100% identical to SEQ ID NO: 91 or SEQ ID NO: 160, or variants thereof that retain functionality.

In one embodiment the bispecific antibody comprises a light chain and a heavy chain of a first Fab fragment specifically binding to CEA, wherein the heavy chain variable region comprises an affinity matured variant of SEQ ID NO: 159 or thereof; and a light chain variable region comprising an affinity matured variant of SEQ ID NO: 160. Affinity matured variants in this embodiment means that independently 1, 2, 3 or 4 amino acids of SEQ ID. NO. 159 and/or SEQ ID. NO. 160 are exchanged.

In a further embodiment, the bispecific antibody comprises a first Fab fragment comprising an antigen binding site that is specific for CEA comprising a heavy chain variable region sequence that is at least about 80%, 85%, 90%, 95%, 96%, 97%, 98%, 99% or 100% identical to SEQ ID NO: 90 and a light chain variable region sequence that is at least about 80%, 85%, 90%, 95%, 96%, 97%, 98%, 99% or 100% identical to SEQ ID NO: 91, or variants thereof that retain functionality, and a light chain and a heavy chain of a second Fab fragment specific for CD3 comprising one or more amino acid sequences as defined in any of the embodiments described herein.

In a further embodiment, the bispecific antibody comprises a first Fab fragment comprising an antigen binding site that is specific for CEA comprising a heavy chain variable region sequence that is at least about 80%, 85%, 90%, 95%, 96%, 97%, 98%, 99% or 100% identical to SEQ ID NO: 159 and a light chain variable region sequence that is at least about 80%, 85%, 90%, 95%, 96%, 97%, 98%, 99% or 100% identical to SEQ ID NO: 160, or variants thereof that retain functionality, and a light chain and a heavy chain of a second Fab fragment specific for CD3 comprising one or more amino acid sequences as defined in any of the embodiments described herein.

In one embodiment the bispecific antibody comprises a light chain and a heavy chain of a first Fab fragment specifically binding to CEA, wherein the heavy chain variable region comprises an affinity matured variant of SEQ ID NO: 159; and a light chain variable region comprising an affinity matured variant of SEQ ID NO: 160 and a light chain and a heavy chain of a second Fab fragment specific for CD3 comprising one or more amino acid sequences as defined in any of the embodiments described herein. Affinity matured variants in this embodiment means that independently 1, 2, 3 or 4 amino acids of SEQ ID. NO. 159 and/or SEQ ID. NO. 160 are exchanged.

In a further embodiment, the bispecific antibody comprises a first and a third Fab fragment comprising an antigen binding site that is specific for CEA comprising a heavy chain variable region sequence that is at least about 80%, 85%, 90%, 95%, 96%, 97%, 98%, 99% or 100% identical to SEQ ID NO: 90 or SEQ ID NO: 159 and a light chain variable region sequence that is at least about 80%, 85%, 90%, 95%, 96%, 97%, 98%, 99% or 100% identical to SEQ ID NO: 91 or SEQ ID NO: 160, or variants thereof that retain functionality, and a light chain and a heavy chain of a second Fab fragment specific for CD3 comprising one or more amino acid sequences as defined in any of the embodiments described herein. Affinity matured variants in this embodiment means that independently 1, 2, 3 or 4 amino acids of SEQ ID. NO. 159 and/or SEQ ID. NO. 160 are exchanged.

In a further embodiment, the bispecific antibody comprises a first and a third Fab fragment comprising an antigen binding site that is specific for CEA wherein the heavy chain variable region comprises an affinity matured variant of SEQ ID NO: 159; and the light chain variable region comprising an affinity matured variant of SEQ ID NO: 160. Affinity matured variants in this embodiment means that independently 1, 2, 3 or 4 amino acids of SEQ ID. NO. 159 and/or SEQ ID. NO. 160 are exchanged.

In one embodiment the T cell activating bispecific antibody comprises at least one antigen binding site that is specific for CD33. In one embodiment, the antigen binding site that is specific for CD33 comprises the heavy chain CDR1 of SEQ ID NO: 92, the heavy chain CDR2 of SEQ ID NO: 93, the heavy chain CDR3 of SEQ ID NO: 94, the light chain CDR1 of SEQ ID NO: 95, the light chain CDR2 of SEQ ID NO: 96, and the light chain CDR3 of SEQ ID NO: 97. In a further embodiment, the antigen binding site that is specific for CD33 comprises a heavy chain variable region sequence that is at least about 80%, 85%, 90%, 95%, 96%, 97%, 98%, 99% or 100% identical to SEQ ID NO: 98 and a light chain variable region sequence that is at least about 80%, 85%, 90%, 95%, 96%, 97%, 98%, 99% or 100% identical to SEQ ID NO: 99, or variants thereof that retain functionality.

In a further embodiment, the bispecific antibody comprises a first Fab fragment comprising an antigen binding site that is specific for CD33 comprising a heavy chain variable region sequence that is at least about 80%, 85%, 90%, 95%, 96%, 97%, 98%, 99% or 100% identical to SEQ ID NO: 98 and a light chain variable region sequence that is at least about 80%, 85%, 90%, 95%, 96%, 97%, 98%, 99% or 100% identical to SEQ ID NO: 99, or variants thereof that retain functionality, and a light chain and a heavy chain of a second Fab fragment specific for CD3 comprising one or more amino acid sequences as defined in any of the embodiments described herein.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 100, SEQ ID NO: 101 and SEQ ID NO: 102.

In one embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 151, SEQ ID NO. 152 and SEQ ID NO. 153.

In yet another embodiment said bispecific antibody comprises one or more amino acid sequences selected from the group of SEQ ID NO: 100, SEQ ID NO: 101, SEQ ID NO: 151, SEQ ID NO. 152 and SEQ ID NO. 153.

In one embodiment of the invention the bispecific antibody is a humanized antibody, as detailed below.

In another embodiment of the invention the bispecific antibody is a human antibody, as detailed below.

In a second object the present invention relates to a pharmaceutical composition comprising a bispecific antibody of the present invention.

In a third object the present invention relates to a bispecific antibody of the present invention for the treatment of cancer. In another embodiment, use of the bispecific antibody as a medicament is provided. Preferably said use is for the treatment of cancer.

In further objects the present invention relates to a nucleic acid sequence comprising a sequence encoding a heavy chain of a bispecific antibody of the present invention, a nucleic acid sequence comprising a sequence encoding a light chain of a bispecific antibody of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

In a further embodiment an immunoconjugate comprising the bispecific antibody of the invention and a cytotoxic agent is provided.

In further objects the present invention relates to a nucleic acid sequence comprising a sequence encoding a heavy chain of a bispecific antibody of the present invention, a nucleic acid sequence comprising a sequence encoding a light chain of a bispecific antibody of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, and SEQ ID NO: 67.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 107, SEQ ID NO: 108, SEQ ID NO: 109, SEQ ID NO: 110, SEQ ID NO: 111, and SEQ ID NO: 112.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 113, SEQ ID NO: 114, SEQ ID NO: 115, SEQ ID NO: 116, SEQ ID NO: 117, SEQ ID NO: 118, SEQ ID NO: 119, and SEQ ID NO: 120.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 121, SEQ ID NO: 122, SEQ ID NO: 123, SEQ ID NO: 124, SEQ ID NO: 125, SEQ ID NO: 126, SEQ ID NO: 127, and SEQ ID NO: 128.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 129, SEQ ID NO: 130, SEQ ID NO: 131, SEQ ID NO: 132, SEQ ID NO: 133, SEQ ID NO: 134, SEQ ID NO: 135, and SEQ ID NO: 136.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 105, SEQ ID NO: 106, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 154, SEQ ID NO: 155 and SEQ ID NO: 156.

In a specific embodiment the T cell activating bispecific antibody comprises a polypeptide sequence encoded by a polynucleotide sequence that is at least about 80%, 85%, 90%, 95%, 96%, 97%, 98%, 99% or 100% identical to a sequence selected from the group of SEQ ID NO: 165 and SEQ ID NO: 166.

In a further aspect, a bispecific antibody according to any of the above embodiments may incorporate any of the features, singly or in combination, as described in Sections 1-5 below:

1. Antibody Affinity

The affinity of the bispecific antibody provided herein for a target antigen can be determined in accordance with the methods set forth in the Examples by surface plasmon resonance (SPR), using standard instrumentation such as a BIACORE® instrument (GE Healthcare), and receptors or target proteins such as may be obtained by recombinant expression. Alternatively, binding of bispecific antibodies for different receptors or target antigens may be evaluated using cell lines expressing the particular receptor or target antigen, for example by flow cytometry (FACS).

In certain embodiments, a bispecific antibody provided herein has a dissociation constant (KD) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

According to one embodiment, KD is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates (ka or $k_{on}$) and dissociation rates (kd or $k_{off}$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Chimeric and Humanized Antibodies

In certain embodiments, a bispecific antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall' Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

3. Human Antibodies

In certain embodiments, a bispecific antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006).

Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Bispecific antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N. J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N. J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

5. Antibody Variants

In certain embodiments, amino acid sequence variants of the bispecific antibodies provided herein are contemplated. For example, it may be desirable to improve the binding affinity and/or other biological properties of the bispecific antibody. Amino acid sequence variants of a bispecific antibody may be prepared by introducing appropriate modifications into the nucleotide sequence encoding the bispecific antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding or decreased immunogenicity.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Cysteine Engineered Antibody Variants

In certain embodiments, it may be desirable to create cysteine engineered bispecific antibodies, e.g., "thioMAbs," in which one or more residues of a bispecific antibody are substituted with cysteine residues. In particular embodiments, the substituted residues occur at accessible sites of the bispecific antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain and A118 (EU numbering) of the heavy chain. Cysteine engineered antibodies may be generated as described, e.g., in U.S. Pat. No. 7,521,541.

c) Antibody Derivatives

In certain embodiments, a bispecific antibody provided herein may be further modified to contain additional non-proteinaceous moieties that are known in the art and readily available. The moieties suitable for derivatization of the bispecific antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of a bispecific antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

C. Recombinant Methods and Compositions

Bispecific antibodies of the invention may be obtained, for example, by solid-state peptide synthesis (e.g. Merrifield solid phase synthesis) or recombinant production. For recombinant production one or more polynucleotide encoding the bispecific anitbody (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a bispecific antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the bispecific antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antibody (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoter inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule is desired, DNA encoding a signal sequence may be placed upstream of the nucleic acid encoding a bispecific antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the bispecific antibody may be included within or at the ends of the bispecific antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a bispecific antibody of the invention. As used herein, the term "host cell" refers to any kind of cellular system which can be engineered to generate the bispecific antibodies of the invention or fragments thereof. Host cells suitable for replicating and for supporting expression of bispecific antibodies are well known in the art. Such cells may be transfected or transduced as appropriate with the particular expression vector and large quantities of vector containing cells can be grown for seeding large scale fermenters to obtain sufficient quantities of the bispecific antibody for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr$^-$ CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain. In one embodiment, a method of producing a bispecific antibody according to the invention is provided, wherein the method comprises culturing a host cell comprising a polynucleotide encoding the bispecific antibody, as provided herein, under conditions suitable for expression of the bispecific antigen binding molecule, and recovering the bispecific antibody from the host cell (or host cell culture medium).

The components of the bispecific antibody are genetically fused to each other. bispecific antibody can be designed such that its components are fused directly to each other or indirectly through a linker sequence. The composition and length of the linker may be determined in accordance with methods well known in the art and may be tested for efficacy. Examples of linker sequences between different components of bispecific antibodies are found in the sequences provided herein. Additional sequences may also be included to incorporate a cleavage site to separate the individual components of the fusion if desired, for example an endopeptidase recognition sequence.

In certain embodiments the one or more antigen binding moieties of the bispecific antibodies comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the bispecific antibodies of the invention. Non-limiting antibodies, antibody fragments, antigen binding domains or variable regions useful in the present invention can be of murine, primate, or human origin. If the antibody is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall' Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N. J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the bispecific antibodies of the present invention are engineered to have enhanced binding affinity according to, for example, the methods disclosed in U.S. Pat. Appl. Publ. No. 2004/0132066, the entire contents of which are hereby incorporated by reference. The ability of the bispecific antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE® T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Bispecific antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antibody binds. For example, for affinity chromatography purification of bispecific antibody of the invention, a matrix with protein A or protein G may be used. Sequential Protein A or G affinity chromatography and size exclusion chromatography can be used to isolate a bispecific antibody essentially as described in the Examples. The purity of the bispecific antibodies can be determined by any of a variety of well known analytical methods including gel electrophoresis, high pressure liquid chromatography, and the like.

D. Assays

Bispecific antibodies provided herein may be identified, screened for, or characterized for their physical/chemical properties and/or biological activities by various assays known in the art.

1. Binding Assays and Other Assays

In one aspect, a bispecific antibody of the invention is tested for its antigen binding activity, e.g., by known methods such as ELISA, Western blot, etc.

In another aspect, competition assays may be used to identify an antibody that competes with a specific antibody for binding to the first or second antigen. In certain embodiments, such a competing antibody binds to the same epitope (e.g., a linear or a conformational epitope) that is bound by a specific antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

2. Activity Assays

In one aspect, assays are provided for identifying bispecific antibodies thereof having biological activity. Biological activity may include, e.g., lysis of targeted cells, or induction of apoptosis. Antibodies having such biological activity in vivo and/or in vitro are also provided.

In certain embodiments, a bispecific antibody of the invention is tested for such biological activity. Assays for detecting cell lysis (e.g. by measurement of LDH release) or apoptosis (e.g. using the TUNEL assay) are well known in the art.

E. Immunoconjugates

The invention also provides immunoconjugates comprising a bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 BI); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises a bispecific antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises a bispecific antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of a bispecific antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

F. Methods and Compositions for Diagnostics and Detection

In certain embodiments, any of the bispecific antibodies provided herein is useful for detecting the presence of a first and/or a second antigen in a biological sample. The term "detecting" as used herein encompasses quantitative or qualitative detection. In certain embodiments, a biological sample comprises a cell or tissue.

In one embodiment, a bispecific antibody for use in a method of diagnosis or detection is provided. In a further aspect, a method of detecting the presence of a first and/or a second antigen in a biological sample is provided. In certain embodiments, the method comprises contacting the biological sample with a bispecific antibody as described herein under conditions permissive for binding of the bispecific antibody to a first and/or a second antigen, and detecting whether a complex is formed between the bispecific antibody a first and/or a second antigen. Such method may be an in vitro or in vivo method. In one embodiment, a bispecific antibody is used to select subjects eligible for therapy with a bispecific antibody, e.g. where a first and/or a second antigen is a biomarker for selection of patients.

Exemplary disorders that may be diagnosed using an antibody of the invention include cancer.

In certain embodiments, labeled bispecific antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Pharmaceutical Formulations

Pharmaceutical formulations of a bispecific antibody as described herein are prepared by mixing such bispecific antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the bispecific antibodies provided herein may be used in therapeutic methods.

In one aspect, a bispecific antibody for use as a medicament is provided. In further aspects, a bispecific antibody for use in treating cancer is provided. In certain embodiments, a bispecific antibody for use in a method of treatment is provided. In certain embodiments, the invention provides a bispecific antibody for use in a method of treating an individual having cancer comprising administering to the individual an effective amount of the bispecific antibody. In one such embodiment, the method further comprises administering to the individual an effective amount of at least one additional therapeutic agent, e.g., as described below. An "individual" according to any of the above embodiments is preferably a human.

In a further aspect, the invention provides for the use of a bispecific antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a bispecific antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the bispecific antibodies provided herein, e.g., for use in any of the above therapeutic methods. In one embodiment, a pharmaceutical formulation comprises any of the bispecific antibody provided herein and a pharmaceutically acceptable carrier. In another embodiment, a pharmaceutical formulation comprises any of the bispecific antibodies provided herein and at least one additional therapeutic agent, e.g., as described below.

The bispecific antibodies of the invention can be used either alone or in combination with other agents in a therapy. For instance, a bispecific antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Bispecific antibodies of the invention can also be used in combination with radiation therapy.

A bispecific antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Bispecific antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific antibody of the invention (when used alone or in combination with one or more other additional therapeutic agents) will depend on the type of disease to be treated, the type of antibody, the severity and course of the disease, whether the bispecific antibody is administered for preventive or therapeutic purposes, previous therapy, the patient's clinical history and response to the bispecific antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of bispecific antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the bispecific antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a bispecific antibody of the invention.

I. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody of the invention. The label or package insert indicates that the composition is used for treating the condition of choice. Moreover, the article of manufacture may comprise (a) a first container with a composition contained therein, wherein the composition comprises a bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a bispecific antibody of the invention.

III. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLE 1

Preparation of Fab (MCSP)-CrossFab(CD3)

The resulting variable region of heavy and light chain DNA sequences have were subcloned in frame with either the constant heavy chain or the constant light chain pre-inserted into the respective recipient mammalian expression vector. The antibody expression is driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using a calcium phosphate-transfection. Exponentially growing HEK293-EBNA cells were transfected by the calcium phosphate method. Alternatively, HEK293-EBNA cells growing in suspension were transfected by polyethylenimine. The cells were transfected with the corresponding expression vectors in a 1:1:1 ratio ("vector CH1-VH-CK-VH":"vector light chain":"vector light chain CH1-VL").

For transfection using calcium phosphate cells were grown as adherent monolayer cultures in T-flasks using DMEM culture medium supplemented with 10% (v/v) FCS, and were transfected when they were between 50 and 80% confluent. For the transfection of a T150 flask, 15 million cells were seeded 24 hours before transfection in 25 ml DMEM culture medium supplemented with FCS (at 10% v/v final), and cells were placed at 37° C. in an incubator with a 5% CO2 atmosphere overnight. For each T150 flask to be transfected, a solution of DNA, CaCl2 and water was prepared by mixing 94 µg total plasmid vector DNA divided in the corresponding ratio, water to a final volume of 469 µl and 469 µl of a 1 M CaCl2 solution. To this solution, 938 µl of a 50 mM HEPES, 280 mM NaCl, 1.5 mM Na2HPO4 solution at pH 7.05 were added, mixed immediately for 10 s and left to stand at room temperature for 20 s. The suspension was diluted with 10 ml of DMEM supplemented with 2% (v/v) FCS, and added to the T150 in place of the existing medium. Then additional 13 ml of transfection medium were added. The cells were incubated at 37° C., 5% CO2 for about 17 to 20 hours, then medium was replaced with 25 ml DMEM, 10% FCS. The conditioned culture medium was harvested approx. 7 days post-media exchange by centrifugation for 15 min at 210×g, the solution was sterile filtered (0.22 µm filter) and sodium azide in a final concentration of 0.01% (w/v) was added, and kept at 4° C.

For transfection using polyethylenimine HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 µg DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 (Lonza) was added. After 7 days cultivation supernatant was collected for purification by centrifugation for 15 min at 210×g, the solution was sterile filtered (0.22 µm filter) and sodium azide in a final concentration of 0.01% w/v was added, and kept at 4° C.

The secreted protein was purified from cell culture supernatants by affinity chromatography using Protein A and Protein G affinity chromatography, followed by a size exclusion chromatographic step. For affinity chromatography supernatant was loaded on a HiTrap Protein A HP column (CV=5 ml, GE Healthcare) coupled to a HiTrap Protein G HP column (CV=5 ml, GE Healthcare) each column equilibrated with 30 ml 20 mM sodium phosphate, 20 mM sodium citrate, pH 7.5. Unbound protein was removed by washing both columns with 6 column volume 20 mM sodium phosphate, 20 mM sodium citrate, pH 7.5. Subsequently an additional wash step was necessary to wash only the HiTrap Protein G HP column using at least 8 column volume 20 mM sodium phosphate, 20 mM sodium citrate, pH 7.5. The target protein was eluted from HiTrap Protein G HP column using a step gradient with 7 column volume 8.8 mM formic acid, pH 3.0. Protein solution was neutralized by adding 1/10 of 0.5 M sodium phosphate, pH 8.0. Target protein was concentrated and filtrated prior loading on a HiLoad Superdex 200 column (GE Healthcare) equilibrated with 25 mM potassium phosphate, 125 mM sodium chloride, 100 mM glycine solution of pH 6.7.

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie (SimpleBlue™ SafeStain from Invitrogen). The NuPAGE® Pre-Cast gel system (Invitrogen, USA) was used according to the manufacturer's instruction (4-12% Tris-Acetate gels or 4-12% Bis-Tris). The aggregate content of antibody samples was analyzed using a Superdex 200 10/300GL analytical size-exclusion column (GE Healthcare, Sweden) in 2 mM MOPS, 150 mM NaCl, 0.02% (w/v) NaN3, pH 7.3 running buffer at 25° C.

Figure 1:
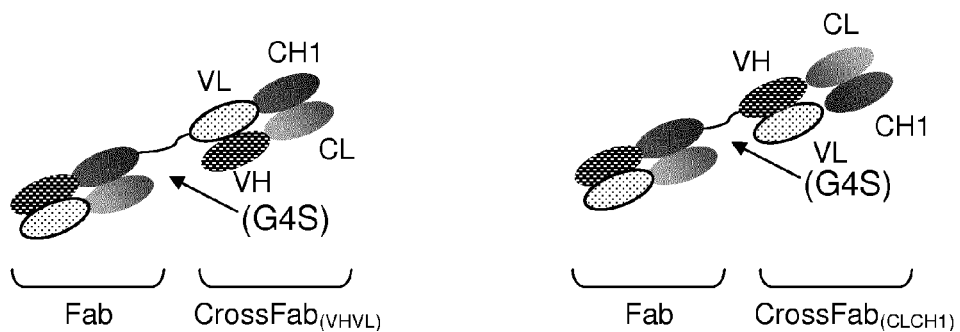
FIGS. 1a-e: Schematic illustration of exemplary bispecific antibody formats wherein the two Fab fragments are connected to each other by one linker. a) Fab-Crossfab molecule C-terminal, b) Fab-Crossfab molecule N-terminal c) (Fab)2-Crossfab molecule C-terminal d) (Fab)2-Crossfab molecule N-terminal e) Fab-Crossfab-Fab molecule.
Figure 1:
Figure 1C:
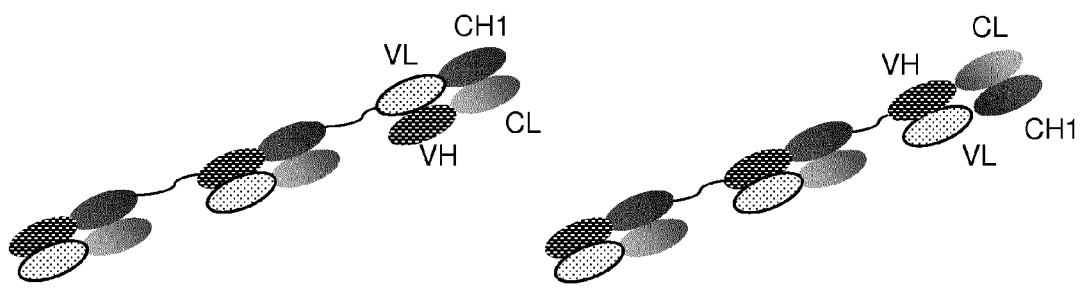
Figure 1:
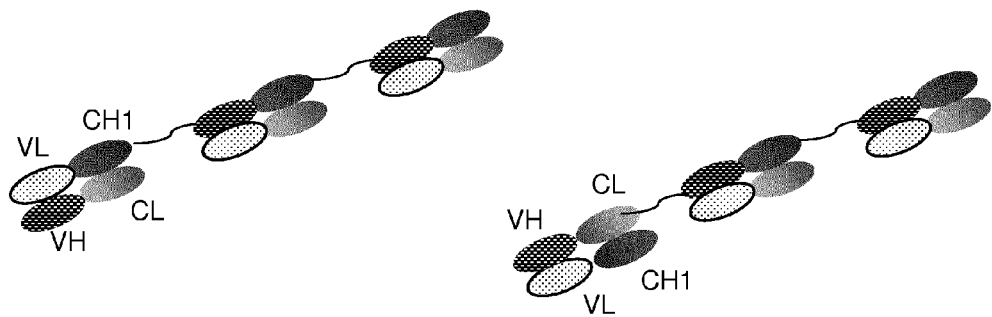
Figure 1E:
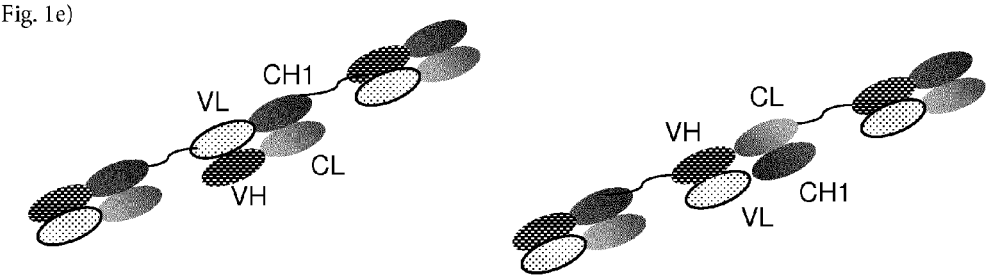
Figure 2:
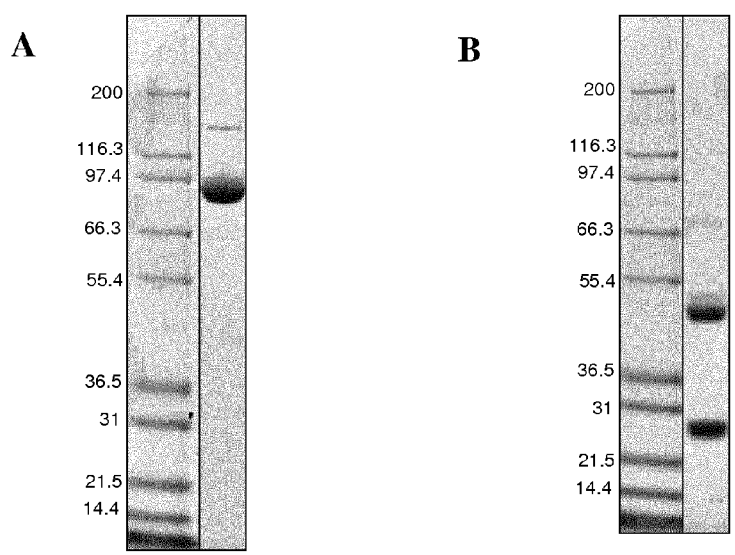
FIGS. 2A-B: Analysis of hu Fab(MCSP)-Crossfab(CD3) production and purification: SDS-Page: 4-12% Bis/Tris (NuPage [invitrogen]; coomassie stained): A 1—Mark 12 (invitrogen), 2—hu Fab(MCSP)-Crossfab(CD3) non reduced; B 1—Mark 12 (invitrogen), 2—hu Fab(MCSP)-Crossfab (CD3) reduced.
Figure 3:
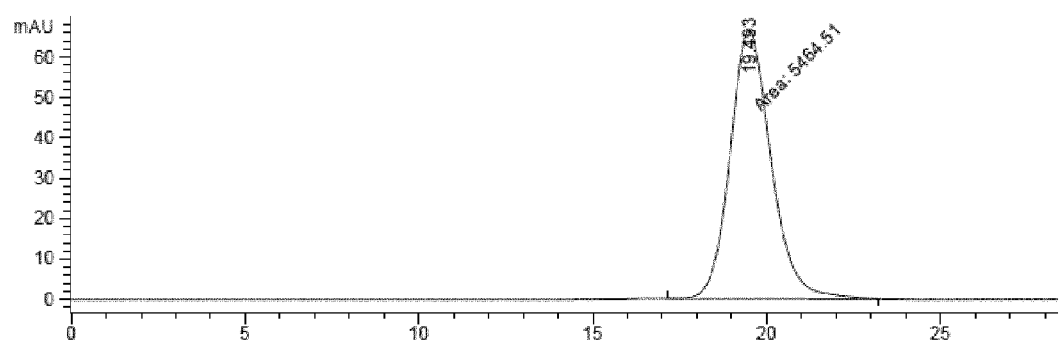
FIG. 3: Analysis Fab(MCSP)-Crossfab(CD3) production and purification. Analytical size exclusion chromatography, Chromatogram A280 (Superdex 200 10/300 GL [GE Healthcare]; 2 mM MOPS pH 7.3, 150 mM NaCl, 0.02% (w/v) NaCl; 50 µg sample were injected).

Analysis of production and purification of an exemplary Fab-Crossfab molecule (consisting of three chains: VHCH1 (MCSP)-VLCH1(CD3$_{v9}$)=SEQ ID NO:25, VLCL(MCSP)= SEQ ID NO: 17 and VHCL(CD3$_{v9}$)=SEQ ID NO:23; with an orientation as depicted in FIG. 1 $a$)) is shown in FIGS. 2 and 3. This molecule is further referred to as Fab (MCSP)-Crossfab (CD3) or hu Fab (MCSP)-Crossfab (CD3).

EXAMPLE 2

Preparation of Fab (MCSP)-Fab (MCSP)-CrossFab (CD3) and Fab (MCSP)-CrossFab(CD3)-Fab (MCSP)

The resulting variable region of heavy and light chain DNA sequences were subcloned in frame with either the constant heavy chain or the constant light chain pre-inserted into the respective recipient mammalian expression vector. The antibody expression is driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using a calcium phosphate-transfection. Exponentially growing HEK293-EBNA cells were transfected by the calcium phosphate method. Alternatively, HEK293-EBNA cells growing in suspension were transfected by polyethylenimine. The cells were transfected with the corresponding expression vectors in a 1:2:1 ratio ("vector CH1-VH-CH1-VH-CK-VH":"vector light chain":"vector light chain CH1-VL").

For transfection using calcium phosphate cells were grown as adherent monolayer cultures in T-flasks using DMEM culture medium supplemented with 10% (v/v) FCS, and were transfected when they were between 50 and 80% confluent. For the transfection of a T150 flask, 15 million cells were seeded 24 hours before transfection in 25 ml DMEM culture medium supplemented with FCS (at 10% v/v final), and cells were placed at 37° C. in an incubator with a 5% CO2 atmosphere overnight. For each T150 flask to be transfected, a solution of DNA, CaCl2 and water was prepared by mixing 94 µg total plasmid vector DNA divided in the corresponding ratio, water to a final volume of 469 µl and 469 µl of a 1 M CaCl2 solution. To this solution, 938 µl of a 50 mM HEPES, 280 mM NaCl, 1.5 mM Na2HPO4 solution at pH 7.05 were added, mixed immediately for 10 s and left to stand at room temperature for 20 s. The suspension was diluted with 10 ml of DMEM supplemented with 2% (v/v) FCS, and added to the T150 in place of the existing medium. Then additional 13 ml of transfection medium were added. The cells were incubated at 37° C., 5% CO2 for about 17 to 20 hours, then medium was replaced with 25 ml DMEM, 10% FCS. The conditioned culture medium was harvested approx. 7 days post-media exchange by centrifugation for 15 min at 210×g, the solution was sterile filtered (0.22 µm filter) and sodium azide in a final concentration of 0.01% (w/v) was added and kept at 4° C. For transfection using polyethylenimine HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 µg DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 (Lonza) was added. After 7 days cultivation supernatant was collected for purification by centrifugation for 15 min at 210×g, the solution was sterile filtered (0.22 μm filter) and sodium azide in a final concentration of 0.01% w/v was added and kept at 4° C.

The secreted protein was purified from cell culture supernatants by affinity chromatography using Protein A and Protein G affinity chromatography, followed by a size exclusion chromatographic step.

For affinity chromatography supernatant was loaded on a HiTrap Protein A HP column (CV=5 ml, GE Healthcare) coupled to a HiTrap Protein G HP column (CV=5 ml, GE Healthcare) each column equilibrated with 30 ml 20 mM sodium phosphate, 20 mM sodium citrate, pH 7.5. Unbound protein was removed by washing both columns with 6 column volume 20 mM sodium phosphate, 20 mM sodium citrate, pH 7.5. Subsequently an additional wash step was necessary to wash only the HiTrap Protein G HP column using at least 8 column volume 20 mM sodium phosphate, 20 mM sodium citrate, pH 7.5. The target protein was eluted from HiTrap Protein G HP column using a step gradient with 7 column volume 8.8 mM formic acid, pH 3.0. Protein solution was neutralized by adding 1/10 of 0.5 M sodium phosphate, pH 8.0. Target protein was concentrated and filtrated prior loading on a HiLoad Superdex 200 column (GE Healthcare) equilibrated with 25 mM potassium phosphate, 125 mM sodium chloride, 100 mM glycine solution of pH 6.7.

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiothreitol) and staining with Coomassie (SimpleBlue™ SafeStain from Invitrogen). The NuPAGE® Pre-Cast gel system (Invitrogen, USA) was used according to the manufacturer's instruction (4-12% Tris-Acetate gels or 4-12% Bis-Tris). The aggregate content of antibody samples was analyzed using a Superdex 200 10/300GL analytical size-exclusion column (GE Healthcare, Sweden) in 2 mM MOPS, 150 mM NaCl, 0.02% (w/v) NaN3, pH 7.3 running buffer at 25° C. and compared with prior art antibody fragment (scFv)2 (results see table below).

| Construct | Yield [mg/l] | Aggregate after 1$^{st}$ purification step [%] | HMW [%] | LMW [%] | Monomer [%] |
|---|---|---|---|---|---|
| (scFv)2 SEQ ID NOs: 149 | 3.84 | 80 | 0 | 0 | 100 |
| Fab-Crossfab SEQ ID NOs: 23, 25, 17 | 7.85 | 13.8 | 0 | 0 | 100 |
| (Fab)2-Crossfab SEQ ID NOs: 42, 17, 23 | 7.8 | 3.6 | 0 | 0 | 100 |
| Fab-Crossfab-Fab SEQ ID NOs: 27, 17, 23 | 5.3 | 1.7 | 0.4 | 0 | 99.56 |

HMW = High Molecular Weight;
LMW = Low Molecular Weight

Figure 4:
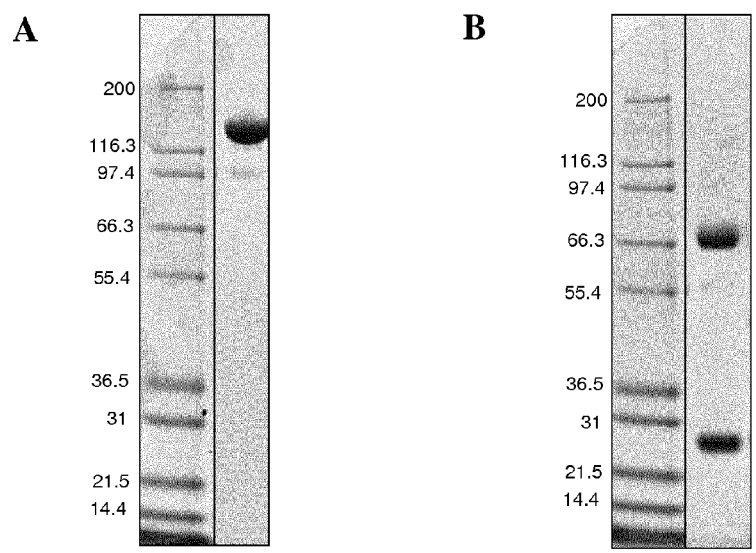
FIGS. 4A-B: Analysis of hu Fab(MCSP)-Fab(MCSP)-Crossfab(CD3) production and purification: SDS-Page: 4-12% Bis/Tris (NuPage [invitrogen]; coomassie stained): A 1—Mark 12 (invitrogen), 2—hu Fab(MCSP)-Fab(MCSP)-Crossfab(CD3) non reduced; B 1—Mark 12 (invitrogen), 2—hu Fab(MCSP)-Fab(MCSP)-Crossfab(CD3) reduced.
Figure 5:
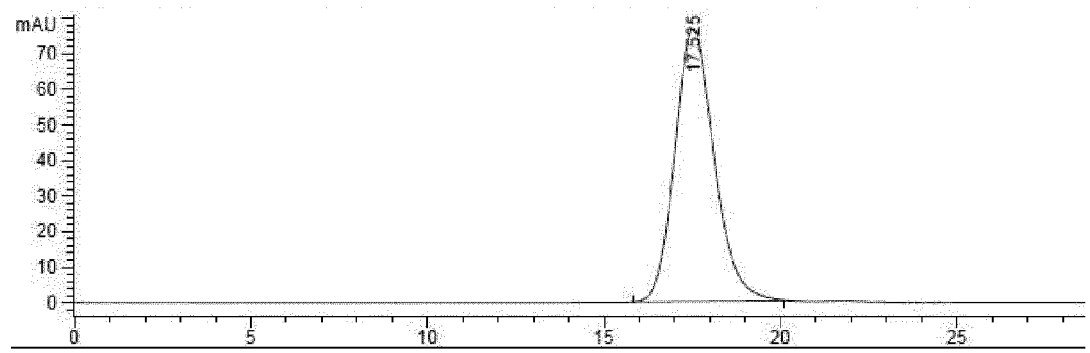
FIG. 5: Analysis of hu Fab(MCSP)-Fab(MCSP)-Crossfab (CD3) production and purification. Analytical size exclusion chromatography, Chromatogram A280 (Superdex 200 10/300 GL [GE Healthcare]; 2 mM MOPS pH 7.3, 150 mM NaCl, 0.02% (w/v) NaCl; 50 g sample were injected).

Analysis of production and purification of an exemplary Fab-Fab-Crossfab molecule (consisting of four chains: VHCH1(MCSP)-VHCH1(MCSP)-VLCH1(CD3$_{v9}$)=SEQ ID NO:26, 2 VLCL(MCSP) chains=SEQ ID NO:17 and one VHCL(CD3$_{v9}$) chain=SEQ ID NO:23; with an orientation as depicted in FIG. 1 c)) is shown in FIGS. 4 and 5. This molecule is further referred to as Fab (MCSP)-Fab (MCSP)-Crossfab (CD3) or hu Fab (MCSP)-Fab (MCSP)-Crossfab (CD3).

Figure 6:
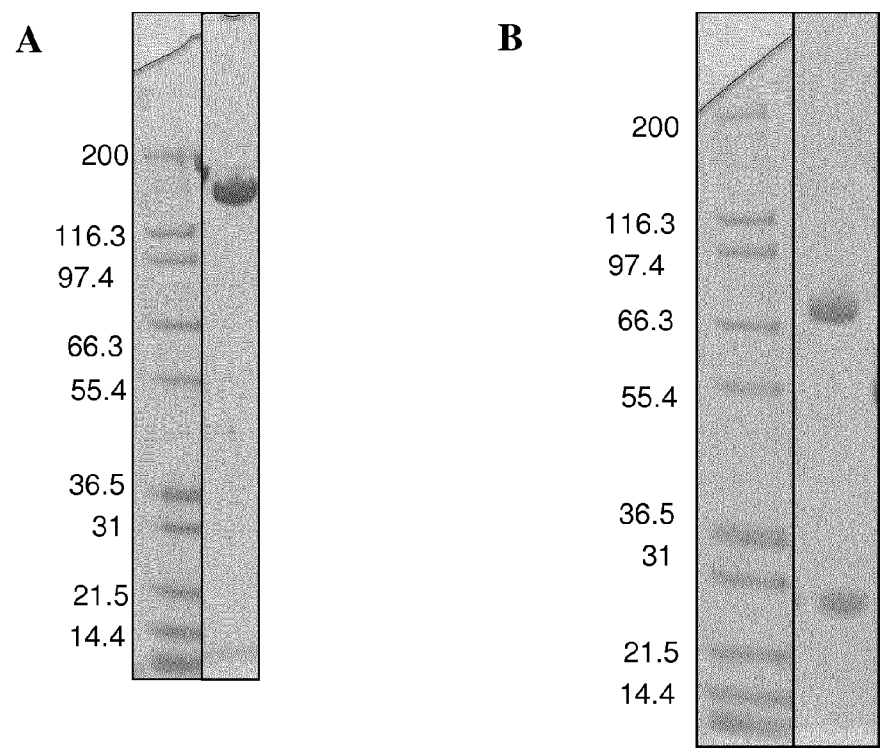
FIGS. 6A-B: Analysis of hu Fab(MCSP)-Crossfab(CD3)-Fab(MCSP) production and purification. SDS-Page: 4-12% Bis/Tris (NuPage [invitrogen]; coomassie stained): A 1—Mark 12 (invitrogen), 2—hu Fab(MCSP)-Crossfab (CD3)-Fab(MCSP) non reduced; B 1—Mark 12 (invitrogen), 2—hu Fab(MCSP)-Crossfab(CD3)-Fab(MCSP) reduced.
Figure 7:
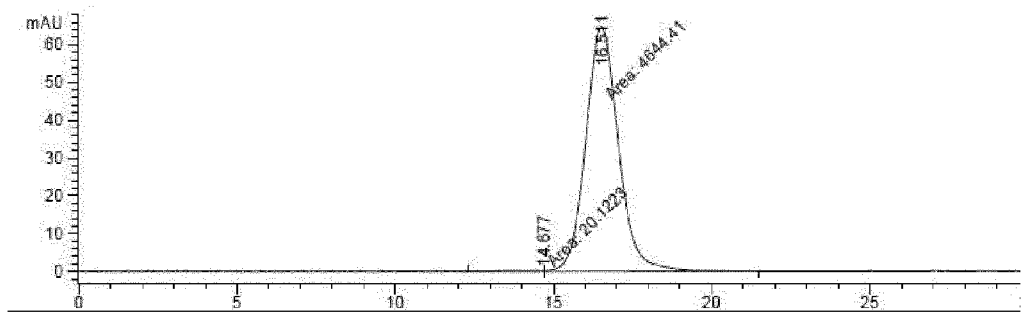
FIG. 7: Analysis of hu Fab(MCSP)-Crossfab(CD3)-Fab (MCSP) production and purification. Analytical size exclusion chromatography, Chromatogram A280 (Superdex 200 10/300 GL [GE Healthcare]; 2 mM MOPS pH 7.3, 150 mM NaCl, 0.02% (w/v) NaCl; 50 g sample were injected).

Analysis of production and purification of an exemplary Fab-Crossfab-Fab molecule (consisting of four chains: VHCH1(MCSP)-VLCH1(CD3$_{v9}$)-VHCH1(MCSP)=SEQ ID NO:27, 2 VLCL(MCSP) chains=SEQ ID NO:17 and one VHCL(CD3$_{v9}$) chain=SEQ ID NO:23; with an orientation as depicted in FIG. 1 e)) is shown in FIGS. 6 and 7. This molecule is further referred to as Fab (MCSP)-Fab (MCSP)-Crossfab (CD3) or hu Fab (MCSP)-Fab (MCSP)-Crossfab (CD3).

Figure 8:
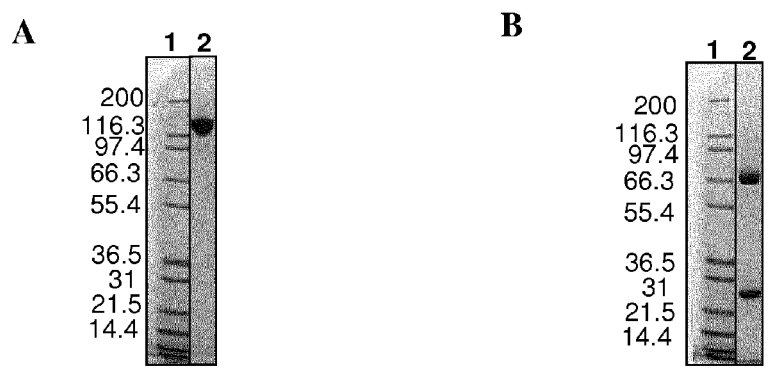
FIGS. 8A-B: Analysis of murine Crossfab(CD3)-Fab (MCSP)-Fab(MCSP) production and purification. SDS-Page: 4-12% Bis/Tris (NuPage [invitrogen]; coomassie stained): A 1—Mark 12 (invitrogen), 2—murine Crossfab (CD3)-Fab(MCSP)-Fab(MCSP) non reduced; B 1—Mark 12 (invitrogen), 2—murine Crossfab(CD3)-Fab(MCSP)-Fab(MCSP) reduced.
Figure 9:
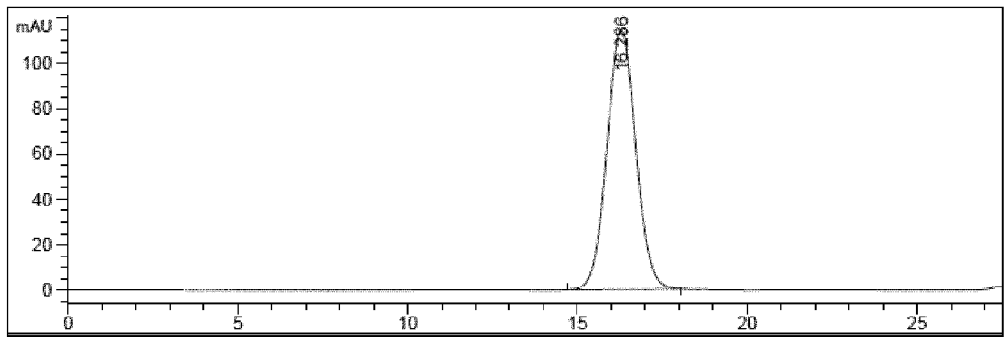
FIG. 9: Analysis of murine Crossfab(CD3)-Fab(MCSP)-Fab(MCSP) production and purification. Analytical size exclusion chromatography, Chromatogram A280 (Superdex 200 10/300 GL [GE Healthcare]; 2 mM MOPS pH 7.3, 150 mM NaCl, 0.02% (w/v) NaCl; 50 µg sample were injected).

Analysis of production and purification of an exemplary Crossfab-Fab-Fab molecule (consisting of four chains: VLCH1(CD3$_{2C11}$)-VHCH1(MCSP)-VHCH1(MCSP)=SEQ ID NO:42, 2 VLCL(MCSP) chains=SEQ ID NO:17 and one VHCL(CD3$_{2C11}$) chain=SEQ ID NO:43; with an orientation as depicted in FIG. 1 d)) is shown in FIGS. 8 and 9. This molecule is further referred to as murine Crossfab (CD3)-Fab (MCSP)-Fab (MCSP).

EXAMPLE 3

Preparation of Fab(CD33)-CrossFab (CD3)

The resulting variable region of heavy and light chain DNA sequences were subcloned in frame with either the constant heavy chain or the constant light chain pre-inserted into the respective recipient mammalian expression vector. The antibody expression is driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using a calcium phosphate-transfection. Exponentially growing HEK293-EBNA cells were transfected by the calcium phosphate method. Alternatively, HEK293-EBNA cells growing in suspension were transfected by polyethylenimine. The cells were transfected with the corresponding expression vectors in a 1:1:1 ratio ("vector CH1-VH-CK-VH":"vector light chain":"vector light chain CH1-VL").

For transfection using calcium phosphate cells were grown as adherent monolayer cultures in T-flasks using DMEM culture medium supplemented with 10% (v/v) FCS, and were transfected when they were between 50 and 80% confluent. For the transfection of a T150 flask, 15 million cells were seeded 24 hours before transfection in 25 ml DMEM culture medium supplemented with FCS (at 10% v/v final), and cells were placed at 37° C. in an incubator with a 5% CO2 atmosphere overnight. For each T150 flask to be transfected, a solution of DNA, CaCl2 and water was prepared by mixing 94 μg total plasmid vector DNA divided in the corresponding ratio, water to a final volume of 469 μl and 469 μl of a 1 M CaCl2 solution. To this solution, 938 μl of a 50 mM HEPES, 280 mM NaCl, 1.5 mM Na2HPO4 solution at pH 7.05 were added, mixed immediately for 10 s and left to stand at room temperature for 20 s. The suspension was diluted with 10 ml of DMEM supplemented with 2% (v/v) FCS, and added to the T150 in place of the existing medium. Then additional 13 ml of transfection medium were added. The cells were incubated at 37° C., 5% CO2 for about 17 to 20 hours, then medium was replaced with 25 ml DMEM, 10% FCS. The conditioned culture medium was harvested approx. 7 days post-media exchange by centrifugation for 15 min at 210×g, the solution was sterile filtered (0.22 μm filter) and sodium azide in a final concentration of 0.01% (w/v) was added, and kept at 4° C.

For transfection using polyethylenimine HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 μg DNA. After addition of 540 μl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 (LONZA) was added. After 7 days cultivation supernatant was collected for purification by centrifugation for 15 min at 210×g, the solution was sterile filtered (0.22 μm filter) and sodium azide in a final concentration of 0.01% w/v was added, and kept at 4° C.

The secreted protein was purified from cell culture supernatants by affinity chromatography using Protein A and ProteinG affinity chromatography, followed by a size exclusion chromatographic step.

For affinity chromatography supernatant was loaded on a HiTrap ProteinA HP column (CV=5 mL, GE Healthcare) coupled to a HiTrap ProteinG HP column (CV=5 mL, GE Healthcare) each column equilibrated with 30 ml 20 mM sodium phosphate, 20 mM sodium citrate, pH 7.5. Unbound protein was removed by washing both columns with 6 column volume 20 mM sodium phosphate, 20 mM sodium citrate, pH 7.5. Subsequently an additional wash step was necessary to wash only the HiTrap ProteinG HP column using at least 8 column volume 20 mM sodium phosphate, 20 mM sodium citrate, pH 7.5. The target protein was eluted from HiTrap ProteinG HP column using a step gradient with 7 column volume 8.8 mM formic acid, pH 3.0. Protein solution was neutralized by adding 1/10 of 0.5M sodium phosphate, pH 8.0. Target protein was concentrated and filtrated prior loading on a HiLoad Superdex 200 column (GE Healthcare) equilibrated with 25 mM potassium phosphate, 125 mM sodium chloride, 100 mM glycine solution of pH 6.7.

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie (SimpleBlue™ SafeStain from Invitrogen). The NuPAGE® Pre-Cast gel system (Invitrogen, USA) was used according to the manufacturer's instruction (4-12% Tris-Acetate gels or 4-12% Bis-Tris). The aggregate content of antibody samples was analyzed using a Superdex 200 10/300GL analytical size-exclusion column (GE Healthcare, Sweden) in 2 mM MOPS, 150 mM NaCl, 0.02% (w/v) NaN3, pH 7.3 running buffer at 25° C.

Figure 17:
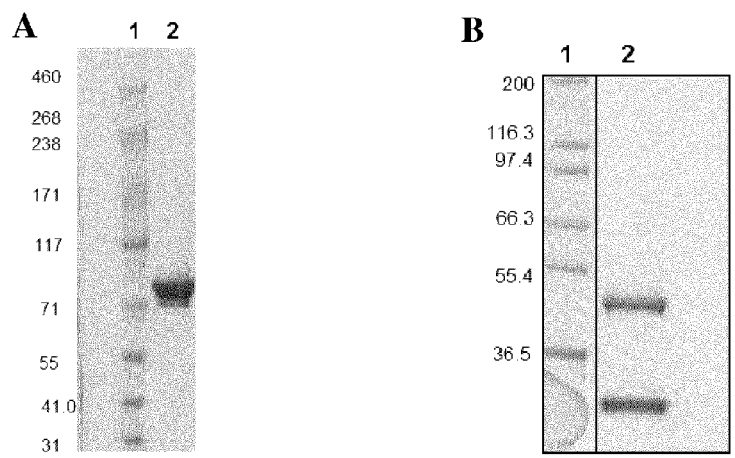

Analysis of production and purification of an exemplary Fab-Crossfab molecule (consisting of three chains: VHCH1 (CD33)-VLCH1(CD3$_{v9}$)=SEQ ID NO:102, VLCL(CD33)= SEQ ID NO:100 and VHCL(CD3$_{v9}$)=SEQ ID NO:23 or SEQ ID NO:101; with an orientation as depicted in FIG. 1 a)) is shown in FIGS. 17 and 18. This molecule is further referred to as Fab(CD33)-CrossFab (CD3) or hu Fab (CD33)-CrossFab (CD3).

EXAMPLE 4

Preparation of the Reference Molecule (scFv)2

Cloning and Production

The resulting variable region of heavy and light chain DNA sequences were subcloned in frame into the respective recipient mammalian expression vector. The antibody expression is driven by an MPSV promoter and carries a synthetic polyA signal sequence at the 3' end of the CDS. In addition each vector contains an EBV OriP sequence.

The molecule was produced by transfecting HEK293-EBNA cells with the mammalian expression vector using polyethylenimine. HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 μg DNA. After addition of 540 μl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 (LONZA) were added. After 7 days cultivation supernatant was collected for purification by centrifugation for 15 min at 210×g, the solution was sterile filtered (0.22 μm filter) and sodium azide in a final concentration of 0.01% w/v was added, and kept at 4° C.

Purification of (scFv)2 (Anti MCSP/Anti huCD3)

The secreted protein was purified from cell culture supernatants by affinity chromatography using Immobilized Metal Ion Affinity Chromatography (IMAC), followed by a size exclusion chromatographic step.

Prior first purification step disturbing components from the supernatant were removed by diafiltration using the tangential flow filtration system Sarcojet (Sartorius) equipped with a 5.000 MWCO membrane (Sartocon Slice Cassette, Hydrosart; Sartorius). Supernatant was concentrated to 210 ml and subsequently diluted in 1 1 20 mM sodium phosphate, 500 mM sodium chloride, pH 6.5. The protein solution was concentrated again to 210 ml. This process was repeated twice to ensure a complete buffer exchange.

For affinity chromatography retentate of the diafiltration process was loaded on a NiNTA Superflow Cartridge (CV=5 mL, Qiagen) equilibrated with 25 ml 20 mM sodium phosphate, 500 mM sodium chloride, 15 mM imidazole, pH 6.5. Unbound protein was removed by washing with at least 2 column volume 20 mM sodium phosphate, 500 mM sodium chloride, 15 mM imidazole, pH 6.5 followed by an additional wash step using 3 column volume 20 mM sodium phosphate, 500 mM sodium chloride, 62.5 mM imidazole, pH 6.5. Target protein was eluted in 2 column volume 20 mM sodium phosphate, 500 mM sodium chloride, 125 mM imidazole, pH 6.5. Column was washed subsequently with 20 mM sodium phosphate, 500 mM sodium chloride, 250 mM imidazole, pH 6.5.

Target protein was concentrated prior loading on a HiLoad Superdex 75 column (GE Healthcare) equilibrated with 25 mM $KH_2PO_4$, 125 mM NaCl, 200 mM Arginine, pH 6.7.

Yields, aggregate content after the first purification step and final monomer content is shown in the table above. Comparison of the aggregate content after the first purification step indicates the superior stability of the Fab-Crossfab construct in contrast to the (scFv)2.

Characterization of (scFv)2

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie (SimpleBlue™ SafeStain from Invitrogen). The NuPAGE® Pre-Cast gel system (Invitrogen, USA) was used according to the manufacturer's instruction (4-12% Tris-Acetate gels or 4-12% Bis-Tris). The aggregate content of antibody samples was analyzed using a Superdex 75 10/300GL analytical size-exclusion column (GE Healthcare, Sweden) in 2 mM MOPS, 150 mM NaCl, 0.02% (w/v) NaN3, pH 7.3 running buffer at 25° C.

A schematic drawing of the (scFv)2 molecule is shown in FIG. 21.

Figure 23:
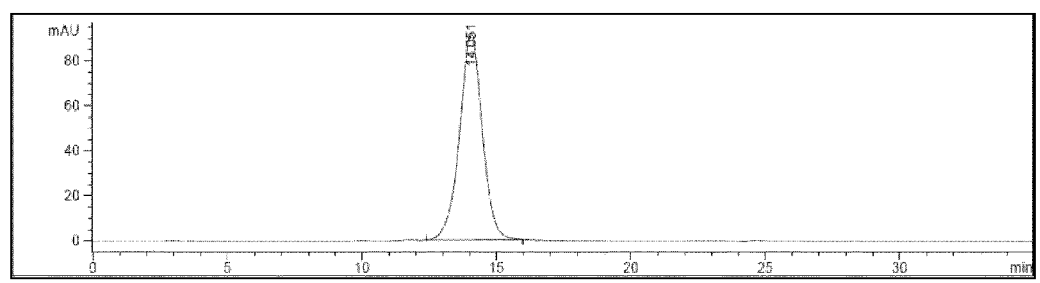

Analysis of production and purification of an exemplary (scFv)2 molecule (antiMCSP/anti huCD3; consisting two single chain Fvs: VL-VH (MCSP) and VH-VL ($CD3_{V9}$)= SEQ ID NO: 149; is shown in FIGS. 22 and 23. This molecule is further referred to as (scFv)2 (antiMCSP/anti huCD3e).

EXAMPLE 5

Isolation of Primary Human Pan T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors.

T-cell enrichment from PBMCs was performed using the Pan T Cell Isolation Kit II (Miltenyi Biotec #130-091-156), according to the manufacturer's instructions. Briefly, the cell pellets were diluted in 40 µl cold buffer per 10 Mio cells (PBS with 0.5% BSA, 2 mM EDTA-sterile filtered) and incubated with 10 µl Biotin-Antibody Cocktail per 10 Mio cells for 10 min at 4° C.

30 µl cold buffer and 20 µl Anti-Biotin magnetic beads per 10 Mio cells were added, and the mixture incubated for another 15 min at 4° C.

Cells were washed by adding 10-20× of labeling volume and a subsequent centrifugation step at 300 g for 10 min. Up to 100 Mio cells were resuspended in 500 µl buffer.

Magnetic separation of unlabeled human pan T cells was performed using LS columns (Miltenyi Biotec #130-042-401) according to the manufacturer's instructions. The resulting T cell population was counted automatically (ViCell) and stored in AIM-V medium at 37° C., 5% CO2 in the incubator until assay start (not longer than 24 h).

EXAMPLE 6

Isolation of Murine Pan T Cells from Splenocytes

Spleens were isolated from C57BL/6 mice, transferred into a GentleMACS C-tube (Miltenyi Biotech #130-093-237) containing MACS buffer (PBS+0.5% BSA+2 mM EDTA) and dissociated with the GentleMACS Dissociator to obtain single-cell suspensions according to the manufacturers' instructions.

The cell suspension was passed through a pre-separation filter to get rid-off remaining undissociated tissue particles. After centrifugation at 400 g for 4 minutes at 4° C., ACK Lysis Buffer was added to lyse red blood cells (incubation for 5 minutes at room temperature). The remaining cells were washed with MACS buffer twice, counted and used for the isolation of murine pan T cells. The negative (magnetic) selection was performed using the Pan T Cell Isolation Kit from Miltenyi Biotec (#130-090-861), following the manufacturers' instructions. The resulting T cell population was counted automatically (ViCell) and used immediately for further assays.

EXAMPLE 7

Re-directed T Cell Cytotoxicity Mediated by Cross-linked Bispecific Constructs Targeting CD3 on T Cells and MCSP on Tumor Cells (LDH Release Assay)

Bispecific constructs targeting CD3 on human, or mouse T cells and human on tumor cells, were analyzed by a LDH release assay regarding their potential to induce T cell-mediated apoptosis of target cells.

Briefly, target cells (human Colo-38, human MDA-MB-435, human melanoma MV-3 or murine B16/F10-huMCSP Fluc 2 clone 48 cells, all expressing human MCSP) were harvested with Cell Dissociation Buffer (MCSP is trypsin-sensitive) or trypsin (and then plated the day before), washed and resuspended in the appropriate cell culture medium (see detailed description of the different figures). 20 000-30 000 cells per well were plated in a round-bottom 96-well-plate and the respective antibody dilution was added as indicated (triplicates). Effector cells were added to obtain a final E:T ratio of 5:1 (for human pan T cells), 10:1 (for human PBMCs).

In addition, 1-10 µg/ml PHA-M (Sigma #L8902), a mixture of isolectins, isolated from *Phaseolus vulgaris*, was used as a mitogenic stimulus to induce human or cynomolgus T cell activation. For murine T cells, a 5% solution of "rat T-Stim with ConA" (BD #354115) was used as a positive control for T cell activation.

For normalization, maximal lysis of the target cells (=100%) was achieved by incubation of the target cells with a final concentration of 1% Triton-X-100. Minimal lysis (=0%) refers to target cells co-incubated with effector cells, but without any construct or antibody.

After an overnight incubation of at least 18 h at 37° C., 5% CO2, LDH release of apoptotic/necrotic target cells into the supernatant was measured with the LDH detection kit (Roche Applied Science, #11 644 793 001), according to the manufacturer's instructions.

LDH Release Assay with Fab (MCSP)-Crossfab (CD3) and Fab (MCSP)-Fab (MCSP)-Crossfab (CD3) Bispecific Constructs Purified Fab (MCSP)-Crossfab (CD3), Fab (MCSP)-Fab (MCSP)-Crossfab (CD3) and the (scFv)2 (antiMCSP/anti huCD3e) reference molecule were analyzed for their potential to induce T cell-mediated apoptosis in tumor target cells upon crosslinkage of the construct via binding of both targeting moieties to the respective antigens on cells. Briefly, huMCSP-expressing MDA-MB-435 human melanoma target cells were harvested with Cell Dissociation Buffer, washed and resuspendend in AIM-V medium (Invitrogen #12055-091). 30 000 cells per well were plated in a round-bottom 96-well-plate and the respective antibody dilution was added at the indicated concentrations. All constructs and controls were adjusted to the same molarity.

Human pan T effector cells were added to obtain a final E:T ratio of 5:1. As a positive control for the activation of human pan T cells, 1 µg/ml PHA-M (Sigma #L8902) was used. For normalization, maximal lysis of the target cells (=100%) was determined by incubation of the target cells with a final concentration of 1% Triton-X-100. Minimal lysis (=0%) refers to target cells co-incubated with effector cells, but without any construct or antibody.

After an overnight incubation of 20 h at 37° C., 5% CO2, LDH release of apoptotic/necrotic target cells into the supernatant was measured with the LDH detection kit (Roche Applied Science, #11 644 793 001), according to the manufacturer's instructions.

Figure 10:
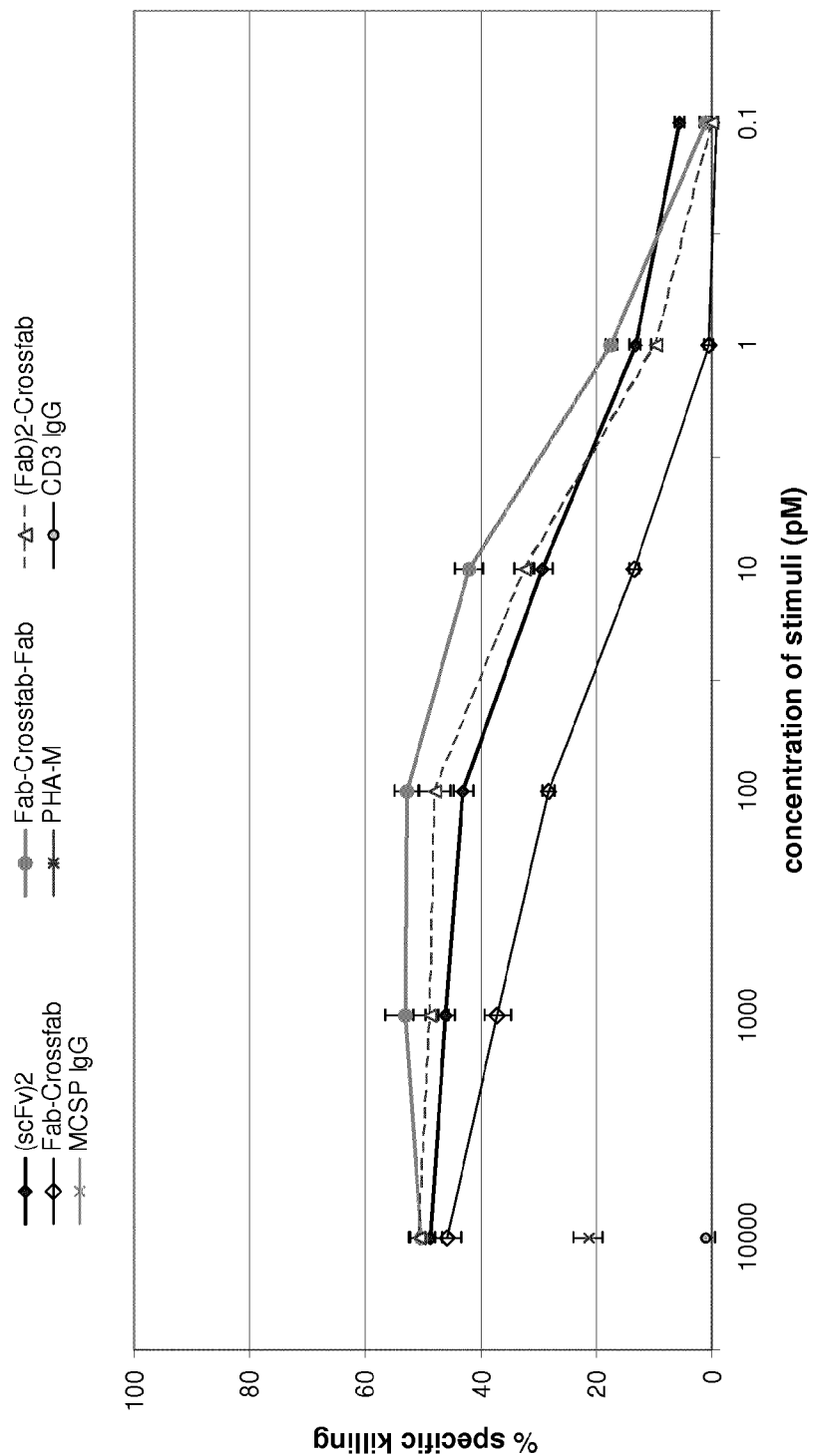
FIG. 10: Killing (as measured by LDH release) of MDA-MB-435 tumor cells upon co-culture with human pan T cells (E:T ratio=5:1) and activation for 20 hours by different concentrations of the hu Fab(MCSP)-Crossfab(CD3) (="Fab-Crossfab"), hu Fab(MCSP)-Crossfab(CD3)-Fab (MCSP) (="Fab-Crossfab-Fab"), hu Fab(MCSP)-Fab (MCSP)-Crossfab(CD3) (="(Fab)2-Crossfab"), as well as the (scFv)2 (antiMCSP/anti huCD3e) (="(scFv)2") bispecific molecules. The constructs with bivalent MCSP-targeting show comparable cytotoxic activity compared to the "(scFv)2" construct, whereas the "Fab-Crossfab" construct with monovalent MCSP binding is clearly less potent.

As depicted in FIG. 10, the constructs with bivalent MCSP-targeting showed comparable cytotoxic activity compared to the (scFv)2 (antiMCSP/anti huCD3e) construct, whereas the Fab (MCSP)-Crossfab (CD3) construct with monovalent MCSP binding was clearly less potent.

LDH Release Assay with Fab (MCSP)-Fab (MCSP)-Crossfab (CD3) Bispecific Construct with MDA-MB-435 Human Melanoma Target Cells Purified Fab (MCSP)-Fab (MCSP)-Crossfab (CD3) and the (scFv)2 (antiMCSP/anti huCD3e) reference molecule were analyzed for their potential to induce T cell-mediated apoptosis in tumor target cells upon crosslinkage of the construct via binding of both targeting moieties to the respective antigens on cells.

Briefly, huMCSP-expressing MDA-MB-435 human melanoma target cells were harvested with Cell Dissociation Buffer, washed and resuspendend in AIM-V medium (Invitrogen #12055-091). 30 000 cells per well were plated in a round-bottom 96-well-plate and the respective antibody dilution was added at the indicated concentrations. All constructs and controls were adjusted to the same molarity.

Human pan T effector cells were added to obtain a final E:T ratio of 5:1. As a positive control for the activation of human pan T cells, 5 µg/ml PHA-M (Sigma #L8902) was used. For normalization, maximal lysis of the target cells (=100%) was determined by incubation of the target cells with a final concentration of 1% Triton-X-100. Minimal lysis (=0%) refers to target cells co-incubated with effector cells, but without any construct or antibody.

After an overnight incubation of 21 h at 37° C., 5% CO2, LDH release of apoptotic/necrotic target cells into the supernatant was measured with the LDH detection kit (Roche Applied Science, #11 644 793 001), according to the manufacturer's instructions.

Figure 11:
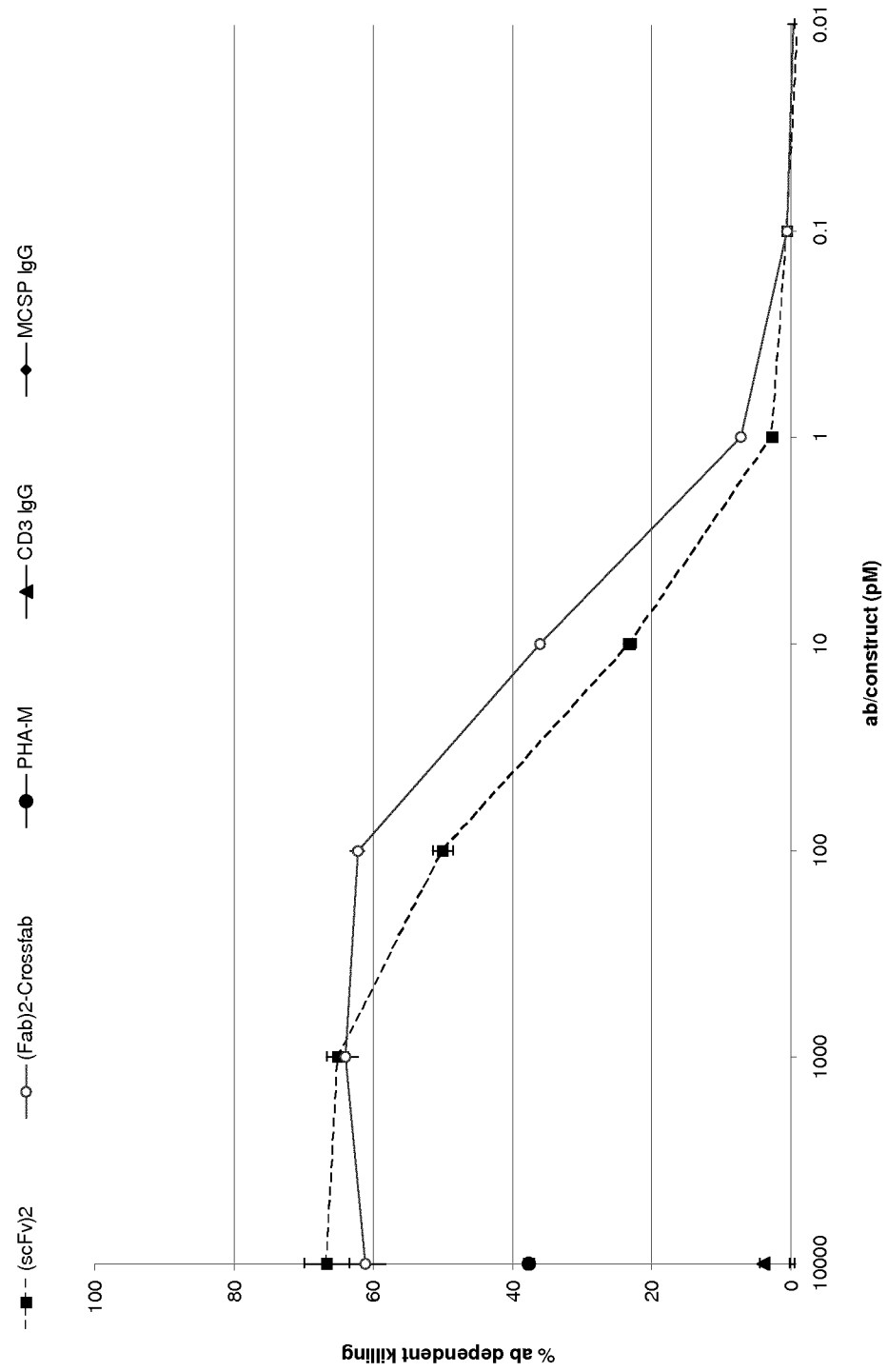
FIG. 11: Comparison of the hu Fab(MCSP)-Fab(MCSP)-Crossfab(CD3) (="(Fab)2-Crossfab") and the (scFv)2 (antiMCSP/anti huCD3e) (="(scFv)2") construct, Depicted is the LDH release from MDA-MB-435 tumor cells upon co-culture with human pan T cells (E/T ratio=5:1), and activation for 21 hours by different concentrations of the bispecific constructs and corresponding IgGs. The "(Fab)2-Crossfab" induces apoptosis in target cells at least comparably good as the (scFv)2 molecule.

As depicted in FIG. 11, the Fab (MCSP)-Fab (MCSP)-Crossfab (CD3) induces apoptosis in target cells at least comparably good as the (scFv)2 (antiMCSP/anti huCD3e) molecule.

LDH Release Assay with Fab (MCSP)-Fab (MCSP)-Crossfab (CD3) Bispecific Construct with MV-3 Human Melanoma Target Cells Purified Fab (MCSP)-Fab (MCSP)-Crossfab (CD3) and the (scFv)2 (antiMCSP/anti huCD3e) molecule were analyzed for their potential to induce T cell-mediated apoptosis in tumor target cells upon crosslinkage of the construct via binding of both targeting moieties to the respective antigens on cells.

Briefly, huMCSP-expressing MV-3 human melanoma target cells were harvested with trypsin on the day before the LDH release assay was started. Cell were washed and resuspendend in the appropriate cell culture medium. 30 000 cells per well were plated in a round-bottom 96-well-plate. The next day, the supernatant was discarded and 100 µl/well AIM-V medium (Invitrogen #12055-091), as well as the respective antibody dilution were added at the indicated concentrations. All constructs and controls were adjusted to the same molarity.

Human PBMC effector cells were added to obtain a final E:T ratio of 10:1. As a positive control for the activation of human pan T cells, 5 µg/ml PHA-M (Sigma #L8902) was used. For normalization, maximal lysis of the target cells (=100%) was determined by incubation of the target cells with a final concentration of 1% Triton-X-100. Minimal lysis (=0%) refers to target cells co-incubated with effector cells, but without any construct or antibody.

After an overnight incubation of 26 h at 37° C., 5% CO2, LDH release of apoptotic/necrotic target cells into the supernatant was measured with the LDH detection kit (Roche Applied Science, #11 644 793 001), according to the manufacturer's instructions.

Figure 12:
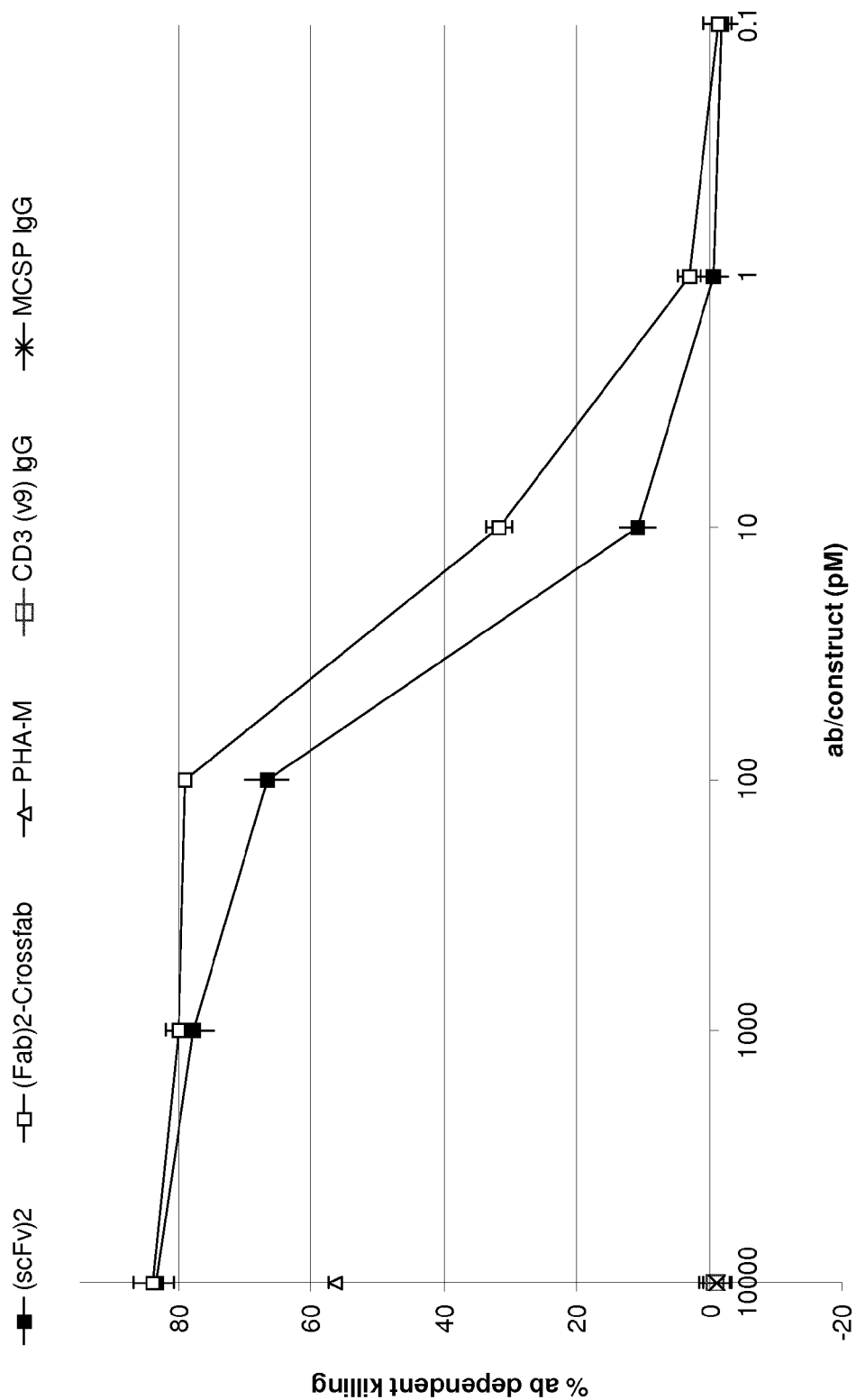
FIG. 12: Comparison of the hu Fab(MCSP)-Fab(MCSP)-Crossfab(CD3) (="(Fab)2-Crossfab") and the (scFv)2 (antiMCSP/anti huCD3e) (="(scFv)2") construct. Depicted is the LDH release from MV-3 human melanoma tumor cells upon co-culture with human PBMCs (E/T ratio=10:1), and activation for 26 hours by different concentrations of the bispecific constructs and corresponding IgGs. The "(Fab)2-Crossfab" induces apoptosis in target cells at least comparably good as the (scFv)2 molecule.

As depicted in FIG. 12, the Fab (MCSP)-Fab (MCSP)-Crossfab (CD3) induces apoptosis in target cells at least comparably good as the (scFv)2 (antiMCSP/anti huCD3e) molecule.

LDH Release Assay with Fab (MCSP)-Crossfab (CD3) Bispecific Construct with MV-3 Human Melanoma Target Cells An LDH release assay was performed as outlined above. FIG. 19 shows killing of huMCSP-positive MV-3 tumor cells upon co-culture with human PBMCs (E:T ratio=10:1), treated with Fab (MCSP)-Crossfab (CD3), respective the (scFv)2 (antiMCSP/anti huCD3e) reference molecule for ~24 hours.

LDH Release Assay with Murine Crossfab (CD3)-Fab (MCSP)-Fab (MCSP) Bispecific Construct Purified with murine Crossfab (CD3)-Fab (MCSP)-Fab (MCSP), targeting murine CD3, as well as human MCSP, was analyzed for its potential to induce T cell-mediated apoptosis in tumor target cells upon crosslinkage of the construct via binding of both targeting moieties to the respective antigens on cells.

Briefly, huMCSP-expressing B16/F10-huMCSP Fluc2 clone 48 tumor target cells were harvested with Cell Dissociation Buffer, washed and resuspendend in RPMI1640 medium, including 1×NEAA, 10 mM Hepes, 50 µm 2-b-ME and 1 mM sodium pyruvate.

20 000 cells per well were plated in a round-bottom 96-well-plate and the respective antibody dilution was added at the indicated concentrations. The bispecific construct and the different IgG controls were adjusted to the same molarity. As an additional control for the activation of murine T cells "T Cell Stim with ConA" (BD #354115) was used, diluted 1:160 with assay medium.

Murine pan T effector cells, isolated from splenocytes (C57BL/6 mice) were added to obtain a final E:T ratio of 10:1. For normalization, maximal lysis of the target cells (=100%) was determined by incubation of the target cells with a final concentration of 1% Triton-X-100. Minimal lysis (=0%) refers to target cells co-incubated with effector cells, but without any construct or antibody.

After an incubation for 70 h at 37° C., 5% CO2, LDH release of apoptotic/necrotic target cells into the supernatant was measured with the LDH detection kit (Roche Applied Science, #11 644 793 001), according to the manufacturer's instructions.

Figure 13:
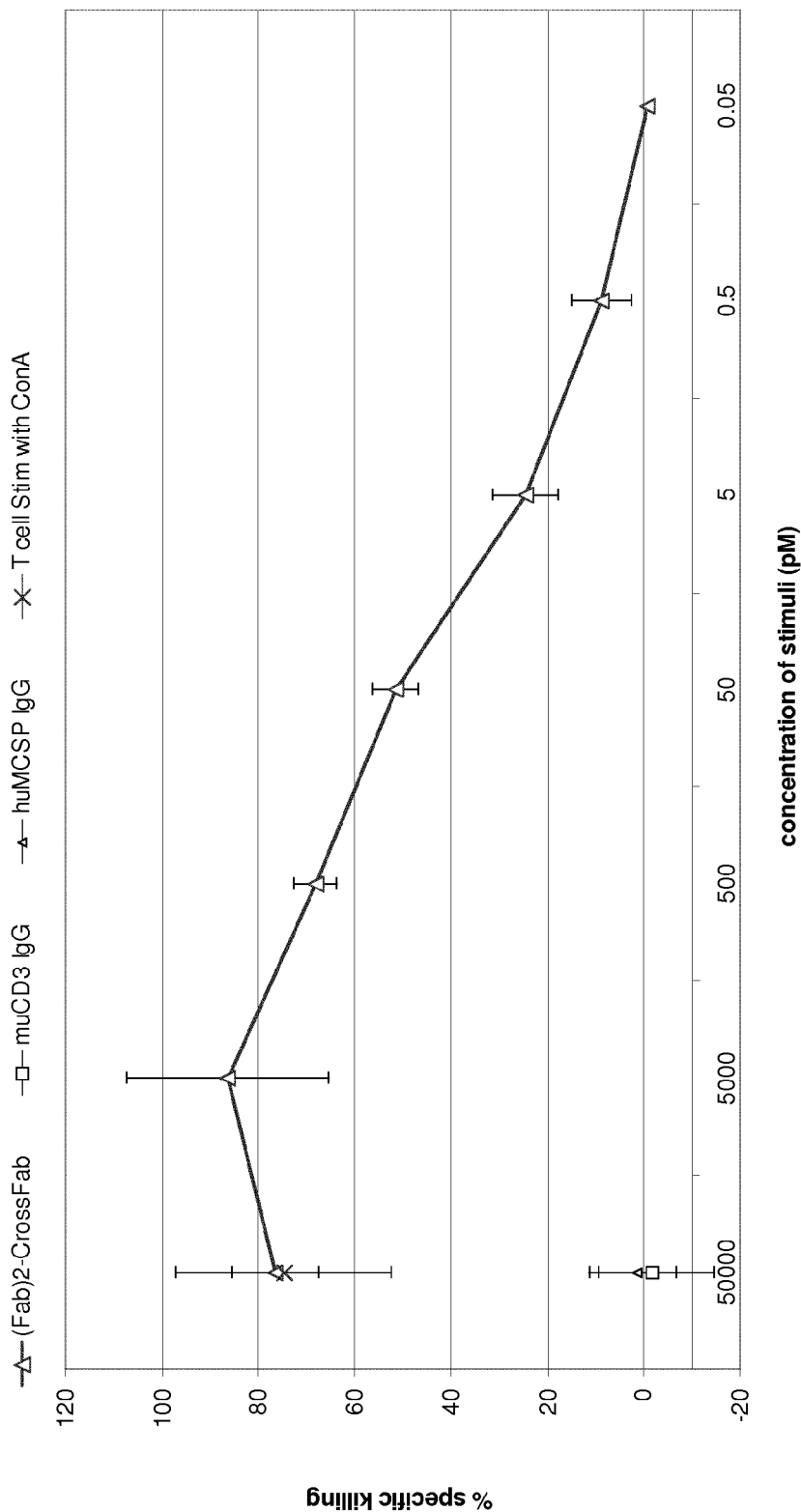
FIG. 13: LDH release from B16/F10-huMCSP Fluc2, clone 48 tumor cells, induced by primary murine T cell activation with the murine Crossfab(CD3)-Fab(MCSP)-Fab (MCSP) construct (=(Fab)2-CrossFab), targeting human MCSP, as well as the murine CD3. The effector to target cell ratio was 5:1. The assay was analyzed after incubation for 23.5 hours at 37° C., 5% CO2. The construct induces concentration-dependent, T cell-mediated apoptosis of human MCSP-expressing target cells.

As depicted in FIG. 13, the bispecific construct induces concentration-dependent LDH release from target cells, comparable to the positive control with "T Cell Stim with ConA".

LDH Release Assay with Murine Crossfab (CD3)-Fab (MCSP)-Fab (MCSP) Bispecific Construct Purified murine Crossfab (CD3)-Fab (MCSP)-Fab (MCSP), targeting murine CD3, as well as human MCSP, was analyzed for its potential to induce T cell-mediated apoptosis in tumor target cells upon crosslinkage of the construct via binding of both targeting moieties to the respective antigens on cells.

Briefly, huMCSP-expressing B16/F10-huMCSP Fluc2 clone 48 tumor target cells were harvested with Cell Dissociation Buffer, washed and resuspendend in RPMI1640 medium, including 1×NEAA, 10 mM Hepes, 50 µM 2-b-ME and 1 mM sodium pyruvate.

20 000 cells per well were plated in a round-bottom 96-well-plate and the respective antibody dilution was added to obtain a final concentration of 50 nM. The bispecific construct and the different IgG controls were adjusted to the same molarity.

Murine pan T effector cells, isolated from splenocytes (C57BL/6 mice) were added to obtain a final E:T ratio of 10:1. To assess the level of hyperactivation of murine T cells in the absence of target cells, control wells with 50 nM bispecific construct and T cells were plated accordingly.

For normalization, maximal lysis of the target cells (=100%) was determined by incubation of the target cells with a final concentration of 1% Triton-X-100. Minimal lysis (=0%) refers to target cells co-incubated with effector cells, but without any construct or antibody.

After an incubation for 70 h at 37° C., 5% CO2, LDH release of apoptotic/necrotic target cells into the supernatant was measured with the LDH detection kit (Roche Applied Science, #11 644 793 001), according to the manufacturer's instructions.

Figure 14:
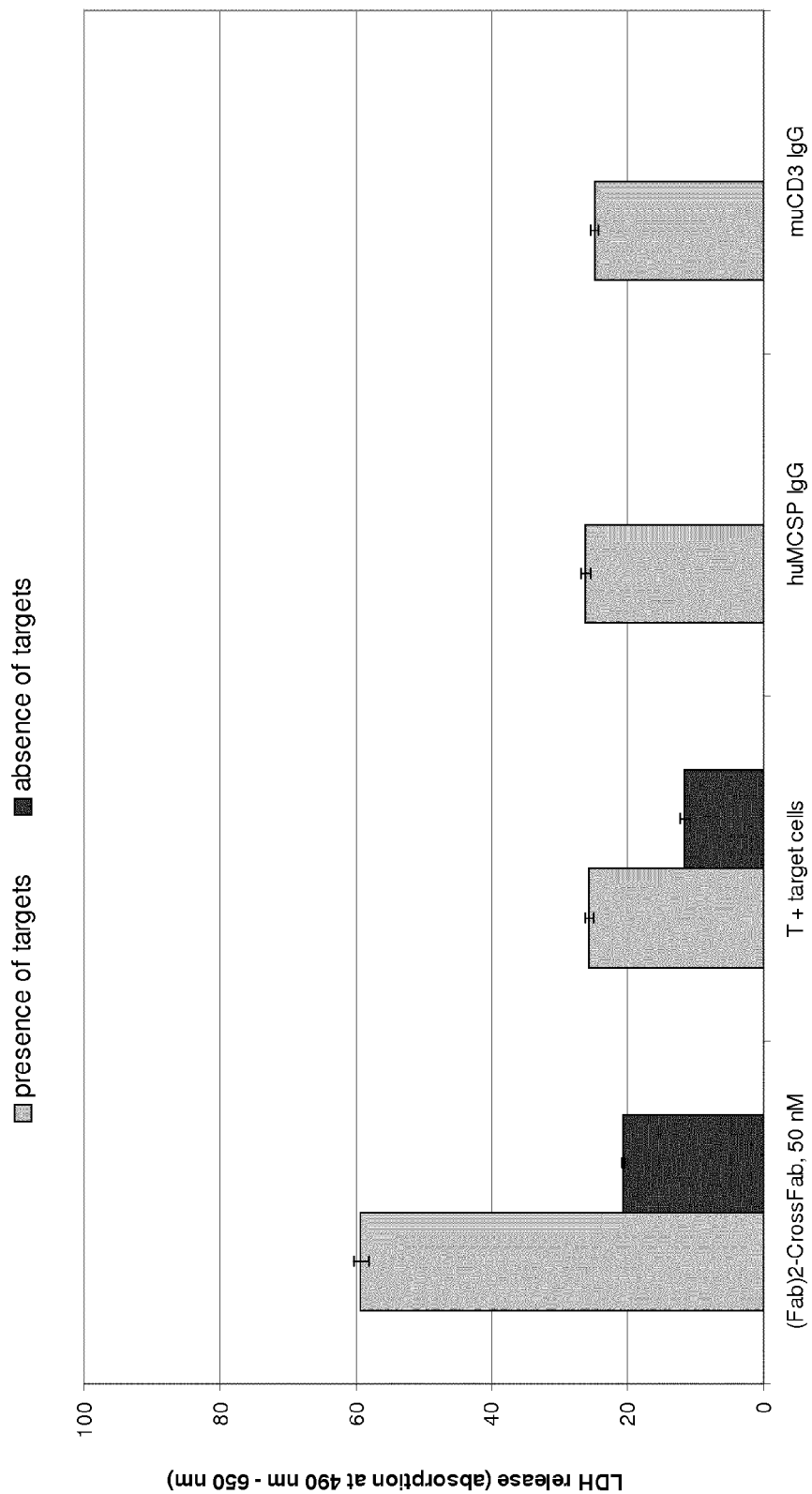
FIG. 14: LDH release from B16/F10-huMCSP Fluc2, clone 48 tumor cells, induced by primary murine T cell activation with 50 nM of the murine Crossfab(CD3)-Fab(MCSP)-Fab(MCSP) construct (=(Fab)2-CrossFab), targeting human MCSP, as well as the murine CD3. The effector to target cell ratio was 5:1. The assay was analyzed after incubation for 23.5 hours at 37° C., 5% CO2. The construct induces T cell-mediated apoptosis of human MCSP-expressing target cells. There is only weak hyperactivation of T cells at this concentration of the construct.

As depicted in FIG. 14, the bispecific construct induces strong LDH release from target cells. In the absence of target cells, there was only a slight increase of LDH (reflecting hyperactivation of T cells) compared to untreated murine T cells, co-incubated with target cells. None of the control IgGs induces LDH release of target cells.

EXAMPLE 8

Cytokine Release Assay (CBA Analysis)

To assess the de novo secretion of different cytokines upon T cell activation with CD3-bispecific constructs in the presence or absence of target cells, human PBMCs were isolated from Buffy Coats and 0.3 Mio cells per well were plated into a round-bottom 96-well plate. Alternatively, 280 µl whole blood from a healthy donor were plated per well of a deep-well 96-well plate.

Tumor target cells (e.g. MDA-MB-435 cells for CD3-MCSP-bispecific constructs) were added to obtain a final E/T-ratio of 10:1. Bispecific constructs and controls were added as indicated. After an incubation of up to 24 h at 37° C., 5% CO2, the assay plate was centrifuged for 5 min at 350 g and the supernatant was transferred into a new deep-well 96-well-plate for the subsequent analysis.

The CBA analysis was performed according to manufacturers' instructions for FACS CantoII, using the combination of the following CBA Flex Sets: human granzyme B (BD 560304), human IFN-γ Flex Set (BD 558269), human TNF Flex Set (BD 558273), human IL-10 Flex Set (BD 558274), human IL-6 Flex Set (BD 558276), human IL-4 Flex Set (BD 558272).

Cytokine Release Assay with MCSP-CD3 Bispecific Constructs

The following purified bispecific constructs targeting human MCSP and human CD3 were analyzed for their ability to induce T cell-mediated de novo secretion of cytokines in the presence (A, B) versus absence (C, D) of tumor target cells: "Fab (MCSP)-Fab (MCSP)-Crossfab (CD3) and the (scFv)2 (antiMCSP/anti huCD3e) reference molecule.

Briefly, 280 µl whole blood from a healthy donor were plated per well of a deep-well 96-well plate. 30 000 Colo-38 tumor target cells, expressing human MCSP, as well as the different bispecific constructs and IgG controls were added were added at 1 nM final concentration. The cells were incubated for 24 h at 37° C., 5% CO2 and then centrifuged for 5 min at 350×g. The supernatant was transferred into a new deep-well 96-well-plate for the subsequent analysis.

The CBA analysis was performed according to manufacturers' instructions for FACS CantoII, using the combination of the following CBA Flex Sets: human granzyme B (BD 560304), human IFN-γ Flex Set (BD 558269), human TNF Flex Set (BD 558273), human IL-10 Flex Set (BD 558274), human IL-6 Flex Set (BD 558276), human IL-4 Flex Set (BD 558272).

Figure 15:
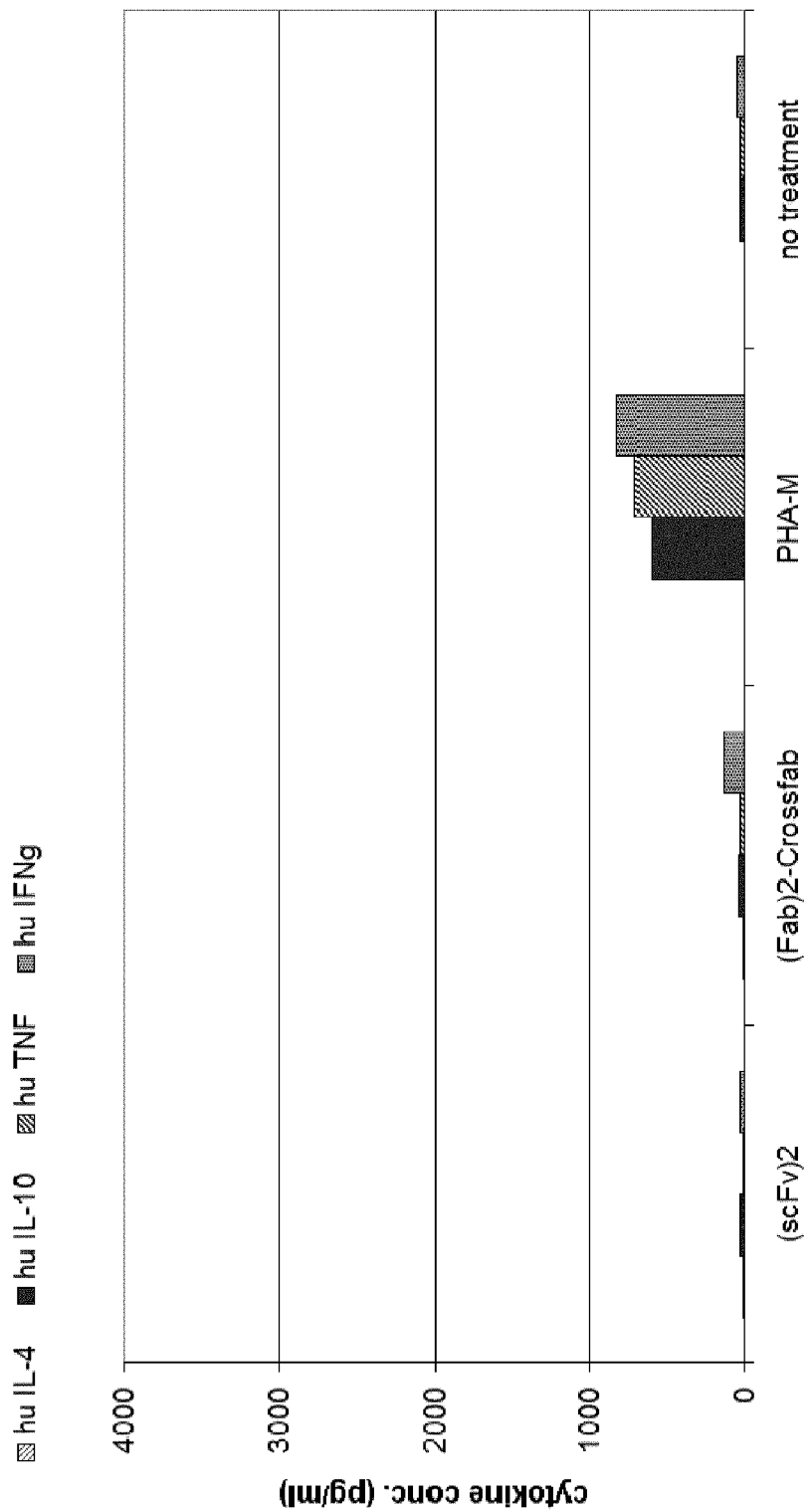
FIGS. 15a: Different cytokine levels measured in the supernatant of whole blood after treatment with 1 nM of different CD3-MCSP bispecific constructs (hu Fab(MCSP)-Fab(MCSP)-Crossfab(CD3) (="(Fab)2-Crossfab") and (scFv)2 (antiMCSP/anti huCD3e) (="(scFv)2")) in the presence (a,b) or absence (c,d) of Colo-38 tumor cells for 24 hours. 280 µl whole blood were plated per well of a 96-well plate and 30 000 Colo-38 cells added, as indicated. The main cytokine that was secreted upon activation of T cells in the presence of Colo-38 tumor cells, is IL-6, followed by IFNgamma. In addition, also the levels of granzyme B increased enormously upon activation of T cells in the presence of target cells. In general, the "(scFv)2" construct elevated the levels of TNF and IFNgamma, as well as granzyme B in the presence of target cells (a and b) a bit more compared to the other bispecific construct.
Figure 15:
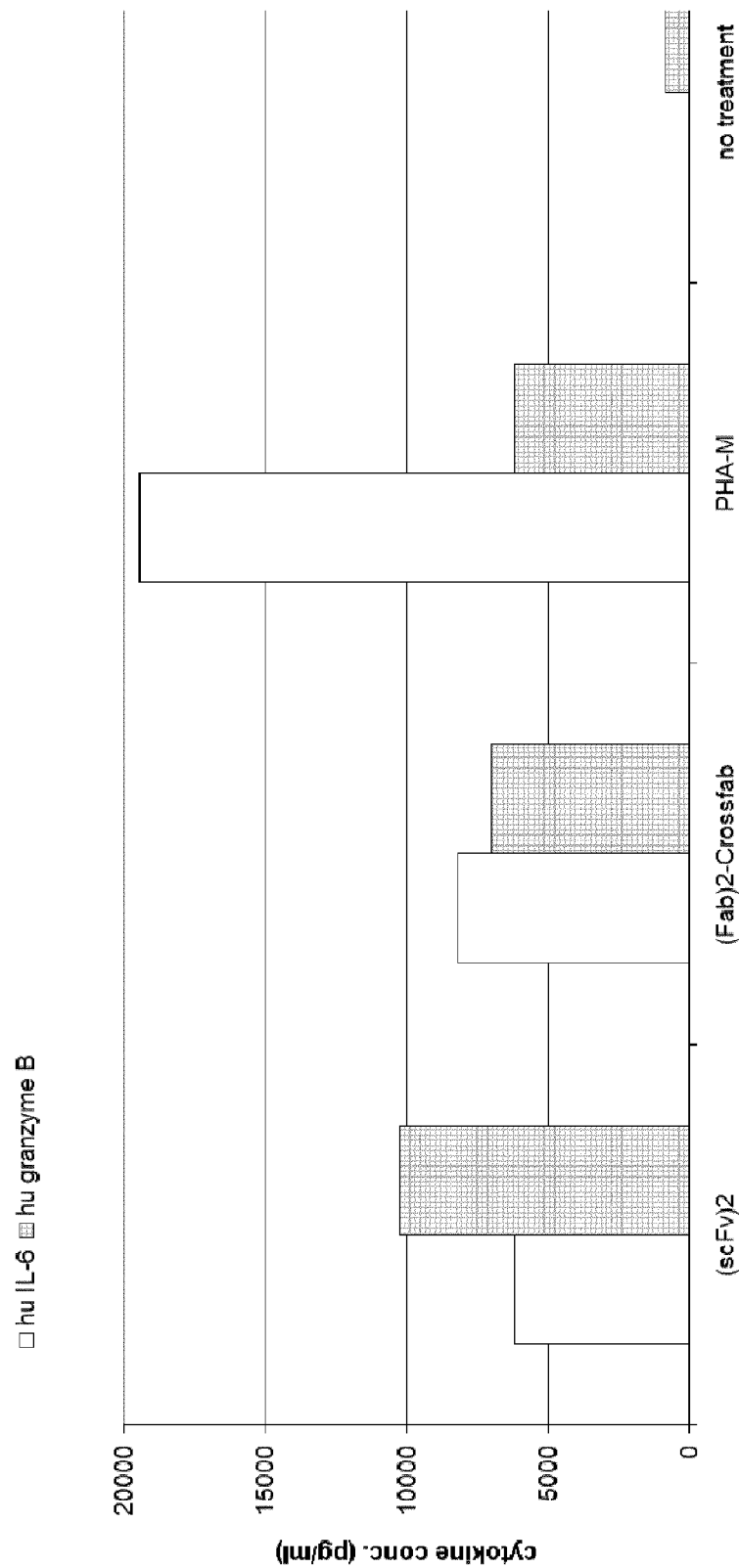
Figure 15:
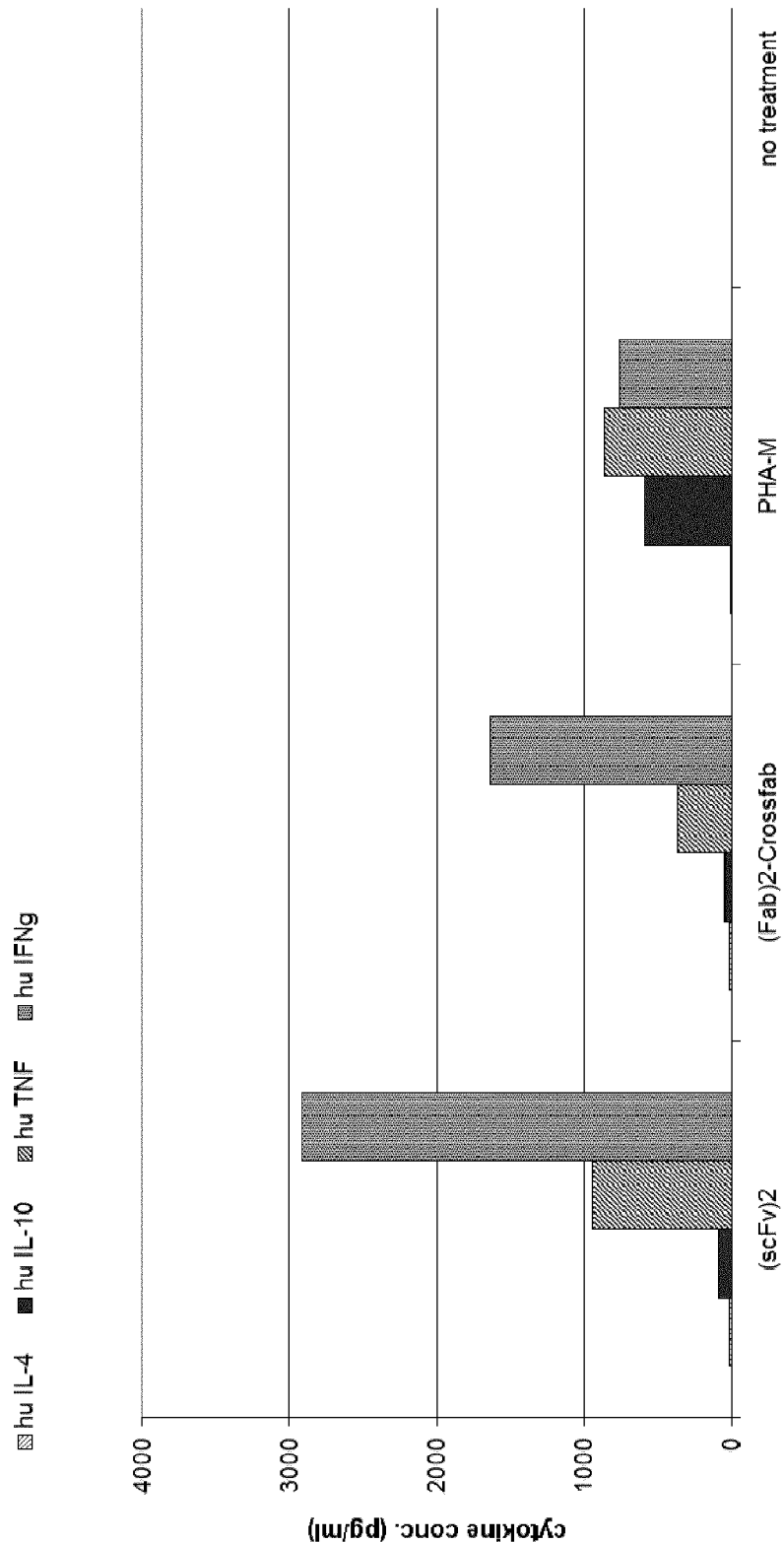

FIG. 15 depicts different cytokine levels, that were measured in the supernatant of whole blood after treatment with 1 nM of different CD3-MCSP bispecific constructs (Fab (MCSP)-Fab (MCSP)-Crossfab (CD3) and the (scFv)2 (antiMCSP/anti huCD3e)) in the presence (A, B) or absence (C,D) of Colo-38 tumor cells for 24 hours. 280 µl whole blood were plated per well of a 96-well plate and 30 000 Colo-38 cells added, as indicated.

The main cytokine that was secreted upon activation of T cells in the presence of Colo-38 tumor cells, was IL-6, followed by IFNgamma. In addition, also the levels of granzyme B increased enormously upon activation of T cells in the presence of target cells. In general, the (scFv)2 (antiMCSP/anti huCD3e) construct elevated the levels of TNF and IFNgamma, as well as granzyme B in the presence of target cells (A and B) a bit more compared to the other bispecific construct.

There was no significant secretion of Th2 cytokines (IL-10 and IL-4) upon activation of T cells by the bispecific constructs in the presence (or absence) of target cells.

In this assay, there was also a weak secretion of IFNgamma, induced by the Fab (MCSP)-Fab (MCSP)-Crossfab (CD3) construct in the absence of target cells.

Cytokine Release Assay with MCSP-murineCD3 Bispecific Constructs

The purified huMCSP-muCD3-targeting bispecific molecule as murine Crossfab (CD3)-Fab (MCSP)-Fab (MCSP) was tested by flow cytometry for its potential to up-regulate the late activation marker CD25 on CD8+ T cells in the presence of human MCSP-expressing tumor cells.

Briefly, MCSP-positive B16/F10-huMCSP Fluc2 clone 48 tumor cells were harvested with Cell Dissociation buffer, counted and checked for viability. Cells were adjusted to $0.3 \times 10^6$ (viable) cells per ml in RPMI1640 medium (including 1×NEAA, 10 mM Hepes, 50 μm 2-b-ME, 1 mM sodium pyruvate), 100 μl of this cell suspension were pipetted per well into a round-bottom 96-well plate (as indicated). 50 μl of the (diluted) bispecific construct was added to the cell-containing wells to obtain a final concentration of 50 nM. Human murine T effector cells were isolated from splenocytes (C57BL/6 mice) and adjusted to $3 \times 10^6$ (viable) cells per ml in AIM-V medium. 50 μl of this cell suspension was added per well of the assay plate (see above) to obtain a final E:T ratio of 10:1. To analyze, if the bispecific construct was able to activate T cells only in the presence of target cells, expressing huMCSP, wells were included that contained 50 nM of the respective bispecific molecule, as well as T effector, but no target cells.

After incubation for 70 hours at 37° C., 5% CO2, cells were centrifuged (5 min, 350×g) and washed twice with 150 l/well PBS, including 0.1% BSA.

Surface staining for CD8a (rat IgG2a; clone 53-6.7; BioLegend #100712) and CD25 (rat IgG2b; clone 3C7; BD #553075) was performed according to the suppliers' suggestions. Cells were washed twice with 150 l/well PBS, including 0.1% BSA and fixed for 15 min at 4° C., using 100 l/well fixation buffer (BD ##554655).

After centrifugation, the samples were resuspended in 200 μl/well PBS, 0.1% BSA and analyzed using a FACS CantoII machine (Software FACS Diva).

FIG. 16 shows that the as murine Crossfab (CD3)-Fab (MCSP)-Fab (MCSP) construct induces up-regulation of CD25 in the presence of target cells only.

EXAMPLE 9

Expression of Surface Activation Markers on Primary Human T Cells Upon Engagement of Bispecific Constructs To check for specific activation of T cells upon binding of CD3 bispecific constructs exclusively in the presence of tumor target cells, primary human PBMCs (isolated as described above) were incubated with the indicated concentrations of bispecific constructs for at least 24 h in the presence or absence of tumor antigen-positive target cells.

Briefly, 0.3 million primary human PBMCs were plated per well of a flat-bottom 96-well plate, containing the huMCSP-positive target cells (MV-3 tumor cells) or medium. The final effector to target cell (E:T) ratio was 10:1. The cells were incubated with the indicated concentration of the CD3-MCSP bispecific constructs (Fab (MCSP)-Crossfab (CD3); designated as "1+1 non-Fc", and the (scFv)2 (antiMCSP/anti huCD3e) reference molecule (designated as "(scFv)2") for the indicated incubation times at 37° C., 5% CO2. The effector cells were stained for CD8, and the early activation marker CD69 or the late activation marker CD25 and analyzed by FACS CantoII.

Figure 20:
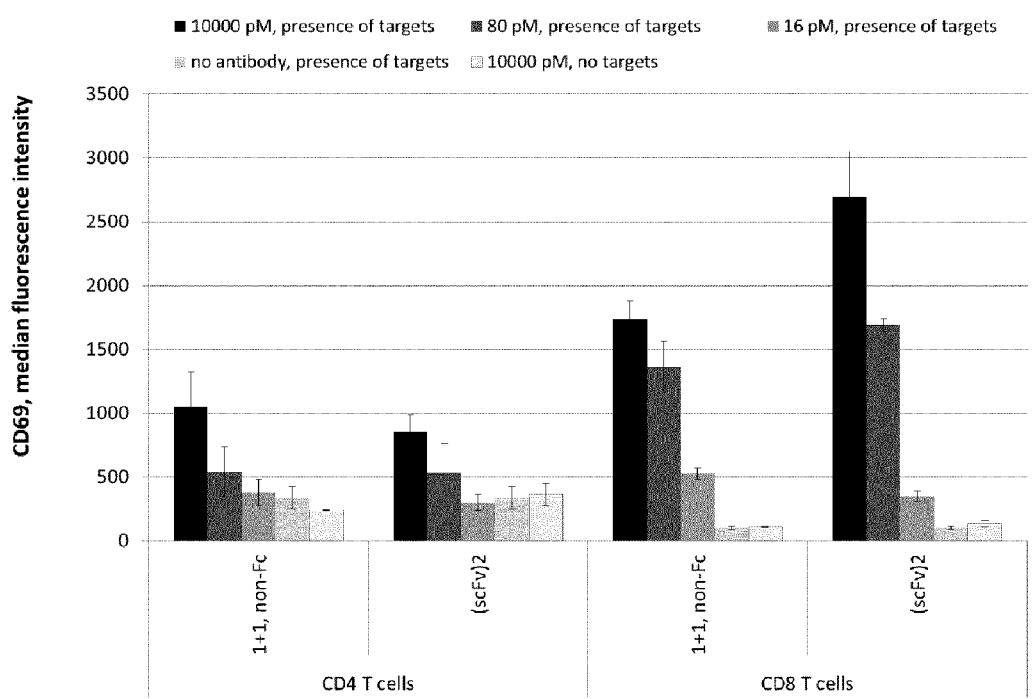
Figure 20:
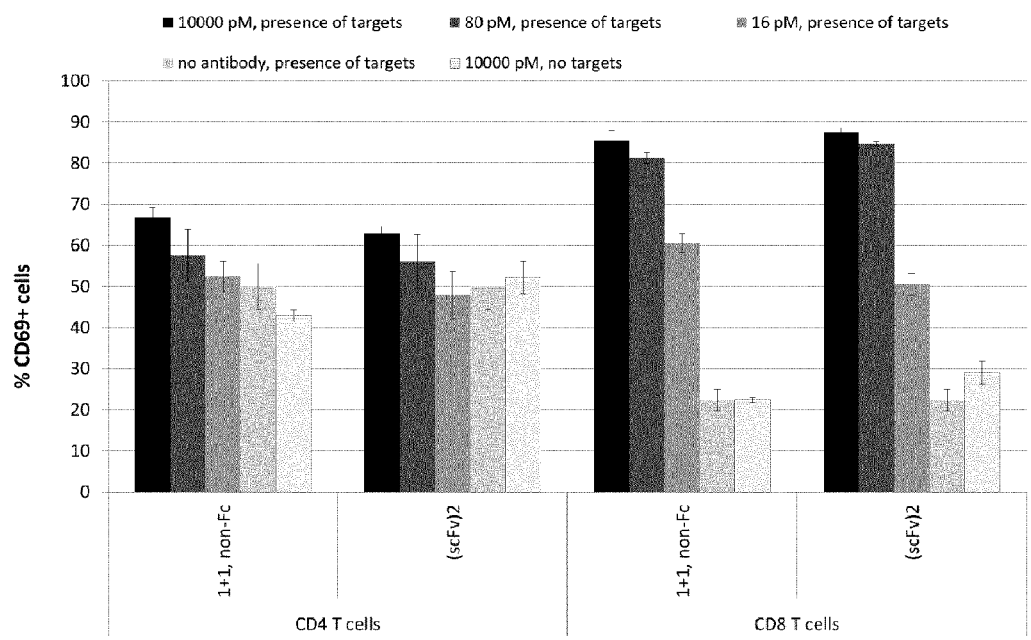

FIG. 20 shows the result of this experiment.

EXAMPLE 10

Preparation of Fab-CrossFab Linked Light Chain (Fab-Crossfab with Two Linkers)

The molecule was produced by co-transfecting HEK293-EBNA cells growing in suspension with the mammalian expression vectors using by polyethylenimine. The cells were transfected with the corresponding expression vectors in a 1:1 ratio ("vector heavy chain" "vector linked light chain").

HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 μg DNA. After addition of 540 μl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution was sterile filtered (0.22 μm filter) and sodium azide in a final concentration of 0.01% w/v was added, and kept at 4° C.

The secreted protein was purified from cell culture supernatants by affinity chromatography using ProteinG affinity chromatography, followed by a size exclusion chromatographic step.

For affinity chromatography supernatant was loaded on a HiTrap ProteinG HP column (CV=5 mL, GE Healthcare) equilibrated with 30 ml 20 mM sodium phosphate, 20 mM sodium citrate, pH 7.5. Unbound protein was removed by washing both columns with 6 column volume 20 mM sodium phosphate, 20 mM sodium citrate, pH 7.5. Subsequently column was washed using at least 8 column volume 20 mM sodium phosphate, 20 mM sodium citrate, pH 7.5. The target protein was eluted from HiTrap ProteinG HP column using a step gradient with 7 column volume 8.8 mM formic acid, pH 3.0. Protein solution was directly loaded on a HiLoad Superdex 200 column (GE Healthcare) equilibrated with 25 mM potassium phosphate, 125 mM sodium chloride, 100 mM glycine solution of pH 6.7.

The protein concentration of purified protein samples was determined by measuring the optical density (OD) at 280 nm, using the molar extinction coefficient calculated on the basis of the amino acid sequence.

Purity and molecular weight of the construct was analyzed by SDS-PAGE in the presence and absence of a reducing agent (5 mM 1,4-dithiothreitol) and staining with Coomassie (SimpleBlue™ SafeStain from Invitrogen). The NuPAGE® Pre-Cast gel system (Invitrogen, USA) was used according to the manufacturer's instruction (4-12% Bis-Tris).

The aggregate content of antibody samples was analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C. Final monomer content was 99.4%.

| Construct MCSP | Yield [mg/l] | Aggregate after 1st purification step [%] | HMW [%] | LMW [%] | Monomer [%] |
|---|---|---|---|---|---|
| 1 + 1 Fab-Crossfab linked light chain (hu Fab (MCSP) = Crossfab (CD3)) SEQ ID NOs 163 and 164 | 0.67 | 27.0 | 0.6 | 0 | 99.4 |

Figure 24:
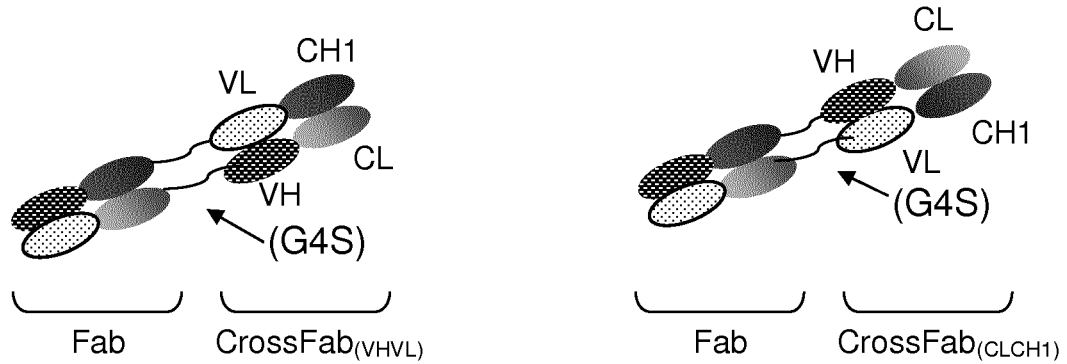
Figure 24:
Figure 24:
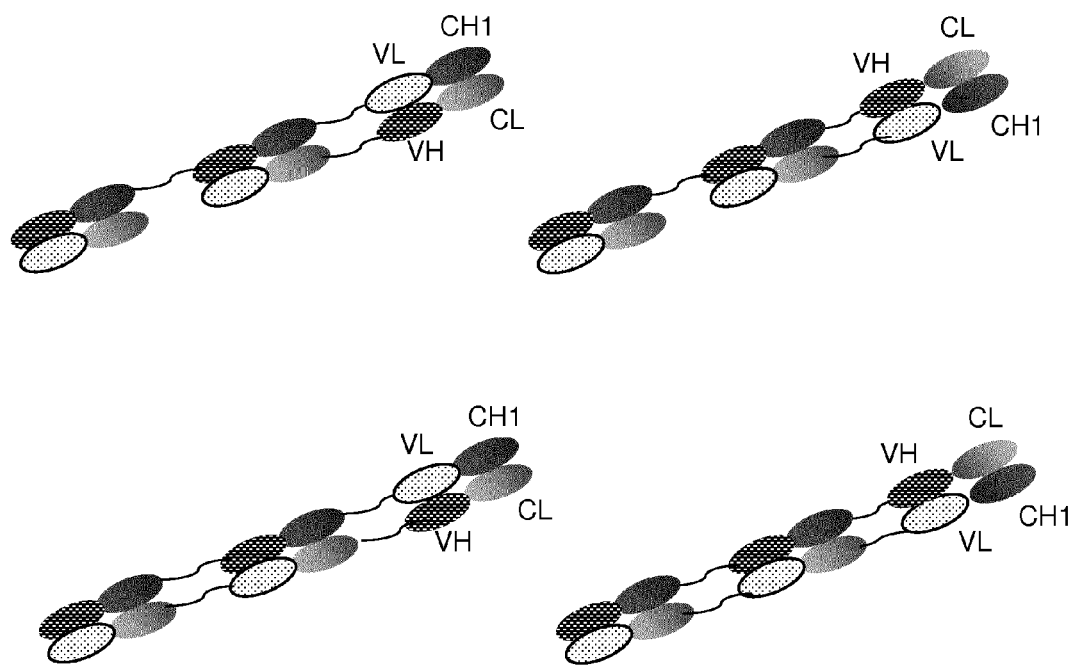
Figure 24:
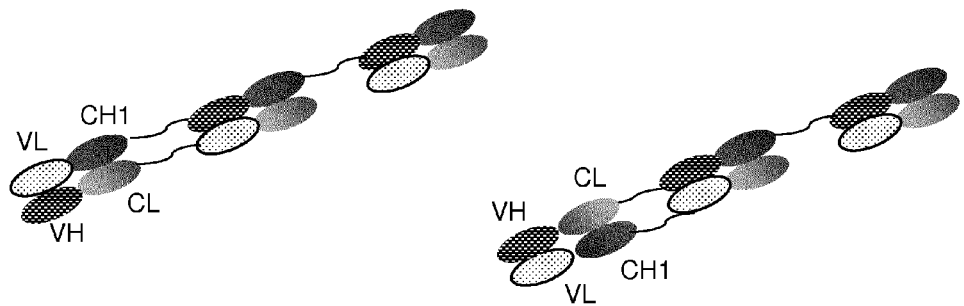
Figure 24:
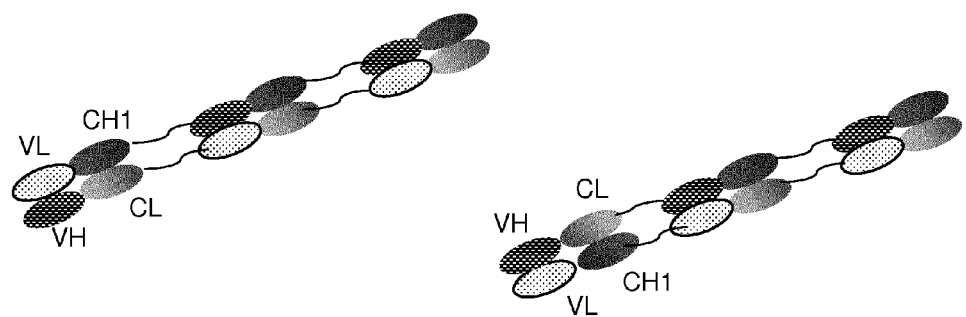
Figure 24:
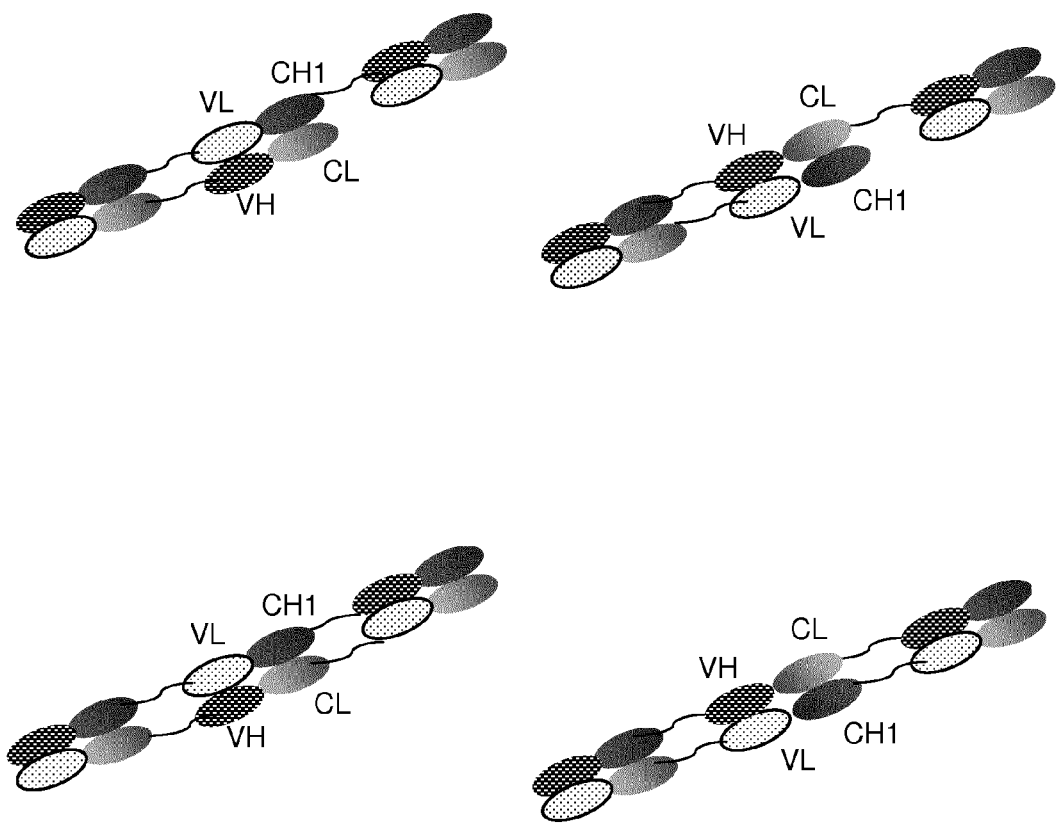

Analysis of production and purification of an exemplary Fab-Crossfab molecule with two linkers (consisting of two chains: VHCH1(MCSP)-(G4S)2-VLCH1(CD3$_{v9}$)=SEQ ID NO: 164, VLCL(MCSP)-(G4S)2-VHCL(CD3$_{v9}$)=SEQ ID NO: 163; with an orientation as depicted in FIG. 24 a) is shown in FIG. 25. This molecule is further referred to as Fab (MCSP)=Crossfab (CD3) or hu Fab (MCSP)=Crossfab (CD3).

Thermal Stability of Fab-CrossFab Linked Light Chain

Thermal stability of the protein was monitored by Dynamic Light Scattering (DLS). 30 μg of filtered protein sample with a protein concentration of 1 mg/ml was applied in duplicate to a Dynapro plate reader (Wyatt Technology Corporation; USA). The temperature was ramped from 25 to 75° C. at 0.05° C./min, with the radius and total scattering intensity being collected.

The results are shown in FIG. 28. Thermal stability was analyzed for the an exemplary Fab-Crossfab molecule with two linkers (consisting of two chains: VHCH1(MCSP)-(G4S)2-VLCH1(CD3$_{v9}$)=SEQ ID NO: 164, VLCL(MCSP)-(G4S)2-VHCL(CD3$_{v9}$)=SEQ ID NO: 163; with an orientation as depicted in FIG. 24 a) in comparison to the (scFv)2 molecule. The aggregation temperature of the Fab-CrossFab linked light chain molecule was measured at 63° C. (black line). The (scFv)2 molecule was inferior to the Fab-Crossfab molecule with two linkers since it starts to aggregate already at 45° C. (grey line).

The Fab-Crossfab molecule with two linkers has a higher stability and thus more developable than the (scFv)2 molecule.

EXAMPLE 11

Analysis of Fab-Crossfab with Two Linkers (Fab (MCSP)=Crossfab (CD3))

Isolation of Primary Human PBMCs from Fresh Blood or Buffy Coat

Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched-off), part of the plasma above the PBMC containing interphase was discarded. Transfer the PBMCs into new 50 ml falcon tubes and fill-up the tubes with PBS to 50 ml total volume. Switch-on the brake and centrifuge at room temperature for 10 minutes at 400×g. Discard the supernatant and wash the PBMC pellet twice with sterile PBS (centrifugation steps at 4° C. for 10 minutes at 350×g).

The resulting PBMC population was counted automatically (ViCell) and stored in RPMI1640 medium, containing 10% FCS and 1% L-alanyl-L-glutamine (Biochrom, K0302) at 37° C., 5% $CO_2$ in the incubator until assay start.

FACS Analysis of Surface Activation Markers on Primary Human T Cells Upon Engagement of Bispecific Constructs To check for specific activation of T cells upon binding of CD3 bispecific constructs exclusively in the presence of tumor target cells, primary human PBMCs were incubated with the indicated concentrations of bispecific constructs for at least 22 h in the presence or absence of MCSP-positive target cells. Briefly, 0.3 million primary human PBMCs were plated per well of a flat-bottom 96-well plate, containing the MCSP-positive target cells (or medium). The final effector to target cell (E:T) ratio was 10:1. The cells were incubated with the indicated concentration of the bispecific constructs and controls for the indicated incubation times at 37° C., 5% $CO_2$. The effector cells were stained for CD8, and the early activation marker CD69 or the late activation marker CD25 and analyzed by FACS CantoII.

Figure 27:
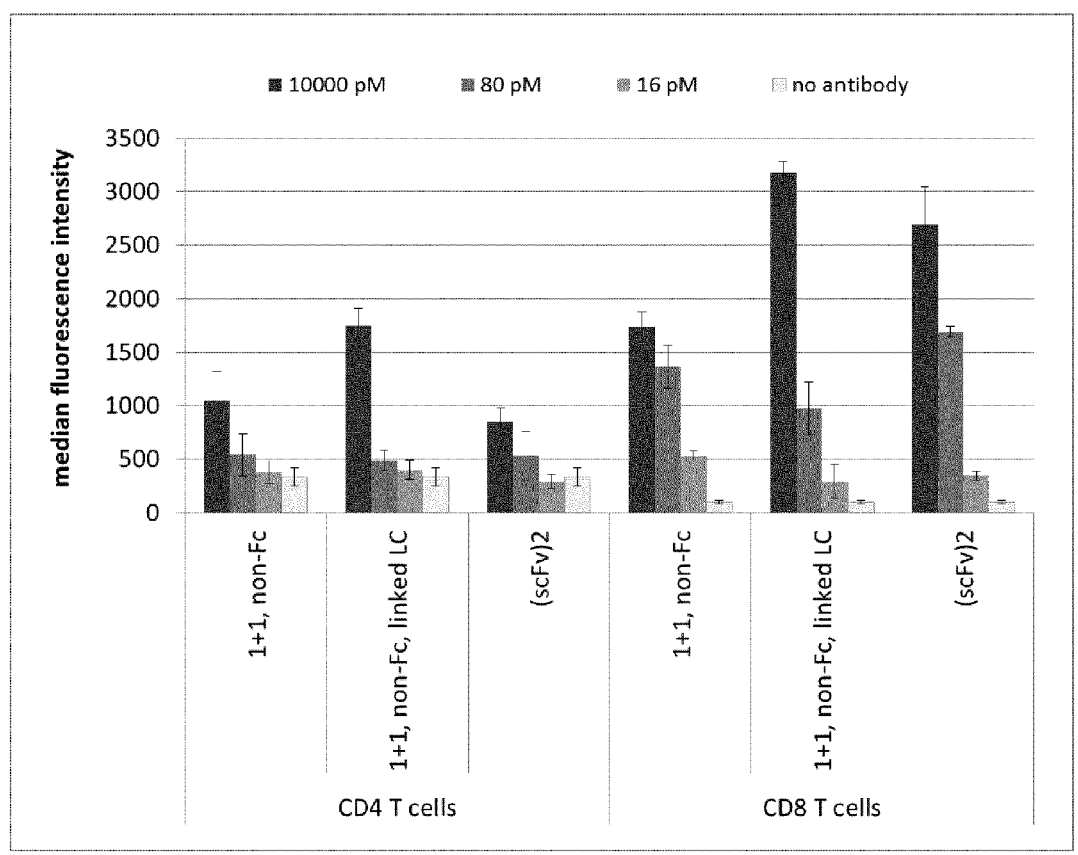
Figure 27:
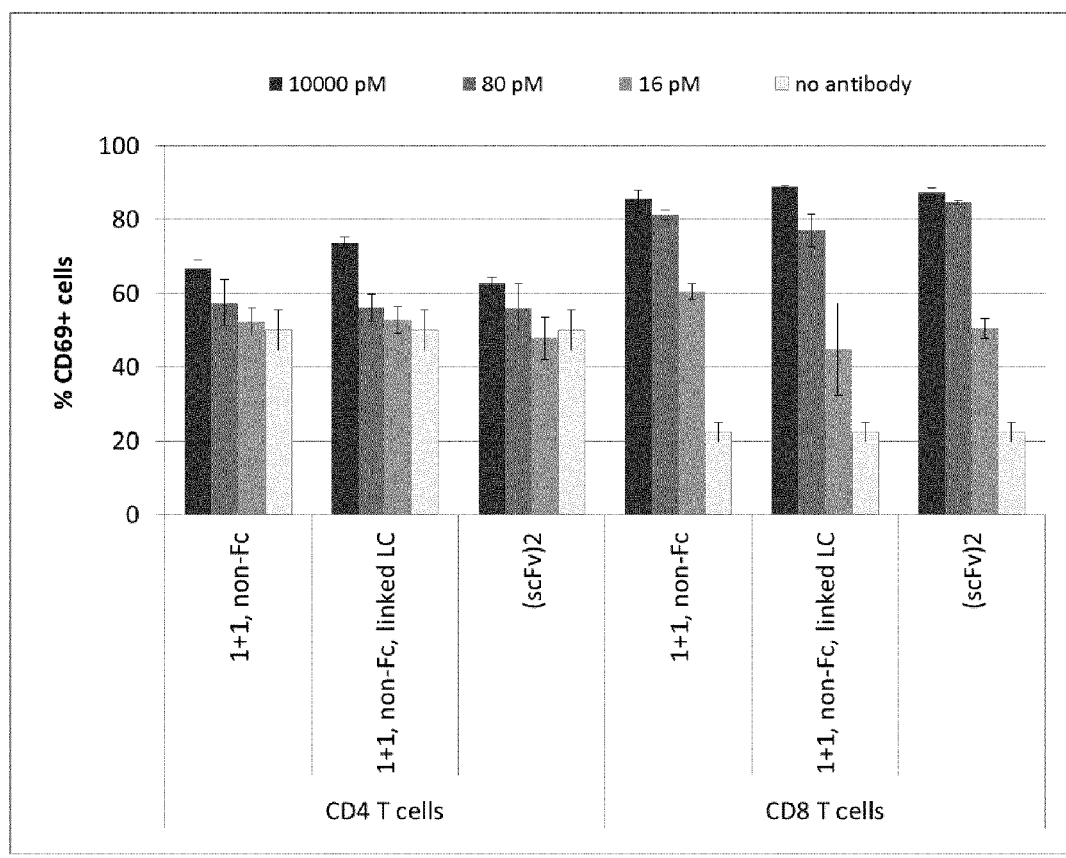

FIG. 27 shows the results of this assay: Activation of CD4+ and CD8+ T cells, mediated by different CD3-MCSP bispecific constructs in the presence versus absence of MCSP-positive MV-3 tumor cells after 24 hours (E:T=10:1), measured as up-regulation of CD69 median fluorescence (A), respective percent of CD69 positive cells (B).

LDH Release Assay

Bispecific constructs targeting CD3 on human T cells, and human MCSP on tumor cells were analyzed by a LDH release assay for their potential to induce T cell-mediated apoptosis of target cells. Briefly, target cells (human Colo-38 or human MV-3 melanoma cells) were harvested with Cell Dissociation Buffer on the day of the assay (or with trypsin one day before the assay was started), washed and resuspended in the appropriate cell culture medium (as indicated). 20 000-30 000 cells per well were plated in a flat-bottom 96-well plate and the respective antibody dilution was added as indicated (triplicates). Effector cells were added to obtain a final E:T ratio of 10:1. All constructs and controls were adjusted to the same molarity. For normalization, maximal lysis of the target cells (=100%) was achieved by incubation of the target cells with a final concentration of 1% Triton X-100. Minimal lysis (=0%) refers to target cells co-incubated with effector cells, but without any bispecific construct. After an overnight incubation of at least 22 h at 37° C., 5% $CO_2$, LDH release of apoptotic/necrotic target cells into the supernatant was measured, using the LDH detection kit (Roche Applied Science, #11 644 793 001), according to the manufacturer's instructions.

FIG. 26 shows the results of this assay: Killing (as measured by LDH release) of MCSP-positive MV-3 tumor cells upon co-culture with human PBMCs (E:T ratio=10:1), treated with different CD3-MCSP bispecific constructs for ~24 hours.

EC50 values were determined using Graph Pad Prism software.

|  | hu Fab (MCSP)-Crossfab (CD3) (1 linker) SEQ ID NO: 25, 23, 17 | hu Fab (MCSP) = Crossfab (CD3) (2 linkers) SEQ ID NOs: 163, 164 | (scFv)2 SEQ ID NO: 149 |
|---|---|---|---|
| EC50 (pM) | 25.35 | 89.78 | 57.1 |

While there are shown and described presently preferred embodiments of the invention, it is to be distinctly understood that the invention is not limited thereto but may be

EXAMPLE 12

Affinity Maturation of Anti-MCSP Antibody M4-3/ML2

The affinity maturation is described in European patent application EP 13156686.1, which is incorporated by reference in its entirety.

Affinity maturation was performed via the oligonucleotide-directed mutagenesis procedure. For this the heavy chain variant M4-3, and the light chain variant ML2 were cloned into a phagemid vector, similar to those described by Hoogenboom, (Hoogenboom et al., Nucleic Acids Res. 1991, 19, 4133-4137). Residues to be randomized were identified by first generating a 3D model of that antibody via classical homology modeling and then identifying the solvent accessible residues of the complementary determining regions (CDRs) of heavy and light chain. Oligonucleotides with randomization based on trinucleotide synthesis as shown in table 3 were purchased from Ella-biotech (Munich, Germany). Three independent sublibraries were generated via classical PCR, and comprised randomization in CDR-H1 together with CDR-H2, or CDR-L1 together with CDR-L2, CDR-L3 was randomized in a separate approach. The DNA fragments of those libraries were cloned into the phagemid via restriction digest and ligation, and subsequently electroporated into TG1 bacteria.

Library Selection.

The antibody variants thus generated were displayed in a monovalent fashion from filamentous phage particles as fusions to the gene III product of M13 packaged within each particle. The phage-displayed variants were then screened for their biological activities (here: binding affinity) and candidates that have one or more improved activities were used for further development. Methods for making phage display libraries can be found in Lee et al., J. Mol. Biol. (2004) 340, 1073-1093), Selections with all affinity maturation libraries were carried out in solution according to the following procedure: 1. binding of ~1012 phagemid particles of each affinity maturation libraries to 100 nM biotinylated hu-MCSP(D3 domain)-avi-his(SEQ ID NO. 118) for 0.5 h in a total volume of 1 ml, 2. capture of biotinylated hu-MCSP(D3 domain)-avi-his and specifically bound phage particles by addition of 5.4×107 streptavidin-coated magnetic beads for 10 min, 3. washing of beads using 5-10x 1 ml PBS/Tween20™ and 5-10x 1 ml PBS, 4. elution of phage particles by addition of 1 ml 100 mM TEA (triethylamine) for 10 min and neutralization by adding 500 ul 1 M Tris/HCl pH 7.4 and 5. re-infection of exponentially growing $E.$ $coli$ TG1 bacteria, infection with helper phage VCSM13 and subsequent PEG/NaCl precipitation of phagemid particles to be used in subsequent selection rounds. Selections were carried out over 3-5 rounds using either constant or decreasing (from 10-7 M to 2×10-9 M) antigen concentrations. In round 2, capture of antigen: phage complexes was performed using neutravidin plates instead of streptavidin beads. Specific binders were identified by ELISA as follows: 100 ul of 10 nM biotinylated hu-MCSP(D3 domain)-avi-his per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using PROTEON™ XPR36 (Bio-Rad). Clones expressing Fabs with the highest affinity constants were identified and the corresponding phagemids were sequenced.

TABLE 3

(excluded were always Cys, and Met. Lys was excluded on top in those cases where the oligonucleotide was a reverse primer)

| Position | Randomization |
|---|---|
| Heavy chain CDR1 | |
| Ser31 | S (40%), test (60%, 4% each) |
| Gly32 | G (40%), rest (60%, 4% each). |
| Tyr33 | Y (40%), rest (60%, 4% each) |
| Tyr34 | Y (40%), rest (60%, 4% each) |
| CDR2 | |
| Tyr50 | Y 40%, (F, W, L, A, I, 30%, 6% each), rest (30%, 2.5% each) |
| Thr52 | T (60%), rest (40%, 2.5% each) |
| Tyr53 | Y (40%), rest (60%, 3.8% each) |
| Asp54 | D (40%), rest (60%, 3.8% each) |
| Ser56 | S (40%), rest (60%, 3.8% each) |
| Light chain CDR1 | |
| Gln27 | Q (40%), (E, D, N, S, T, R, 40%, 6.7% each), rest (total 20%, 2.2% each) |
| Gly28 | G (40%), (N, T, S, Q, Y, D, E, 40%, 5.7% each), rest (20%, 2.5% each) |
| Asn31 | N (40%), (S, T, G, Q, Y, D, E, R, 50%, 6.3% each), rest (10%, 1.4% each) |
| Tyr32 | Y (40%), (W, S, R, 30%, 10% each), rest (30%, 2.3% each) |
| CDR2 | |
| Tyr50 | Y (70%), (E, R, K, A, Q, T, S, D, G, W, F, 30%, 2.7% each) |
| Thr51 | T (50%), (S, A, G, N, Q, V, 30%, 5% each), rest (20%, 2% each) |
| Ser52 | S (50%), rest (50%, 3.1% each) |
| Ser53 | S (40%), (N, T, Q, Y, D, E, I, 40%, 5.7% each), rest (20%, 2.2% each) |
| CDR3 | |
| Tyr91 | Y (50%), rest (50%, 3.1% each) |
| Ser92 | S (50%), (N, Q, T, A, G 25%, 5% each), rest (25%, 2.3% each) |
| Lys93 | K (50%), S (5%), T (5%), N (5%), rest (35%, 2.7% each) |
| Leu94 | L (50%), (Y, F, S, I, A, V, 30%, 5% each), rest (20%, 2% each) |
| Pro95 | P (50%), (S, A, 20%, 10% each), rest (30%, 2.1% each) |
| Trp96 | W 50%, (Y, R, L, 15%, 5% each), rest (35%, 2.5% each) |

Heavy chain randomization was performed only in the CDR1 and 2. Light chain randomization was performed in CDR1 and 2, and independently in CDR3.

During selection, a few mutations in the frameworks occured like F71Y in clone G3 or Y87H in clone E10.

Production and Purification of Human IgG1

The variable region of heavy and light chain DNA sequences of the affinity matured variants were subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contained an EBV OriP sequence.

The molecule was produced by co-transfecting HEK293-EBNA cells with the mammalian expression vectors using polyethylenimine. The cells were transfected with the corresponding expression vectors in a 1:1 ratio. For transfection HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant was replaced by pre-warmed 20 ml CD CHO medium. Expression vectors were mixed in 20 ml CD CHO medium to a final amount of 200 µg DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution was sterile filtered (0.22 µm filter) and sodium azide in a final concentration of 0.01% w/v was added, and kept at 4° C.

The secreted protein was purified from cell culture supernatants by affinity chromatography using ProteinA. Supernatant was loaded on a HiTrap ProteinA HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volume 20 mM sodium phosphate, 20 mM sodium citrate, 0.5 M sodium chloride, pH 7.5. Target protein was eluted during a gradient over 20 column volume from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM Histidine, 140 mM sodium chloride solution of pH 6.0.

The protein concentration of purified protein samples was determined by measuring the optical density (OD) at 280 nm, using the molar extinction coefficient calculated on the basis of the amino acid sequence. Purity and molecular weight of molecules were analyzed by CE-SDS analyses in the presence and absence of a reducing agent. The Caliper LABCHIP® GXII system (Caliper lifescience) was used according to the manufacturer's instruction. 2ug sample is used for analyses. The aggregate content of antibody samples is analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C.

Affinity Determination
ProteOn Analysis

KD was measured by surface plasmon resonance using a PROTEON™ XPR36 machine (BioRad) at 25° C. with anti-human F(ab')2 fragment specific capture antibody (Jackson ImmunoResearch #109-005-006) immobilized by amine coupling on CM5 chips and subsequent capture of Fabs from bacterial supernatant or from purified Fab preparations. Briefly, carboxymethylated dextran biosensor chips (CM5, GE Healthcare) were activated with N-ethyl-N'-(3-dimethylaminopropyl)-carbodiimide hydrochloride (EDC) and N-hydroxysuccinimide (NHS) according to the supplier's instructions. Anti-human F(ab')2 fragment specific capture antibody was diluted with 10 mM sodium acetate, pH 5.0 at 50 µg/ml before injection at a flow rate of 10 µl/minute to achieve approximately up to 10.000 response units (RU) of coupled capture antibody. Following the injection of the capture antibody, 1 M ethanolamine is injected to block unreacted groups. For kinetics measurements, Fabs from bacterial supernatant or purified Fabs were injected at a flow rate of 10 ul/minute for 300s and a dissociation of 300s for capture baseline stabilization. Capture levels were in the range of 100-500 RU. In a subsequent step, human MCSP (D3 domain)-avi-his analyte was injected either as a single concentration or as a concentration series (depending of clone affinity in a range between 100 nM and 250 pM) diluted into HBS-EP+ (GE Healthcare, 10 mM HEPES, 150 mM NaCl, 3 mM EDTA, 0.05% Surfactant P20, pH 7.4) at 25° C. at a flow rate of 50 µl/min. The surface of the sensorchip was regenerated by injection of glycine pH 1.5 for 30s at 90 ul/min followed by injection of NaOH for 20s at the same flow rate. Association rates (kon) and dissociation rates (koff) were calculated using a simple one-to-one Langmuir binding model (PROTEON™ XPR36 Evaluation Software or Scrubber software (BioLogic)) by simultaneously fitting the association and dissociation sensorgrams. The equilibrium dissociation constant (KD) was calculated as the ratiokoff/kon. . This data was used to determine the comparative binding affinity of the affinity matured variants with the parental antibody. Table 4a shows the data generated from these assays.

G3, E10, C5 for the Light Chain, and D6, A7, B7, B8, C1 for the Heavy Chain were chosen for conversion into human IgG1 format. Since CDR1 and 2 of the light chain were randomized independent from CDR3, the obtained CDRs were combined during IgG conversion.

In the IgG format affinities were measured again to the human MCSP antigen in addition also to the cynomolgus homologue.

Method exactly as described for the Fab fragments, just purified IgG from mammalian production were used.

TABLE 4a

MCSP acuity matured clones: Proteon data

| Variant | Human MCSP Fab KD | Human MCSP IgG KD | Cyno MCSP IgG KD | Human MCSP IgG KD Comparative binding affinity - Fold increase over parent | Cyno MCSP IgG KD Comparative binding affinity - Fold increase over parent |
|---|---|---|---|---|---|
| | | Proteon generated affinity data | | | |
| Parental M4-3/ML2 | $5*10^{-9}$ | $2*10^{-9}$ | $2*10^{-9}$ | | |
| M4-3/ML2(G3) | $4*10^{-10}$ | $3*10^{-10}$ | $6*10^{-10}$ | 6.7 | 3.3 |
| M4-3/ML2 (E10) | $7*10^{-10}$ | $1*10^{-9}$ | $2*10^{-9}$ | 2.0 | 1.0 |
| M4-3/ML2 (E10/G3) | | $4*10^{-10}$ | $9*10^{-10}$ | 5.0 | 2.2 |
| M4-3/ML2 (C5) | $7*10^{-10}$ | $4*10^{-10}$ | $1*10^{-9}$ | 5.0 | 2.0 |
| M4-3/ML2 (C5/G3) | | $7*10^{-10}$ | $1*10^{-9}$ | 2.9 | 2.0 |
| M4-3(D6)/ML2 | $2*10^{-9}$ | $4*10^{-10}$ | $1*10^{-9}$ | 5.0 | 2.0 |
| M4-3(A7)/ML2 | $2*10^{-11}$ | $8*10^{-10}$ | $1*10^{-9}$ | 2.5 | 2.0 |
| M4-3(B7)/ML2 | | $5*10^{-10}$ | $7*10^{-10}$ | 4.0 | 2.9 |
| M4-3(B8)/ML2 | $3*10^{-10}$ | $9*10^{-10}$ | $1*10^{-9}$ | 2.2 | 2.0 |
| M4-3(C1)/ML2 | $6*10^{-10}$ | $9*10^{-10}$ | $8*10^{-10}$ | 2.2 | 2.5 |
| M4-3(C1)/ML2(G3) | | $7*10^{-11}$ | $2*10^{-10}$ | 28.6 | 10.0 |
| M4-3(C1)/ML2(E10) | | $5*10^{-10}$ | $6*10^{-10}$ | 4.0 | 3.3 |
| M4-3(A7)/ML2(G3) | | $7*10^{-11}$ | $2*10^{-10}$ | 28.6 | 10.0 |
| M4-3(A7)/ML2(E10) | | $3*10^{-10}$ | $7*10^{-10}$ | 6.7 | 2.9 |
| M4-3(C1)/ML2(C5) | | $2*10^{-10}$ | $3*10^{-10}$ | 10.0 | 6.7 |
| M4-3(A7)/ML2(C5) | | $7*10^{-11}$ | $2*10^{-10}$ | 28.6 | 10.0 |

Affinity Determination by Surface Plasmon Resonance (SPR) Using Biacore T200

Surface plasmon resonance (SPR) experiments to determine the affinity and the avidity of the affinity matured IgGs were performed on a BIACORE® T200 at 25° C. with HBS-EP as running buffer (0.01 M HEPES pH 7.4, 0.15 M NaCl, 3 mM EDTA, 0.005% Surfactant P20, Biacore, Freiburg/Germany).

For analyzing the avidity of the interaction of different antiMCSP IgGs to human and cynomolgus MCSP D3 direct coupling of around 9,500 resonance units (RU) of the anti-Penta His antibody (Qiagen) ("PentaHis" disclosed as SEQ ID NO: 208) was performed on a CM5 chip at pH 5.0 using the standard amine coupling kit (Biacore, Freiburg/Germany). Antigens were captured for 60 s at 30 nM with 10 µl/min respectively. IgGs were passed at a concentration of 0.0064-100 nM with a flowrate of 30 µl/min through the flow cells over 280 s. The dissociation was monitored for 180 s. Bulk refractive index differences were corrected for by subtracting the response obtained on reference flow cell. Here, the IgGs were flown over a surface with immobilized anti-Penta His antibody ("PentaHis" disclosed as SEQ ID NO: 208) but on which HBS-EP has been injected rather than human MCSP D3 or cynomolgus MCSP D3.

For affinity measurements IgGs were captured on a CM5 sensorchip surface with immobilized anti human Fc. Capture IgG was coupled to the sensorchip surface by direct immobilization of around 9,500 resonance units (RU) at pH 5.0 using the standard amine coupling kit (Biacore, Freiburg/Germany). IgGs are captured for 25 s at 10 nM with 30 µl/min. Human and cynomolgus MCSP D3 were passed at a concentration of 2-500 nM with a flowrate of 30 µl/min through the flow cells over 120 s. The dissociation is monitored for 60 s. Association and dissociation for concentration 166 and 500 nM was monitored for 1200 and 600 s respectively. Bulk refractive index differences were corrected for by subtracting the response obtained on reference flow cell. Here, the antigens were flown over a surface with immobilized anti-human Fc antibody but on which HBS-EP has been injected rather than anti MCSP IgGs.

Kinetic constants were derived using the BIACORE® T200 Evaluation Software (vAA, Biacore AB, Uppsala/Sweden), to fit rate equations for 1:1 Langmuir binding by numerical integration.

Higher affinity to human and cynomolgus MCSP D3 were confirmed by surface plasmon resonance measurements using BIACORE® T200. In addition avidity measurements showed an up to 3fold increase in bivalent binding (Table 4b).

TABLE 4b

Affinity and avidity of anti MCSP IgGs to human MCSP-D3 and cynomolgus MCSP D3.

| $K_D$ in nM | Human MCSP D3 | | Cynomolgus MCSP D3 | |
| --- | --- | --- | --- | --- |
| T = 25° C. | Affinity | Avidity | Affinity | Avidity |
| M4-3(C1) ML2(G3) | 1.8 | 0.0045 | 1.4 | 0.0038 |
| M4-3(C1) ML2(E10) | 4.6 | 0.0063 | 3.8 | 0.0044 |
| M4-3(C1) ML2(C5) | 1.8 | 0.0046 | 1.3 | 0.0044 |
| M4-3 ML2 (parental) | 8.6 | 0.0090 | 11.4 | 0.0123 |

Sequences

Legend: GA201=EGFR binder, 3F2=FAP binder, CH1A1A=CEA binder.
Protein Sequences

| SEQ ID NO. | Description | Sequence |
| --- | --- | --- |
| 1 | CDR1 VL MCSP | SASQGIRNYLN |
| 2 | CDR2 VL MCSP | YTSSLHS |
| 3 | CDR3 VL MCSP | QQYSKLPWT |
| 4 | CDR1 VH MCSP | GYSITSGYYWN |
| 5 | CDR2 VH MCSP | YITYDGSNNYNPSLKN |
| 6 | CDR3 VH MCSP | FDY |
| 7 | CDR1 VL CD3 $_{(V9)}$ | RASQDIRNYLN |
| 8 | CDR2 VL CD3 $_{(V9)}$ | YTSRLES |
| 9 | CDR3 VL CD3 $_{(V9)}$ | QQGNTLPWT |
| 10 | CDR1 VH CD3 $_{(V9)}$ | GYTMN |
| 11 | CDR2 VH CD3 $_{(V9)}$ | LINPYKGVSTYNQKFKD |
| 12 | CDR3 VH CD3 $_{(V9)}$ | SGYYGDSDWYFDV |
| 29 | CDR1 VL CD3 $_{(H2C)}$ | GSSTGAVTSGYYPN |
| 30 | CDR2 VL CD3 $_{(H2C)}$ | GTKFLAP |
| 31 | CDR3 VL CD3 $_{(H2C)}$ | ALWYSNRWV |
| 32 | CDR1 VH CD3 $_{(H2C)}$ | GFTFNKYAMN |
| 33 | CDR2 VH CD3 $_{(H2C)}$ | RIRSKYNNYATYYADSVKD |
| 34 | CDR3 VH CD3 $_{(H2C)}$ | HGNFGNSYISYWAY |
| 13 | VL MCSP | DIVLTQSPSSLSASLGDRVTISCSASQG IRNYLNWYQQRPDGTVKLLIYYTSSLHS GVPSRFSGSGSGTDYSLTISNLEPEDIA TYYCQQYSKLPWTFGGGTKLEIK |
| 14 | VH MCSP | EVQLQESGPGLVKPSQSLSLTCSVTGYS ITSGYYWNWIRQFPGNKLEWMGYITYDG SNNYNPSLKNRISITRDTSKNQFFLKLN SVTTEDTATYYCADFDYWGQGTTLTVSS |
| 15 | CL MCSP | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 16 | CH1 MCSP | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCD |
| 17 | LIGHT CHAIN MCSP | DIVLTQSPSSLSASLGDRVTISCSASQG IRNYLNWYQQRPDGTVKLLIYYTSSLHS GVPSRFSGSGSGTDYSLTISNLEPEDIA TYYCQQYSKLPWTFGGGTKLEIKRTVAA PSVFIFPPSDEQLKSGTASVVCLLNNFY PREAKVQWKVDNALQSGNSQESVTEQDS KDSTYSLSSTLTLSKADYEKHKVYACEV THQGLSSPVTKSFNRGEC |
| 18 | HEAVY CHAIN MCSP | EVQLQESGPGLVKPSQSLSLTCSVTGYS ITSGYYWNWIRQFPGNKLEWMGYITYDG SNNYNPSLKNRISITRDTSKNQFFLKLN SVTTEDTATYYCADFDYWGQGTTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCD |
| 19 | VL CD3 $_{(V9)}$ | DIQMTQSPSSLSASVGDRVTITCRASQD IRNYLNWYQQKPGKAPKLLIYYTSRLES GVPSRFSGSGSGTDYTLTISSLQPEDFA TYYCQQGNTLPWTFGQGTKVEIK |

| SEQ ID. NO. | Description | Sequence |
|---|---|---|
| 20 | VH CD3 $_{(I2V9)}$ | EVQLVESGGGLVQPGGSLRLSCAASGYS FTGYTMNWVRQAPGKGLEWVALINPYKG VSTYNQKFKDRFTISVDKSKNTAYLQMN SLRAEDTAVYYCARSGYYGDSDWYFDVW GQGTLVTVSS |
| 21 | CL CD3 $_{(I2V9)}$ | VAAPSVFIFPPSDEQLKSGTASVVCLLN NFYPREAKVQWKVDNALQSGNSQESVTE QDSKDSTYSLSSTLTLSKADYEKHKVYA CEVTHQGLSSPVTKSFNRGEC |
| 22 | CH CD3 $_{(I2V9)}$ | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSC |
| 23 | LIGHT CHAIN CD3 $_{(I2V9)}$ (VHCL) | EVQLVESGGGLVQPGGSLRLSCAASGYS FTGYTMNWVRQAPGKGLEWVALINPYKG VSTYNQKFKDRFTISVDKSKNTAYLQMN SLRAEDTAVYYCARSGYYGDSDWYFDVW GQGTLVTVSSVAAPSVFIFPPSDEQL KSGTASVVCLLNNFYPREAKVQWKVDNA LQSGNSQESVTEQDSKDSTYSLSSTLTL SKADYEKHKVYACEVTHQGLSSPVTKSF NRGEC |
| 24 | HEAVY CHAIN CD3 $_{(I2V9)}$ (VLCH1) | DIQMTQSPSSLSASVGDRVTITCRASQD IRNYLNWYQQKPGKAPKLLIYYTSRLES GVPSRFSGSGSGTDYTLTISSLQPEDFA TYYCQQGNTLPWTFGQGTKVEIKSSAST KGPSVFPLAPSSKSTSGGTAALGCLVKD YFPEPVTVSWNSGALTSGVHTFPAVLQS SGLYSLSSVVTVPSSSLGTQTYICNVNH KPSNTKVDKKVEPKSC |
| 35 | VL CD3 $_{(H2C)}$ | QTVVTQEPSLTVSPGGTVTLTCGSSTGA VTSGYYPNWVQQKPGQAPRGLIGGTKFL APGTPARFSGSLLGGKAALTLSGVQPED EAEYYCALWYSNRWVFGGGTKLTVL |
| 36 | VH CD3 $_{(H2C)}$ | EVQLVESGGGLVQPGGSLKLSCAASGFT FNKYAMNWVRQAPGKGLEWVARIRSKYN NYATYYADSVKDRFTISRDDSKNTAYLQ MNNLKTEDTAVYYCVRHGNFGNSYISYW AYWGQGTLVTVSS |
| 37 | CL CD3 $_{(H2C)}$ | VAAPSVFIFPPSDEQLKSGTASVVCLLN NFYPREAKVQWKVDNALQSGNSQESVTE QDSKDSTYSLSSTLTLSKADYEKHKVYA CEVTHQGLSSPVTKSFNRGEC |
| 38 | CH1 CD3 $_{(H2C)}$ | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSC |
| 39 | LIGHT CHAIN CD3 $_{(H2C)}$ (VHCL) | EVQLVESGGGLVQPGGSLKLSCAASGFT FNKYAMNWVRQAPGKGLEWVARIRSKYN NYATYYADSVKDRFTISRDDSKNTAYLQ MNNLKTEDTAVYYCVRHGNFGNSYISYW AYWGQGTLVTVSSASVAAPSVFIFPPSD EQLKSGTASVVCLLNNFYPREAKVQWKV DNALQSGNSQESVTEQDSKDSTYSLSST LTLSKADYEKHKVYACEVTHQGLSSPVT KSFNRGEC |
| 40 | HEAVY CHAIN CD3 $_{(H2C)}$ (VLCH1) | QTVVTQEPSLTVSPGGTVTLTCGSSTGA VTSGYYPNWVQQKPGQAPRGLIGGTKFL APGTPARFSGSLLGGKAALTLSGVQPED EAEYYCALWYSNRWVFGGGTKLTVLSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSC |
| 25 | FAB (MCSP)- XFAB (CD3 $_{(I2V9)}$) (VH-CH1-VL-CH1) | EVQLQESGPGLVKPSQSLSLTCSVTGYS ITSGYYWNWIRQPPGNKLEWMGYITYDG SNNYNPSLKNRISITRDTSKNQFFLKLN SVTTEDTATYYCADFDYWGQGTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDGGGGSGGG GSDIQMTQSPSSLSASVGDRVTITCRAS QDIRNYLNWYQQKPGKAPKLLIYYTSRL ESGVPSRFSGSGSGTDYTLTISSLQPED FATYYCQQGNTLPWTFGQGTKVEIKSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSC |
| 26 | FAB (MCSP)- FAB (MCSP)- XFAB (CD3 $_{(I2V9)}$) (VH-CH1-VH CH1-VL-CH1) | EVQLQESGPGLVKPSQSLSLTCSVTGYS ITSGYYWNWIRQPPGNKLEWMGYITYDG SNNYNPSLKNRISITRDTSKNQFFLKLN SVTTEDTATYYCADFDYWGQGTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDGGGGSGGG GSEVQLQESGPGLVKPSQSLSLTCSVTG YSITSGYYWNWIRQPPGNKLEWMGYITY DGSNNYNPSLKNRISITRDTSKNQFFLK LNSVTTEDTATYYCADFDYWGQGTTLTV SSASTKGPSVFPLAPSSKSTSGGTAALG CLVKDYFPEPVTVSWNSGALTSGVHTFP AVLQSSGLYSLSSVVTVPSSSLGTQTYI CNVNHKPSNTKVDKKVEPKSCDGGGGSG GGGSDIQMTQSPSSLSASVGDRVTITCR ASQDIRNYLNWYQQKPGKAPKLLIYYTS RLESGVPSRFSGSGSGTDYTLTISSLQP EDFATYYCQQGNTLPWTFGQGTKVEIKS SASTKGPSVFPLAPSSKSTSGGTAALGC LVKDYFPEPVTVSWNSGALTSGVHTFPA VLQSSGLYSLSSVVTVPSSSLGTQTYIC NVNHKPSNTKVDKKVEPKSC |
| 27 | FAB (MCSP)- XFAB (CD3 $_{(I2V9)}$)- FAB (MCSP) (VH-CH1-VL-CH1-VH-CH1) | EVQLQESGPGLVKPSQSLSLTCSVTGYS ITSGYYWNWIRQPPGNKLEWMGYITYDG SNNYNPSLKNRISITRDTSKNQFFLKLN SVTTEDTATYYCADFDYWGQGTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDGGGGSGGG GSDIQMTQSPSSLSASVGDRVTITCRAS QDIRNYLNWYQQKPGKAPKLLIYYTSRL ESGVPSRFSGSGSGTDYTLTISSLQPED FATYYCQQGNTLPWTFGQGTKVEIKSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSCGGGGSGGGGS EVQLQESGPGLVKPSQSLSLTCSVTGYS ITSGYYWNWIRQPPGNKLEWMGYITYDG SNNYNPSLKNRISITRDTSKNQFFLKLN SVTTEDTATYYCADFDYWGQGTTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSC |
| 28 | LINKER 1 | GGGGSGGGGS |
| 41 | FAB (MCSP)- FAB (MCSP)- XFAB (CD3 $_{(H2C)}$) (VH-CH1-VH-CH1-VL-CH1) | EVQLQESGPGLVKPSQSLSLTCSVTGYS ITSGYYWNWIRQPPGNKLEWMGYITYDG SNNYNPSLKNRISITRDTSKNQFFLKLN SVTTEDTATYYCADFDYWGQGTTLTVSS ASTKGPSVFPLAPSSKSTSGGTAALGCL |

| SEQ ID. NO. | Description | Sequence |
|---|---|---|
| | | VKDYFPEPVTVSWNSGALTSGVHTFPAV LQSSGLYSLSSVVTVPSSSLGTQTYICN VNHKPSNTKVDKKVEPKSCDGGGGSGGG GSEVQLQESGPGLVKPSQSLSLTCSVTG YSITSGYYWNWIRQFPGNKLEWMGYITY DGSNNYNPSLKNRISITRDTSKNQFFLK LNSVTTEDTATYYCADFDYWGQGTTLTV SSASTKGPSVFPLAPSSKSTSGGTAALG CLVKDYFPEPVTVSWNSGALTSGVHTFP AVLQSSGLYSLSSVVTVPSSSLGTQTYI CNVNHKPSNTKVDKKVEPKSCDGGGGSG GGGSQTVVTQEPSLTVSPGGTVTLTCGS STGAVTSGYYPNWVQQKPGQAPRGLIGG TKFLAPGTPARFSGSLLGGKAALTLSGV QPEDEAEYYCALWYSNRWVFGGGTKLTV LSSASTKGPSVFPLAPSSKSTSGGTAAL GCLVKDYFPEPVTVSWNSGALTSGVHTF PAVLQSSGLYSLSSVVTVPSSSLGTQTY ICNVNHKPSNTKVDKKVEPKSC |
| 42 | Murine LIGHT CHAIN CD3$_{(2C11)}$ (VHCL) | EVQLVESGGGLVQPGKSLKLSCEASGFT FSGYGMHWVRQAPGRGLESVAYITSSSI NIKYADAVKGRFTVSRDNAKNLLFLQMN ILKSEDTAMYYCARFDWDKNYWGQGTMV TVSSASVAAPSVFIFPPSDEQLKSGTAS VVCLLNNFYPREAKVQWKVDNALQSGNS QESVTEQDSKDSTYSLSSTLTLSKADYE KHKVYACEVTHQGLSSPVTKSFNRGEC |
| 43 | Murine XFAB (CD3$_{(2C11)}$)- FAB (MCSP)- FAB (MCSP) (VL-CH1-VH- CH1-VH-CH1) | DIQMTQSPSSLPASLGDRVTINCQASQD ISNYLNWYQQKPGKAPKLLIYYTNKLAD GVPSRFSGSGSGRDSSFTISSLESEDIG SYYCQQYYNYPWTFGPGTKLEIKSSAST KGPSVFPLAPSSKSTSGGTAALGCLVKD YFPEPVTVSWNSGALTSGVHTFPAVLQS SGLYSLSSVVTVPSSSLGTQTYICNVNH KPSNTKVDKKVEPKSCGGGGSGGGGSEV QLQESGPGLVKPSQSLSLTCSVTGYSIT SGYYWNWIRQFPGNKLEWMGYITYDGSN NYNPSLKNRISITRDTSKNQFFLKLNSV TTEDTATYYCADFDYWGQGTTLTVSSAS TKGPSVFPLAPSSKSTSGGTAALGCLVK DYFPEPVTVSWNSGALTSGVHTFPAVLQ SSGLYSLSSVVTVPSSSLGTQTYICNVN HKPSNTKVDKKVEPKSCDGGGGSGGGGS EVQLQESGPGLVKPSQSLSLTCSVTGYS ITSGYYWNWIRQFPGNKLEWMGYITYDG SNNYNPSLKNRISITRDTSKNQFFLKLN SVTTEDTATYYCADFDYWGQGTTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCD |
| 68 | GA201 CDR1 VH | DYKIH |
| 69 | GA201 CDR2 VH | YFNPNSGYSTYAQKFQG |
| 70 | GA201 CDR3 VH | LSPGGYYVMDA |
| 71 | GA201 CDR1 VL | RASQGINNYLN |
| 72 | GA201 CDR2 VL | NTNNLQT |
| 73 | GA201 CDR3 VL | LQHNSFPT |
| 74 | GA201 VH | QVQLVQSGAEVKKPGSSVKVSCKASGFT FTDYKIHWVRQAPGQGLEWMGYFNPNSG YSTYAQKFQGRVTITADKSTSTAYMELS SLRSEDTAVYYCARLSPGGYYVMDAWGQ GTTVTVSS |
| 75 | GA201 VL | DIQMTQSPSSLSASVGDRVTITCRASQG INNYLNWYQQKPGKAPKRLIYNTNNLQT GVPSRFSGSGSGTEFTLTISSLQPEDFA TYYCLQHNSFPTFGQGTKLEIK |
| 76 | 3F2 CDR1 VH | SYAMS |
| 77 | 3F2 CDR2 VH | AISGSGGSTYYADSVK |
| 78 | 3F2 CDR3 VH | YCAKGWFG |
| 79 | 3F2 CDR1 VL | RASQSVTSSYL |
| 80 | 3F2 CDR2 VL | NVGSRRA |
| 81 | 3F2 CDR3 VL | CQQGIMLPP |
| 82 | 3F2 VH | EVQLLESGGGLVQPGGSLRLSCAASGFT FSSYAMSWVRQAPGKGLEWVSAISGSGG STYYADSVKGRFTISRDNSKNTLYLQMN SLRAEDTAVYYCAKGWFGGFNYWGQGTL VTVSS |
| 83 | 3F2 VL | EIVLTQSPGTLSLSPGERATLSCRASQS VTSSYLAWYQQKPGQAPRLLINVGSRRA TGIPDRFSGSGSGTDFTLTISRLEPEDF AVYYCQQGIMLPPTFGQGTKVEIK |
| 84 | CH1A1A CDR1 VH | EFGMN |
| 85 | CH1A1A CDR2 VH | WINTKTGEATYVEEFKG |
| 86 | CH1A1A CDR3 VH | WDFAYYVEAMDY |
| 87 | CH1A1A CDR1 VL | KASAAVGTYVA |
| 88 | CH1A1A CDR2 VL | SASYRKR |
| 89 | CH1A1A CDR3 VL | HQYYTYPLFT |
| 90 | CH1A1A VH | QVQLVQSGAEVKKPGASVKVSCKASGYT FTEFGMNWVRQAPGQGLEWMGWINTKTG EATYVEEFKGRVTFTTDTSTSTAYMELR SLRSDDTAVYYCARWDFAYYVEAMDYWG QGTTVTVSS |
| 91 | CH1A1A VL | DIQMTQSPSSLSASVGDRVTITCKASAA VGTYVAWYQQKPGKAPKLLIYSASYRKR GVPSRFSGSGSGTDFTLTISSLQPEDFA TYYCHQYYTYPLFTFGQGTKLEIK |
| 92 | Anti-CD33 CDR1 VH | GYTITDSNIH |
| 93 | Anti-CD33 CDR2 VH | YIYPYNGGTDYNQ |
| 94 | Anti-CD33 CDR3 VH | GNPWLAY |
| 95 | Anti-CD33 CDR1 VL | RASESLDNYGIRFLT |
| 96 | Anti-CD33 CDR1 VL | AASNQGS |
| 97 | Anti-CD33 CDR1 VL | QQTKEVPWS |
| 98 | Anti-CD33 VH | EVQLVQSGAEVKKPGSSVKVSCKASGYT ITDSNIHWVRQAPGQSLEWIGYIYPYNG GTDYNQKFKNRATLTVDNPTNTAYMELS SLRSEDTAFYYCVNGNPWLAYWGQGTLV TVSS |
| 99 | Anti-CD33 VL | DIQLTQSPSTLSASVGDRVTITCRASES LDNYGIRFLTWFQQKPGKAPKLLMYAAS NQGSGVPSRFSGSGSGTEFTLTISSLQP DDFATYYCQQTKEVPWSFGQGTKVEVK |
| 100 | Light Chain antiCD33 | DIQMTQSPSSLSASVGDRVTITCRASES VDNYGISFMNWFQQKPGKAPKLLIYAAS NQGSGVPSRFSGSGSGTDFTLTISSLQP |

| SEQ ID. NO. | Description | Sequence |
|---|---|---|
|  |  | DDFATYYCQQSKEVPWTFGQGTKVEIKR TVAAPSVFIFPPSDEQLKSGTASVVCLL NNFYPREAKVQWKVDNALQSGNSQESVT EQDSKDSTYSLSSTLTLSKADYEKHKVY ACEVTHQGLSSPVTKSFNRGEC |
| 101 | Light Chain CD3 (v9) (VH-CL) | EVQLVESGGGLVQPGGSLRLSCAASGYS FTGYTMNWVRQAPGKGLEWVALINPYKG VSTYNQKFKDRFTISVDKSKNTAYLQMN SLRAEDTAVYYCARSGYYGDSDWYFDVW GQGTLVTVSSASVAAPSVFIFPPSDEQL KSGTASVVCLLNNFYPREAKVQWKVDNA LQSGNSQESVTEQDSKDSTYSLSSTLTL SKADYEKHKVYACEVTHQGLSSPVTKSF NRGEC |
| 102 | Fab (CD33)- XFab (CD3 (v9)) (VH-CH1-VL- CH1) | QVQLVQSGAEVKKPGSSVKVSCKASGYT FTDYNMHWVRQAPGQGLGEWIGYIYPYNG GTGYNQKFKSKATITADESTNTAYMELS SLRSEDTAVYYCARGRPAMDYWGQGTLV TVSSASTKGPSVFPLAPSSKSTSGGTAA LGCLVKDYFPEPVTVSWNSGALTSGVHT FPAVLQSSGLYSLSSVVTVPSSSLGTQT YICNVNHKPSNTKVDKKVEPKSCDGGGG SGGGGSDIQMTQSPSSLSASVGDRVTIT CRASQDIRNYLNWYQQKPGKAPKLLIYY TSRLESGVPSRFSGSGSGTDYTLTISSL QPEDFATYYCQQGNTLPWTFGQGTKVEI KSSASTKGPSVFPLAPSSKSTSGGTAAL GCLVKDYFPEPVTVSWNSGALTSGVHTF PAVL |
| 145 | Linker 2 | EPKSCGGGGSGGGGS |
| 146 | Linker 3 | EPKSCDGGGGSGGGGS |
| 147 | Linker 4 | GGGGSGGGGSGGGGSGGGGSGGGGSGGG GSGGG |
| 148 | Linker 5 | SGGGGSGGGSEGGGSEGGGSEGGGSEGGG SGGGGSG |
| 149 | (scFv)2 antiMCSP/anti huCD3e (MCSP(VL- VH)- CD3 (v9) (VH-VL)) | DIVLTQSPSSLSASLGDRVTISCSASQG IRNYLNWYQQRPDGTVKLLIYYTSSLHS GVPSRFSGSGSGTDYSLTISNLEPEDIA TYYCQQYSKLPWTFGGGTKLEIKGGGGS GGGGSGGGGSEVQLVESGGGLVQPSQSL SLTCSVTGYSITSGYYWNWIRQFPGNKL EWMGYITYDGSNNYNPSLKNRISITRDT SKNQFFLKLNSVTTEDTATYYCADFDYW GQGTTLTVSSGGGGSEVQLVESGGGLVQ PGGSLRLSCAASGYSFTGYTMNWVRQAP GKGLEWVALINPYKGVSTYNQKFKDRFT ISVDKSKNTAYLQMNSLRAEDTAVYYCA RSGYYGDSDWYFDVWGQGTLVTVSSVEG GSGGSGGSGGSGGVDDIQMTQSPSSLSA SVGDRVTITCRASQDIRNYLNWYQQKPG KAPKLLIYYTSRLESGVPSRFSGSGSGT DYTLTISSLQPEDFATYYCQQGNTLPWT FGQGTKVEIKHHHHHH |
| 151 | Light Chain antiCD33 (Myelotarg) | DIQLTQSPSTLSASVGDRVTITCRASES LDNYGIRFLTWFQQKPGKAPKLLMYAAS NQGSGVPSRFSGSGSGTEFTLTISSLQP DDFATYYCQQTKEVPWSFGQGTKVEVKR TVAAPSVFIFPPSDEQLKSGTASVVCLL NNFYPREAKVQWKVDNALQSGNSQESVT EQDSKDSTYSLSSTLTLSKADYEKHKVY ACEVTHQGLSSPVTKSFNRGEC |
| 152 | Light Chain CD3 (v9) (VL-CH1) | DIQMTQSPSSLSASVGDRVTITCRASQD IRNYLNWYQQKPGKAPKLLIYYTSRLES GVPSRFSGSGSGTDYTLTISSLQPEDFA TYYCQQGNTLPWTFGQGTKVEIKSSAST KGPSVFPLAPSSKSTSGGTAALGCLVKD |
| 153 | Fab (CD33(Myelotarg)- XFab (CD3 (v9)) (VH-CH1-VH- CL) | YFPEPVTVSWNSGALTSGVHTFPAVLQS SGLYSLSSVVTVPSSSLGTQTYICNVNH KPSNTKVDKKVEPKSC EVQLVQSGAEVKKPGSSVKVSCKASGYT ITDSNIHWVRQAPGQSLEWIGYIYPYNG GTDYNQKFKNRATLTVDNPTNTAYMELS SLRSEDTAFYYCVNGNPWLAYWGQGTLV TVSSASTKGPSVFPLAPSSKSTSGGTAA LGCLVKDYFPEPVTVSWNSGALTSGVHT FPAVLQSSGLYSLSSVVTVPSSSLGTQT YICNVNHKPSNTKVDKKVEPKSCDGGGG SGGGGSEVQLVESGGGLVQPGGSLRSC AASGYSFTGYTMNWVRQAPGKGLEWVAL INPYKGVSTYNQKFKDRFTISVDKSKNT AYLQMNSLRAEDTAVYYCARSGYYGDSD WYFDVWGQGTLVTVSSASVAAPSVFIFPP PSDEQLKSGTASVVCLLNNFYPREAKVQ WKVDNALQSGNSQESVTEQDSKDSTYSL SSTLTLSKADYEKHKVYACEVTHQGLSS PVTKSFNRGEC |
| 157 | CD3 (CH2527) VL | QAVVTQESALTTSPGETVTLTCRSSTGA VTTSNYANWVQEKPDHLFTGLIGGTNKR APGVPARFSGSLIGDKAALTITGAQTED EAIYFCALWYSNLWVFGGGTKLTVL |
| 158 | CD3 (CH2527) VH | EVQLVESGGGLVQPGKSLKLSCAASGFT FNTYAMNWVRQAPGKGLEWVARIRSKYN NYATYYADSVKDRFTISRDDSQSILYLQ MNNLKTEDTAMYYCVRHGNFGNSYVSWF AYWGQGTLVTVSA |
| 159 | CEA (CH1A1A (98/99)) VH | QVQLVQSGAEVKKPGASVKVSCKASGYT FTEFGMNWVRQAPGQGLEWMGWINTKTG EATYVEEFKGRVTFTTDTSTSTAYMELR SLRSDDTAVYYCARWDFAYYVEAMDYWG QGTTVTVSS |
| 160 | CEA (CH1A1A (98/99)) VL | DIQMTQSPSSLSASVGDRVTITCKASAA VGTYVAWYQQKPGKAPKLLIYSASYRKR GVPSRFSGSGSGTDFTLTISSLQPEDFA TYYCHQYYTYPLFTFGQGTKLEIK |
| 161 | MCSP (M4-3 ML2) | VHQVQLQESGPGLVKPSQTLSLTCTVSG GSITSGYYWNWIRQHPGKGLEWIGYITY DGSNNYNPSLKSRVTISRDTSKNQFSLK LSSVTAADTAVYYCADFDYWGQGTLVTV SS |
| 162 | MCSP (M4-3 ML2) | VLDIQMTQSPSSLSASVGDRVTITCRAS QGIRNYLNWYQQKPGKAPKLLIYYTSSL HSGVPSRFSGSGSGTDFTLTISSLQPED FATYYCQQYSKLPWTFGQGTKVEIK |
| 163 | VLCL(MCSP) - (G4S)2- VHCL(CD3 v9) | EVQLVESGGGLVQPGGSLRLSCAASGYS FTGYTMNWVRQAPGKGLEWVALINPYKG VSTYNQKFKDRFTISVDKSKNTAYLQMN SLRAEDTAVYYCARSGYYGDSDWYFDVW GQGTLVTVSSASVAAPSVFIFPPSDEQL KSGTASVVCLLNNFYPREAKVQWKVDNA LQSGNSQESVTEQDSKDSTYSLSSTLTL SKADYEKHKVYACEVTHQGLSSPVTKSF NRGECDGGGGSGGGGSDIVLTQSPSSLS ASLGDRVTISCSASQGIRNYLNWYQQRP DGTVKLLIYYTSSLHSGVPSRFSGSGSG TDYSLTISNLEPEDIATYYCQQYSKLPW TFGGGTKLEIKRTVAAPSVFIFPPSDEQ LKSGTASVVCLLNNFYPREAKVQWKVDN ALQSGNSQESVTEQDSKDSTYSLSSTLT LSKADYEKHKVYACEVTHQGLSSPVTKS FNRGEC |

| SEQ ID. NO. | Description | Sequence |
|---|---|---|
| 164 | VHCH1(MCSP)-(G4S)2-VLCH1(CD3_v9) | EVQLQESGPGLVKPSQSLSLTCSVTGYS ITSGYYWNWIRQFPGNKLEWMGYITYDG SNNYNPSLKNRISITRDTSKNQFFLKLN SVTTEDTATYYCADFDYWGQGTTLTVSS ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDGGGGSGGG GSDIQMTQSPSSLSASVGDRVTITCRAS QDIRNYLNWYQQKPGKAPKLLIYYTSRL ESGVPSRFSGSGSGTDYTLTISSLQPED FATYYCQQGNTLPWTFGQGTKVEIKSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSC |

Protein Sequences: Humanised CD3 Binders and Affinity Matured MCSP Binders

| | CD3 $_{CH2527}$ | | SEQ ID NO. |
|---|---|---|---|
| Heavy chain "CD3 $_{CH2527\ (VH\_3-23(12))}$" | | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCVRHGNFGNSYVSWFAYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSDG SFFLYSKLTVDKSRWQQGNVFSCSVMHEALHNHYTQKSLSL SPGK | 167 |
| Light chain "CD3 $_{CH2527\ (VL\_7-46(13))}$" | | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLGQPKAAPSVTLFPP SSEELQANKATLVCLISDFYPGAVTVAWKADSSPVKAGVET TTPSKQSNNKYAASSYLSLTPEQWKSHRSYSCQVTHEGSTV EKTVAPTECS | 168 |
| VH "CD3 $_{CH2527\ (VH\_3-23(12))}$" | | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCVRHGNFGNSYVSWFAYWGQGTLVTV SS | 169 |
| VH CDR H1 "CD3 $_{CH2527\ (VH\_3-23(12))}$" | | TYAMN | 170 |
| VH CDR H2 "CD3 $_{CH2527\ (VH\_3-23(12))}$" | | RIRSKYNNYATYYADSVKG | 171 |
| VH CDR H3 "CD3 $_{CH2527\ (VH\_3-23(12))}$" | | HGNFGNSYVSWFAY | 172 |
| VL "CD3 $_{CH2527\ (VL\_7-46(13))}$" | | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVL | 173 |
| VL CDR L1 "CD3 $_{CH2527\ (VL\_7-46(13))}$" | | GSSTGAVTTSNYAN | 174 |
| VL CDR L2 "CD3 $_{CH2527\ (VL\_7-46(13))}$" | | GTNKRAP | 175 |
| VL CDR L3 "CD3 $_{CH2527\ (VL\_7-46(13))}$" | | ALWYSNLWV | 176 |

| | MCSP $_{M4-3(C1)ML2(G3)}$ | | SEQ ID NO |
|---|---|---|---|
| Heavy chain ,,MCSP $_{M4-3(C1)}$" | | QVQLQESGPGLVKPSQTLSLTCTVSGGSITSGYYWNWIRQH PGKGLEWIGYITFDGSNNYNPSLKSRVTISRDTSKNQFSLK LSSVTAADTAVYYCADFDYWGQGTLVTVSSASTKGPSVFPL APSSKSTSGGTAALGCLVKDYFPEPVTVSWNSGALTSGVHT FPAVLQSSGLYSLSSVVTVPSSSLGTQTYICNVNHKPSNTK VDKKVEPKSCDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVYTLPPSRDELTKNQVSLTCLVKGFYP SDIAVEWESNGQPENNYKTTPPVLDSDGSFFLYSKLTVDKS RWQQGNVFSCSVMHEALHNHYTQKSLSLSPGK | 177 |

| | | |
|---|---|---|
| Light chain "MCSP_ML2(G3)" | DIQMTQSPSSLSASVGDRVTITCRASQGIRNYLNWYQQKPG KAPKLLIYYTSSLHSGVPSRFSGSGSGTDYTLTISSLQPED FATYYCQQYSALPWTFGQGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC | 178 |
| VH "MCSP_M4-3(C1)" | QVQLQESGPGLVKPSQTLSLTCTVSGGSITSGYYWNWIRQH PGKGLEWIGYITFDGSNNYNPSLKSRVTISRDTSKNQFSLK LSSVTAADTAVYYCADFDYWGQGTLVTVSS | 179 |
| VH CDR H1 "MCSP_M4-3(C1)" | SGYYWN | 180 |
| VH CDR H2 "MCSP_M4-3(C1)" | YITFDGSNNYNPSLKS | 181 |
| VH CDR H3 "MCSP_M4-3(C1)" | FDY | 6 |
| VL "MCSP_ML2(G3)" | DIQMTQSPSSLSASVGDRVTITCRASQGIRNYLNWYQQKPG KAPKLLIYYTSSLHSGVPSRFSGSGSGTDYTLTISSLQPED FATYYCQQYSALPWTFGQGTKVEIK | 182 |
| VL CDR L1 "MCSP_ML2(G3)" | RASQGIRNYLN | 183 |
| VL CDR L2 "MCSP_ML2(G3)" | YTSSLHS | 2 |
| VL CDR L3 "MCSP_ML2(G3)" | QQYSALPWT | 184 |

| CD3 VL_7-43(11)/VH_3-23(12) | | SEQ ID NO. |
|---|---|---|
| VH "CD3_CH2527(VH_3-23(12))" | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCVRHGNFGNSYVSWFAYWGQGTLVTV SS | 169 |
| VH CDR H1 "CD3_CH2527(VH_3-23(12))" | TYAMN | 170 |
| VH CDR H2 "CD3_CH2527(VH_3-23(12))" | RIRSKYNNYATYYADSVKG | 171 |
| VH CDR H3 "CD3_CH2527(VH_3-23(12))" | HGNFGNSYVSWFAY | 172 |
| VL "CD3_CH2527(VL_7-43(11))" | QTVVTQEPSLTVSPGGTVTLTCGSSTGAVTTSNYANWVQQK PGQAPRGLIGGTNKRAPGTPARFSGSLLGGKAALTLSGVQP EDEAEYYCALWYSNLWVFGGGTKLTVLSS | 185 |
| VL CDR L1 "CD3_CH2527(VL_7-43(11))" | GSSTGAVTTSNYAN | 174 |
| VL CDR L2 "CD3_CH2527(VL_7-43(11))" | GTNKRAP | 175 |
| VL CDR L3 "CD3_CH2527(VL_7-43(11))" | ALWYSNLWV | 176 |

| CD3 VL_7-43(11)/VHcomboA49SV93A | | |
|---|---|---|
| VH "CD3_CH2527(VHcomboA49SV93A)" | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCARHGNFGNSYVSWFAYWGQGTLVTV SS | 186 |
| VH CDR H1 "CD3_CH2527(VHcomboA49SV93A)" | TYAMN | 170 |
| VH CDR H2 "CD3_CH2527(VHcomboA49SV93A)" | RIRSKYNNYATYYADSVKG | 171 |
| VH CDR H3 "CD3_CH2527(VHcomboA49SV93A)" | HGNFGNSYVSWFAY | 172 |

| | | |
|---|---|---|
| VL "CD3 CH2527(VL_7-43(11))" | QTVVTQEPSLTVSPGGTVTLTCGSSTGAVTTSNYANWVQQK PGQAPRGLIGGTNKRAPGTPARFSGSLLGKAALTLSGVQP EDEAEYYCALWYSNLWVFGGGTKLTVLSS | 185 |
| VL CDR L1 "CD3 CH2527(VL_7-43(11))" | GSSTGAVTTSNYAN | 174 |
| VL CDR L2 "CD3 CH2527(VL_7-43(11))" | GTNKRAP | 175 |
| VL CDR L3 "CD3 CH2527(VL_7-43(11))" | ALWYSNLWV | 176 |
| CD3 VL_7-46(13)/VHcomboA49SV93A | | |
| VH ,,CD3 CH2527(VHcomboA49SV93A)" | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCARHGNFGNSYVSWFAYWGQGTLVTV SS | 186 |
| VH CDR H1 ,,CD3 CH2527(VHcomboA49SV93A)" | TYAMN | 170 |
| VH CDR H2 ,,CD3 CH2527(VHcomboA49SV93A)" | RIRSKYNNYATYYADSVKG | 171 |
| VH CDR H3 ,,CD3 CH2527(VHcomboA49SV93A)" | HGNFGNSYVSWFAY | 172 |
| VL "CD3 CH2527(VL_7-46(13))" | QAVVTQEPSLTVSPGGTVTLTCGSSTGAVTTSNYANWVQEK PGQAFRGLIGGTNKRAPGTPARFSGSLLGKAALTLSGAQP EDEAEYYCALWYSNLWVFGGGTKLTVL | 173 |
| VL CDR L1 "CD3 CH2527(VL_7-46(13))" | GSSTGAVTTSNYAN | 174 |
| VL CDR L2 "CD3 CH2527(VL_7-46(13))" | GTNKRAP | 175 |
| VL CDR L3 "CD3 CH2527(VL_7-46(13))" | ALWYSNLWV | 176 |
| CD3 VL_7-43(11)/VHcomboA49SV93AR94K | | |
| VH ,,CD3 CH2527 (VHcomboA49SV93AR94K)" | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCAKHGNFGNSYVSWFAYWGQGTLVTV SS | 187 |
| VH CDR H1 ,,CD3 CH2527 (VHcomboA49SV93AR94K)" | TYAMN | 170 |
| VH CDR H2 ,,CD3 CH2527 (VHcomboA49SV93AR94K)" | RIRSKYNNYATYYADSVKG | 171 |
| VH CDR H3 ,,CD3 CH2527 (VHcomboA49SV93AR94K)" | HGNFGNSYVSWFAY | 172 |
| VL "CD3 CH2527(VL_7-43(11))" | QTVVTQEPSLTVSPGGTVTLTCGSSTGAVTTSNYANWVQQK PGQAPRGLIGGTNKRAPGTPARFSGSLLGKAALTLSGVQP EDEAEYYCALWYSNLWVFGGGTKLTVLSS | 185 |
| VL CDR L1 "CD3 CH2527(VL_7-43(11))" | GSSTGAVTTSNYAN | 174 |
| VL CDR L2 "CD3 CH2527(VL_7-43(11))" | GTNKRAP | 175 |
| VL CDR L3 "CD3 CH2527(VL_7-43(11))" | ALWYSNLWV | 176 |

-continued

| CD3 $_{VL\_7-46(13)}$ / VHcomboA95SV93AR94K | | |
|---|---|---|
| VH ,,CD3 $_{CH2527}$ $_{(VHcomboA49SV93AR94K)}$" | EVQLLESGGGLVQPGGSLRLSCAASGFTFSTYAMNWVRQAP GKGLEWVSRIRSKYNNYATYYADSVKGRFTISRDDSKNTLY LQMNSLRAEDTAVYYCAKHGNFGNSYVSWFAYWGQGTLVTV SS | 187 |
| VH CDR H1 ,,CD3 $_{CH2527}$ $_{(VHcomboA49SV93AR94K)}$" | TYAMN | 170 |
| VH CDR H2 ,,CD3 $_{CH2527}$ $_{(VHcomboA49SV93AR94K)}$" | RIRSKYNNYATYYADSVKG | 171 |
| VH CDR H3 ,,CD3 $_{CH2527}$ $_{(VHcomboA49SV93AR94K)}$" | HGNFGNSYVSWFAY | 172 |
| VL "CD3 $_{CH2527(VL\_7-46(13))}$" | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVL | 173 |
| VL CDR L1 "CD3 $_{CH2527(VL\_7-46(13))}$" | GSSTGAVTTSNYAN | 174 |
| VL CDR L2 "CD3 $_{CH2527(VL\_7-46(13))}$" | GTNKRAP | 175 |
| VL CDR L3 "CD3 $_{CH2527(VL\_7-46(13))}$" | ALWYSNLWV | 176 |

| MCSP | | SEQ ID NO |
|---|---|---|
| VH ,,MCSP $_{M4-3(D6)}$" | QVQLQESGPGLVKPSQTLSLTCTVSGGSITSGYYWNWIRQH PGKGLEWIGYITFDGKNNYNPSLKSRVTISRDTSKNQFSLK LSSVTAADTAVYYCADFDYWGQGTLVTVSS | 188 |
| VH CDR H1 ,,MCSP $_{M4-3(D6)}$" | SGYYWN | 180 |
| VH CDR H2 ,,MCSP $_{M4-3(D6)}$" | ITFDGKNNYNPSLKS | 189 |
| VH CDR H3 ,,MCSP $_{M4-3(D6)}$" | FDY | 6 |
| VH ,,MCSP $_{M4-3(A7)}$" | QVQLQESGPGLVKPSQTLSLTCTVSGGSITDGYYWNWIRQH PGKGLEWIGYITFDGRNNYNPSLKSRVTISRDTSKNQFSLK LSSVTAADTAVYYCADFDYWGQGTLVTVSS | 190 |
| VH CDR H1 ,,MCSP $_{M4-3(A7)}$" | DGYYWN | 191 |
| VH CDR H2 ,,MCSP $_{M4-3(A7)}$" | ITFDGRNNYNPSLKS | 192 |
| VH CDR H3 ,,MCSP $_{M4-3(A7)}$" | FDY | 6 |
| VH ,,MCSP $_{M4-3(B7)}$" | QVQLQESGPGLVKPSQTLSLTCTVSGGSITSGYYWNWIRQH PGKGLEWIGYITFDGINNYNPSLKSRVTISRDTSKNQFSLK LSSVTAADTAVYYCADFDYWGQGTLVTVSS | 193 |
| VH CDR H1 ,,MCSP $_{M4-3(B7)}$" | SGYYWN | 180 |
| VH CDR H2 ,,"MCSP $_{M4-3(B7)}$" | ITFDGINNYNPSLKS | 194 |
| VH CDR H3 ,,MCSP $_{M4-3(B7)}$" | FDY | 6 |
| VH ,,MCSP $_{M4-3(B8)}$" | QVQLQESGPGLVKPSQTLSLTCTVSGGSITSGYYWNWIRQH PGKGLEWIGYITFDGRNNYNPSLKSRVTISRDTSKNQFSLK LSSVTAADTAVYYCADFDYWGQGTLVTVSS | 195 |
| VH CDR H1 ,,MCSP $_{M4-3(B8)}$" | SGYYWN | 180 |

| Description | Sequence | SEQ ID NO. |
|---|---|---|
| VH CDR H2 "MCSP M4-3(B8)" | ITFDGRNNYNPSLKS | 192 |
| VH CDR H3 "MCSP M4-3(B8)" | FDY | 6 |
| Parental VH MCSP M4-3 | QVQLQESGPGLVKPSQTLSLTCTVSGGSITSGYYWNWIRQH PGKGLEWIGYITYDGSNNYNPSLKSRVTISRDTSKNQFSLK LSSVTAADTAVYYCADFDYWGQGTLVTVSS | 161 |
| VL "MCSP ML2(E10)" | DIQMTQSPSSLSASVGDRVTITCRASYGIRGYLNWYQQKPG KAPKLLIYYTSSLHSGVPSRFSGSGSGTDFTLTISSLQPED FATYHCQQYSKLPWTFGQGTKVEIK | 196 |
| VL CDR L1 "MCSP ML2(E10)" | RASYGIRGYLN | 197 |
| VL CDR L2 "MCSP ML2(E10)" | YTSSLHS | 2 |
| VL CDR L3 "MCSP ML2(E10)" | QQYSKLPWT | 3 |
| VL "MCSP ML2(E10-G3)" | DIQMTQSPSSLSASVGDRVTITCRASYGIRGYLNWYQQKPG KAPKLLIYYTSSLHSGVPSRFSGSGSGTDFTLTISSLQPED FATYHCQQYSALPWTFGQGTKVEIK | 198 |
| VL CDR L1 "MCSP ML2(E10-G3)" | RASYGIRGYLN | 197 |
| VL CDR L2 "MCSP ML2(E10-G3)" | YTSSLHS | 2 |
| VL CDR L3 "MCSP ML2(E10-G3)" | QQYSKLPWT | 3 |
| VL "MCSP ML2(C5)" | DIQMTQSPSSLSASVGDRVTITCRASRGIREYLNWYQQKPG KAPKLLIYYTGSLHSGVPSRFSGSGSGTDFTLTISSLQPED FATYYCQQYSELPWTFGQGTKVEIK | 199 |
| VL CDR L1 "MCSP ML2(C5)" | RASRGIREYLN | 200 |
| VL CDR L2 "MCSP ML2(C5)" | YTGSLHS | 201 |
| VL CDR L3 "MCSP ML2(C5)" | QQYSELPWT | 202 |
| VL "MCSP ML2(C5-G3)" | DIQMTQSPSSLSASVGDRVTITCRASRGIREYLNWYQQKPG KAPKLLIYYTGSLHSGVPSRFSGSGSGTDFTLTISSLQPED FATYYCQQYSALPWTFGQGTKVEIK | 203 |
| VL CDR L1 "MCSP ML2(C5-G3)" | RASRGIREYLN | 200 |
| VL CDR L2 "MCSP ML2(C5-G3)" | YTGSLHS | 201 |
| VL CDR L3 "MCSP ML2(C5-G3)" | QQYSKLPWT | 3 |
| Parental VL MCSP ML2 | DIQMTQSPSSLSASVGDRVTITCRASQGIRNYLNWYQQKPG KAPKLLIYYTSSLHSGVPSRFSGSGSGTDFTLTISSLQPED FATYYCQQYSKLPWTFGQGTKVEIK | 162 |

DNA Sequences

| SEQ ID NO. | Description | Sequence |
|---|---|---|
| 44 | VL MCSP | GATATTGTGCTCACACAGTCTCCATCCTCCC TGTCTGCCTCTCTGGGAGACAGAGTCACCAT CAGTTGCAGTGCAAGTCAGGGCATTAGAAAT TATTTAAACTGGTATCAGCAGAGACCAGATG GAACTGTTAAACTCCTGATCTATTACACATC AAGTTTACACTCAGGAGTCCCATCAAGGTTC AGTGGCAGTGGGTCTGGGACAGATTATTCTC |

| SEQ ID. NO. | Description | Sequence |
|---|---|---|
| | | TCACCATCAGCAACCTGGAACCTGAAGATAT TGCCACTTACTATTGTCAGCAGTATAGTAAG CTTCCTTGGACGTTCGGTGGAGGCACCAAGC TGGAAATCAAA |
| 45 | VH MCSP | GAGGTGCAGCTGCAGGAATCTGGGCCCTGGCC TGGTCAAGCCAAGCCAGAGTCTGAGCCTGAC CTGCAGCGTGACCGGCTACAGCATTACCAGC GGCTACTACTGGAACTGGATTCGGCAGTTCC CCGGCAATAAGCTGGAATGGATGGGCTACAT CACCTACGACGGCAGCAACAACTACAACCCC AGCCTGAAGAACCGGATCAGCATCACCCGGG ACACCAGCAAGAACCAGTTCTTCCTGAAGCT GAACAGCGTGACCACCGAGGACACCGCCACA TACTATTGCGCCGACTTCGACTACTGGGGCC AGGGCACCACCCTGACCGTGTCCAGC |
| 46 | CL MCSP | CGTACGGTTGGCTGCACCATCTGTCTTCATCT TCCCGCCATCTGATGAGCAGTTGAAATCTGG AACTGCCTCTGTTGTGTGCCTGCTGAATAAC TTCTATCCCAGAGAGGCCAAAGTACAGTGGA AGGTGGATAACGCCCTCCAATCGGGTAACTC CCAGGAGAGTGTCACAGAGCAGGACAGCAAG GACAGCACCTACAGCCTCAGCAGCACCCTGA CGCTGAGCAAAGCAGACTACGAGAAACACAA AGTCTACGCCTGCGAAGTCACCCATCAGGGC CTGAGCTCGCCCGTCACAAAGAGCTTCAACA GGGGAGAGTGTTAG |
| 47 | CH1 MCSP | GCCAGCACAAAGGGCCCTAGCGTGTTCCCTC TGGCCCCCAGCAGCAAGAGCACAAGCGGCGG AACAGCCGCCCTGGGCTGCCTCGTGAAGGAC TACTTCCCCGAGCCCGTGACAGTGTCTTGGA ACAGCGGAGCCCTGACAAGCGGCGTGCACAC CTTCCCTGCCGTGCTGCAGAGCAGCGGCCTG TACTCCCTGAGCAGCGTGGTCACCGTGCCTA GCAGCAGCCTGGGCACCCAGACCTACATCTG CAACGTGAACCACAAGCCCAGCAACACCAAA GTGGACAAGAAGGTGGAGCCCAAGAGCTGTG AT |
| 48 | LIGHT CHAIN MCSP | ATGGACATGAGGGTCCCCGCTCAGCTCCTGG GCCTCCTGCTGCTCTGGTTCCCAGGTGCCAG GTGTGATATTGTGCTCACACAGTCTCCATCC TCCCTGTCTGCCTCTCGGGAGACAGAGTCA CCATCAGTTGCAGTGCAAGTCAGGGCATTAG AAATTATTTAAACTGGTACAGCAGAAGACCA GATGGAACTGTTAAACTCCTGATCTATTACA CATCAAGTTTACACTCAGGAGTCCCATCAAG GTTCAGTGGCAGTGGGTCTGGGACAGATTAT TCTCTCACCATCAGCAACCTGGAACCTGAAG ATATTGCCACTTACTATTGTCAGCAGTATAG TAAGCTTCCTTGGACGTTCGGTGGAGGCACC AAGCTGGAAATCAAACGTACGGTTGGCTGCAC CATCTGTCTTCATCTTCCCGCCATCTGATGA GCAGTTGAAATCTGGAACTGCCTCTGTTGTG TGCCTGCTGAATAACTTCTATCCCAGAGAGG CCAAAGTACAGTGGAAGGTGGATAACGCCCT CCAATCGGGTAACTCCCAGGAGAGTGTCACA GAGCAGGACAGCAAGGACAGCACCTACAGCC TCAGCAGCACCCTGACGCTGAGCAAAGCAGA CTACGAGAAACACAAAGTCTACGCCTGCGAA GTCACCCATCAGGGCCTGAGCTCGCCCGTCA CAAAGAGCTTCAACAGGGGAGAGTGTTAG |
| 49 | HEAVY CHAIN MCSP | ATGGGATGGAGCTGTATCATCCTCTTCTTGG TAGCAACAGCTACCGGTGTGCATTCGGAGGT GCAGCTGCAGGAATCTGGGCCCTGGCCTGGTC AAGCCAAGCCAGAGTCTGAGCCTGACCTGCA GCGTGACCGGCTACAGCATTACCAGCGGCTA CTACTGGAACTGGATTCGGCAGTTCCCCGGC AATAAGCTGGAATGGATGGGCTACATCACCT ACGACGGCAGCAACAACTACAACCCCAGCCT GAAGAACCGGATCAGCATCACCCGGGACACC AGCAAGAACCAGTTCTTCCTGAAGCTGAACA |

| SEQ ID. NO. | Description | Sequence |
|---|---|---|
| | | GCGTGACCACCGAGGACACCGCCACATACTA TTGCGCCGACTTCGACTACTGGGGCCAGGGC ACCACCCTGACCGTGTCCAGCGCCAGCACAA AGGGCCCTAGCGTGTTCCCTCTGGCCCCCAG CAGCAAGAGCACAAGCGGCGGAACAGCCGCC CTGGGCTGCCTCGTGAAGGACTACTTCCCCG AGCCCGTGACAGTGTCTTGGAACAGCGGAGC CCTGACAAGCGGCGTGCACACCTTCCCTGCC GTGCTGCAGAGCAGCGGCCTGTACTCCCTGA GCAGCGTGGTCACCGTGCCTAGCAGCAGCCT GGGCACCCAGACCTACATCTGCAACGTGAAC CACAAGCCCAGCAACACCAAAGTGGACAAGA AGGTGGAGCCCAAGAGCTGTGAT |
| 50 | VL CD3 (V9) | GACATCCAGATGACCCAGAGCCCCTCTAGCC TGAGCGCCAGCGTGGGCGACAGAGTGACCAT CACCTGTCGGGCCAGCCAGGACATCAGAAAC TACCTGAACTGGTATCAGCAGAAGCCCGGCA AGGCCCCCAAGCTGCTGATCTACTACACCTC TAGACTGGAAAGCGGCGTGCCCAGCCGGTTT AGCGGCAGCGGCTCCGGCACCGACTACACCC TGACCATCAGCAGCCTGCAGCCCGAGGACTT CGCCACCTACTACTGCCAGCAGGGCAACACA CTCCCCTGGACCTTCGGCCAGGGCACCAAGG TGGAGATCAAGTCCAGC |
| 51 | VH CD3 (V9) | GAGGTGCAGCTGGTCGAGAGCGGAGGCGGCC TGGTGCAGCCTGGCGGCAGCCTGAGACTGAG CTGCGCCGCCAGCGGCTACAGCTTCACCGGC TACACCATGAACTGGGTCCGGCAGGCACCTG GCAAGGGACTGGAATGGGTGGCCCTGATCAA CCCCTACAAGGGCGTGAGCACCTACAACCAG AAGTTCAAGGACCGGTTCACCATCAGCGTGG ACAAGAGCAAGAACACCGCCTATCTGCAGAT GAACAGCCTGCGGGCCGAGGACACCGCCGTG TACTACTGCGCCAGAAGCGGCTACTACGGCG ACAGCGACTGGTACTTCGACGTGTGGGGCCA GGGCACCCTCGTGACCGTGTCTAGC |
| 52 | CL CD3 (V9) | GTGGCTGCACCATCTGTCTTCATCTTCCCGC CATCTGATGAGCAGTTGAAATCTGGAACTGC CTCTGTTGTGTGCCTGCTGAATAACTTCTAT CCCAGAGAGGCCAAAGTACAGTGGAAGGTGG ATAACGCCCTCCAATCGGGTAACTCCCAGGA GAGTGTCACAGAGCAGGACAGCAAGGACAGC ACCTACAGCCTCAGCAGCACCCTGACGCTGA GCAAAGCAGACTACGAGAAACACAAAGTCTA CGCCTGCGAAGTCACCCATCAGGGCCTGAGC TCGCCCGTCACAAAGAGCTTCAACAGGGGAG AGTGTTGA |
| 53 | CH CD3 (V9) | ACCAAGGGCCCCTCCGTGTTCCCCCTGGCCC CCAGCAGCAAGAGCACCAGCGGCGGCACAGC CGCCCTCGGCTGCCTGGTCAAGGACTACTTC CCCGAGCCCGTGACCGTGTCCTGGAACAGCG GAGCCCTGACCTCCGGCGTGCACACCTTCCC CGCCGTGCTGCAGAGCAGCGGCCTGTACAGC CTGTCCAGCGTGGTCACCGTGCCCTCCAGCA GCCTGGGCACCCAGACCTACATCTGCAACGT GAACCACAAGCCCAGCAATACCAAGGTGGAC AAGAAGGTGGAGCCCAAGAGCTGCTGA |
| 54 | LIGHT CHAIN CD3 (V9) (VHCL) | ATGGGATGGAGCTGTATCATCCTCTTCTTGG TAGCAACAGCTACCGGTGTGCATTCCGAGGT GCAGCTGGTCGAGAGCGGAGGCGGCCTGGTG CAGCCTGGCGGCAGCCTGAGACTGAGCTGCG CCGCCAGCGGCTACAGCTTCACCGGCTACAC CATGAACTGGGTCCGGCAGGCACCTGGCAAG GGACTGGAATGGGTGGCCCTGATCAACCCCT ACAAGGGCGTGAGCACCTACAACCAGAAGTT CAAGGACCGGTTCACCATCAGCGTGGACAAG AGCAAGAACACCGCCTATCTGCAGATGAACA GCCTGCGGGCCGAGGACACCGCCGTGTACTA CTGCGCCAGAAGCGGCTACTACGGCGACAGC GACTGGTACTTCGACGTGTGGGGCCAGGGCA |

| SEQ ID. NO. | Description | Sequence |
|---|---|---|
| | | CCCTCGTGACCGTGTCTAGCGCTAGCGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTGA |
| 55 | HEAVY CHAIN CD3 $_{(V9)}$ (VLCH1) | GACATCCAGATGACCCAGAGCCCCTCTAGCCTGAGCGCCAGCGTGGGCGACAGAGTGACCATCACCTGTCGGGCCAGCCAGGACATCAGAAACTACCTGAACTGGTATCAGCAGAAGCCCGGCAAGGCCCCCAAGCTGCTGATCTACTACACCTCTAGACTGGAAAGCGGCGTGCCCAGCCGGTTTAGCGGCAGCGGCTCCGGCACCGACTACACCCTGACCATCAGCAGCCTGCAGCCCGAGGACTTCGCCACCTACTACTGCCAGCAGGGCAACACACTCCCCTGGACCTTCGGCCAGGGCACCAAGGTGGAGATCAAGTCCAGCGCTAGCACCAAGGGCCCCTCCGTGTTCCCCCTGGCCCCCAGCAGCAAGAGCACCAGCGGCGCACAGCCGCCCTCGGCTGCCTGGTCAAGGACTACTTCCCCGAGCCCGTGACCGTGTCCTGGAACAGCGGAGCCCTGACCTCCGGCGTGCACACCTTCCCCGCCGTGCTGCAGAGCAGCGGCCTGTACAGCCTGTCCAGCGTGGTCACCGTGCCCTCCAGCAGCCTGGGCACCCAGACCTACATCTGCAACGTGAACCACAAGCCCAGCAATACCAAGGTGGACAAGAAGGTGGAGCCCAAGAGCTGCTGA |
| 56 | VL CD3 $_{(H2C)}$ | CAGACCGTGGTGACACAGGAACCCAGCCTGACCGTCTCCCCTGGCGGCACCGTGACCCTGACCTGTGGAAGCAGCACAGGCGCCGTGACCAGCGGCTACTACCCCAACTGGGTGCAGCAGAAGCCCGGCCAGGCCCCTAGAGGACTGATCGGCGGCACCAAGTTTCTGGCCCCTGGCACCCCCGCCAGATTCTCTGGCTCTCTGCTGGGCGGCAAGGCCGCCCTGACACTGTCTGGCGTGCAGCCTGAGGACGAGGCCGAGTACTACTGCGCCCTGTGGTACAGCAACAGATGGGTGTTCGGCGGAGGCACCAAGCTGACCGTGCTGAGCAGC |
| 57 | VH CD3 $_{(H2C)}$ | GAGGTGCAGCTGGTGGAAAGCGGCGGAGGACTGGTGCAGCCTGGCGGAAGCCTGAAGCTGTCTTGCGCCGCCAGCGGCTTCACCTTCAACAAATACGCCATGAACTGGGTGCGCCAGGCCCCTGGCAAGGGACTGGAATGGGTGGCCCGGATCAGAAGCAAGTACAACAACTACGCCACCTACTACGCCGACAGCGTGAAGGACCGGTTCACCATCAGCCGGGACGACAGCAAGAACACCGCCTACCTGCAGATGAACAACCTGAAAACCGAGGACACCGCCGTGTACTACTGCGTGCGGCACGGCAACTTCGGCAACAGCTACATCAGCTACTGGGCCTACTGGGGACAGGGCACCCTGGTGACAGTGTCCAGC |
| 58 | CL CD3 $_{(H2C)}$ | GTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTGA |
| 59 | CH1 CD3 $_{(H2C)}$ | ACCAAGGGCCCCTCCGTGTTCCCCCTGGCCCCCAGCAGCAAGAGCACCAGCGGCGGCACAGCCGCCCTCGGCTGCCTGGTCAAGGACTACTTCCCCGAGCCCGTGACCGTGTCCTGGAACAGCGGAGCCCTGACCTCCGGCGTGCACACCTTCCCCGCCGTGCTGCAGAGCAGCGGCCTGTACAGCCTGTCCAGCGTGGTCACCGTGCCCTCCAGCAGCCTGGGCACCCAGACCTACATCTGCAACGTGAACCACAAGCCCAGCAATACCAAGGTGGACAAGAAGGTGGAGCCCAAGAGCTGCTGA |
| 60 | LIGHT CHAIN CD3 $_{(H2C)}$ (VHCL) | ATGGGATGGAGCTGTATCATCCTCTTCTTGGTAGCAACAGCTACCGGTGTGCATTCCGAGGTGCAGCTGGTGGAAAGCGGCGGAGGACTGGTGCAGCCTGGCGGAAGCCTGAAGCTGTCTTGCGCCGCCAGCGGCTTCACCTTCAACAAATACGCCATGAACTGGGTGCGCCAGGCCCCTGGCAAGGGACTGGAATGGGTGGCCCGGATCAGAAGCAAGTACAACAACTACGCCACCTACTACGCCGACAGCGTGAAGGACCGGTTCACCATCAGCCGGGACGACAGCAAGAACACCGCCTACCTGCAGATGAACAACCTGAAAACCGAGGACACCGCCGTGTACTACTGCGTGCGGCACGGCAACTTCGGCAACAGCTACATCAGCTACTGGGCCTACTGGGGACAGGGCACCCTGGTGACAGTGTCCAGCGCTAGCGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTGA |
| 61 | HEAVY CHAIN CD3 $_{(H2C)}$ (VLCH1) | CAGACCGTGGTGACACAGGAACCCAGCCTGACCGTCTCCCCTGGCGGCACCGTGACCCTGACCTGTGGAAGCAGCACAGGCGCCGTGACCAGCGGCTACTACCCCAACTGGGTGCAGCAGAAGCCCGGCCAGGCCCCTAGAGGACTGATCGGCGGCACCAAGTTTCTGGCCCCTGGCACCCCCGCCAGATTCTCTGGCTCTCTGCTGGGCGGCAAGGCCGCCCTGACACTGTCTGGCGTGCAGCCTGAGGACGAGGCCGAGTACTACTGCGCCCTGTGGTACAGCAACAGATGGGTGTTCGGCGGAGGCACCAAGCTGACCGTGCTGAGCAGCGCTAGCACCAAGGGCCCCTCCGTGTTCCCCCTGGCCCCCAGCAGCAAGAGCACCAGCGGCGGCACAGCCGCCCTCGGCTGCCTGGTCAAGGACTACTTCCCCGAGCCCGTGACCGTGTCCTGGAACAGCGGAGCCCTGACCTCCGGCGTGCACACCTTCCCCGCCGTGCTGCAGAGCAGCGGCCTGTACAGCCTGTCCAGCGTGGTCACCGTGCCCTCCAGCAGCCTGGGCACCCAGACCTACATCTGCAACGTGAACCACAAGCCCAGCAATACCAAGGTGGACAAGAAGGTGGAGCCCAAGAGCTGCTGA |
| 62 | FAB (MCSP)-XFAB (CD3) $_{(V9)}$ (VH-CH1-VL-CH1) | ATGGGATGGAGCTGTATCATCCTCTTCTTGGTAGCAACAGCTACCGGTGTGCATTCGGAGGTGCAGCTGCAGGAAAGCGGCCCTGGCCTGGTGAAACCCAGCCAGACCCTGAGCCTGACCTGCAGCGTGACCGGCTACAGCATCACCAGCGGCTACTACTGGAACTGGATCAGACAGTTCCCCGGCAACAAGCTGGAATGGATGGGCTACATCACCTACGACGGCAGCAACAACTACAACCCCAGCCTGAAGAACAGAATCAGCATCACCCGGGACACCAGCAAGAACCAGTTCTTCCTGAAGCTGAACAGCGTGACCACCGAGGACACCGCCACCTACTACTGCGCCCGACTTCGACTACTGGGGCCAGGGCACCACCCTGACCGTGTCCTCCGCTAGCACCAGGGACCCAGCGTGTTCCCCCTGGCACCCAGCAGCAAGAGCACATCTGGCGGAACAGCCGCT |

| SEQ ID. NO. | Description | Sequence |
|---|---|---|
| | | CTGGGCTGTCTGGTGAAAGACTACTTCCCCG AGCCCGTGACCGTGTCTTGGAACTCTGGCGC CCTGACCAGCGGCGTGCACACCTTTCCAGCC GTGCTGCAGAGCAGCGGCCTGTACTCCCTGA GCAGCGTGGTGACAGTGCCCAGCAGCAGCCT GGGAACCCAGACCTACATCTGCAACGTGAAC CACAAGCCCAGCAACACCAAGGTGGACAAGA AGGTGGAACCCAAGAGCTGCGATGGCGGAGG AGGCTCCGGAGGCGGAGGCTCTGATATCCAG ATGACCCAGAGCCCCAGCTCTCTGAGCGCCA GCGTGGGCGACAGAGTGACCATCACCTGTCG GGCCAGCCAGGACATCAGAAACTACCTGAAC TGGTATCAGCAGAAGCCCGGCAAGGCCCCCA AGCTGCTGATCTACTACACCAGCAGACTGGA AAGCGGCGTGCCCTCCAGATTTTCCGGCAGC GGCTCCGGCACCGACTACACCCTGACCATCA GCAGCCTGCAGCCCGAGGATTTCGCCACATA TTACTGCCAGCAGGGCAATACCCTGCCCTGG ACCTTCGGACAGGGCACAAAAGTGGAAATCA AG |
| 63 | FAB (MCSP)- FAB (MCSP)- XFAB (CD3)$_{(T9)}$ (VH-CH1-VH- CH1-VL-CH1) | ATGGGATGGAGCTGTATCATCCTCTTCTTGG TAGCAACAGCTACCGGTGTGCATTCGGAGGT GCAGCTGCAGGAATCTGGCCCTGGCCTGGTC AAGCCAAGCCAGAGTCTGAGCCTGACCTGCA GCGTGACCGGCTACAGCATTACCAGCGGCTA CTACTGGAACTGGATTCGGCAGTTCCCCGGC AATAAGCTGGAATGGATGGGCTACATCACCT ACGACGGCAGCAACAACTACAACCCCAGCCT GAAGAACCGGATCAGCATCACCCGGGACACC AGCAAGAACCAGTTCTTCCTGAAGCTGAACA GCGTGACCACCGAGGACACCGCCACCTACTA TTGCGCCGACTTCGACTACTGGGGCCAGGGC ACCACCCTGACCGTGTCCAGCGCCAGCACAA AGGGCCCTAGCGTGTTCCCTCTGGCCCCCAG CAGCAAGAGCACAAGCGGCGGAACAGCCGCC CTGGGCTGCCTCGTGAAGGACTACTTCCCCG AGCCCGTGACAGTGTCTTGGAACAGCGGAGC CCTGACAAGCGGCGTGCACACCTTCCCTGCC GTGCTGCAGAGCAGCGGCCTGTACTCCCTGA GCAGCGTGGTCACCGTGCCTAGCAGCAGCCT GGGCACCCAGACCTACATCTGCAACGTGAAC CACAAGCCCAGCAACACCAAGGTGGACAAGA AGGTGGAGCCCAAGAGCTGTGATGGCGGAGG AGGGTCCGGAGGCGGTGGCTCCGAGGTGCAG CTGCAGGAATCTGGCCCTGGCCTGGTCAAGC CAAGCCAGAGTCTGAGCCTGACCTGCAGCGT GACCGGCTACAGCATTACCAGCGGCTACTAC TGGAACTGGATTCGGCAGTTCCCCGGCAATA AGCTGGAATGGATGGGCTACATCACCTACGA CGGCAGCAACAACTACAACCCCAGCCTGAAG AACCGGATCAGCATCACCCGGGACACCAGC AAGAACCAGTTCTTCCTGAAGCTGAACAGCG TGACCACCGAGGACACCGCCACATACTATTG CGCCGACTTCGACTACTGGGGCCAGGGCACC ACCCTGACCGTGTCCAGCGCCAGCACAAAGG GCCCTAGCGTGTTCCCTCTGGCCCCCAGCAG CAAGAGCACAAGCGGCGGAACAGCCGCCCTG GGCTGCCTCGTGAAGGACTACTTCCCCGAGC CCGTGACAGTGTCTTGGAACAGCGGAGCCCT GACAAGCGGCGTGCACACCTTCCCTGCCGTG CTGCAGAGCAGCGGCCTGTACTCCCTGAGCA GCGTGGTCACCGTGCCTAGCAGCAGCCTGGG CACCCAGACCTACATCTGCAACGTGAACCAC AAGCCCAGCAACACCAAAGTGGACAAGAAGG TGGAGCCCAAGAGCTGTGATGGCGGAGGAGG GTCCGGCGGCGTGGATCCGACATCCAGATG ACCCAGAGCCCCTCTAGCCTGAGCGCCAGCG TGGGCGACAGAGTGACCATCACCTGTCGGGC CAGCCAGGACATCAGAAACTACCTGAACTGG TATCAGCAGAAGCCGGCAAGGCCCCCAAGC TGCTGATCTACTACACCTAGACTGGAAAG CGGCGTGCCCAGCCGGTTTAGCGGCAGCGGC TCCGGCACCGACTACACCCTGACCATCAGCA GCCTGCAGCCCGAGGACTTCGCCACCTACTA |
| | | CTGCCAGCAGGGCAACACACTCCCCTGGACC TTCGGCCAGGGCACCAAGGTGGAGATCAAGT CCAGCGCTAGCACCAAGGGCCCCTCCGTGTT CCCCCTGGCCCCCAGCAGCAAGAGCACCAGC GGCGGCACAGCCGCCCTCGGCTGCCTGGTCA AGGACTACTTCCCCGAGCCCGTGACCGTGTC CTGGAACAGCGGAGCCCTGACCTCCGGCGTG CACACCTTCCCCGCCGTGCTGCAGAGCAGCG GCCTGTACAGCCTGTCCAGCGTGGTCACCGT GCCCTCCAGCAGCCTGGGCACCCAGACCTAC ATCTGCAACGTGAACCACAAGCCCAGCAATA CCAAGGTGGACAAGAAGGTGGAGCCCAAGAG CTGCTGA |
| 64 | FAB (MCSP)- XFAB (CD3$_{(T9)}$)- FAB (MCSP) (VH-CH1-VL- CH1-VH- CH1) | ATGGGATGGAGCTGTATCATCCTCTTCTTGG TAGCAACAGCTACCGGTGTGCATTCGGAGGT GCAGCTGCAGGAAAGCGGCCCTGGCCTGGTG AAACCCAGCCAGAGCCTGAGCCTGACCTGCA GCGTGACCGGCTACAGCATCACCAGCGGCTA CTACTGGAACTGGATCAGACAGTTCCCCGGC AACAAGCTGGAATGGATGGGCTACATCACCT ACGACGGCAGCAACAACTACAACCCCAGCCT GAAGAACAGAATCAGCATCACCCGGGACACC AGCAAGAACCAGTTCTTCCTGAAGCTGAACA GCGTGACCACCGAGGACACCGCCACCTACTA CTGCGCCGACTTCGACTACTGGGGCCAGGGC ACCACCCTGACCGTGTCCTCCGCTAGCACCA AGGGACCCAGCGTGTTCCCCCTGGCACCCAG CAGCAAGAGCACATCTGGCGGAACAGCCGCT CTGGGCTGTCTGGTGAAAGACTACTTCCCCG AGCCCGTGACCGTGTCTTGGAACTCTGGCGC CCTGACCAGCGGCGTGCACACCTTTCCAGCC GTGCTGCAGAGCAGCGGCCTGTACTCCCTGA GCAGCGTGGTGACAGTGCCCAGCAGCAGCCT GGGAACCCAGACCTACATCTGCAACGTGAAC CACAAGCCCAGCAACACCAAGGTGGACAAGA AGGTGGAACCCAAGAGCTGCGATGGCGGAGG AGGCTCCGGAGGCGGAGGCTCTGATATCCAG ATGACCCAGAGCCCCAGCTCTCTGAGCGCCA GCGTGGGCGACAGAGTGACCATCACCTGTCG GGCCAGCCAGGACATCAGAAACTACCTGAAC TGGTATCAGCAGAAGCCCGGCAAGGCCCCCA AGCTGCTGATCTACTACACCAGCAGACTGGA AAGCGGCGTGCCCTCCAGATTTTCCGGCAGC GGCTCCGGCACCGACTACACCCTGACCATCA GCAGCCTGCAGCCCGAGGATTTCGCCACATA TTACTGCCAGCAGGGCAATACCCTGCCCTGG ACCTTCGGACAGGGCACAAAAGTGGAAATCA AGAGCAGCGCTTCCACCAAAGGCCCTTCCGT GTTTCCTCTGGCTCCTAGCTCCAAGTCCACC TCTGGAGGCACCGCTGCTCTCGGATGCCTCG TGAAGGATTATTTTCCTGAGCCTGTGACAGT GTCCTGGAATAGCGGAGCACTGACCTCTGGA GTGCATACTTTCCCCGCTGTGCTGCAGTCCT CTGGACTGTACAGCCTGAGCAGCGTGGTGAC AGTGCCCAGCAGCAGCCTGGGCACCCAGACC TACATCTGCAACGTGAACCACAAGCCCAGCA ACACCAAGGTGGACAAGAAGGTGGAACCCAA GTCTTGTGCGGCAGGCGGATCCGGCGGAGGG GGATCTGAGGTGCAGCTGCAGGAAAGCGGCC CTGGCCTGGTGAAACCCAGCCAGAGCCTGAG CCTGACCTGCAGCGTGACCGGCTACAGCATC ACCAGCGGCTACTACTGGAACTGGATCAGAC AGTTCCCCGGCAACAAGCTGGAATGGATGGG CTACATCACCTACGACGGCAGCAACAACTAC AACCCCAGCCTGAAGAACAGAATCAGCATCA CCCGGGACACCAGCAAGAACCAGTTCTTCCT GAAGCTGAACAGCGTGACCACCGAGGACACC GCCACCTACTACTGCGCCGACTTCGACTACT GGGGCCAGGGCACCACCCTGACCGTGTCCTC CGCCTCTACCAAGGGCCCCAGCGTGTTCCCC CTGGCACCCAGCAGCAAGAGCACATCTGGCG GAACAGCCGCTCTGGGCTGTCTGGTGAAAGA CTACTTCCCCGAGCCCGTGACCGTGTCTTGG AACTCTGGCGCCCTGACCAGCGGCGTGCACA |

| SEQ ID. NO. | Description | Sequence |
|---|---|---|
| | | CCTTTCCAGCCGTGCTGCAGAGCAGCGGCCT GTACTCCCTGTCCTCCGTGGTCACCGTGCCC TCTAGCTCCCTGGGAACACAGACATATATCT GTAATGTCAATCACAAGCCTTCCAACACCAA AGTCGATAAGAAAGTCGAGCCCAAGAGCTGC TGA |
| 65 | FAB (MCSP)- FAB (MCSP)- XFAB (CD3$_{(H2C)}$) (VH-CH1-VH- CH1-VL-CH1) | ATGGGATGGAGCTGTATCATCCTCTTCTTGG TAGCAACAGCTACCGGTGTGCATTCGGAGGT GCAGCTGCAGGAATCTGGCCCTGGCCTGGTC AAGCCAAGCCAGAGTCTGAGCCTGACCTGCA GCGTGACCGGCTACAGCATTACCAGCGGCTA CTACTGGAACTGGATTCGGCAGTTCCCCGGC AATAAGCTGGAATGGATGGGCTACATCACCT ACGACGGCAGCAACAACTACAACCCCAGCCT GAAGAACCGGATCAGCATCACCCGGGACACC AGCAAGAACCAGTTCTTCCTGAAGCTGAACA GCGTGACCACCGAGGACACCGCCACATACTA TTGCGCCGACTTCGACTACTGGGGCCAGGGC ACCACCCTGACCGTGTCCAGCGCCAGCACAA AGGGCCCTAGCGTGTTCCCTCTGGCCCCCAG CAGCAAGAGCACAAGCGGCGGAACAGCCGCC CTGGGCTGCCTCGTGAAGGACTACTTCCCCG AGCCCGTGACAGTGTCTTGGAACAGCGGAGC CCTGACAAGCGGCGTGCACACCTTCCCTGCC GTGCTGCAGAGCAGCGGCCTGTACTCCCTGA GCAGCGTGGTCACCGTGCCTAGCAGCAGCCT GGGCACCCAGACCTACATCTGCAACGTGAAC CACAAGCCCAGCAACACCAAAGTGGACAAGA AGGTGGAGCCCAAGAGCTGTGATGGCGGAGG AGGGTCCGGAGGCGGTGGCTCCGAGGTGCAG CTGCAGGAATCTGGCCCTGGCCTGGTCAAGC CAAGCCAGAGTCTGAGCCTGACCTGCAGCGT GACCGGCTACAGCATTACCAGCGGCTACTAC TGGAACTGGATTCGGCAGTTCCCCGGCAATA AGCTGGAATGGATGGGCTACATCACCTACGA CGGCAGCAACAACTACAACCCCAGCCTGAAG AACCGGATCAGCATCACCCGGGACACCAGCA AGAACCAGTTCTTCCTGAAGCTGAACAGCGT GACCACCGAGGACACCGCCACATACTATTGC GCCGACTTCGACTACTGGGGCCAGGGCACCA CCCTGACCGTGTCCAGCGCCAGCACAAAGGG CCCTAGCGTGTTCCCTCTGGCCCCCAGCAGC AAGAGCACAAGCGGCGGAACAGCCGCCCTGG GCTGCCTCGTGAAGGACTACTTCCCCGAGCC CGTGACAGTGTCTTGGAACAGCGGAGCCCTG ACAAGCGGCGTGCACACCTTCCCTGCCGTGC TGCAGAGCAGCGGCCTGTACTCCCTGAGCAG CGTGGTCACCGTGCCTAGCAGCAGCCTGGGC ACCCAGACCTACATCTGCAACGTGAACCACA AGCCCAGCAACACCAAAGTGGACAAGAAGGT GGAGCCCAAGAGCTGTGATGGCGGAGGAGGG TCCGGCGGCGGTGGATCCCAGACCGTGGTGA CACAGGAACCCAGCCTGACCGTCTCCCCTGG CGGCACCGTGACCCTGACCTGTGGAAGCAGC ACAGGCGCCGTGACCAGCGGCTACTACCCCA ACTGGGTGCAGCAGAAGCCCGGCCAGGCCCC TAGAGGACTGATCGGCGGCACCAAGTTTCTG GCCCCTGGCACCCCCGCCAGATTCTCTGGCT CTCTGCTGGGCGGCAAGGCCGCCCTGACACT GTCTGGCGTGCAGCCTGAGGACGAGGCCGAG TACTACTGCGCCCTGTGGTACAGCAACAGAT GGGTGTTCGGCGGAGGCACCAAGCTGACCGT GCTGAGCAGCGCTAGCACCAAGGGCCCCTCC GTGTTCCCCCTGGCCCCCAGCAGCAAGAGCA CCAGCGGCGGCACAGCCGCCCTCGGCTGCCT GGTCAAGGACTACTTCCCCGAGCCCGTGACC GTGTCCTGGAACAGCGGAGCCCTGACCTCCG GCGTGCACACCTTCCCCGCCGTGCTGCAGAG CAGCGGCCTGTACAGCCTGTCCAGCGTGGTC ACCGTGCCCTCCAGCAGCCTGGGCACCCAGA CCTACATCTGCAACGTGAACCACAAGCCCAG CAATACCAAGGTGGACAAGAAGGTGGAGCCC AAGAGCTGCTGA |
| 66 | Murine LIGHT CHAIN CD3$_{(2C11)}$ (VHCL) | ATGGGATGGAGCTGTATCATCCTCTTCTTGG TAGCAACAGCTACCGGTGTGCATTCCGAGGT GCAGCTGGTGGAAAGCGGCGGAGGCCTGGTG CAGCCCGGCAAGAGCCTGAAGCTGAGCTGCG AGGCCAGCGGCTTCACCTTCAGCGGCTACGG CATGCACTGGGTGAGACAGGCCCCTGGCAGA GGACTGGAAAGCGTGGCCTACATCACCAGCA GCAGCATCAACATTAAGTACGCCGACGCCGT GAAGGGCCGGTTCACCGTGTCCAGGGATAAC GCCAAGAACCTGCTGTTCCTGCAGATGAACA TCCTGAAGTCCGAGGACACCGCTATGTATTA CTGCGCCAGATTCGACTGGGACAAGAACTAC TGGGGCCAGGGCACCATGGTCACAGTGTCTA GCGCTAGCTGGCTGCACCATCTGTCTTCAT CTTCCCGCCATCTGATGAGCAGTTGAAATCT GGAACTGCCTCTGTTGTGTGCCTGCTGAATA ACTTCTATCCCAGAGAGGCCAAAGTACAGTG GAAGGTGGATAACGCCCTCCAATCGGGTAAC TCCCAGGAGAGTGTCACAGAGCAGGACAGCA AGGACAGCACCTACAGCCTCAGCAGCACCCT GACGCTGAGCAAAGCAGACTACGAGAAACAC AAAGTCTACGCCTGCGAAGTCACCCATCAGG GCCTGAGCTCGCCCGTCACAAAGAGCTTCAA CAGGGGAGAGTGTTGA |
| 67 | Murine XFAB (CD3$_{(2C11)}$)- FAB (MCSP)- FAB (MCSP) (VL-CH1-VH- CH1-VH- CH1) | ATGGGATGGAGCTGTATCATCCTCTTCTTGG TAGCAACAGCTACCGGTGTGCATTCCGACAT CCAGATGACCCAGAGCCCCAGCAGCCTGCCT GCCAGCCTGGGCGACAGAGTGACCATCAACT GCCAGGCCAGCCAGGACATCAGCAACTACCT GAACTGGTATCAGCAGAAGCCTGGCAAGGCC CCCAAGCTGCTGATCTACTACACCAACAAGC TGGCCGACGGCGTGCCCAGCAGATTCAGCGG CAGCGGCTCCGGCAGAGACAGCAGCTTCACC ATCTCCAGCCTGGAAAGCGAGGACATCGGCA GCTACTACTGCCAGCAGTACTACAACTACCC CTGGACCTTCGGCCCTGGCACCAAGCTGGAA ATCAAGCAGCAGCCTTCCACCAAAGGCCCTT CCGTGTTTCCTCTGGCTCCTAGCTCCAAGTC CACCTCTGGAGGCACCGCTGCTCTCGGATGC CTCGTGAAGGATTATTTTCCTGAGCCTGTGA CAGTGTCCTGGAATAGCGGAGCACTGACCTC TGGAGTGCATACTTTCCCCGCTGTGCTGCAG TCCTCTGGACTGTACAGCCTGAGCAGCGTGG TGACAGTGCCCAGCAGCAGCCTGGGCACCCA GACCTACATCTGCAACGTGAACCACAAGCCC AGCAACACCAAGGTGGACAAGAAGGTGGAAC CCAAGTCTTGTGGCGGAGGCGGATCCGGCGG AGGAGGGTCCGAGGTGCAGCTGCAGGAATCT GGCCCTGGCCTGGTCAAGCCAAGCCAGAGTC TGAGCCTGACCTGCAGCGTGACCGGCTACAG CATTACCAGCGGCTACTACTGGAACTGGATT CGGCAGTTCCCCGGCAATAAGCTGGAATGGA TGGGCTACATCACCTACGACGGCAGCAACAA CTACAACCCCAGCCTGAAGAACCGGATCAGC ATCACCCGGGACACCAGCAAGAACCAGTTCT TCCTGAAGCTGAACAGCGTGACCACCGAGGA CACCGCCACATACTATTGCGCCGACTTCGAC TACTGGGGCCAGGGCACCACCCTGACCGTGT CCAGCGCCAGCACAAAGGGCCCTAGCGTGTT CCCTCTGGCCCCCAGCAGCAAGAGCACAAGC GGCGGAACAGCCGCCCTGGGCTGCCTCGTGA AGGACTACTTCCCCGAGCCCGTGACAGTGTC TTGGAACAGCGGAGCCCTGACAAGCGGCGTG CACACCTTCCCTGCCGTGCTGCAGAGCAGCG GCCTGTACTCCCTGAGCAGCGTGGTCACCGT GCCTAGCAGCAGCCTGGGCACCCAGACCTAC ATCTGCAACGTGAACCACAAGCCCAGCAACA CCAAAGTGGACAAGAAGGTGGAGCCCAAGAG CTGTGATGGCGGAGGAGGGTCCGGAGGCGGT GGCTCCGAGGTGCAGCTGCAGGAATCTGGCC CTGGCCTGGTCAAGCCAAGCCAGAGTCTGAG CCTGACCTGCAGCGTGACCGGCTACAGCATT ACCAGCGGCTACTACTGGAACTGGATTCGGC AGTTCCCCGGCAATAAGCTGGAATGGATGGG |

| SEQ ID. NO. | Description | Sequence |
|---|---|---|
| | | CTACATCACCTACGACGGCAGCAACAACTAC AACCCCAGCCTGAAGAACCGGATCAGCATCA CCCGGGACACCAGCAAGAACCAGTTCTTCCT GAAGCTGAACAGCGTGACCACCGAGGACACC GCCACATACTATTGCGCCGACTTCGACTACT GGGGCCAGGGCACCACCCTGACCGTGTCCAG CGCCAGCACAAAGGGCCCTAGCGTGTTCCCT CTGGCCCCCAGCAGCAAGAGCACAAGCGGCG GAACAGCCGCCCTGGGCTGCCTCGTGAAGGA CTACTTCCCCGAGCCCGTGACAGTGTCTTGG AACAGCGGAGCCCTGACAAGCGGCGTGCACA CCTTCCCTGCCGTGCTGCAGAGCAGCGGCCT GTACTCCCTGAGCAGCGTGGTCACCGTGCCT AGCAGCAGCCTGGGCACCCAGACCTACATCT GCAACGTGAACCACAAGCCCAGCAACACCAA AGTGGACAAGAAGGTGGAGCCCAAGAGCTGT GATTGA |
| 104 | Light Chain antiCD33 | ATGGGATGGAGCTGTATCATCCTCTTCTTGG TAGCAACAGCTACCGGTGTGCATTCCGACAT CCAGATGACCCAGAGCCCCAGCAGCCTGAGC GCCAGCGTGGGCGACAGAGTGACCATCACCT GTCGGGCCAGCGAGAGCGTGGACAACTACGG CATCAGCTTCATGAACTGGTTCCAGCAGAAG CCCGGCAAGGCCCCCAAGCTGCTGATCTACG CCGCCAGCAATCAGGGCAGCGGCGTGCCAGC CAGATTCAGCGGCTCTGGCAGCGGCACCGAC TTCACCCTGACCATCAGCAGCCTGCAGCCCG ACGACTTCGCCACCTACTACTGCCAGCAGAG CAAAGAGGTGCCCTGGACCTTCGGCCAGGGC ACCAAGGTGGAAATCAAGCGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAACGC CCTCCAATCGGGTAACTCCCAGGAGAGTGTC ACAGAGCAGGACAGCAAGGACAGCACCTACA GCCTCAGCAGCACCCTGACGCTGAGCAAAGC AGACTACGAGAAACACAAAGTCTACGCCTGC GAAGTCACCCATCAGGGCCTGAGCTCGCCCG TCACAAAGAGCTTCAACAGGGGAGAGTGTTA G |
| 105 | Light Chain (CD3(F9)) (VH-CL) | ATGGGATGGAGCTGTATCATCCTCTTCTTGG TAGCAACAGCTACCGGTGTGCATTCCGAGGT GCAGCTGGTCGAGAGCGGAGGCGGCCTGGTG CAGCCTGGCGGCAGCCTGAGACTGAGCTGCG CCGCCAGCGGCTACAGCTTCACCGGCTACAC CATGAACTGGGTCCGGCAGGCACCTGGCAAG GGACTGGAATGGGTGGCCCTGATCAACCCCT ACAAGGGCGTGAGCACCTACAACCAGAAGTT CAAGGACCGGTTCACCATCAGCGTGGACAAG AGCAAGAACACCGCCTATCTGCAGATGAACA GCCTGCGGGCCGAGGACACCGCCGTGTACTA CTGCGCCAGAAGCGGCTACTACGGCGACAGC GACTGGTACTTCGACGTGTGGGGCCAGGGCA CCCTCGTGACCGTGTCTAGCGCTAGCGTGGC TGCACCATCTGTCTTCATCTTCCCGCCATCT GATGAGCAGTTGAAATCTGGAACTGCCTCTG TTGTGTGCCTGCTGAATAACTTCTATCCCAG AGAGGCCAAAGTACAGTGGAAGGTGGATAAC GCCCTCCAATCGGGTAACTCCCAGGAGAGTG TCACAGAGCAGGACAGCAAGGACAGCACCTA CAGCCTCAGCAGCACCCTGACGCTGAGCAAA GCAGACTACGAGAAACACAAAGTCTACGCCT GCGAAGTCACCCATCAGGGCCTGAGCTCGCC CGTCACAAAGAGCTTCAACAGGGGAGAGTGT TGA |
| 106 | Fab (CD33)- CrossFab (CD3(F9)) (VH-CH1-VL- CH1) | ATGGGATGGAGCTGTATCATCCTCTTCTTGG TAGCAACAGCTACCGGTGTGCATTCCCAGGT GCAGCTGGTGCAGTCTGGCGCCGAAGTGAAG AAACCCGGCAGCAGCGTGAAGGTGTCCTGCA AGGCCAGCGGCTACACCTTCACCGACTACAA CATGCACTGGGTCCGCCAGGCCCCCAGGCCAG |

| SEQ ID. NO. | Description | Sequence |
|---|---|---|
| | | GGACTGGAATGGATCGGCTACATCTACCCCT ACAACGGCGGCACCGGCTACAACCAGAAGTT CAAGAGCAAGGCCACCATCACCGCCGACGAG AGCACCAACACCGCCTACATGGAACTGAGCA GCCTGCGGAGCGAGGACACCGCCGTGTACTA CTGCGCCAGAGGCAGACCCGCCATGGACTAC TGGGGCCAGGGCACCCTGGTGACAGTGTCCA GCGCCAGCACAAAGGGCCCTAGCGTGTTCCC TCTGGCCCCCAGCAGCAAGAGCACAAGCGGC GGAACAGCCGCCCTGGGCTGCCTCGTGAAGG ACTACTTCCCCGAGCCCGTGACAGTGTCTTG GAACAGCGGAGCCCTGACAAGCGGCGTGCAC ACCTTCCCTGCCGTGCTGCAGAGCAGCGGCC TGTACTCCCTGAGCAGCGTGGTCACCGTGCC TAGCAGCAGCCTGGGCACCCAGACCTACATC TGCAACGTGAACCACAAGCCCAGCAACACCA AAGTGGACAAGAAGGTGGAGCCCAAGAGCTG TGATGGCGGAGGAGGGTCCGGAGGCGGTGGA TCCGACATCCAGATGACCCAGAGCCCCTCTA GCCTGAGCGCCAGCGTGGGCGACAGAGTGAC CATCACCTGTCGGGCCAGCCAGGACATCAGA AACTACCTGAACTGGTATCAGCAGAAGCCCG GCAAGGCCCCCAAGCTGCTGATCTACTACAC CTCTAGACTGGAAAGCGGCGTGCCCAGCCGG TTTAGCGGCAGCGGCTCCGGCACCGACTACA CCCTGACCATCAGCAGCCTGCAGCCCGAGGA CTTCGCCACCTACTACTGCCAGCAGGGCAAC ACACTCCCTGGACCTTCGGCCAGGGCACCA AGGTGGAGATCAAGTCCAGCGCTAGCACCAA GGGCCCCTCCGTGTTCCCCCTGGCCCCCAGC AGCAAGAGCACCAGCGGCGGCACAGCCGCCC TCGGCTGCCTGGTCAAGGACTACTTCCCCGA GCCCGTGACCGTGTCCTGGAACAGCGGAGCC CTGACCTCCGGCGTGCACACCTTCCCCGCCG TGCTGCAGAGCAGCGCCCTGTACAGCCTGTC CAGCGTGGTCACCGTGCCCTCCAGCAGCCTG GGCACCCAGACCTACATCTGCAACGTGAACC ACAAGCCCAGCAATACCAAGGTGGACAAGAA GGTGGAGCCCAAGAGCTGCTGA |
| 107 | MCSP CDR1 VH | GGCTACTCCATCACCAGTGGTTATTACTGGA AC |
| 108 | MCSP CDR2 VH | TACATAACCTACGACGGTAGCAATAACTACA ACCCATCTCTCAAAAAT |
| 109 | MCSP CDR3 VH | TTTGACTAC |
| 110 | MCSP CDR1 VL | AGTGCAAGTCAGGGCATTAGAAATTATTTAA AC |
| 111 | MCSP CDR2 VL | TACACATCAAGTTTACACTCA |
| 112 | MCSP CDR3VL | CAGCAGTATAGTAAGCTTCCTTGGACG |
| 113 | GA201 CDR1 VH | GACTACAAGATACAC |
| 114 | GA201 CDR2 VH | TATTTCAACCCTAACAGCGGTTATAGTACCT ACGCACAGAAGTTCCAGGGC |
| 115 | GA201 CDR3 VH | CTATCCCCAGGCGGTTACTATGTTATGGATG CC |
| 116 | GA201 CDR1 VL | CGGGCAAGTCAGGGCATTAACAATTACTTAA AT |
| 117 | GA201 CDR2 VL | AATACCAACAACTTGCAGACA |
| 118 | GA201 CDR3 VL | TTGCAGCATAATAGTTTTCCCACG |

| SEQ ID. NO. | Description | Sequence |
|---|---|---|
| 119 | GA201 VH | CAGGTGCAGCTGGTGCAGTCTGGGGCTGAGG TGAAGAAGCCTGGGTCCTCGGTGAAGGTCTC CTGCAAGGCCTCTGGTTTCACATTCACTGAC TACAAGATACACTGGGTGCGACAGGCCCCTG GACAAGGGCTCGAGTGGATGGGATATTTCAA CCCTAACAGCGGTTATAGTACCTACGCACAG AAGTTCCAGGGCAGGGTCACCATTACCGCGG ACAAATCCACGAGCACAGCCTACATGGAGCT GAGCAGCCTGAGATCTGAGGACACGGCCGTG TATTACTGTGCGAGACTATCCCCAGGCGGTT ACTATGTTATGGATGCCTGGGGCCAAGGGAC CACCGTGACCGTCTCCTCA |
| 120 | GA201 VL | GATATCCAGATGACCCAGTCTCCATCCTCCC TGTCTGCATCTGTCGGAGACCGGGTCACCAT CACCTGCCGGGCAAGTCAGGGCATTAACAAT TACTTAAATTGGTACCAGCAGAAGCCAGGGA AAGCCCCTAAGCGCCTGATCTATAATACCAA CAACTTGCAGACAGGCGTCCCATCAAGGTTC AGCGGCAGTGGATCCGGGACAGAATTCACTC TCACCATCAGCAGCCTGCAGCCTGAAGATTT TGCCACTTATTACTGTTTGCAGCATAATAGT TTTCCCACGTTTTGGCCAGGGCACCAAGCTCG AGATCAAG |
| 121 | 3F2 CDR1 VH | AGCTACGCCATGAGC |
| 122 | 3F2 CDR2 VH | GCCATCTCCGGCAGCGGAGGCAGCACCTACT ACGCCGACAGCGTGAAG |
| 123 | 3F2 CDR3 VH | TATTGCGCCAAGGGATGGTTCGGC |
| 124 | 3F2 CDR1 VL | AGAGCCAGCCAGAGCGTGACCAGCAGCTACC TG |
| 125 | 3F2 CDR2 VL | AACGTGGGCAGCAGACGGGCC |
| 126 | 3F2 CDR3 VL | TGCCAGCAGGGCATCATGCTGCCCCCC |
| 127 | 3F2 VH | GAGGTGCAGCTGCTGGAATCTGGAGGCGGCC TGGTGCAGCCTGGCGGCAGCCTGAGACTGTC TTGCGCCGCCAGCGGCTTCACCTTCAGCAGC TACGCCATGAGCTGGGTCCGACAGGCTCCTG GCAAGGGACTGGAATGGGTGTCCGCCATCTC CGGCAGCGGAGGCAGCACCTACTACGCCGAC AGCGTGAAGGGCCGGTTCACCATCAGCAGAG ACAACAGCAAGAACACCCTGTACCTGCAGAT GAACAGCCTGCGGGCCGAGGATACCGCCGTG TATTATTGCGCCAAGGGATGGTTCGGCGGCT TCAACTACTGGGGCCAGGGAACCCTGGTGAC AGTGTCCAGC |
| 128 | 3F2 VL | GAGATCGTGCTGACCCAGTCTCCCGGCACCC TGAGCCTGAGCCCTGGCGAGAGAGCCACCCT GAGCTGCAGAGCCAGCCAGAGCGTGACCAGC AGCTACCTGGCCTGGTATCAGCAGAAGCCCG GCCAGGCCCCCAGACTGCTGATCAACGTGGG CAGCAGACGGGCCACCGGCATCCCCGATAGA TTCAGCGGCAGCGGCTCCGGCACCGACTTCA CCCTGACCATCAGCCGGCTGGAACCCGAGGA CTTCGCCGTGTACTACTGCCAGCAGGGCATC ATGCTGCCCCCCACCTTCGGCCAGGGCACCA AGGTGGAAATCAAG |
| 129 | CH1A1A CDR1 VH | GAGTTCGGCATGAAC |
| 130 | CH1A1A CDR2 VH | TGGATCAACACCAAGACCGGCGAGGCCACCT ACGTGGAAGAGTTCAAGGGC |
| 131 | CH1A1A CDR3 VH | TGGGACTTCGCCTATTACGTGGAAGCCATGG ACTAC |
| 132 | CH1A1A CDR1 VL | AAGGCCAGTGCGGCTGTGGGTACGTATGTTG CG |
| 133 | CH1A1A CDR2 VL | TCGGCATCCTACCGCAAAAGG |
| 134 | CH1A1A CDR3 VL | CACCAATATTACACCTATCCTCTATTCACG |
| 135 | CH1A1A VH | CAGGTGCAGCTGGTGCAGTCTGGCGCCGAAG TGAAGAAACCTGGAGCTAGTGTGAAGGTGTC CTGCAAGGCCAGCGGCTACACCTTCACCGAG TTCGGCATGAACTGGGTCCGACAGGCTCCAG GCCAGGGCCTGAATGGATGGGCTGGATCAA CACCAAGACCGGCGAGGCCACCTACGTGGAA GAGTTCAAGGGCAGAGTGACCTTCACCACGG ACACCAGCACCAGCACCGCCTACATGGAACT GCGGAGCCTGAGAAGCGACGACACCGCCGTG TACTACTGCGCCAGATGGGACTTCGCCTATT ACGTGGAAGCCATGGACTACTGGGGCCAGGG CACCACCGTGACCGTGTCTAGC |
| 136 | CH1A1A VL | GATATCCAGATGACCCAGTCTCCATCCTCCC TGTCTGCATCTGTGGGAGACAGAGTCACCAT CACTTGCAAGGCCAGTGCGGCTGTGGGTACG TATGTTGCGTGGTATCAGCAGAAACCAGGGA AAGCACCTAAGCTCCTGATCTATTCGGCATC CTACCGCAAAAGGGGAGTCCCATCAAGGTTC AGTGGCAGTGGATCTGGGACAGATTTCACTC TCACCATCAGCAGTCTGCAACCTGAAGATTT CGCAACTTACTACTGTCACCAATATTACACC TATCCTCTATTCACGTTTGGCCAGGGCACCA AGCTCGAGATCAAG |
| 137 | Anti-CD33 CDR1 VH | GGCTACACCATCACCGACAGCAACATCCAC |
| 138 | Anti-CD33 CDR2 VH | TACATCTACCCCTACAACGGCGGCACCGACT ACAACCAG |
| 139 | Anti-CD33 CDR3 VH | GGCAACCCCTGGCTGGCCTAT |
| 140 | Anti-CD33 CDR1 VL | CGGGCCAGCGAGAGCCTGGACAACTACGGCA TCCGGTTTCTGACC |
| 141 | Anti-CD33 CDR2 VL | GCCGCCAGCAACCAGGGCAGC |
| 142 | Anti-CD33 CDR3 VL | CAGCAGACCAAAGAGGTGCCCTGGTCC |
| 143 | Anti-CD33 VH | GAAGTGCAGCTGGTGCAGTCTGGCGCCGAAG TGAAGAAACCCGGCAGCAGCGTGAAGGTGTC CTGCAAGGCCAGCGGCTACACCATCACCGAC AGCAACATCCACTGGGTCCGACAGGCCCCTG GGCAGAGCCTGGAATGGATCGGCTACATCTA CCCCTACAACGGCGGCACCGACTACAACCAG AAGTTCAAGAACCGGGCCACCCTGACCGTGG ACAACCCCACCAACACCGCCTACATGGAACT GAGCAGCCTGCGGAGCGAGGACACCGCCTTC TACTACTGCGTGAACGGCAACCCCTGGCTGG CCTATTGGGGCCAGGGAACCCTGGTCACCGT GTCTAGC |
| 144 | Anti-CD33 VL | GACATCCAGCTGACCCAGAGCCCCAGCACCC TGTCTGCCAGCGTGGGCGACAGAGTGACCAT CACCTGTCGGGCCAGCGAGAGCCTGGACAAC TACGGCATCCGGTTTCTGACCTGGTTCCAGC AGAAGCCCGGCAAGGCCCCCAAGCTGCTGAT GTACGCCGCCAGCAACCAGGGCAGCGGCGTG CCAAGCAGATTCAGCGGCAGCGGCTCCGGCA CCGAGTTCACCCTGACCATCAGCAGCCTGCA GCCCGACGACTTCGCCACCTACTACTGCCAG CAGACCAAAGAGGTGCCCTGGTCCTTCGGCC AGGGCACCAAGGTGGAAGTGAAG |

-continued

| SEQ ID. NO. | Description | Sequence |
|---|---|---|
| 150 | (scFv)2 antiMCSP/antihuCD3 (LC007(VL-VH)-V9(VH-VL)) | ATGGGCTGGTCCTGCATCATCCTGTTTCTGG TGGCCACAGCCACCGGTGTGCATTCCGACAT CGTGCTGACCCAGAGCCCCAGCAGCCTGAGC GCCAGCCTGGGCGACAGAGTGACCATCAGCT GCAGCGCCTCCCAGGGCATCAGAAACTACCT GAACTGGTATCAGCAGCGGCCCGACGGCACC GTGAAGCTGCTGATCTACTACACCAGCTCCC TGCACAGCGGCGTGCCCAGCAGATTTTCAGG CAGCGGCAGCGGCACTGACTACAGCCTGACC ATCTCCAACCTGGAACCCGAGGACATTGCCA CCTACTACTGCCAGCAGTACAGCAAGCTGCC CTGGACCTTCGGCGAGGCACCAAGCTGGAA ATCAAGGGCGGAGGCGGATCCGGCGGAGGTG GAAGTGGCGGCGGAGGCTCTGAGGTGCAATT GCAGGAAAGCGGCCCTGGCCTGGTGAAACCC AGCCAGAGCCTGAGCCTGACCTGCAGCGTGA CCGGCTACTCCATCACCAGCGGCTACTACTG GAACTGGATCAGACAGTTCCCCGGAAACAAG CTGGAATGGATGGGCTACATCACCTACGACG GCAGCAACAACTACAACCCCAGCCTGAAGAA CCGGATCAGCATCACCCGGGACACCAGCAAG AACCAGTTCTTCCTGAAGCTGAACAGCGTGA CCACCGAGGATACCGCCACCTATTACTGTGC CGACTTCGACTACTGGGGCCAGGGCACCACC CTGACCGTGTCATCCGGTGGCGGCGGATCCG AAGTGCAGCTGGTGGAGTCTGGCGGTGGACT GGTGCAGCCAGGCGGCTCCCTGAGACTGAGC TGCGCCGCCTCCGGCTACAGCTTCACCGGCT ACACCATGAATTGGGTCCGCCAGGCCCTGG AAAGGACTGGAATGGGTGGCCCTGATCAAC CCCTACAAGGGCGTGAGCACCTACAACCAGA AGTTCAAGGACCGGTTCACCATCAGCGTGGA CAAGAGCAAGAACACAGCCTACCTGCAGATG AACTCCCTGAGAGCCGAGGATACCGCCGTGT ATTACTGTGCCCGCAGCGGCTACTACGGCGA CTCCGACTGGTACTTCGACGTGTGGGGGCAG GGAACCCTGGTCACCGTGTCCAGCGTGGAAG GCGGCAGCGGAGGATCTGGCGGCTCTGGCGG AAGCGGCGGAGTGGACGATATCCAGATGACA CAGTCCCCCAGCTCCCTGAGCGCCAGCGTGG GCGACAGAGTGACCATCACCTGTCGGGCCAG CCAGGACATCCGGAATTATCTCAATTGGTAT CAGCAGAAACCTGGCAAAGCTCCTAAACTGC TGATCTACTACACCTCCCGGCTGGAAAGCGG CGTGCCCAGCAGATTTTCCGGCAGCGGGAGC GGCACCGATTACACACTGACCATCAGCAGCC TGCAGCCCGAGGACTTTGCCACCTACTATTG CCAGCAGGGCAACACCCTGCCCTGGACCTTT GGGCAGGGCACAAAGGTGGAGATCAAGCACC ACCACCATCACCACTGA |
| 154 | Light Chain antiCD33 (Myelotarg) | ATGGGATGGAGCTGTATCATCCTCTTCTTGG TAGCAACAGCTACCGGTGTGCATTCCGACAT CCAGCTGACCCAGAGCCCCTCCACACTCTCT GCCTCAGTGGGCGATAGGGTCACCATTACTT GCAGAGCTAGCGAGTCCCTGGACAACTACGG AATCCGCTTCCTTACATGGTTTCAGCAGAAG CCTGGAAAAGCACCAAAGCTGCTCATGTATG CCGCTTCTAATCAAGGCAGTGGTGTGCCCAG CCGGTTCTCCGGGTCTGGCTCAGGAACCGAA TTTACTCTGACCATTAGCTCCTTGCAGCCTG ATGACTTCGCAACATACTATTGTCAGCAGAC CAAGGAGGTCCCATGGTCTTTTGGTCAAGGC ACAAAAGTGGAGGTTAAGCGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAACGC CCTCCAATCGGGTAACTCCCAGGAGAGTGTC ACAGAGCAGGACAGCAAGGACAGCACCTACA GCCTCAGCAGCACCCTGACGCTGAGCAAAGC AGACTACGAGAAACACAAAGTCTACGCCTGC GAAGTCACCCATCAGGGCCTGAGCTCGCCCG TCACAAAGAGCTTCAACAGGGGAGAGTGTTA G |
| 155 | Light Chain CD3 (V9) (VL-CH1) | ATGGGATGGAGCTGTATCATCCTCTTCTTGG TAGCAACAGCTACCGGTGTGCATTCCGATAT TCAGATGACCCAGAGCCCCAGCTCTCTGAGC GCCAGCGTGGGCGACAGAGTGACCATCACCT GTCGGGCCAGCCAGGACATCAGAAACTACCT GAACTGGTATCAGCAGAAGCCCGGCAAGGCC CCCAAGCTGCTGATCTACTACACCAGCAGAC TGGAAAGCGGCGTGCCCTCCAGATTTTCCGG CAGCGGCTCCGGCACCGACTACACCCTGACC ATCAGCAGCCTGCAGCCCGAGGATTTCGCCA CATATTACTGCCAGCAGGGCAATACCCTGCC CTGGACCTTCGGACAGGGCACAAAAGTGGAA ATCAAGAGCAGCGCTTCCACCAAAGGCCCTT CCGTGTTTCCTCTGGCTCCTAGCTCCAAGTC CACCTCTGGAGGCACCGCTGCTCTCGGATGC CTCGTGAAGGATTATTTTCCTGAGCCTGTGA CAGTGTCCTGGAATAGCGGAGCACTGACCTC TGGAGTGCATACTTTCCCGCTGTGCTGCAG TCCTCTGGACTGTACAGCCTGAGCAGCGTGG TGACAGTGCCCAGCAGCAGCCTGGGCACCCA GACCTACATCTGCAACGTGAACCACAAGCCC AGCAACACCAAGGTGGACAAGAAGGTGGAAC CCAAGTCTTGTTGA |
| 156 | Fab (CD33 (Myelotarg))-XFab (CD3 (V9)) (VH-CH1-VH-CL) | ATGGGATGGAGCTGTATCATCCTCTTCTTGG TAGCAACAGCTACCGGTGTGCATTCCGAGGT GCAGCTGGTGCAGTCTGGCGCCGAAGTGAAG AAACCCGGCAGCAGCGTGAAGGTGTCCTGCA AGGCCAGCGGCTACACCATCACCGACGGCAA CATCCACTGGGTGCGCCAGGCCCCTGGCCAG CTGTCTGGAATGGATCGGCTACATCTACCCCT ACAACGGCGGCACCGACTACAACCAGAAGTT CAAGAACCGGGCCACCCTGACCGTGGACAAC CCCACCAATACCGCCTACATGGAACTGAGCA GCCTGCGGAGCGAGGACACCGCCTTCTACTA CTGCGTGAACGGCAACCCCTGGCTGGCCTAT TGGGGCCAGGGAACACTCGTGACCGTGTCCA GCGCTAGCACCAAGGGCCCTAGCGTGTTCCC TCTGGCCCCCTAGCAGCAAGAGCACCTCTGGC GGAACAGCCGCCCTGGGCTGCCTCGTGAAGG ACTACTTTCCCGAGCCCGTGACAGTGTCCTG GAACTCTGGCGCCCTGACAAGCGGCGTGCAC ACCTTTCCAGCCGTGCTGCAGTCTAGCGGCC TGTACAGCCTGAGCAGCGTCGTGACTGTGCC CAGCAGCAGCCTGGGAACCCAGACCTACATC TGCAACGTGAACCACAAGCCCAGCAACACCA AGGTGGACAAGAAGGTGGAACCCAAGAGCTG CGACGGCGGAGGCGGATCCGGGGAGGGGA TCTGAAGTGCAGCTGGTGGAAAGCGGCGGAG GCCTGGTGCAGCCTGGGGGATCTCTGAGACT GAGCTGTGCCGCCTCCGGCTACAGCTTCACC GGCTACACAATGAATTGGGTGCGCCAGGCTC CCGGCAAGGGCCTGGAATGGGTGGCCCTGAT CAACCCCTTACAAGGGCGTGTCCACCTATAAT CAGAAGTTTAAGGACCGCTTCACCATCAGCG TGGACAAGTCCAAGAACACCGCCTACCTGCA GATGAACTCCCTGCGGGCCGAGGATACAGCC GTGTACTACTGTGCCAGAAGCGGCTACTACG GCGACAGCGACTGGTACTTCGACGTGTGGG ACAGGGCACCCTGGTGACCGTGTCTAGTGCC TCTGTGGCCCTCCAGCGTGTTCATCTTCC CACCTAGCGACGAGCAGCTGAAGTCCGGCAC CGCTTCTGTCGTGTGCCTGCTGAACAACTTC TACCCCCGCGAGGCCAAGGTGCAGTGGAAAG TGGACAATGCCCTGCAGAGCGGCAACAGCCA GGAAAGCGTGACCGAGCAGGACAGCAAGGAC TCCACCTACAGCCTGTCCAGCACCCTGACAC TGAGCAAGGCCGACTACGAGAAGCACAAGGT GTACGCCTGCGAAGTGACCCACCAGGGCCTG TCTAGCCCCGTGACCAAGAGCTTCAACCGGG GCGAGTGCTGA |

| SEQ ID. NO. | Description | Sequence |
|---|---|---|
| 165 | VLCL(MCSP)-(G4S)2-VHCL(CD3 $_{r9}$) | CATTCCGAGGTGCAGCTGGTGGAATCTGGCG GCGGACTGGTGCAGCCTGGCGGATCTCTGAG ACTGAGCTGTGCCGCCAGCGGCTACAGCTTC ACCGGCTACACCATGAACTGGGTGCGCCAGG CCCCTGGCAAGGGACTGGAATGGGTGGCCCT GATCAACCCCTACAAGGGCGTGTCCACCTAC AACCAGAAGTTCAAGGACCGGTTCACCATCA GCGTGGACAAGAGCAAGAACACCGCCTACCT GCAGATGAACAGCCTGCGGGCCGAGGACACC GCCGTGTACTATTGTGCCAGAAGCGGCTACT ACGGCGACAGCGACTGGTACTTCGACGTGTG GGGCCAGGGCACACTCGTGACCGTGTCAAGC GCTAGCGTGGCCGCTCCCAGCGTGTTCATCT TCCCACCTAGCGACGAGCAGCTGAAGTCCGG CACAGCCTCTGTCGTGTGCCTGCTGAACAAC TTCTACCCCCGCGAGGCCAAGGTGCAGTGGA AGGTGGACAATGCCCTGCAGAGCGGCAACAG CCAGGAAAGCGTGACCGAGCAGGACAGCAAG GATAGCACCTACAGCCTGAGCAGCACCCTGA CCCTGAGCAAGGCCGACTACGAGAAGCACAA GGTGTACGCCTGCGAAGTGACCCACCAGGGC CTGTCTAGCCCCGTGACCAAGAGCTTCAACC GGGGCGAGTGTGATGGCGGAGGCGGATCCGG GGGAGGCGGCTCTGATATTGTGCTGACCCAG AGCCCCAGCAGCCTGTCTGCCTCTCTGGGCG ACAGAGTGACCATCAGCTGTAGCGCCTCTCA GGGCATCCGGAACTACCTGAACTGGTATCAG CAGCGGCCCGACGGCACCGTGAAGCTGCTGA TCTACTACACCAGCTCCCTGCACTCCGGCGT GCCCAGCAGATTTTCTGGCAGCGGCTCCGGC ACCGACTACTCCCTGACCATCTCCAACCTGG AACCCGAGGATATCGCCACCTACTACTGCCA GCAGTACTCCAAGCTGCCCTGGACCTTTGGA GGCGGCACCAAGCTGGAAATCAAGCGTACGG TGGCTGCCCCCTCCGTGTTTATCTTTCCCCC ATCCGATGAACAGCTGAAAAGCGGCACCGCC AGCGTCGTGTGTCTGCTGAACAATTTTTACC CTAGGGAAGCTAAAGTGCAGTGGAAAGTGGA TAACGCACTGCAGTCCGGCAACTCCCAGGAA TCTGTGACAGAACAGGACTCTAAGGACAGCA CATACTCCCTGTCCTCCACCCTGACACTGTC TAAGGCTGATTATGAGAAACACAAAGTGTAT GCTTGTGAAGTGACACATCAGGGACTGAGCA GCCCTGTGACAAAGTCCTTCAACAGAGGCGA GTGCTGATGAA |
| 166 | VHCH1(MCSP)-(G4S)2-VLCH1(CD3 $_{r9}$) | ATGGGATGGAGCTGTATCATCCTCTTCTTGG TAGCAACAGCTACCGGTGTGCATTCGGAGGT GCAGCTGCAGGAATCTGGCCCTGGCCTGGTC AAGCCAAGCCAGAGTCTGAGCCTGACCTGCA GCGTGACCGGCTACAGCATTACCAGCGGCTA CTACTGGAACTGGATTCGGCAGTTCCCCGGC AATAAGCTGGAATGGATGGGCTACATCACCT ACGACGGCAGCAACAACTACAACCCCAGCCT GAAGAACCGGATCAGCATCACCCGGGACACC AGCAAGAACCAGTTCTTCCTGAAGCTGAACA GCGTGACCACCGAGGACACCGCCACATACTA TTGCGCCGACTTCGACTACTGGGGCCAGGGC ACCACCCTGACCGTGTCCAGCGCCAGCACAA AGGGCCCTAGCGTGTTCCCTCTGGCCCCCAG CAGCAAGAGCACAAGCGGCGGAACAGCCGCC CTGGGCTGCCTCGTGAAGGACTACTTCCCCG AGCCCGTGACAGTGTCTTGGAACAGCGGAGC CCTGACAAGCGGCGTGCACACCTTCCCTGCC GTGCTGCAGAGCAGCGGCCTGTACTCCCTGA GCAGCGTGGTCACCGTGCCTAGCAGCAGCCT GGGCACCCAGACCTACATCTGCAACGTGAAC CACAAGCCCAGCAACACCAAAGTGGACAAGA AGGTGGAGCCCAAGAGCTGTGATGGCGGAGG AGGGTCCGGAGGCGGTGGATCCGACATCCAG ATGACCCAGAGCCCCTCTAGCCTGAGCGCCA GCGTGGGCGACAGAGTGACCATCACCTGTCG GGCCAGCCAGGACATCAGAAACTACCTGAAC TGGTATCAGCAGAAGCCCGGCAAGGCCCCCA AGCTGCTGATCTACTACACCTCTAGACTGGA AAGCGGCGTGCCCAGCCGGTTTAGCGGCAGC GGCTCCGGCACCGACTACACCCTGACCATCA GCAGCCTGCAGCCCGAGGACTTCGCCACCTA CTACTGCCAGCAGGGCAACACACTCCCCTGG ACCTTCGGCCAGGGCACCAAGGTGGAGATCA AGTCCAGCGCTAGCACCAAGGGCCCCTCCGT GTTCCCCCTGGCCCCCAGCAGCAAGAGCACC AGCGGCGGCACAGCCGCCCTCGGCTGCCTGG TCAAGGACTACTTCCCCGAGCCCGTGACCGT GTCCTGGAACAGCGGAGCCCTGACCTCCGGC GTGCACACCTTCCCCGCCGTGCTGCAGAGCA GCGGCCTGTACAGCCTGTCCAGCGTGGTCAC CGTGCCCTCCAGCAGCCTGGGCACCCAGACC TACATCTGCAACGTGAACCACAAGCCCAGCA ATACCAAGGTGGACAAGAAGGTGGAGCCCAA GAGCTGCTGA |

While there are shown and described presently preferred embodiments of the invention, it is to be distinctly understood that the invention is not limited thereto but may be otherwise variously embodied and practiced within the scope of the following claims.

The invention claimed is:

1. A bispecific antibody comprising a first and a second Fab fragment, wherein:
   (a) the first Fab fragment comprises one antigen binding site specific for a tumor antigen;
   (b) the second Fab fragment comprises one antigen binding site specific for a CD3 T-cell co-receptor (CD3) antigen, wherein the second Fab fragment is a crossover Fab fragment; and
   (c) the two Fab fragments are connected to each other by two peptide linkers, wherein:
      (i) each peptide linker connects a C-terminus of the first Fab fragment with an N-terminus of the second Fab fragment, or
      (ii) each peptide linker connects an N-terminus of the first Fab fragment with a C-terminus of the second Fab fragment;
   and wherein the bispecific antibody is devoid of a Fc domain.

2. The bispecific antibody of claim 1, additionally comprising a third Fab fragment.

3. The bispecific antibody of claim 2, wherein the third Fab fragment comprises one antigen binding site specific for the tumor antigen.

4. The bispecific antibody of claim 2 or 3, wherein the third Fab fragment is connected to the first Fab fragment by one or two peptide linkers.

5. The bispecific antibody of claim 2 or 3, wherein the third Fab fragment is connected to the second Fab fragment by one or two peptide linkers.

6. The bispecific antibody of any one of claim 1, 2, and 3, wherein the tumor antigen is selected from the group of melanoma-associated chondroitin sulfate proteoglycan (MCSP), epidermal growth factor receptor (EGFR), carcinoembryonic antigen (CEA), fibroblast activation protein (FAP), and CD33.

7. The bispecific antibody of claim 6, wherein the tumor antigen is MCSP.

8. A pharmaceutical composition comprising a bispecific antibody of any one of claim 1, 2, and 3.

9. A prokaryotic or eukaryotic host cell comprising vectors comprising nucleic acid molecules encoding the bispecific antibody of any one of claim 1, 2, and 3.

10. A method of producing the antibody of any one of claim 1, 2, and 3 comprising culturing the host cell of claim 9 so that the antibody is produced.

11. A bispecific antibody comprising a first and a second Fab fragment, wherein:
   (a) the first Fab fragment comprises one antigen binding site specific for MCSP, and the second Fab fragment comprises one antigen binding site specific for a CD3 antigen, wherein the variable heavy chain region and variable light chain region of the second Fab fragment are exchanged;
   (b) the two Fab fragments are connected to each other by a first and second peptide linker, wherein the first peptide linker connects the C-terminus of a constant light chain region of the first Fab fragment with the N-terminus of the variable heavy chain region of the second Fab fragment, and the second peptide linker connects the C-terminus of a constant heavy chain 1 region of the first Fab fragment with the N-terminus of the variable light chain region of the second Fab fragment; and
   (c) the bispecific antibody is devoid of a Fc domain.

12. The bispecific antibody of claim 1 or 11, comprising a first polypeptide having the amino acid sequence of SEQ ID NO: 163 and a second polypeptide having the amino acid sequence of SEQ ID NO: 164.

* * * * *

UNITED STATES PATENT AND TRADEMARK OFFICE
CERTIFICATE OF CORRECTION

PATENT NO. : 10,087,250 B2
APPLICATION NO. : 14/434168
DATED : October 2, 2018
INVENTOR(S) : Peter Bruenker et al.

It is certified that error appears in the above-identified patent and that said Letters Patent is hereby corrected as shown below:

In the Specification

Column 6, Line 33, replace "A 1" with --A) 1--;
  Line 34, replace "B 1" with --B) 1--.

Column 14, Line 61, replace "<1 μM" with --≤1 μM--.

Column 16, Line 22, replace "CD3ϵ" with --CDε--.

Column 26, Line 56, replace "a cell" with --a T cell--.

Column 27, Line 4, replace "In one embodiment" with --    In one embodiment--.

Column 30, Line 7, replace "chain of 15 second" with --chain of second--.

Column 54, Line 65, replace "BI" with --B1--.

Column 61, Line 66, replace "Analysis" with --  Analysis--.

Column 73, Line 25, replace "150 l/well" with --150 μl/well--.

Column 88, Line 43, replace "MCSP$_{(M4\text{-}3\ ML2)}$" with --MCSP$_{(M4\text{-}3\ ML2)}$VH--;
  Replace "VHQVQ" with --QVQ--;
  Line 47, replace "MCSP$_{(M4\text{-}3\ ML2)}$" with --MCSP$_{(M4\text{-}3\ ML2)}$VL--;
  Replace "VLDIQ" with --DIQ--.

Signed and Sealed this
Twenty-sixth Day of March, 2019

Andrei Iancu
*Director of the United States Patent and Trademark Office*

SEQUENCE LISTING

<160> NUMBER OF SEQ ID NOS: 209

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR1 VL MCSP peptide

<400> SEQUENCE: 1

Ser Ala Ser Gln Gly Ile Arg Asn Tyr Leu Asn
1               5                   10

<210> SEQ ID NO 2
<211> LENGTH: 7
<212> TYPE: PRT

<210> SEQ ID NO 2
<213> ORGANISM: Artificial Sequence
<220> FEATURE:
<223> OTHER INFORMATION: Description of Artificial Sequence: Synthetic
      CDR2 VL MCSP peptide

<400> SEQUENCE: 2

Tyr Thr Ser Ser Leu His Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR3 VL MCSP peptide

<400> SEQUENCE: 3

Gln Gln Tyr Ser Lys Leu Pro Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR1 VH MCSP peptide

<400> SEQUENCE: 4

Gly Tyr Ser Ile Thr Ser Gly Tyr Tyr Trp Asn
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR2 VH MCSP peptide

<400> SEQUENCE: 5

Tyr Ile Thr Tyr Asp Gly Ser Asn Asn Tyr Asn Pro Ser Leu Lys Asn
1               5                   10                  15

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      CDR3  VH MCSP peptide

<400> SEQUENCE: 6

Phe Asp Tyr
1

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR1 VL CD3 peptide

<400> SEQUENCE: 7

Arg Ala Ser Gln Asp Ile Arg Asn Tyr Leu Asn
1               5                   10

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR2 VL CD3 peptide

<400> SEQUENCE: 8

Tyr Thr Ser Arg Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR3 VL CD3 peptide

<400> SEQUENCE: 9

Gln Gln Gly Asn Thr Leu Pro Trp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      CDR1 VH CD3 peptide

<400> SEQUENCE: 10

Gly Tyr Thr Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR2 VH CD3 peptide

<400> SEQUENCE: 11

Leu Ile Asn Pro Tyr Lys Gly Val Ser Thr Tyr Asn Gln Lys Phe Lys
1               5                   10                  15

Asp

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR3 VH CD3 peptide

<400> SEQUENCE: 12

Ser Gly Tyr Tyr Gly Asp Ser Asp Trp Tyr Phe Asp Val
1               5                   10

<210> SEQ ID NO 13
<211> LENGTH: 107
<212> TYPE: PRT
<213> ORGANISM: Artificial Sequence
<220> FEATURE:
```

<223> OTHER INFORMATION: Description of Artificial Sequence: Synthetic
    VL MCSP polypeptide

<400> SEQUENCE: 13

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
    VH MCSP polypeptide

<400> SEQUENCE: 14

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Leu Thr Val Ser Ser
            100                 105                 110

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
    CL MCSP polypeptide

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

<210> SEQ ID NO 16
<211> LENGTH: 104
<212> TYPE: PRT
<213> ORGANISM: Artificial Sequence
<220> FEATURE:
<223> OTHER INFORMATION: Description of Artificial Sequence: Synthetic
      CH1 MCSP polypeptide

<400> SEQUENCE: 16

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp
                100
```

<210> SEQ ID NO 17
<211> LENGTH: 214
<212> TYPE: PRT
<213> ORGANISM: Artificial Sequence
<220> FEATURE:
<223> OTHER INFORMATION: Description of Artificial Sequence: Synthetic
      LIGHT CHAIN MCSP polypeptide

<400> SEQUENCE: 17

```
Asp Ile Val Leu Thr Gln Ser Pro Ser Ser Leu Ser Ala Ser Leu Gly
  1               5                  10                  15

Asp Arg Val Thr Ile Ser Cys Ser Ala Ser Gln Gly Ile Arg Asn Tyr
                 20                  25                  30

Leu Asn Trp Tyr Gln Gln Arg Pro Asp Gly Thr Val Lys Leu Leu Ile
             35                  40                  45

Tyr Tyr Thr Ser Ser Leu His Ser Gly Val Pro Ser Arg Phe Ser Gly
         50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Trp
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
```

```
            130               135               140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 18
<211> LENGTH: 216
<212> TYPE: PRT
<213> ORGANISM: Artificial Sequence
<220> FEATURE:
<223> OTHER INFORMATION: Description of Artificial Sequence: Synthetic
      HEAVY CHAIN MCSP polypeptide

<400> SEQUENCE: 18

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
                35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp
    210                 215

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      VL CD3 (V9) polypeptide
```

```
<400> SEQUENCE: 19

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      VH CD3 (V9) polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 21
<211> LENGTH: 105
<212> TYPE: PRT
<213> ORGANISM: Artificial Sequence
<220> FEATURE:
<223> OTHER INFORMATION: Description of Artificial Sequence: Synthetic
      CL CD3 (V9) polypeptide

<400> SEQUENCE: 21

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
```

```
                 50                  55                  60
Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Cys
                100                 105

<210> SEQ ID NO 22
<211> LENGTH: 103
<212> TYPE: PRT
<213> ORGANISM: Artificial Sequence
<220> FEATURE:
<223> OTHER INFORMATION: Description of Artificial Sequence: Synthetic
      CH1 CD3 (V9) polypeptide

<400> SEQUENCE: 22

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
                100

<210> SEQ ID NO 23
<211> LENGTH: 229
<212> TYPE: PRT
<213> ORGANISM: Artificial Sequence
<220> FEATURE:
<223> OTHER INFORMATION: Description of Artificial Sequence: Synthetic
      Light chain CD3 (VHCL) (V9) polypeptide

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Ala Ser Gly Tyr Ser Phe Thr Gly Tyr
                 20                  25                  30

Thr Met Asn Trp Val Arg Gln Ala Pro Gly Lys Gly Leu Glu Trp Val
             35                  40                  45

Ala Leu Ile Asn Pro Tyr Lys Gly Val Ser Thr Tyr Asn Gln Lys Phe
         50                  55                  60

Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Ala Ser Val Ala Ala Pro
             115                 120                 125

Ser Val Phe Ile Phe Pro Pro Ser Asp Glu Gln Leu Lys Ser Gly Thr
```

```
                130             135             140
Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
            195                 200                 205

Cys Glu Val Thr His Gln Gly Leu Ser Ser Pro Val Thr Lys Ser Phe
        210                 215                 220

Asn Arg Gly Glu Cys
225

<210> SEQ ID NO 24
<211> LENGTH: 212
<212> TYPE: PRT
<213> ORGANISM: Artificial Sequence
<220> FEATURE:
<223> OTHER INFORMATION: Description of Artificial Sequence: Synthetic
      Heavy Chain CD3 (VLCH1) V9 polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 25
<211> LENGTH: 438
<212> TYPE: PRT
<213> ORGANISM: Artificial Sequence
<220> FEATURE:
```

<223> OTHER INFORMATION: Description of Artificial Sequence: Synthetic
      FAB (MCSP)-XFAB (CD3) polypeptide

<400> SEQUENCE: 25

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Gly Gly Gly Ser Gly Gly Gly
    210                 215                 220

Gly Ser Asp Ile Gln Met Thr Gln Ser Pro Ser Ser Leu Ser Ala Ser
225                 230                 235                 240

Val Gly Asp Arg Val Thr Ile Thr Cys Arg Ala Ser Gln Asp Ile Arg
                245                 250                 255

Asn Tyr Leu Asn Trp Tyr Gln Gln Lys Pro Gly Lys Ala Pro Lys Leu
            260                 265                 270

Leu Ile Tyr Tyr Thr Ser Arg Leu Glu Ser Gly Val Pro Ser Arg Phe
        275                 280                 285

Ser Gly Ser Gly Ser Gly Thr Asp Tyr Thr Leu Thr Ile Ser Ser Leu
    290                 295                 300

Gln Pro Glu Asp Phe Ala Thr Tyr Tyr Cys Gln Gln Gly Asn Thr Leu
305                 310                 315                 320

Pro Trp Thr Phe Gly Gln Gly Thr Lys Val Glu Ile Lys Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400
```

Ser Ser Val Val Thr Val Pro Ser Ser Leu Gly Thr Gln Thr Tyr
            405                 410                 415

Ile Cys Asn Val Asn His Lys Pro Ser Asn Thr Lys Val Asp Lys Lys
            420                 425                 430

Val Glu Pro Lys Ser Cys
            435

<210> SEQ ID NO 26
<211> LENGTH: 664
<212> TYPE: PRT
<213> ORGANISM: Artificial Sequence
<220> FEATURE:
<223> OTHER INFORMATION: Description of Artificial Sequence: Synthetic
      FAB (MCSP)-FAB (MCSP)-XFAB (CD3) polypeptide

<400> SEQUENCE: 26

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
            35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
            85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Gly Gly Gly Ser Gly Gly Gly
            210                 215                 220

Gly Ser Glu Val Gln Leu Gln Glu Ser Gly Pro Gly Leu Val Lys Pro
225                 230                 235                 240

Ser Gln Ser Leu Ser Leu Thr Cys Ser Val Thr Gly Tyr Ser Ile Thr
            245                 250                 255

Ser Gly Tyr Tyr Trp Asn Trp Ile Arg Gln Phe Pro Gly Asn Lys Leu
            260                 265                 270

Glu Trp Met Gly Tyr Ile Thr Tyr Asp Gly Ser Asn Asn Tyr Asn Pro
            275                 280                 285

Ser Leu Lys Asn Arg Ile Ser Ile Thr Arg Asp Thr Ser Lys Asn Gln
            290                 295                 300

Phe Phe Leu Lys Leu Asn Ser Val Thr Thr Glu Asp Thr Ala Thr Tyr

```
                305                 310                 315                 320
Tyr Cys Ala Asp Phe Asp Tyr Trp Gly Gln Gly Thr Thr Leu Thr Val
                325                 330                 335
Ser Ser Ala Ser Thr Lys Gly Pro Ser Val Phe Pro Leu Ala Pro Ser
                340                 345                 350
Ser Lys Ser Thr Ser Gly Gly Thr Ala Ala Leu Gly Cys Leu Val Lys
                355                 360                 365
Asp Tyr Phe Pro Glu Pro Val Thr Val Ser Trp Asn Ser Gly Ala Leu
                370                 375                 380
Thr Ser Gly Val His Thr Phe Pro Ala Val Leu Gln Ser Ser Gly Leu
385                 390                 395                 400
Tyr Ser Leu Ser Ser Val Val Thr Val Pro Ser Ser Ser Leu Gly Thr
                405                 410                 415
Gln Thr Tyr Ile Cys Asn Val Asn His Lys Pro Ser Asn Thr Lys Val
                420                 425                 430
Asp Lys Lys Val Glu Pro Lys Ser Cys Asp Gly Gly Gly Gly Ser Gly
                435                 440                 445
Gly Gly Gly Ser Asp Ile Gln Met Thr Gln Ser Pro Ser Ser Leu Ser
450                 455                 460
Ala Ser Val Gly Asp Arg Val Thr Ile Thr Cys Arg Ala Ser Gln Asp
465                 470                 475                 480
Ile Arg Asn Tyr Leu Asn Trp Tyr Gln Gln Lys Pro Gly Lys Ala Pro
                485                 490                 495
Lys Leu Leu Ile Tyr Tyr Thr Ser Arg Leu Glu Ser Gly Val Pro Ser
                500                 505                 510
Arg Phe Ser Gly Ser Gly Ser Gly Thr Asp Tyr Thr Leu Thr Ile Ser
                515                 520                 525
Ser Leu Gln Pro Glu Asp Phe Ala Thr Tyr Tyr Cys Gln Gln Gly Asn
                530                 535                 540
Thr Leu Pro Trp Thr Phe Gly Gln Gly Thr Lys Val Glu Ile Lys Ser
545                 550                 555                 560
Ser Ala Ser Thr Lys Gly Pro Ser Val Phe Pro Leu Ala Pro Ser Ser
                565                 570                 575
Lys Ser Thr Ser Gly Gly Thr Ala Ala Leu Gly Cys Leu Val Lys Asp
                580                 585                 590
Tyr Phe Pro Glu Pro Val Thr Val Ser Trp Asn Ser Gly Ala Leu Thr
                595                 600                 605
Ser Gly Val His Thr Phe Pro Ala Val Leu Gln Ser Ser Gly Leu Tyr
                610                 615                 620
Ser Leu Ser Ser Val Val Thr Val Pro Ser Ser Ser Leu Gly Thr Gln
625                 630                 635                 640
Thr Tyr Ile Cys Asn Val Asn His Lys Pro Ser Asn Thr Lys Val Asp
                645                 650                 655
Lys Lys Val Glu Pro Lys Ser Cys
                660

<210> SEQ ID NO 27
<211> LENGTH: 663
<212> TYPE: PRT
<213> ORGANISM: Artificial Sequence
<220> FEATURE:
<223> OTHER INFORMATION: Description of Artificial Sequence: Synthetic
      FAB (MCSP)-XFAB (CD3)-FAB (MCSP) polypeptide

<400> SEQUENCE: 27
```

```
Glu Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Gly Gly Gly Ser Gly Gly Gly
            210                 215                 220

Gly Ser Asp Ile Gln Met Thr Gln Ser Pro Ser Ser Leu Ser Ala Ser
225                 230                 235                 240

Val Gly Asp Arg Val Thr Ile Thr Cys Arg Ala Ser Gln Asp Ile Arg
            245                 250                 255

Asn Tyr Leu Asn Trp Tyr Gln Gln Lys Pro Gly Lys Ala Pro Lys Leu
            260                 265                 270

Leu Ile Tyr Tyr Thr Ser Arg Leu Glu Ser Gly Val Pro Ser Arg Phe
            275                 280                 285

Ser Gly Ser Gly Ser Gly Thr Asp Tyr Thr Leu Thr Ile Ser Ser Leu
            290                 295                 300

Gln Pro Glu Asp Phe Ala Thr Tyr Tyr Cys Gln Gln Gly Asn Thr Leu
305                 310                 315                 320

Pro Trp Thr Phe Gly Gln Gly Thr Lys Val Glu Ile Lys Ser Ser Ala
            325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
            355                 360                 365

Pro Glu Pro Val Thr Val Ser Trp Asn Ser Gly Ala Leu Thr Ser Gly
            370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Leu Gly Thr Gln Thr Tyr
            405                 410                 415

Ile Cys Asn Val Asn His Lys Pro Ser Asn Thr Lys Val Asp Lys Lys
```

```
            420                 425                 430
Val Glu Pro Lys Ser Cys Gly Gly Gly Ser Gly Gly Gly Gly Ser
            435                 440                 445

Glu Val Gln Leu Gln Glu Ser Gly Pro Gly Leu Val Lys Pro Ser Gln
450                 455                 460

Ser Leu Ser Leu Thr Cys Ser Val Thr Gly Tyr Ser Ile Thr Ser Gly
465                 470                 475                 480

Tyr Tyr Trp Asn Trp Ile Arg Gln Phe Pro Gly Asn Lys Leu Glu Trp
                485                 490                 495

Met Gly Tyr Ile Thr Tyr Asp Gly Ser Asn Asn Tyr Asn Pro Ser Leu
            500                 505                 510

Lys Asn Arg Ile Ser Ile Thr Arg Asp Thr Ser Lys Asn Gln Phe Phe
            515                 520                 525

Leu Lys Leu Asn Ser Val Thr Thr Glu Asp Thr Ala Thr Tyr Tyr Cys
            530                 535                 540

Ala Asp Phe Asp Tyr Trp Gly Gln Gly Thr Thr Leu Thr Val Ser Ser
545                 550                 555                 560

Ala Ser Thr Lys Gly Pro Ser Val Phe Pro Leu Ala Pro Ser Ser Lys
                565                 570                 575

Ser Thr Ser Gly Gly Thr Ala Ala Leu Gly Cys Leu Val Lys Asp Tyr
            580                 585                 590

Phe Pro Glu Pro Val Thr Val Ser Trp Asn Ser Gly Ala Leu Thr Ser
            595                 600                 605

Gly Val His Thr Phe Pro Ala Val Leu Gln Ser Ser Gly Leu Tyr Ser
            610                 615                 620

Leu Ser Ser Val Val Thr Val Pro Ser Ser Ser Leu Gly Thr Gln Thr
625                 630                 635                 640

Tyr Ile Cys Asn Val Asn His Lys Pro Ser Asn Thr Lys Val Asp Lys
                645                 650                 655

Lys Val Glu Pro Lys Ser Cys
            660

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      Linker Sequence peptide

<400> SEQUENCE: 28

Gly Gly Gly Gly Ser Gly Gly Gly Gly Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      CDR1 VL CD3 (H2C) peptide

<400> SEQUENCE: 29

Gly Ser Ser Thr Gly Ala Val Thr Ser Gly Tyr Tyr Pro Asn
1               5                   10

<210> SEQ ID NO 30
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      CDR2 VL CD3 (H2C) peptide

<400> SEQUENCE: 30

Gly Thr Lys Phe Leu Ala Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR3 VL CD3 (H2C) peptide

<400> SEQUENCE: 31

Ala Leu Trp Tyr Ser Asn Arg Trp Val
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 VH CD3 (H2C) peptide

<400> SEQUENCE: 32

Gly Phe Thr Phe Asn Lys Tyr Ala Met Asn
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR2 VH CD3 (H2C) peptide

<400> SEQUENCE: 33

Arg Ile Arg Ser Lys Tyr Asn Asn Tyr Ala Thr Tyr Tyr Ala Asp Ser
1               5                   10                  15

Val Lys Asp

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      CDR3 VH CD3 (H2C) peptide

<400> SEQUENCE: 34

His Gly Asn Phe Gly Asn Ser Tyr Ile Ser Tyr Trp Ala Tyr
1               5                   10

<210> SEQ ID NO 35
<211> LENGTH: 109
<212> TYPE: PRT
<213> ORGANISM: Artificial Sequence
<220> FEATURE:
<223> OTHER INFORMATION: Description of Artificial Sequence: Synthetic
      VL CD3 (H2C) polypeptide

<400> SEQUENCE: 35
```

```
Gln Thr Val Val Thr Gln Glu Pro Ser Leu Thr Val Ser Pro Gly
1               5                   10                  15

Thr Val Thr Leu Thr Cys Gly Ser Ser Thr Gly Ala Val Thr Ser Gly
                20                  25                  30

Tyr Tyr Pro Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
                100                 105
```

<210> SEQ ID NO 36
<211> LENGTH: 125
<212> TYPE: PRT
<213> ORGANISM: Artificial Sequence
<220> FEATURE:
<223> OTHER INFORMATION: Description of Artificial Sequence: Synthetic
    VH CD3 (H2C) polypeptide

<400> SEQUENCE: 36

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 37
<211> LENGTH: 105
<212> TYPE: PRT
<213> ORGANISM: Artificial Sequence
<220> FEATURE:
<223> OTHER INFORMATION: Description of Artificial Sequence: Synthetic
    CL CD3 (H2C) polypeptide

<400> SEQUENCE: 37

```
Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
        50                  55                  60
```

```
Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Cys
            100                 105

<210> SEQ ID NO 38
<211> LENGTH: 103
<212> TYPE: PRT
<213> ORGANISM: Artificial Sequence
<220> FEATURE:
<223> OTHER INFORMATION: Description of Artificial Sequence: Synthetic
      CH1 CD3 (H2C) polypeptide

<400> SEQUENCE: 38

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100

<210> SEQ ID NO 39
<211> LENGTH: 232
<212> TYPE: PRT
<213> ORGANISM: Artificial Sequence
<220> FEATURE:
<223> OTHER INFORMATION: Description of Artificial Sequence: Synthetic
      LIGHT CHAIN CD3 (VHCL) polypeptide

<400> SEQUENCE: 39

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
    130                 135                 140
```

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 40
<211> LENGTH: 214
<212> TYPE: PRT
<213> ORGANISM: Artificial Sequence
<220> FEATURE:
<223> OTHER INFORMATION: Description of Artificial Sequence: Synthetic
      HEAVY CHAIN CD3 (VLCH1) polypeptide

<400> SEQUENCE: 40

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 41
<211> LENGTH: 666
<212> TYPE: PRT
<213> ORGANISM: Artificial Sequence
<220> FEATURE:
<223> OTHER INFORMATION: Description of Artificial Sequence: Synthetic
      FAB(MCSP)-FAB(MCSP)-XFAB(CD3) polypeptide

<400> SEQUENCE: 41

| | | | | | | | | | | | | | | |
|---|---|---|---|---|---|---|---|---|---|---|---|---|---|---|
|Glu|Val|Gln|Leu|Gln|Glu|Ser|Gly|Pro|Gly|Leu|Val|Lys|Pro|Ser|Gln|
|1| | | |5| | | | |10| | | | |15| |
|Ser|Leu|Ser|Leu|Thr|Cys|Ser|Val|Thr|Gly|Tyr|Ser|Ile|Thr|Ser|Gly|
| | | |20| | | | |25| | | | |30| | |
|Tyr|Tyr|Trp|Asn|Trp|Ile|Arg|Gln|Phe|Pro|Gly|Asn|Lys|Leu|Glu|Trp|
| | |35| | | | |40| | | | |45| | | |
|Met|Gly|Tyr|Ile|Thr|Tyr|Asp|Gly|Ser|Asn|Asn|Tyr|Asn|Pro|Ser|Leu|
| |50| | | | |55| | | | |60| | | | |
|Lys|Asn|Arg|Ile|Ser|Ile|Thr|Arg|Asp|Thr|Ser|Lys|Asn|Gln|Phe|Phe|
|65| | | | |70| | | | |75| | | | |80|
|Leu|Lys|Leu|Asn|Ser|Val|Thr|Thr|Glu|Asp|Thr|Ala|Thr|Tyr|Tyr|Cys|
| | | | |85| | | | |90| | | | |95| |
|Ala|Asp|Phe|Asp|Tyr|Trp|Gly|Gln|Gly|Thr|Thr|Leu|Thr|Val|Ser|Ser|
| | | |100| | | | |105| | | | |110| | |
|Ala|Ser|Thr|Lys|Gly|Pro|Ser|Val|Phe|Pro|Leu|Ala|Pro|Ser|Ser|Lys|
| | |115| | | | |120| | | | |125| | | |
|Ser|Thr|Ser|Gly|Gly|Thr|Ala|Ala|Leu|Gly|Cys|Leu|Val|Lys|Asp|Tyr|
| |130| | | | |135| | | | |140| | | | |
|Phe|Pro|Glu|Pro|Val|Thr|Val|Ser|Trp|Asn|Ser|Gly|Ala|Leu|Thr|Ser|
|145| | | | |150| | | | |155| | | | |160|
|Gly|Val|His|Thr|Phe|Pro|Ala|Val|Leu|Gln|Ser|Ser|Gly|Leu|Tyr|Ser|
| | | | |165| | | | |170| | | | |175| |
|Leu|Ser|Ser|Val|Val|Thr|Val|Pro|Ser|Ser|Ser|Leu|Gly|Thr|Gln|Thr|
| | | |180| | | | |185| | | | |190| | |
|Tyr|Ile|Cys|Asn|Val|Asn|His|Lys|Pro|Ser|Asn|Thr|Lys|Val|Asp|Lys|
| | |195| | | | |200| | | | |205| | | |
|Lys|Val|Glu|Pro|Lys|Ser|Cys|Asp|Gly|Gly|Gly|Gly|Ser|Gly|Gly|Gly|
| |210| | | | |215| | | | |220| | | | |
|Gly|Ser|Glu|Val|Gln|Leu|Gln|Glu|Ser|Gly|Pro|Gly|Leu|Val|Lys|Pro|
|225| | | | |230| | | | |235| | | | |240|
|Ser|Gln|Ser|Leu|Ser|Leu|Thr|Cys|Ser|Val|Thr|Gly|Tyr|Ser|Ile|Thr|
| | | | |245| | | | |250| | | | |255| |
|Ser|Gly|Tyr|Tyr|Trp|Asn|Trp|Ile|Arg|Gln|Phe|Pro|Gly|Asn|Lys|Leu|
| | | |260| | | | |265| | | | |270| | |
|Glu|Trp|Met|Gly|Tyr|Ile|Thr|Tyr|Asp|Gly|Ser|Asn|Asn|Tyr|Asn|Pro|
| | |275| | | | |280| | | | |285| | | |
|Ser|Leu|Lys|Asn|Arg|Ile|Ser|Ile|Thr|Arg|Asp|Thr|Ser|Lys|Asn|Gln|
| |290| | | | |295| | | | |300| | | | |
|Phe|Phe|Leu|Lys|Leu|Asn|Ser|Val|Thr|Thr|Glu|Asp|Thr|Ala|Thr|Tyr|
|305| | | | |310| | | | |315| | | | |320|
|Tyr|Cys|Ala|Asp|Phe|Asp|Tyr|Trp|Gly|Gln|Gly|Thr|Thr|Leu|Thr|Val|
| | | | |325| | | | |330| | | | |335| |
|Ser|Ser|Ala|Ser|Thr|Lys|Gly|Pro|Ser|Val|Phe|Pro|Leu|Ala|Pro|Ser|
| | | |340| | | | |345| | | | |350| | |
|Ser|Lys|Ser|Thr|Ser|Gly|Gly|Thr|Ala|Ala|Leu|Gly|Cys|Leu|Val|Lys|
| | |355| | | | |360| | | | |365| | | |
|Asp|Tyr|Phe|Pro|Glu|Pro|Val|Thr|Val|Ser|Trp|Asn|Ser|Gly|Ala|Leu|
| |370| | | | |375| | | | |380| | | | |
|Thr|Ser|Gly|Val|His|Thr|Phe|Pro|Ala|Val|Leu|Gln|Ser|Ser|Gly|Leu|
|385| | | | |390| | | | |395| | | | |400|
|Tyr|Ser|Leu|Ser|Ser|Val|Val|Thr|Val|Pro|Ser|Ser|Ser|Leu|Gly|Thr|

```
                    405                 410                 415
Gln Thr Tyr Ile Cys Asn Val Asn His Lys Pro Ser Asn Thr Lys Val
                420                 425                 430

Asp Lys Lys Val Glu Pro Lys Ser Cys Asp Gly Gly Gly Ser Gly
            435                 440                 445

Gly Gly Gly Ser Gln Thr Val Thr Gln Glu Pro Ser Leu Thr Val
450                 455                 460

Ser Pro Gly Gly Thr Val Thr Leu Thr Cys Gly Ser Ser Thr Gly Ala
465                 470                 475                 480

Val Thr Ser Gly Tyr Tyr Pro Asn Trp Val Gln Gln Lys Pro Gly Gln
                485                 490                 495

Ala Pro Arg Gly Leu Ile Gly Thr Lys Phe Leu Ala Pro Gly Thr
            500                 505                 510

Pro Ala Arg Phe Ser Gly Ser Leu Leu Gly Gly Lys Ala Ala Leu Thr
                515                 520                 525

Leu Ser Gly Val Gln Pro Glu Asp Glu Ala Glu Tyr Tyr Cys Ala Leu
                530                 535                 540

Trp Tyr Ser Asn Arg Trp Val Phe Gly Gly Gly Thr Lys Leu Thr Val
545                 550                 555                 560

Leu Ser Ser Ala Ser Thr Lys Gly Pro Ser Val Phe Pro Leu Ala Pro
                565                 570                 575

Ser Ser Lys Ser Thr Ser Gly Gly Thr Ala Ala Leu Gly Cys Leu Val
                580                 585                 590

Lys Asp Tyr Phe Pro Glu Pro Val Thr Val Ser Trp Asn Ser Gly Ala
                595                 600                 605

Leu Thr Ser Gly Val His Thr Phe Pro Ala Val Leu Gln Ser Ser Gly
            610                 615                 620

Leu Tyr Ser Leu Ser Ser Val Val Thr Val Pro Ser Ser Ser Leu Gly
625                 630                 635                 640

Thr Gln Thr Tyr Ile Cys Asn Val Asn His Lys Pro Ser Asn Thr Lys
                645                 650                 655

Val Asp Lys Lys Val Glu Pro Lys Ser Cys
                660                 665

<210> SEQ ID NO 42
<211> LENGTH: 223
<212> TYPE: PRT
<213> ORGANISM: Artificial Sequence
<220> FEATURE:
<223> OTHER INFORMATION: Description of Artificial Sequence: Synthetic
      LIGHT CHAIN CD3 polypeptide

<400> SEQUENCE: 42

Glu Val Gln Leu Val Glu Ser Gly Gly Leu Val Gln Pro Gly Lys
1               5                   10                  15

Ser Leu Lys Leu Ser Cys Glu Ala Ser Gly Phe Thr Phe Ser Gly Tyr
                20                  25                  30

Gly Met His Trp Val Arg Gln Ala Pro Gly Arg Gly Leu Glu Ser Val
            35                  40                  45

Ala Tyr Ile Thr Ser Ser Ser Ile Asn Ile Lys Tyr Ala Asp Ala Val
        50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95
```

```
Ala Arg Phe Asp Trp Asp Lys Asn Tyr Trp Gly Gln Gly Thr Met Val
            100                 105                 110

Thr Val Ser Ser Ala Ser Val Ala Ala Pro Ser Val Phe Ile Phe Pro
        115                 120                 125

Pro Ser Asp Glu Gln Leu Lys Ser Gly Thr Ala Ser Val Val Cys Leu
        130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
        180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
        210                 215                 220

<210> SEQ ID NO 43
<211> LENGTH: 664
<212> TYPE: PRT
<213> ORGANISM: Mus musculus

<400> SEQUENCE: 43

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Leu Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
        180                 185                 190

Asn Val Asn His Lys Pro Ser Asn Thr Lys Val Asp Lys Lys Val Glu
        195                 200                 205

Pro Lys Ser Cys Gly Gly Gly Ser Gly Gly Gly Ser Glu Val
        210                 215                 220

Gln Leu Gln Glu Ser Gly Pro Gly Leu Val Lys Pro Ser Gln Ser Leu
225                 230                 235                 240

Ser Leu Thr Cys Ser Val Thr Gly Tyr Ser Ile Thr Ser Gly Tyr Tyr
                245                 250                 255
```

```
Trp Asn Trp Ile Arg Gln Phe Pro Gly Asn Lys Leu Glu Trp Met Gly
                260                 265                 270

Tyr Ile Thr Tyr Asp Gly Ser Asn Asn Tyr Asn Pro Ser Leu Lys Asn
            275                 280                 285

Arg Ile Ser Ile Thr Arg Asp Thr Ser Lys Asn Gln Phe Phe Leu Lys
        290                 295                 300

Leu Asn Ser Val Thr Glu Asp Thr Ala Thr Tyr Tyr Cys Ala Asp
305                 310                 315                 320

Phe Asp Tyr Trp Gly Gln Gly Thr Thr Leu Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
370                 375                 380

His Thr Phe Pro Ala Val Leu Gln Ser Ser Gly Leu Tyr Ser Leu Ser
385                 390                 395                 400

Ser Val Val Thr Val Pro Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Gly Gly Gly Ser Gly Gly Gly Gly Ser
        435                 440                 445

Glu Val Gln Leu Gln Glu Ser Gly Pro Gly Leu Val Lys Pro Ser Gln
        450                 455                 460

Ser Leu Ser Leu Thr Cys Ser Val Thr Gly Tyr Ser Ile Thr Ser Gly
465                 470                 475                 480

Tyr Tyr Trp Asn Trp Ile Arg Gln Phe Pro Gly Asn Lys Leu Glu Trp
                485                 490                 495

Met Gly Tyr Ile Thr Tyr Asp Gly Ser Asn Asn Tyr Asn Pro Ser Leu
            500                 505                 510

Lys Asn Arg Ile Ser Ile Thr Arg Asp Thr Ser Lys Asn Gln Phe Phe
        515                 520                 525

Leu Lys Leu Asn Ser Val Thr Thr Glu Asp Thr Ala Thr Tyr Tyr Cys
530                 535                 540

Ala Asp Phe Asp Tyr Trp Gly Gln Gly Thr Thr Leu Thr Val Ser Ser
545                 550                 555                 560

Ala Ser Thr Lys Gly Pro Ser Val Phe Pro Leu Ala Pro Ser Ser Lys
                565                 570                 575

Ser Thr Ser Gly Gly Thr Ala Ala Leu Gly Cys Leu Val Lys Asp Tyr
            580                 585                 590

Phe Pro Glu Pro Val Thr Val Ser Trp Asn Ser Gly Ala Leu Thr Ser
        595                 600                 605

Gly Val His Thr Phe Pro Ala Val Leu Gln Ser Ser Gly Leu Tyr Ser
        610                 615                 620

Leu Ser Ser Val Val Thr Val Pro Ser Ser Leu Gly Thr Gln Thr
625                 630                 635                 640

Tyr Ile Cys Asn Val Asn His Lys Pro Ser Asn Thr Lys Val Asp Lys
                645                 650                 655

Lys Val Glu Pro Lys Ser Cys Asp
            660
```

-continued

<210> SEQ ID NO 44
<211> LENGTH: 321
<212> TYPE: DNA
<213> ORGANISM: Artificial Sequence
<220> FEATURE:
<223> OTHER INFORMATION: Description of Artificial Sequence: Synthetic
      VL MCSP DNA polynucleotide

<400> SEQUENCE: 44
gatattgtgc tcacacagtc tccatcctcc ctgtctgcct ctctgggaga cagagtcacc      60
atcagttgca gtgcaagtca gggcattaga aattatttaa actggtatca gcagagacca     120
gatggaactg ttaaactcct gatctattac acatcaagtt tacactcagg agtcccatca     180
aggttcagtg gcagtgggtc tgggacagat tattctctca ccatcagcaa cctggaacct     240
gaagatattg ccacttacta ttgtcagcag tatagtaagc ttccttggac gttcggtgga     300
ggcaccaagc tggaaatcaa a                                              321

<210> SEQ ID NO 45
<211> LENGTH: 336
<212> TYPE: DNA
<213> ORGANISM: Artificial Sequence
<220> FEATURE:
<223> OTHER INFORMATION: Description of Artificial Sequence: Synthetic
      VH MCSP DNA polynucleotide

<400> SEQUENCE: 45
gaggtgcagc tgcaggaatc tggccctggc ctggtcaagc caagccagag tctgagcctg      60
acctgcagcg tgaccggcta cagcattacc agcggctact actggaactg gattcggcag     120
ttccccggca ataagctgga atggatgggc tacatcacct acgacggcag caacaactac     180
aaccccagcc tgaagaaccg gatcagcatc acccgggaca ccagcaagaa ccagttcttc     240
ctgaagctga acagcgtgac caccgaggac accgccacat actattgcgc cgacttcgac     300
tactggggcc agggcaccac cctgaccgtg tccagc                              336

<210> SEQ ID NO 46
<211> LENGTH: 324
<212> TYPE: DNA
<213> ORGANISM: Artificial Sequence
<220> FEATURE:
<223> OTHER INFORMATION: Description of Artificial Sequence: Synthetic
      CL MCSP DNA polynucleotide

<400> SEQUENCE: 46
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                           324

<210> SEQ ID NO 47
<211> LENGTH: 312
<212> TYPE: DNA
<213> ORGANISM: Artificial Sequence
<220> FEATURE:
<223> OTHER INFORMATION: Description of Artificial Sequence: Synthetic
      CH1 MCSP DNA polynucleotide

<400> SEQUENCE: 47

```
gccagcacaa agggccctag cgtgttccct ctggccccca gcagcaagag cacaagcggc    60
ggaacagccg ccctgggctg cctcgtgaag gactacttcc ccgagccgt gacagtgtct    120 tggaacagcg gagccctgac aagcggcgtg cacaccttcc ctgccgtgct gcagagcagc    180
ggcctgtact ccctgagcag cgtggtcacc gtgcctagca gcagcctggg cacccagacc    240
tacatctgca acgtgaacca caagcccagc aacaccaaag tggacaagaa ggtggagccc    300
aagagctgtg at                                                       312

<210> SEQ ID NO 48
<211> LENGTH: 711
<212> TYPE: DNA
<213> ORGANISM: Artificial Sequence
<220> FEATURE:
<223> OTHER INFORMATION: Description of Artificial Sequence: Synthetic
      LIGHT CHAIN MCSP DNA polynucleotide

<400> SEQUENCE: 48
atggacatga gggtccccgc tcagctcctg ggcctcctgc tgctctggtt cccaggtgcc    60
aggtgtgata ttgtgctcac acagtctcca tcctccctgt ctgcctctct gggagacaga    120
gtcaccatca gttgcagtgc aagtcagggc attagaaatt atttaaactg gtatcagcag    180
agaccagatg gaactgttaa actcctgatc tattacacat caagtttaca ctcaggagtc    240
ccatcaaggt tcagtggcag tgggtctggg acagattatt ctctcaccat cagcaacctg    300
gaacctgaag atattgccac ttactattgt cagcagtata gtaagcttcc ttggacgttc    360
ggtggaggca ccaagctgga aatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g            711

<210> SEQ ID NO 49
<211> LENGTH: 705
<212> TYPE: DNA
<213> ORGANISM: Artificial Sequence
<220> FEATURE:
<223> OTHER INFORMATION: Description of Artificial Sequence: Synthetic
      HEAVY CHAIN MCSP DNA polynucleotide

<400> SEQUENCE: 49
atgggatgga gctgtatcat cctcttcttg gtagcaacag ctaccggtgt gcattcggag    60
gtgcagctgc aggaatctgg ccctggcctg gtcaagccaa gccagagtct gagcctgacc    120
tgcagcgtga ccggctacag cattaccagc ggctactact ggaactggat cggcagttc    180 cccggcaata gctggaatg gatgggctac atcacctacg acggcagcaa caactacaac    240
cccagcctga agaaccggat cagcatcacc cgggacacca gcaagaacca gttcttcctg    300
aagctgaaca gcgtgaccac cgaggacacc gccacatact attgcgccga cttcgactac    360
tggggccagg gcaccaccct gaccgtgtcc agcgccagca caagggccc tagcgtgttc    420 cctctggccc ccagcagcaa gagcacaagc ggcggaacag ccgccctggg ctgcctcgtg    480
aaggactact ccccgagcc cgtgacagtg tcttggaaca gcggagccct gacaagcggc    540
gtgcacacct tccctgccgt gctgcagagc agcggcctgt actccctgag cagcgtggtc    600
```

| | |
|---|---|
| accgtgccta gcagcagcct gggcacccag acctacatct gcaacgtgaa ccacaagccc | 660 |
| agcaacacca aagtggacaa gaaggtggag cccaagagct gtgat | 705 |

<210> SEQ ID NO 50
<211> LENGTH: 327
<212> TYPE: DNA
<213> ORGANISM: Artificial Sequence
<220> FEATURE:
<223> OTHER INFORMATION: Description of Artificial Sequence: Synthetic
      VL CD3 DNA polynucleotide

<400> SEQUENCE: 50

| | |
|---|---|
| gacatccaga tgacccagag cccctctagc ctgagcgcca gcgtgggcga cagagtgacc | 60 |
| atcacctgtc gggccagcca ggacatcaga aactacctga actggtatca gcagaagccc | 120 |
| ggcaaggccc ccaagctgct gatctactac acctctagac tggaaagcgg cgtgcccagc | 180 |
| cggtttagcg gcagcggctc cggcaccgac tacaccctga ccatcagcag cctgcagccc | 240 |
| gaggacttcg ccacctacta ctgccagcag ggcaacacac tcccctggac cttcggccag | 300 |
| ggcaccaagg tggagatcaa gtccagc | 327 |

<210> SEQ ID NO 51
<211> LENGTH: 366
<212> TYPE: DNA
<213> ORGANISM: Artificial Sequence
<220> FEATURE:
<223> OTHER INFORMATION: Description of Artificial Sequence: Synthetic
      VH CD3 DNA polynucleotide

<400> SEQUENCE: 51

| | |
|---|---|
| gaggtgcagc tggtcgagag cggaggcggc ctggtgcagc ctggcggcag cctgagactg | 60 |
| agctgcgccg ccagcggcta cagcttcacc ggctacacca tgaactgggt ccggcaggca | 120 |
| cctggcaagg gactggaatg ggtggccctg atcaacccct acaagggcgt gagcacctac | 180 |
| aaccagaagt tcaaggaccg gttcaccatc agcgtggaca gagcaagaa caccgcctat | 240 |
| ctgcagatga acagcctgcg ggccgaggac accgccgtgt actactgcgc cagaagcggc | 300 |
| tactacggcg acagcgactg gtacttcgac gtgtggggcc agggcaccct cgtgaccgtg | 360 |
| tctagc | 366 |

<210> SEQ ID NO 52
<211> LENGTH: 318
<212> TYPE: DNA
<213> ORGANISM: Artificial Sequence
<220> FEATURE:
<223> OTHER INFORMATION: Description of Artificial Sequence: Synthetic
      CL CD3 DNA polynucleotide

<400> SEQUENCE: 52

| | |
|---|---|
| gtggctgcac catctgtctt catcttcccg ccatctgatg agcagttgaa atctggaact | 60 |
| gcctctgttg tgtgcctgct gaataacttc tatcccagag aggccaaagt acagtggaag | 120 |
| gtggataacg ccctccaatc gggtaactcc caggagagtg tcacagagca ggacagcaag | 180 |
| gacagcacct acagcctcag cagcaccctg acgctgagca agcagacta cgagaaacac | 240 |
| aaagtctacg cctgcgaagt cacccatcag ggcctgagct cgcccgtcac aaagagcttc | 300 |
| aacaggggag agtgttga | 318 |

<210> SEQ ID NO 53
<211> LENGTH: 306
<212> TYPE: DNA

```
<213> ORGANISM: Artificial Sequence
<220> FEATURE:
<223> OTHER INFORMATION: Description of Artificial Sequence: Synthetic
      CH1 CD3 DNA polynucleotide

<400> SEQUENCE: 53
accaagggcc ctccgtgtt ccccctggcc cccagcagca agagcaccag cggcggcaca    60
gccgccctcg gctgcctggt caaggactac ttccccgagc ccgtgaccgt gtcctggaac   120
agcggagccc tgacctccgg cgtgcacacc ttccccgccg tgctgcagag cagcggcctg   180
tacagcctgt ccagcgtggt caccgtgccc tccagcagcc tgggcaccca gacctacatc   240
tgcaacgtga accacaagcc cagcaatacc aaggtggaca gaaaggtgga gcccaagagc   300
tgctga                                                              306

<210> SEQ ID NO 54
<211> LENGTH: 747
<212> TYPE: DNA
<213> ORGANISM: Artificial Sequence
<220> FEATURE:
<223> OTHER INFORMATION: Description of Artificial Sequence: Synthetic
      LIGHT CHAIN CD3 (VHCL) DNA polynucleotide

<400> SEQUENCE: 54
atgggatgga gctgtatcat cctcttcttg gtagcaacag ctaccggtgt gcattccgag    60
gtgcagctgg tcgagagcgg aggcggcctg gtgcagcctg gcggcagcct gagactgagc   120
tgcgccgcca gcggctacag cttcaccggc tacaccatga actgggtccg gcaggcacct   180
ggcaagggac tggaatgggt ggccctgatc aaccctaca agggcgtgag cacctacaac   240
cagaagttca aggaccggtt caccatcagc gtggacaaga gcaagaacac cgcctatctg   300
cagatgaaca gcctgcgggc cgaggacacc gccgtgtact actgcgccag aagcggctac   360
tacggcgaca cgactggta cttcgacgtg tggggccagg gcaccctcgt gaccgtgtct   420
agcgctagcg tggctgcacc atctgtcttc atcttcccgc catctgatga gcagttgaaa   480
tctggaactg cctctgttgt gtgcctgctg aataacttct atcccagaga ggccaaagta   540
cagtggaagg tggataacgc cctccaatcg ggtaactccc aggagagtgt cacagagcag   600
gacagcaagg acagcaccta cagcctcagc agcaccctga cgctgagcaa agcagactac   660
gagaaacaca aagtctacgc ctgcgaagtc acccatcagg gcctgagctc gcccgtcaca   720
aagagcttca acaggggaga gtgttga                                       747

<210> SEQ ID NO 55
<211> LENGTH: 639
<212> TYPE: DNA
<213> ORGANISM: Artificial Sequence
<220> FEATURE:
<223> OTHER INFORMATION: Description of Artificial Sequence: Synthetic
      HEAVY CHAIN (VLCH1) CD3 DNA polynucleotide

<400> SEQUENCE: 55
gacatccaga tgacccagag ccctctagc ctgagcgcca gcgtgggcga cagagtgacc    60
atcacctgtc gggccagcca ggacatcaga aactacctga actggtatca gcagaagccc   120
ggcaaggccc ccaagctgct gatctactac acctctagac tggaaagcgg cgtgcccagc   180
cggtttagcg gcagcggctc cggcaccgac tacaccctga ccatcagcag cctgcagccc   240
gaggacttcg ccacctacta ctgccagcag ggcaacacac tccccctggac cttcggccag   300 ggcaccaagg tggagatcaa gtccagcgct agcaccaagg gccctccgt gttccccctg   360
```

```
gcccccagca gcaagagcac cagcggcggc acagccgccc tcggctgcct ggtcaaggac    420
tacttccccg agcccgtgac cgtgtcctgg aacagcggag ccctgacctc cggcgtgcac    480
accttccccg ccgtgctgca gagcagcggc ctgtacagcc tgtccagcgt ggtcaccgtg    540
ccctccagca gcctgggcac ccagacctac atctgcaacg tgaaccacaa gcccagcaat    600
accaaggtgg acaagaaggt ggagcccaag agctgctga                           639
```

<210> SEQ ID NO 56
<211> LENGTH: 333
<212> TYPE: DNA
<213> ORGANISM: Artificial Sequence
<220> FEATURE:
<223> OTHER INFORMATION: Description of Artificial Sequence: Synthetic
      VL CD3 DNA polynucleotide

<400> SEQUENCE: 56

```
cagaccgtgg tgacacagga acccagcctg accgtctccc ctggcggcac cgtgaccctg     60
acctgtggaa gcagcacagg cgccgtgacc agcggctact accccaactg ggtgcagcag    120
aagcccggcc aggcccctag aggactgatc ggcggcacca gtttctggc ccctggcacc    180 cccgccagat tctctggctc tctgctgggc ggcaaggccg ccctgacact gtctggcgtg    240
cagcctgagg acgaggccga gtactactgc gccctgtggt acagcaacag atgggtgttc    300
ggcggaggca ccaagctgac cgtgctgagc agc                                 333
```

<210> SEQ ID NO 57
<211> LENGTH: 375
<212> TYPE: DNA
<213> ORGANISM: Artificial Sequence
<220> FEATURE:
<223> OTHER INFORMATION: Description of Artificial Sequence: Synthetic
      VH CD3 DNA polynucleotide

<400> SEQUENCE: 57

```
gaggtgcagc tggtggaaag cggcggagga ctggtgcagc ctggcggaag cctgaagctg     60
tcttgcgccg ccagcggctt caccttcaac aaatacgcca tgaactgggt gcgccaggcc    120
cctggcaagg gactggaatg ggtggcccgg atcagaagca agtacaacaa ctacgccacc    180
tactacgccg acagcgtgaa ggaccggttc accatcagcc gggacgacag caagaacacc    240
gcctacctgc agatgaacaa cctgaaaacc gaggacaccg ccgtgtacta ctgcgtgcgg    300
cacggcaact tcggcaacag ctacatcagc tactgggcct actggggaca gggcaccctg    360
gtgacagtgt ccagc                                                     375
```

<210> SEQ ID NO 58
<211> LENGTH: 318
<212> TYPE: DNA
<213> ORGANISM: Artificial Sequence
<220> FEATURE:
<223> OTHER INFORMATION: Description of Artificial Sequence: Synthetic
      CL CD3 DNA polynucleotide

<400> SEQUENCE: 58

```
gtggctgcac catctgtctt catcttcccg ccatctgatg agcagttgaa atctggaact     60
gcctctgttg tgtgcctgct gaataacttc tatcccagag aggccaaagt acagtggaag    120
gtggataacg ccctccaatc gggtaactcc caggagagtg tcacagagca ggacagcaag    180
gacagcacct acagcctcag cagcaccctg acgctgagca agcagactac gagaaacac    240 aaagtctacg cctgcgaagt cacccatcag ggcctgagct cgcccgtcac aaagagcttc    300
```

```
                                                    aacaggggag agtgttga                                                318
```

<210> SEQ ID NO 59
<211> LENGTH: 306
<212> TYPE: DNA
<213> ORGANISM: Artificial Sequence
<220> FEATURE:
<223> OTHER INFORMATION: Description of Artificial Sequence: Synthetic
      CH1 CD3 DNA polynucleotide

<400> SEQUENCE: 59

```
accaagggcc cctccgtgtt ccccctggcc cccagcagca agagcaccag cggcggcaca      60
gccgccctcg gctgcctggt caaggactac ttccccgagc ccgtgaccgt gtcctggaac     120
agcggagccc tgacctccgg cgtgcacacc ttccccgccg tgctgcagag cagcggcctg     180
tacagcctgt ccagcgtggt caccgtgccc tccagcagcc tgggcaccca gacctacatc     240
tgcaacgtga accacaagcc cagcaatacc aaggtggaca gaaggtgga gcccaagagc     300
tgctga                                                               306
```

<210> SEQ ID NO 60
<211> LENGTH: 756
<212> TYPE: DNA
<213> ORGANISM: Artificial Sequence
<220> FEATURE:
<223> OTHER INFORMATION: Description of Artificial Sequence: Synthetic
      LIGHT CHAIN CD3 (VHCL) DNA polynucleotide

<400> SEQUENCE: 60

```
atgggatgga gctgtatcat cctcttcttg gtagcaacag ctaccggtgt gcattccgag      60
gtgcagctgg tggaaagcgg cggaggactg gtgcagcctg gcggaagcct gaagctgtct     120
tgcgccgcca gcggcttcac cttcaacaaa tacgccatga actgggtgcg ccaggccct      180
ggcaagggac tggaatgggt ggcccggatc agaagcaagt acaacaacta cgccacctac     240
tacgccgaca gcgtgaagga ccggttcacc atcagccggg acgacagcaa gaacaccgcc     300
tacctgcaga tgaacaacct gaaaaccgag gacaccgccg tgtactactg cgtgcggcac     360
ggcaacttcg gcaacagcta catcagctac tgggcctact ggggacaggg caccctggtg     420
acagtgtcca gcgctagcgt ggctgcacca tctgtcttca tcttcccgcc atctgatgag     480
cagttgaaat ctggaactgc ctctgttgtg tgcctgctga ataacttcta tcccagagag     540
gccaaagtac agtggaaggt ggataacgcc ctccaatcgg gtaactccca ggagagtgtc     600
acagagcagg acagcaagga cagcacctac agcctcagca gcaccctgac gctgagcaaa     660
gcagactacg agaaacacaa agtctacgcc tgcgaagtca cccatcaggg cctgagctcg     720
cccgtcacaa agagcttcaa caggggagag tgttga                              756
```

<210> SEQ ID NO 61
<211> LENGTH: 645
<212> TYPE: DNA
<213> ORGANISM: Artificial Sequence
<220> FEATURE:
<223> OTHER INFORMATION: Description of Artificial Sequence: Synthetic
      HEAVY CHAIN CD3 (VLCH1) DNA polynucleotide

<400> SEQUENCE: 61

```
cagaccgtgg tgacacagga acccagcctg accgtctccc ctggcggcac cgtgaccctg      60
acctgtggaa gcagcacagg cgccgtgacc agcggctact accccaactg ggtgcagcag     120
aagcccggcc aggcccctag aggactgatc ggcggcacca agtttctggc ccctggcacc     180
```

```
cccgccagat tctctggctc tctgctgggc ggcaaggccg ccctgacact gtctggcgtg    240
cagcctgagg acgaggccga gtactactgc gccctgtggt acagcaacag atgggtgttc    300
ggcggaggca ccaagctgac cgtgctgagc agcgctagcc caagggccc ctccgtgttc    360 cccctggccc ccagcagcaa gagcaccagc ggcggcacag ccgccctcgg ctgcctggtc    420
aaggactact cccccgagcc cgtgaccgtg tcctggaaca gcggagccct gacctccggc    480
gtgcacacct tccccgccgt gctgcagagc agcggcctgt acagcctgtc cagcgtggtc    540
accgtgccct ccagcagcct gggcacccag acctacatct gcaacgtgaa ccacaagccc    600
agcaatacca aggtggacaa gaaggtggag cccaagagct gctga                    645

<210> SEQ ID NO 62
<211> LENGTH: 1056
<212> TYPE: DNA
<213> ORGANISM: Artificial Sequence
<220> FEATURE:
<223> OTHER INFORMATION: Description of Artificial Sequence: Synthetic
      FAB(MCSP)-XFAB (CD3) DNA polynucleotide

<400> SEQUENCE: 62
atgggatgga gctgtatcat cctcttcttg gtagcaacag ctaccggtgt gcattcggag     60
gtgcagctgc aggaaagcgg ccctggcctg gtgaaaccca gccagagcct gagcctgacc    120
tgcagcgtga ccggctacag catcaccagc ggctactact ggaactggat cagacagttc    180
cccggcaaca agctggaatg gatgggctac atcacctacg acggcagcaa caactacaac    240
cccagcctga gaacagaat cagcatcacc cgggacacca gcaagaacca gttcttcctg    300
aagctgaaca gcgtgaccac cgaggacacc gccacctact actgcgccga cttcgactac    360
tggggccagg gcaccaccct gaccgtgtcc tccgctagca ccaagggacc cagcgtgttc    420
cccctggcac ccagcagcaa gagcacatct ggcggaacag ccgctctggg ctgtctggtg    480
aaagactact cccccgagcc cgtgaccgtg tcttggaact ctggcgccct gaccagcggc    540
gtgcacacct ttccagccgt gctgcagagc agcggcctgt actccctgag cagcgtggtg    600
acagtgccca gcagcagcct gggaacccag acctacatct gcaacgtgaa ccacaagccc    660
agcaacacca aggtggacaa gaaggtggaa cccaagagct gcgatggcgg aggaggctcc    720
ggaggcggag gctctgatat ccagatgacc cagagcccca gctctctgag cgccagcgtg    780
ggcgacagag tgaccatcac ctgtcgggcc agccaggaca tcagaaacta cctgaactgg    840
tatcagcaga gcccggcaa ggcccccaag ctgctgatct actacaccag cagactggaa    900
agcggcgtgc cctccagatt tccggcagc ggctccggca ccgactacac cctgaccatc    960
agcagcctgc agcccgagga tttcgccaca tattactgcc agcagggcaa tccctgccc   1020 tggaccttcg gacagggcac aaaagtggaa atcaag                             1056

<210> SEQ ID NO 63
<211> LENGTH: 2052
<212> TYPE: DNA
<213> ORGANISM: Artificial Sequence
<220> FEATURE:
<223> OTHER INFORMATION: Description of Artificial Sequence: Synthetic
      FAB(MCSP)-FAB(MCSP)-XFAB (CD3) DNA polynucleotide

<400> SEQUENCE: 63
atgggatgga gctgtatcat cctcttcttg gtagcaacag ctaccggtgt gcattcggag     60
gtgcagctgc aggaatctgg ccctggcctg gtcaagccaa gccagagtct gagcctgacc    120
tgcagcgtga ccggctacag cattaccagc ggctactact ggaactggat cggcagttc    180
```

```
cccggcaata agctggaatg gatgggctac atcacctacg acggcagcaa caactacaac    240
cccagcctga agaaccggat cagcatcacc cgggacacca gcaagaacca gttcttcctg    300
aagctgaaca gcgtgaccac cgaggacacc gccacatact attgcgccga cttcgactac    360
tggggccagg gcaccaccct gaccgtgtcc agcgccagca caagggccc tagcgtgttc    420 cctctggccc ccagcagcaa gagcacaagc ggcggaacag ccgccctggg ctgcctcgtg    480
aaggactact ccccgagcc cgtgacagtg tcttggaaca gcggagccct gacaagcggc    540
gtgcacacct ccctgccgt gctgcagagc agcggcctgt actccctgag cagcgtggtc    600
accgtgccta gcagcagcct gggcacccag acctacatct gcaacgtgaa ccacaagccc    660
agcaacacca agtggacaa gaaggtggag cccaagagct gtgatggcgg aggagggtcc    720
ggaggcggtg gctccgaggt gcagctgcag gaatctggcc ctggcctggt caagccaagc    780
cagagtctga gcctgacctg cagcgtgacc ggctacagca ttaccagcgg ctactactgg    840
aactggattc ggcagttccc cggcaataag ctggaatgga tgggctacat cacctacgac    900
ggcagcaaca actacaaccc cagcctgaag aaccggatca gcatcacccg ggacaccagc    960
aagaaccagt tcttcctgaa gctgaacagc gtgaccaccg aggacaccgc cacatactat   1020
tgcgccgact tcgactactg ggccagggc accaccctga ccgtgtccag cgccagcaca   1080
aagggcccta gcgtgttccc tctggccccc agcagcaaga gcacaagcgg cggaacagcc   1140
gccctgggct gcctcgtgaa ggactacttc cccgagcccg tgacagtgtc ttggaacagc   1200
ggagccctga caagcggcgt gcacaccttc cctgccgtgc tgcagagcag cggcctgtac   1260
tccctgagca gcgtggtcac cgtgcctagc agcagcctgg gcacccagac ctacatctgc   1320
aacgtgaacc acaagcccag caacaccaaa gtggacaaga aggtggagcc caagagctgt   1380
gatggcggag gagggtccgg cggcgtgga tccgacatcc agatgaccca gagcccctct   1440
agcctgagcg ccagcgtggg cgacagagtg accatcacct gtcgggccag ccaggacatc   1500
agaaactacc tgaactggta tcagcagaag cccggcaagg cccccaagct gctgatctac   1560
tacacctcta actggaaag cggcgtgccc agccggttta gcggcagcgg ctccggcacc   1620
gactacaccc tgaccatcag cagcctgcag cccgaggact cgccaccta ctactgccag   1680 cagggcaaca cactcccctg gaccttcggc cagggcacca aggtggagat caagtccagc   1740
gctagcacca agggcccctc cgtgttcccc ctggccccca gcagcaagag caccagcggc   1800
ggcacagccg ccctcggctg cctggtcaag gactacttcc ccgagcccgt gaccgtgtcc   1860
tggaacagcg gagccctgac ctccggcgtg cacaccttcc ccgccgtgct gcagagcagc   1920
ggcctgtaca gcctgtccag cgtggtcacc gtgccctcca gcagcctggg cacccagacc   1980
tacatctgca acgtgaacca caagcccagc aataccaagg tggacaagaa ggtggagccc   2040
aagagctgct ga                                                      2052
```

<210> SEQ ID NO 64
<211> LENGTH: 2049
<212> TYPE: DNA
<213> ORGANISM: Artificial Sequence
<220> FEATURE:
<223> OTHER INFORMATION: Description of Artificial Sequence: Synthetic
      FAB(MCSP)-XFAB(CD3)-FAB(MCSP) polynucleotide

<400> SEQUENCE: 64

```
atgggatgga gctgtatcat cctcttcttg gtagcaacag ctaccggtgt gcattcggag     60
gtgcagctgc aggaaagcgg ccctggcctg gtgaaaccca gccagagcct gagcctgacc    120
```

```
tgcagcgtga ccggctacag catcaccagc ggctactact ggaactggat cagacagttc      180
cccggcaaca agctggaatg gatgggctac atcacctacg acggcagcaa caactacaac      240
cccagcctga agaacagaat cagcatcacc cgggacacca gcaagaacca gttcttcctg      300
aagctgaaca gcgtgaccac cgaggacacc gccacctact actgcgccga cttcgactac      360
tggggccagg gcaccaccct gaccgtgtcc tccgctagca ccaagggacc cagcgtgttc      420
cccctggcac ccagcagcaa gagcacatct ggcggaacag ccgctctggg ctgtctggtg      480
aaagactact cccccgagcc cgtgaccgtg tcttggaact ctggcgccct gaccagcggc      540
gtgcacacct tccagccgt gctgcagagc agcggcctgt actccctgag cagcgtggtg      600
acagtgccca gcagcagcct gggaacccag acctacatct gcaacgtgaa ccacaagccc      660
agcaacacca aggtggacaa gaaggtggaa cccaagagct gcgatggcgg aggaggctcc      720
ggaggcggag gctctgatat ccagatgacc cagagcccca gctctctgag cgccagcgtg      780
ggcgacagag tgaccatcac ctgtcgggcc agccaggaca tcagaaacta cctgaactgg      840
tatcagcaga agcccggcaa ggcccccaag ctgctgatct actacaccag cagactggaa      900
agcggcgtgc cctccagatt ttccggcagc ggctccggca ccgactacac cctgaccatc      960
agcagcctgc agcccgagga tttcgccaca tattactgcc agcagggcaa taccctgccc     1020
tggaccttcg gacagggcac aaaagtggaa atcaagagca cgcttccac caaaggccct     1080 tccgtgtttc ctctggctcc tagctccaag tccacctctg gaggcaccgc tgctctcgga     1140
tgcctcgtga aggattattt tcctgagcct gtgacagtgt cctggaatag cggagcactg     1200
acctctggag tgcatacttt ccccgctgtg ctgcagtcct ctggactgta cagcctgagc     1260
agcgtggtga cagtgcccag cagcagcctg ggcacccaga cctacatctg caacgtgaac     1320
cacaagccca gcaacaccaa ggtggacaag aaggtggaac ccaagtcttg tggcggaggc     1380
ggatccggcg gaggggatc tgaggtgcag ctgcaggaaa gcggccctgg cctggtgaaa     1440
cccagccaga gcctgagcct gacctgcagc gtgaccggct acagcatcac cagcggctac     1500
tactggaact ggatcagaca gttccccggc aacaagctgg aatggatggg ctacatcacc     1560
tacgacggca gcaacaacta caaccccagc ctgaagaaca gaatcagcat cacccgggac     1620
accagcaaga accagttctt cctgaagctg aacagcgtga ccaccgagga caccgccacc     1680
tactactgcg ccgacttcga ctactgggc cagggcacca ccctgaccgt gtcctccgcc     1740
tctaccaagg gcccagcgt gttccccctg gcacccagca gcaagagcac atctggcgga     1800
acagccgctc tgggctgtct ggtgaaagac tacttccccg agcccgtgac cgtgtcttgg     1860
aactctggcg ccctgaccag cggcgtgcac acctttccag ccgtgctgca gagcagcggc     1920
ctgtactccc tgtcctccgt ggtcaccgtg ccctctagct ccctgggaac acagacatat     1980
atctgtaatg tcaatcacaa gccttccaac accaaagtcg ataagaaagt cgagcccaag     2040
agctgctga                                                            2049
```

<210> SEQ ID NO 65
<211> LENGTH: 2058
<212> TYPE: DNA
<213> ORGANISM: Artificial Sequence
<220> FEATURE:
<223> OTHER INFORMATION: Description of Artificial Sequence: Synthetic
      FAB (MCSP)-FAB(MCSP)-XFAB (CD3) DNA polynucleotide

<400> SEQUENCE: 65

```
atgggatgga gctgtatcat cctcttcttg gtagcaacag ctaccggtgt gcattcggag       60
```

```
gtgcagctgc aggaatctgg ccctggcctg gtcaagccaa gccagagtct gagcctgacc    120
tgcagcgtga ccggctacag cattaccagc ggctactact ggaactggat tcggcagttc    180
cccggcaata agctggaatg gatgggctac atcacctacg acggcagcaa caactacaac    240
cccagcctga gaaccggatc agcatcaccc gggacaccag caagaaccag gttcttcctg    300
aagctgaaca gcgtgaccac cgaggacacc gccacatact attgcgccga cttcgactac    360
tggggccagg gcaccaccct gaccgtgtcc agcgccagca aagggcccta gcgtgttc     420
cctctggccc ccagcagcaa gagcacaagc ggcggaacag ccgccctggg ctgcctcgtg    480
aaggactact cccccgagcc cgtgacagtg tcttggaaca gcggagccct gacaagcggc    540
gtgcacacct ccctgccgt gctgcagagc agcggcctgt actccctgag cagcgtggtc    600
accgtgccta gcagcagcct gggcacccag acctacatct gcaacgtgaa ccacaagccc    660
agcaacacca agtggacaa gaaggtggag cccaagagct gtgatggcgg aggagggtcc    720
ggaggcggtg gctccgaggt gcagctgcag gaatctggcc ctggcctggt caagccaagc    780
cagagtctga gcctgacctg cagcgtgacc ggctacagca ttaccagcgg ctactactgg    840
aactggattc ggcagttccc cggcaataag ctggaatgga tgggctacat cacctacgac    900
ggcagcaaca actacaaccc cagcctgaag aaccggatca gcatcacccg ggacaccagc    960
aagaaccagt tcttcctgaa gctgaacagc gtgaccaccg aggacaccgc cacatactat   1020
tgcgccgact tcgactactg gggccagggc accaccctga ccgtgtccag cgccagcaca   1080
aagggcccta gcgtgttccc tctggccccc agcagcaaga gcacaagcgg cggaacagcc   1140
gccctgggct gcctcgtgaa ggactacttc cccgagcccg tgacagtgtc ttggaacagc   1200
ggagccctga caagcggcgt gcacaccttc cctgccgtgc tgcagagcag cggcctgtac   1260
tccctgagca gcgtggtcac cgtgcctagc agcagcctgg gcacccagac ctacatctgc   1320
aacgtgaacc acaagcccag caacaccaaa gtggacaaga aggtggagcc caagagctgt   1380
gatggcggag gagggtccgg cggcggtgga tcccagaccg tggtgacaca ggaacccagc   1440
ctgaccgtct cccctggcgg caccgtgacc ctgacctgtg aagcagcac aggcgccgtg   1500
accagcggct actaccccaa ctgggtgcag cagaagcccg gccaggcccc tagaggactg   1560
atcggcggca ccaagtttct ggcccctggc accccgcca gattctctgg ctctctgctg   1620
ggcggcaagg ccgccctgac actgtctggc gtgcagcctg aggacgaggc cgagtactac   1680
tgcgccctgt ggtacagcaa cagatggggtg ttcggcggag gcaccaagct gaccgtgctg   1740
agcagcgcta gcaccaaggg cccctccgtg ttcccctgg ccccagcag caagagcacc   1800
agcggcggca gccgccct cggctgcctg gtcaaggact acttccccga gcccgtgacc   1860
gtgtcctgga cagcggagc cctgacctcc ggcgtgcaca ccttccccgc cgtgctgcag   1920
agcagcggcc tgtacagcct gtccagcgtg gtcaccgtgc cctccagcag cctgggcacc   1980
cagacctaca tctgcaacgt gaaccacaag cccagcaata ccaaggtgga caagaaggtg   2040
gagcccaaga gctgctga                                                  2058
```

<210> SEQ ID NO 66
<211> LENGTH: 729
<212> TYPE: DNA
<213> ORGANISM: Artificial Sequence
<220> FEATURE:
<223> OTHER INFORMATION: Description of Artificial Sequence: Synthetic
      LIGHT CHAIN CD3 (VHCL) DNA polynucleotide

<400> SEQUENCE: 66

```
atgggatgga gctgtatcat cctcttcttg gtagcaacag ctaccggtgt gcattccgag    60
gtgcagctgg tggaaagcgg cggaggcctg gtgcagcccg gcaagagcct gaagctgagc   120
tgcgaggcca gcggcttcac cttcagcggc tacggcatgc actgggtgag acaggcccct   180
ggcagaggac tggaaagcgt ggcctacatc accagcagca gcatcaacat taagtacgcc   240
gacgccgtga agggccggtt caccgtgtcc agggataacg ccaagaacct gctgttcctg   300
cagatgaaca tcctgaagtc cgaggacacc gctatgtatt actgcgccag attcgactgg   360
gacaagaact actggggcca gggcaccatg gtcacagtgt ctagcgctag cgtggctgca   420
ccatctgtct tcatcttccc gccatctgat gagcagttga aatctggaac tgcctctgtt   480
gtgtgcctgc tgaataactt ctatcccaga gaggccaaag tacagtggaa ggtggataac   540
gcccctccaat cggtaactc ccaggagagt gtcacagagc aggacagcaa ggacagcacc   600
tacagcctca gcagcaccct gacgctgagc aaagcagact acgagaaaca caaagtctac   660
gcctgcgaag tcacccatca gggcctgagc tcgcccgtca caaagagctt caacagggga   720
gagtgttga                                                            729
```

<210> SEQ ID NO 67
<211> LENGTH: 2052
<212> TYPE: DNA
<213> ORGANISM: Artificial Sequence
<220> FEATURE:
<223> OTHER INFORMATION: Description of Artificial Sequence: Synthetic
      XFAB (CD3)-FAB(MCSP)-FAB(MCSP) DNA polynucleotide

<400> SEQUENCE: 67

```
atgggatgga gctgtatcat cctcttcttg gtagcaacag ctaccggtgt gcattccgac    60
atccagatga cccagagccc cagcagcctg cctgccagcc tgggcgacag agtgaccatc   120
aactgccagg ccagccagga catcagcaac tacctgaact ggtatcagca gaagcctggc   180
aaggccccca gctgctgat ctactacacc aacaagctgg ccgacggcgt gcccagcaga   240
ttcagcggca gcggctccgg cagagacagc agcttcacca tctccagcct ggaaagcgag   300
gacatcggca gctactactg ccagcagtac tacaactacc ctggaccctt cggccctggc   360
accaagctgg aaatcaagag cagcgcttcc accaaaggcc cttccgtgtt cctctggct   420
cctagctcca gtccaccctc tggaggcacc gctgctctcg gatgcctcgt gaaggattat   480
tttcctgagc ctgtgacagt gtcctggaat agcggagcac tgacctctgg agtgcatact   540
ttccccgctg tgctgcagtc ctctggactg tacagcctga gcagcgtggt gacagtgccc   600
agcagcagcc tgggcaccca gacctacatc tgcaacgtga accacaagcc cagcaacacc   660
aaggtggaca gaaggtgga acccaagtct tgtggcggag gcggatccgg cggaggaggg   720
tccgaggtgc agctgcagga atctggccct ggcctggtca gccaagcca gagtctgagc   780
ctgacctgca cgtgaccgg ctacagcatt accagcggct actactgaa ctggattcgg   840
cagttccccg caataagct ggaatggatg ggctacatca cctacgacgg cagcaacaac   900
tacaaccca gcctgaagaa ccggatcagc atcacccggg acaccagcaa gaaccagttc   960
ttcctgaagc tgaacagcgt gaccaccgag gacaccgcca catactattg cgccgacttc  1020
gactactggg gccagggcac caccctgacc gtgtccagcg ccagcacaaa gggccctagc  1080
gtgttccctc tggcccccag cagcaagagc acaagcggcg aacagccgc cctgggctgc  1140
ctcgtgaagg actacttccc cgagcccgtg acagtgtctt ggaacagcgg agccctgaca  1200
agcggcgtgc acaccttccc tgccgtgctg cagagcagcg gcctgtactc cctgagcagc  1260
```

```
gtggtcaccg tgcctagcag cagcctgggc acccagacct acatctgcaa cgtgaaccac    1320
aagcccagca acaccaaagt ggacaagaag gtggagccca gagctgtga tggcggagga    1380 gggtccggag gcggtggctc cgaggtgcag ctgcaggaat ctggccctgg cctggtcaag    1440
ccaagccaga gtctgagcct gacctgcagc gtgaccggct acagcattac agcggctac    1500 tactggaact ggattcggca gttccccggc ataagctgg aatggatggg ctacatcacc    1560
tacgacggca gcaacaacta caaccccagc ctgaagaacc ggatcagcat cacccgggac    1620
accagcaaga accagttctt cctgaagctg aacagcgtga ccaccgagga caccgccaca    1680
tactattgcg ccgacttcga ctactgggc agggcacca ccctgaccgt gtccagcgcc    1740
agcacaaagg gcctagcgt gttccctctg ccccccagca gcaagagcac aagcggcgga    1800
acagccgccc tgggctgcct cgtgaaggac tacttcccg agcccgtgac agtgtcttgg    1860
aacagcggag ccctgacaag cggcgtgcac accttccctg ccgtgctgca gagcagcggc    1920
ctgtactccc tgagcagcgt ggtcaccgtg cctagcagca gcctgggcac ccagacctac    1980
atctgcaacg tgaaccacaa gcccagcaac accaaagtgg acaagaaggt ggagcccaag    2040
agctgtgatt ga                                                        2052

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      GA201 HCDR1 peptide

<400> SEQUENCE: 68

Asp Tyr Lys Ile His
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      GA201 HCDR2 peptide

<400> SEQUENCE: 69

Tyr Phe Asn Pro Asn Ser Gly Tyr Ser Thr Tyr Ala Gln Lys Phe Gln
1               5                   10                  15

Gly

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      GA201 HCDR3 peptide

<400> SEQUENCE: 70

Leu Ser Pro Gly Gly Tyr Tyr Val Met Asp Ala
1               5                   10

<210> SEQ ID NO 71
<211> LENGTH: 11
<212> TYPE: PRT
<213> ORGANISM: Artificial Sequence
<220> FEATURE:
```

<223> OTHER INFORMATION: Description of Artificial Sequence: Synthetic
      GA201 LCDR1 peptide

<400> SEQUENCE: 71

Arg Ala Ser Gln Gly Ile Asn Asn Tyr Leu Asn
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      GA201 LCDR2 peptide

<400> SEQUENCE: 72

Asn Thr Asn Asn Leu Gln Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      GA201 LCDR3 peptide

<400> SEQUENCE: 73

Leu Gln His Asn Ser Phe Pro Thr
1               5

<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic
      GA201 VH polypeptide

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
                20                  25                  30

Lys Ile His Trp Val Arg Gln Ala Pro Gly Gln Gly Leu Glu Trp Met
            35                  40                  45

Gly Tyr Phe Asn Pro Asn Ser Gly Tyr Ser Thr Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 75
<211> LENGTH: 106
<212> TYPE: PRT
<213> ORGANISM: Artificial Sequence
<220> FEATURE:
<223> OTHER INFORMATION: Description of Artificial Sequence: Synthetic
      GA201 VL polypeptide

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys
            100                 105

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      3F2 HCDR1 peptide

<400> SEQUENCE: 76

Ser Tyr Ala Met Ser
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      3F2 HCDR2 peptide

<400> SEQUENCE: 77

Ala Ile Ser Gly Ser Gly Gly Ser Thr Tyr Tyr Ala Asp Ser Val Lys
1               5                   10                  15

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      3F2 HCDR3 peptide

<400> SEQUENCE: 78

Tyr Cys Ala Lys Gly Trp Phe Gly
1               5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      3F2 LCDR1 peptide

<400> SEQUENCE: 79

Arg Ala Ser Gln Ser Val Thr Ser Ser Tyr Leu
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      3F2 LCDR2 peptide

<400> SEQUENCE: 80

Asn Val Gly Ser Arg Arg Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      3F2 LCDR3 peptide

<400> SEQUENCE: 81

Cys Gln Gln Gly Ile Met Leu Pro Pro
1               5

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      3F2 VH polypeptide

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      3F2 VL polypeptide

<400> SEQUENCE: 83

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser

```
                    20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      CH1A1A HCDR1 peptide

<400> SEQUENCE: 84

Glu Phe Gly Met Asn
1               5

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      CH1A1A HCDR2 peptide

<400> SEQUENCE: 85

Trp Ile Asn Thr Lys Thr Gly Glu Ala Thr Tyr Val Glu Glu Phe Lys
1               5                   10                  15

Gly

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      CH1A1A HCDR3 peptide

<400> SEQUENCE: 86

Trp Asp Phe Ala Tyr Tyr Val Glu Ala Met Asp Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      CH1A1A LCDR1 peptide

<400> SEQUENCE: 87

Lys Ala Ser Ala Ala Val Gly Thr Tyr Val Ala
1               5                   10

<210> SEQ ID NO 88
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      CH1A1A LCDR2 peptide

<400> SEQUENCE: 88

Ser Ala Ser Tyr Arg Lys Arg
1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      CH1A1A LCDR3 peptide

<400> SEQUENCE: 89

His Gln Tyr Tyr Thr Tyr Pro Leu Phe Thr
1               5                   10

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      CH1A1A VH polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 91
<211> LENGTH: 108
<212> TYPE: PRT
<213> ORGANISM: Artificial Sequence
<220> FEATURE:
<223> OTHER INFORMATION: Description of Artificial Sequence: Synthetic
      CH1A1A VL polypeptide

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
                20                  25                  30

Val Ala Trp Tyr Gln Gln Lys Pro Gly Lys Ala Pro Lys Leu Leu Ile
            35                  40                  45
```

```
Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      Anti-CD33 HCDR1 peptide

<400> SEQUENCE: 92

Gly Tyr Thr Ile Thr Asp Ser Asn Ile His
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      Anti-CD33 HCDR2 peptide

<400> SEQUENCE: 93

Tyr Ile Tyr Pro Tyr Asn Gly Gly Thr Asp Tyr Asn Gln
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD33 HCDR3 peptide

<400> SEQUENCE: 94

Gly Asn Pro Trp Leu Ala Tyr
1               5

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      Anti-CD33 LCDR1 peptide

<400> SEQUENCE: 95

Arg Ala Ser Glu Ser Leu Asp Asn Tyr Gly Ile Arg Phe Leu Thr
1               5                   10                  15

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-CD33 LCDR2 peptide

<400> SEQUENCE: 96
```

Ala Ala Ser Asn Gln Gly Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      Anti-CD33 LCDR3 peptide

<400> SEQUENCE: 97

Gln Gln Thr Lys Glu Val Pro Trp Ser
1               5

<210> SEQ ID NO 98
<211> LENGTH: 116
<212> TYPE: PRT
<213> ORGANISM: Artificial Sequence
<220> FEATURE:
<223> OTHER INFORMATION: Description of Artificial Sequence: Synthetic
      Anti-CD33 VH polypeptide

<400> SEQUENCE: 98

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser
        115

<210> SEQ ID NO 99
<211> LENGTH: 111
<212> TYPE: PRT
<213> ORGANISM: Artificial Sequence
<220> FEATURE:
<223> OTHER INFORMATION: Description of Artificial Sequence: Synthetic
      Anti-CD33 VL polypeptide

<400> SEQUENCE: 99

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys

```
                    85                  90                  95
Glu Val Pro Trp Ser Phe Gly Gln Gly Thr Lys Val Glu Val Lys
                100                 105                 110
```

<210> SEQ ID NO 100
<211> LENGTH: 218
<212> TYPE: PRT
<213> ORGANISM: Artificial Sequence
<220> FEATURE:
<223> OTHER INFORMATION: Description of Artificial Sequence: Synthetic
      Light Chain antiCD33 polypeptide

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 101
<211> LENGTH: 229
<212> TYPE: PRT
<213> ORGANISM: Artificial Sequence
<220> FEATURE:
<223> OTHER INFORMATION: Description of Artificial Sequence: Synthetic
      Light Chain V9 (VH-CL) polypeptide

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
```

```
                 50                  55                  60
Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Ala Ser Val Ala Ala Pro
                115                 120                 125

Ser Val Phe Ile Phe Pro Pro Ser Asp Glu Gln Leu Lys Ser Gly Thr
                130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
                180                 185                 190

Thr Leu Thr Leu Ser Lys Ala Asp Tyr Glu Lys His Lys Val Tyr Ala
                195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 102
<211> LENGTH: 396
<212> TYPE: PRT
<213> ORGANISM: Artificial Sequence
<220> FEATURE:
<223> OTHER INFORMATION: Description of Artificial Sequence: Synthetic
      CD33 Fab-Crossfab (VH-CH1-VL-CH1) polypeptide

<400> SEQUENCE: 102

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Asn Met His Trp Val Arg Gln Ala Pro Gly Gln Gly Leu Glu Trp Ile
                 35                  40                  45

Gly Tyr Ile Tyr Pro Tyr Asn Gly Gly Thr Gly Tyr Asn Gln Lys Phe
             50                  55                  60

Lys Ser Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Pro Ala Met Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Gly Gly Gly Gly
210                 215                 220

Ser Gly Gly Gly Gly Ser Asp Ile Gln Met Thr Gln Ser Pro Ser Ser
225                 230                 235                 240

Leu Ser Ala Ser Val Gly Asp Arg Val Thr Ile Thr Cys Arg Ala Ser
            245                 250                 255

Gln Asp Ile Arg Asn Tyr Leu Asn Trp Tyr Gln Gln Lys Pro Gly Lys
            260                 265                 270

Ala Pro Lys Leu Leu Ile Tyr Tyr Thr Ser Arg Leu Glu Ser Gly Val
            275                 280                 285

Pro Ser Arg Phe Ser Gly Ser Gly Ser Gly Thr Asp Tyr Thr Leu Thr
            290                 295                 300

Ile Ser Ser Leu Gln Pro Glu Asp Phe Ala Thr Tyr Tyr Cys Gln Gln
305                 310                 315                 320

Gly Asn Thr Leu Pro Trp Thr Phe Gly Gln Gly Thr Lys Val Glu Ile
            325                 330                 335

Lys Ser Ser Ala Ser Thr Lys Gly Pro Ser Val Phe Pro Leu Ala Pro
            340                 345                 350

Ser Ser Lys Ser Thr Ser Gly Gly Thr Ala Ala Leu Gly Cys Leu Val
            355                 360                 365

Lys Asp Tyr Phe Pro Glu Pro Val Thr Val Ser Trp Asn Ser Gly Ala
            370                 375                 380

Leu Thr Ser Gly Val His Thr Phe Pro Ala Val Leu
385                 390                 395

<210> SEQ ID NO 103
<211> LENGTH: 105
<212> TYPE: PRT
<213> ORGANISM: Homo sapiens

<400> SEQUENCE: 103

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
            85                  90                  95

Val Cys Glu Asn Cys Met Glu Met Asp
            100                 105

<210> SEQ ID NO 104
<211> LENGTH: 714
<212> TYPE: DNA
<213> ORGANISM: Artificial Sequence
<220> FEATURE:
<223> OTHER INFORMATION: Description of Artificial Sequence: Synthetic
      Light Chain antiCD33 DNA polynucleotide

<400> SEQUENCE: 104

```
atgggatgga gctgtatcat cctcttcttg gtagcaacag ctaccggtgt gcattccgac      60
atccagatga cccagagccc cagcagcctg agcgccagcg tgggcgacag agtgaccatc     120
acctgtcggg ccagcgagag cgtggacaac tacggcatca gcttcatgaa ctggttccag     180
cagaagcccg gcaaggcccc caagctgctg atctacgccg ccagcaatca gggcagcggc     240
gtgcccagca gattcagcgg ctctggcagc ggcaccgact tcaccctgac catcagcagc     300
ctgcagcccg acgacttcgc cacctactac tgccagcaga gcaaagaggt gccctggacc     360
ttcggccagg gcaccaaggt ggaaatcaag cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttag           714
```

<210> SEQ ID NO 105
<211> LENGTH: 747
<212> TYPE: DNA
<213> ORGANISM: Artificial Sequence
<220> FEATURE:
<223> OTHER INFORMATION: Description of Artificial Sequence: Synthetic
      Light Chain V9 (VH-CL) DNA polynucleotide

<400> SEQUENCE: 105

```
atgggatgga gctgtatcat cctcttcttg gtagcaacag ctaccggtgt gcattccgag      60
gtgcagctgg tcgagagcgg aggcggcctg gtgcagcctg gcggcagcct gagactgagc     120
tgcgccgcca gcggctacag cttcaccggc tacaccatga actgggtccg gcaggcacct     180
ggcaagggac tggaatgggt ggccctgatc aaccccacag agggcgtgag cacctacaac     240
cagaagttca ggaccggtt caccatcagc gtggacaaga gcaagaacac cgcctatctg     300
cagatgaaca gcctgcgggc cgaggacacc gccgtgtact actgcgccag aagcggctac     360
tacggcgaca gcgactggta cttcgacgtg tggggccagg gcaccctcgt gaccgtgtct     420
agcgctagcg tggctgcacc atctgtcttc atcttcccgc catctgatga gcagttgaaa     480
tctggaactg cctctgttgt gtgcctgctg aataacttct atcccagaga ggccaaagta     540
cagtggaagg tggataacgc cctccaatcg gtaactccc aggagagtgt cacagagcag     600
gacagcaagg acagcaccta gcctcagc agcaccctga cgctgagcaa agcagactac     660
gagaaacaca agtctacgc ctgcgaagtc acccatcagg gcctgagctc gcccgtcaca     720
aagagcttca caggggaga gtgttga                                          747
```

<210> SEQ ID NO 106
<211> LENGTH: 1386
<212> TYPE: DNA
<213> ORGANISM: Artificial Sequence
<220> FEATURE:
<223> OTHER INFORMATION: Description of Artificial Sequence: Synthetic
      CD33 Fab-Crossfab (VH-CH1-VL-CH1) DNA polynucleotide

<400> SEQUENCE: 106

```
atgggatgga gctgtatcat cctcttcttg gtagcaacag ctaccggtgt gcattccag       60
gtgcagctgg tgcagtctgg cgccgaagtg aagaacccg gcagcagcgt gaaggtgtcc     120
```

```
tgcaaggcca gcggctacac cttcaccgac tacaacatgc actgggtccg ccaggcccca    180
ggccagggac tggaatggat cggctacatc taccccctaca acggcggcac cggctacaac    240
cagaagttca agagcaaggc caccatcacc gccgacgaga gcaccaacac cgcctacatg    300
gaactgagca gcctgcggag cgaggacacc gccgtgtact actgcgccag aggcagaccc    360
gccatggact actggggcca gggcaccctg gtgacagtgt ccagcgccag cacaaagggc    420
cctagcgtgt tccctctggc ccccagcagc aagagcacaa gcggcggaac agccgccctg    480
ggctgcctcg tgaaggacta cttccccgag cccgtgacag tgtcttggaa cagcggagcc    540
ctgacaagcg gcgtgcacac cttccctgcc gtgctgcaga gcagcggcct gtactccctg    600
agcagcgtgg tcaccgtgcc tagcagcagc ctgggcaccc agacctacat ctgcaacgtg    660
aaccacaagc ccagcaacac caaagtggac aagaaggtgg agcccaagag ctgtgatggc    720
ggaggagggt ccggaggcgg tggatccgac atccagatga cccagagccc ctctagcctg    780
agcgccagcg tgggcgacag agtgaccatc acctgtcggg ccagccagga catcagaaac    840
tacctgaact ggtatcagca gaagcccggc aaggccccca gctgctgat ctactacacc    900 tctagactgg aaagcggcgt gcccagccgg tttagcggca gcggctccgg caccgactac    960
accctgacca tcagcagcct gcagcccgag gacttcgcca cctactactg ccagcagggc    1020
aacacactcc cctggacctt cggccagggc accaaggtgg agatcaagtc cagcgctagc    1080
accaagggcc cctccgtgtt cccctggcc ccagcagca gagcaccag cggcggcaca    1140 gccgccctcg gctgcctggt caaggactac ttccccgagc ccgtgaccgt gtcctggaac    1200
agcggagccc tgacctccgg cgtgcacacc ttccccgccg tgctgcagag cagcggcctg    1260
tacagcctgt ccagcgtggt caccgtgccc tccagcagcc tgggcaccca gacctacatc    1320
tgcaacgtga accacaagcc cagcaatacc aaggtggaca gaaggtgga gcccaagagc    1380 tgctga                                                               1386

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      MCSP CDR1 VH DNA oligonucleotide

<400> SEQUENCE: 107
ggctactcca tcaccagtgg ttattactgg aac                                 33

<210> SEQ ID NO 108
<211> LENGTH: 48
<212> TYPE: DNA
<213> ORGANISM: Artificial Sequence
<220> FEATURE:
<223> OTHER INFORMATION: Description of Artificial Sequence: Synthetic
      MCSP CDR2 VH oligonucleotide

<400> SEQUENCE: 108
tacataacct acgacggtag caataactac aacccatctc tcaaaaat                 48

<210> SEQ ID NO 109
<211> LENGTH: 9
<212> TYPE: DNA
<213> ORGANISM: Artificial Sequence
<220> FEATURE:
<223> OTHER INFORMATION: Description of Artificial Sequence: Synthetic
      MCSP CDR3 VH oligonucleotide
```

```
<400> SEQUENCE: 109 tttgactac                                                                  9

<210> SEQ ID NO 110
<211> LENGTH: 33
<212> TYPE: DNA
<213> ORGANISM: Artificial Sequence
<220> FEATURE:
<223> OTHER INFORMATION: Description of Artificial Sequence: Synthetic
      MCSP CDR1 VL DNA oligonucleotide

<400> SEQUENCE: 110
agtgcaagtc agggcattag aaattattta aac                                       33

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      MCSP CDR2 VL oligonucleotide

<400> SEQUENCE: 111
tacacatcaa gtttacactc a                                                    21

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence: Synthetic
      MCSP CDR3 VL oligonucleotide

<400> SEQUENCE: 112
cagcagtata gtaagcttcc ttggacg                                              27

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      GA201 CDR1 VH oligonucleotide

<400> SEQUENCE: 113
gactacaaga tacac                                                           15

<210> SEQ ID NO 114
<211> LENGTH: 51
<212> TYPE: DNA
<213> ORGANISM: Artificial Sequence
<220> FEATURE:
<223> OTHER INFORMATION: Description of Artificial Sequence: Synthetic
      GA201 CDR2 VH oligonucleotide

<400> SEQUENCE: 114
tatttcaacc ctaacagcgg ttatagtacc tacgcacaga gttccaggg c                    51

<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence: Synthetic
      GA201 CDR3 VH oligonucleotide

<400> SEQUENCE: 115
```
ctatccccag gcggttacta tgttatggat gcc 33

<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence: Synthetic
      GA201 CDR1 VL oligonucleotide

<400> SEQUENCE: 116
cgggcaagtc agggcattaa caattactta aat 33

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      GA201 CDR2 VL oligonucleotide

<400> SEQUENCE: 117
aataccaaca acttgcagac a 21

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      GA201 CDR3 VL oligonucleotide

<400> SEQUENCE: 118
ttgcagcata atagttttcc cacg 24

<210> SEQ ID NO 119
<211> LENGTH: 360
<212> TYPE: DNA
<213> ORGANISM: Artificial Sequence
<220> FEATURE:
<223> OTHER INFORMATION: Description of Artificial Sequence: Synthetic
      GA201 VH polynucleotide

<400> SEQUENCE: 119
caggtgcagc tggtgcagtc tggggctgag gtgaagaagc ctgggtcctc ggtgaaggtc     60
tcctgcaagg cctctggttt cacattcact gactacaaga tacactgggt gcgacaggcc    120
cctggacaag gctcgagtg gatgggatat ttcaacccta cagcggtta tagtacctac    180
gcacagaagt tccagggcag ggtcaccatt accgcggaca atccacgag cacagcctac    240
atggagctga gcagcctgag atctgaggac acggccgtgt attactgtgc gagactatcc    300
ccaggcggtt actatgttat ggatgcctgg ggccaaggga ccaccgtgac cgtctcctca    360

<210> SEQ ID NO 120
<211> LENGTH: 318
<212> TYPE: DNA
<213> ORGANISM: Artificial Sequence
<220> FEATURE:
<223> OTHER INFORMATION: Description of Artificial Sequence: Synthetic
      GA201 VL polynucleotide

<400> SEQUENCE: 120
gatatccaga tgacccagtc tccatcctcc ctgtctgcat ctgtcggaga ccgggtcacc     60
atcacctgcc gggcaagtca gggcattaac aattacttaa attggtacca gcagaagcca    120

```
gggaaagccc ctaagcgcct gatctataat accaacaact tgcagacagg cgtcccatca      180
aggttcagcg gcagtggatc cgggacagaa ttcactctca ccatcagcag cctgcagcct      240
gaagattttg ccacctatta ctgcttgcag cataatagtt ttcccacgtt tggccagggc      300
accaagctcg agatcaag                                                    318
```

<210> SEQ ID NO 121
<211> LENGTH: 15
<212> TYPE: DNA
<213> ORGANISM: Artificial Sequence
<220> FEATURE:
<223> OTHER INFORMATION: Description of Artificial Sequence: Synthetic
       3F2 CDR1 VH oligonucleotide

<400> SEQUENCE: 121

```
agctacgcca tgagc                                                        15
```

<210> SEQ ID NO 122
<211> LENGTH: 48
<212> TYPE: DNA
<213> ORGANISM: Artificial Sequence
<220> FEATURE:
<223> OTHER INFORMATION: Description of Artificial Sequence: Synthetic
       3F2 CDR2 VH oligonucleotide

<400> SEQUENCE: 122

```
gccatctccg gcagcggagg cagcacctac tacgccgaca gcgtgaag                    48
```

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
       3F2 CDR3 VH oligonucleotide

<400> SEQUENCE: 123

```
tattgcgcca agggatggtt cggc                                              24
```

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: Synthetic
       3F2 CDR1 VL oligonucleotide

<400> SEQUENCE: 124

```
agagccagcc agagcgtgac cagcagctac ctg                                    33
```

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
       3F2 CDR2 VL oligonucleotide

<400> SEQUENCE: 125

```
aacgtgggca gcagacgggc c                                                 21
```

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      3F2 CDR3 VL oligonucleotide

<400> SEQUENCE: 126
tgccagcagg gcatcatgct gcccccc                                              27

<210> SEQ ID NO 127
<211> LENGTH: 351
<212> TYPE: DNA
<213> ORGANISM: Artificial Sequence
<220> FEATURE:
<223> OTHER INFORMATION: Description of Artificial Sequence: Synthetic
      3F2 VH polynucleotide

<400> SEQUENCE: 127
gaggtgcagc tgctggaatc tggaggcggc ctggtgcagc ctggcggcag cctgagactg           60
tcttgcgccg ccagcggctt caccttcagc agctacgcca tgagctgggt ccgacaggct          120
cctggcaagg gactggaatg ggtgtccgcc atctccggca gcggaggcag cacctactac          180
gccgacagcg tgaagggccg gttcaccatc agcagagaca acagcaagaa caccctgtac          240
ctgcagatga acagcctgcg ggccgaggat accgccgtgt attattgcgc aagggatgg           300 ttcggcggct tcaactactg gggccaggga accctggtga cagtgtccag c                   351

<210> SEQ ID NO 128
<211> LENGTH: 324
<212> TYPE: DNA
<213> ORGANISM: Artificial Sequence
<220> FEATURE:
<223> OTHER INFORMATION: Description of Artificial Sequence: Synthetic
      3F2 VL polynucleotide

<400> SEQUENCE: 128
gagatcgtgc tgacccagtc tcccggcacc ctgagcctga gccctggcga gagagccacc           60
ctgagctgca gagccagcca gagcgtgacc agcagctacc tggcctggta tcagcagaag          120
cccggccagg cccccagact gctgatcaac gtgggcagca cgggccac cggcatcccc            180 gatagattca gcggcagcgg ctccggcacc gacttcaccc tgaccatcag ccggctggaa          240
cccgaggact tcgccgtgta ctactgccag cagggcatca tgctgccccc caccttcggc          300
cagggcacca aggtggaaat caag                                                 324

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      CH1A1A CDR1 VH oligonucleotide

<400> SEQUENCE: 129
gagttcggca tgaac                                                           15

<210> SEQ ID NO 130
<211> LENGTH: 51
<212> TYPE: DNA
<213> ORGANISM: Artificial Sequence
<220> FEATURE:
<223> OTHER INFORMATION: Description of Artificial Sequence: Synthetic
      CH1A1A CDR2 VH oligonucleotide

<400> SEQUENCE: 130
tggatcaaca ccaagaccgg cgaggccacc tacgtggaag agttcaaggg c                   51

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
CH1A1A CDR3 VH oligonucleotide

<400> SEQUENCE: 131
tgggacttcg cctattacgt ggaagccatg gactac                                36

<210> SEQ ID NO 132
<211> LENGTH: 33
<212> TYPE: DNA
<213> ORGANISM: Artificial Sequence
<220> FEATURE:
<223> OTHER INFORMATION: Description of Artificial Sequence: Synthetic
CH1A1A CDR1 VL oligonucleotide

<400> SEQUENCE: 132
aaggccagtg cggctgtggg tacgtatgtt gcg                                   33

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
CH1A1A CDR2 VL oligonucleotide

<400> SEQUENCE: 133
tcggcatcct accgcaaaag g                                                21

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
CH1A1A CDR3 VL oligonucleotide

<400> SEQUENCE: 134
caccaatatt acacctatcc tctattcacg                                       30

<210> SEQ ID NO 135
<211> LENGTH: 363
<212> TYPE: DNA
<213> ORGANISM: Artificial Sequence
<220> FEATURE:
<223> OTHER INFORMATION: Description of Artificial Sequence: Synthetic
CH1A1A VH polynucleotide

<400> SEQUENCE: 135
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca gaccggcga ggccacctac      180 gtggaagagt tcaagggcag agtgaccttc accacggaca ccagcaccag caccgcctac     240
atggaactgc ggagcctgag aagcgacgac accgccgtgt actactgcgc cagatgggac     300
ttcgcctatt acgtggaagc catggactac tggggccagg gcaccaccgt gaccgtgtct     360
agc                                                                  363

```
<210> SEQ ID NO 136
<211> LENGTH: 324
<212> TYPE: DNA
<213> ORGANISM: Artificial Sequence
<220> FEATURE:
<223> OTHER INFORMATION: Description of Artificial Sequence: Synthetic
      CH1A1A VL polynucleotide

<400> SEQUENCE: 136
gatatccaga tgacccagtc tccatcctcc ctgtctgcat ctgtgggaga cagagtcacc    60
atcacttgca aggccagtgc ggctgtgggt acgtatgttg cgtggtatca gcagaaacca   120
gggaaagcac ctaagctcct gatctattcg catcctacc gcaaaagggg agtcccatca   180
aggttcagtg gcagtggatc tgggacagat ttcactctca ccatcagcag tctgcaacct   240
gaagatttcg caacttacta ctgtcaccaa tattacacct atcctctatt cacgtttggc   300
cagggcacca agctcgagat caag                                           324

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      Anti-CD33 CDR1 VH oligonucleotide

<400> SEQUENCE: 137
ggctacacca tcaccgacag caacatccac                                      30

<210> SEQ ID NO 138
<211> LENGTH: 39
<212> TYPE: DNA
<213> ORGANISM: Artificial Sequence
<220> FEATURE:
<223> OTHER INFORMATION: Description of Artificial Sequence: Synthetic
      Anti-CD33 CDR2 VH oligonucleotide

<400> SEQUENCE: 138
tacatctacc cctacaacgg cggcaccgac tacaaccag                            39

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      Anti-CD33 CDR3 VH oligonucleotide

<400> SEQUENCE: 139
ggcaacccct ggctggccta t                                               21

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: Synthetic
      Anti-CD33 CDR1 VL oligonucleotide

<400> SEQUENCE: 140
cgggccagcg agagcctgga caactacggc atccggtttc tgacc                     45

<210> SEQ ID NO 141
<211> LENGTH: 21
<212> TYPE: DNA
<213> ORGANISM: Artificial Sequence
```

<220> FEATURE:
<223> OTHER INFORMATION: Description of Artificial Sequence: Synthetic
Anti-CD33 CDR2 VL oligonucleotide

<400> SEQUENCE: 141
gccgccagca accagggcag c    21

<210> SEQ ID NO 142
<211> LENGTH: 27
<212> TYPE: DNA
<213> ORGANISM: Artificial Sequence
<220> FEATURE:
<223> OTHER INFORMATION: Description of Artificial Sequence: Synthetic
Anti-CD33 CDR3 VL oligonucleotide

<400> SEQUENCE: 142
cagcagacca aagaggtgcc ctggtcc    27

<210> SEQ ID NO 143
<211> LENGTH: 348
<212> TYPE: DNA
<213> ORGANISM: Artificial Sequence
<220> FEATURE:
<223> OTHER INFORMATION: Description of Artificial Sequence: Synthetic
Anti-CD33 VH polynucleotide

<400> SEQUENCE: 143
gaagtgcagc tggtgcagtc tggcgccgaa gtgaagaaac ccggcagcag cgtgaaggtg    60
tcctgcaagg ccagcggcta caccatcacc gacagcaaca tccactgggt ccgacaggcc    120
cctgggcaga gcctggaatg gatcggctac atctacccct acaacggcgg caccgactac    180
aaccagaagt tcaagaaccg ggccaccctg accgtggaca cccccaccaa caccgcctac    240
atggaactga gcagcctgcg gagcgaggac accgccttct actactgcgt gaacggcaac    300
ccctggctgg cctattgggg ccagggaacc ctggtcaccg tgtctagc    348

<210> SEQ ID NO 144
<211> LENGTH: 333
<212> TYPE: DNA
<213> ORGANISM: Artificial Sequence
<220> FEATURE:
<223> OTHER INFORMATION: Description of Artificial Sequence: Synthetic
Anti-CD33 VL polynucleotide

<400> SEQUENCE: 144
gacatccagc tgacccagag ccccagcacc ctgtctgcca gcgtgggcga cagagtgacc    60
atcacctgtc gggccagcga gagcctggac aactacggca tccggtttct gacctggttc    120
cagcagaagc ccggcaaggc ccccaagctg ctgatgtacg ccgccagcaa ccagggcagc    180
ggcgtgccaa gcagattcag cggcagcggc tccggcaccg agttcaccct gaccatcagc    240
agcctgcagc ccgacgactt cgccacctac tactgccagc agaccaaaga ggtgccctgg    300
tccttcggcc agggcaccaa ggtggaagtg aag    333

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
Linker 2 peptide

<400> SEQUENCE: 145

Glu Pro Lys Ser Cys Gly Gly Gly Gly Ser Gly Gly Gly Gly Ser

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
    Linker 3 peptide

<400> SEQUENCE: 146

Glu Pro Lys Ser Cys Asp Gly Gly Gly Gly Ser Gly Gly Gly Gly Ser
1               5                   10                  15

<210> SEQ ID NO 147
<211> LENGTH: 32
<212> TYPE: PRT
<213> ORGANISM: Artificial Sequence
<220> FEATURE:
<223> OTHER INFORMATION: Description of Artificial Sequence: Synthetic
    Linker 4 polypeptide

<400> SEQUENCE: 147

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
    Linker 5 polypeptide

<400> SEQUENCE: 148

Ser Gly Gly Gly Ser Gly Gly Gly Ser Glu Gly Gly Gly Ser Glu Gly
1               5                   10                  15

Gly Gly Ser Glu Gly Gly Gly Ser Glu Gly Gly Gly Ser Gly Gly Gly
            20                  25                  30

Ser Gly

<210> SEQ ID NO 149
<211> LENGTH: 492
<212> TYPE: PRT
<213> ORGANISM: Artificial Sequence
<220> FEATURE:
<223> OTHER INFORMATION: Description of Artificial Sequence: Synthetic
    (scFV)2 CD3-MCSP polypeptide

<400> SEQUENCE: 149

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp

```
                    85                  90                  95
Thr Phe Gly Gly Gly Thr Lys Leu Glu Ile Lys Gly Gly Gly Ser
                100                 105                 110
Gly Gly Gly Gly Ser Gly Gly Gly Ser Glu Val Gln Leu Gln Glu
            115                 120                 125
Ser Gly Pro Gly Leu Val Lys Pro Ser Gln Ser Leu Ser Leu Thr Cys
    130                 135                 140
Ser Val Thr Gly Tyr Ser Ile Thr Ser Gly Tyr Tyr Trp Asn Trp Ile
145                 150                 155                 160
Arg Gln Phe Pro Gly Asn Lys Leu Glu Trp Met Gly Tyr Ile Thr Tyr
                165                 170                 175
Asp Gly Ser Asn Asn Tyr Asn Pro Ser Leu Lys Asn Arg Ile Ser Ile
            180                 185                 190
Thr Arg Asp Thr Ser Lys Asn Gln Phe Phe Leu Lys Leu Asn Ser Val
        195                 200                 205
Thr Thr Glu Asp Thr Ala Thr Tyr Tyr Cys Ala Asp Phe Asp Tyr Trp
    210                 215                 220
Gly Gln Gly Thr Thr Leu Thr Val Ser Ser Gly Gly Gly Ser Glu
225                 230                 235                 240
Val Gln Leu Val Glu Ser Gly Gly Gly Leu Val Gln Pro Gly Gly Ser
                245                 250                 255
Leu Arg Leu Ser Cys Ala Ala Ser Gly Tyr Ser Phe Thr Gly Tyr Thr
            260                 265                 270
Met Asn Trp Val Arg Gln Ala Pro Gly Lys Gly Leu Glu Trp Val Ala
        275                 280                 285
Leu Ile Asn Pro Tyr Lys Gly Val Ser Thr Tyr Asn Gln Lys Phe Lys
    290                 295                 300
Asp Arg Phe Thr Ile Ser Val Asp Lys Ser Lys Asn Thr Ala Tyr Leu
305                 310                 315                 320
Gln Met Asn Ser Leu Arg Ala Glu Asp Thr Ala Val Tyr Tyr Cys Ala
                325                 330                 335
Arg Ser Gly Tyr Tyr Gly Asp Ser Asp Trp Tyr Phe Asp Val Trp Gly
            340                 345                 350
Gln Gly Thr Leu Val Thr Val Ser Val Glu Gly Ser Gly Gly
        355                 360                 365
Ser Gly Gly Ser Gly Gly Ser Gly Gly Val Asp Asp Ile Gln Met Thr
    370                 375                 380
Gln Ser Pro Ser Ser Leu Ser Ala Ser Val Gly Asp Arg Val Thr Ile
385                 390                 395                 400
Thr Cys Arg Ala Ser Gln Asp Ile Arg Asn Tyr Leu Asn Trp Tyr Gln
                405                 410                 415
Gln Lys Pro Gly Lys Ala Pro Lys Leu Leu Ile Tyr Tyr Thr Ser Arg
            420                 425                 430
Leu Glu Ser Gly Val Pro Ser Arg Phe Ser Gly Ser Gly Ser Gly Thr
        435                 440                 445
Asp Tyr Thr Leu Thr Ile Ser Ser Leu Gln Pro Glu Asp Phe Ala Thr
    450                 455                 460
Tyr Tyr Cys Gln Gln Gly Asn Thr Leu Pro Trp Thr Phe Gly Gln Gly
465                 470                 475                 480
Thr Lys Val Glu Ile Lys His His His His His
                485                 490

<210> SEQ ID NO 150
```

<211> LENGTH: 1536
<212> TYPE: DNA
<213> ORGANISM: Artificial Sequence
<220> FEATURE:
<223> OTHER INFORMATION: Description of Artificial Sequence: Synthetic (scFv)2 MCSP-CD3 DNA polynucleotide

<400> SEQUENCE: 150

```
atgggctggt cctgcatcat cctgtttctg gtggccacag ccaccggtgt gcattccgac    60
atcgtgctga cccagagccc cagcagcctg agcgccagcc tgggcgacag agtgaccatc   120
agctgcagcg cctcccaggg catcagaaac tacctgaact ggtatcagca gcggcccgac   180
ggcaccgtga agctgctgat ctactacacc agctccctgc acagcggcgt gcccagcaga   240
ttttcaggca gcggcagcgg cactgactac agcctgacca tctccaacct ggaacccgag   300
gacattgcca cctactactg ccagcagtac agcaagctgc cctggacctt cggcggaggc   360
accaagctgg aaatcaaggg cggaggcgga tccggcggag gtggaagtgg cggcggaggc   420
tctgaggtgc aattgcagga aagcggccct ggcctggtga acccagcca gagcctgagc   480
ctgacctgca gcgtgaccgg ctactccatc accagcggct actactggaa ctggatcaga   540
cagttccccg gaaacaagct ggaatggatg ggctacatca cctacgacgg cagcaacaac   600
tacaacccca gcctgaagaa ccggatcagc atcacccggg acaccagcaa gaaccagttc   660
ttcctgaagc tgaacagcgt gaccaccgag gataccgcca cctattactg tgccgacttc   720
gactactggg gccagggcac caccctgacc gtgtcatccg gtggcggcgg atccgaagtg   780
cagctggtgg agtctggcgg tggactggtg cagccaggcg gctccctgag actgagctgc   840
gccgcctccg gctacagctt caccggctac accatgaatt gggtccgcca ggcccctgga   900
aagggactgg aatgggtggc cctgatcaac ccctacaagg cgtgagcac ctacaaccag   960
aagttcaagg accggttcac catcagcgtg acaagagca agaacacagc ctacctgcag  1020
atgaactccc tgagagccga ggataccgcc gtgtattact gtgccgcag cggctactac  1080
ggcgactccg actggtactt cgacgtgtgg gggcagggaa ccctggtcac cgtgtccagc  1140
gtggaaggcg gcagcggagg atctggcggc tctggcggaa cggcggagt ggacgatatc  1200
cagatgacac agtcccccag ctccctgagc gccagcgtgg gcgacagagt gaccatcacc  1260
tgtcgggcca gccaggacat ccggaattat ctcaattggt atcagcagaa acctggcaaa  1320
gctcctaaac tgctgatcta ctacacctcc cggctggaaa gcggcgtgcc cagcagattt  1380
tccggcagcg ggagcggcac cgattacaca ctgaccatca gcagcctgca gcccgaggac  1440
tttgccacct actattgcca gcagggcaac accctgccct ggacctttgg cagggcaca  1500
aaggtggaga tcaagcacca ccaccatcac cactga                            1536
```

<210> SEQ ID NO 151
<211> LENGTH: 218
<212> TYPE: PRT
<213> ORGANISM: Artificial Sequence
<220> FEATURE:
<223> OTHER INFORMATION: Description of Artificial Sequence: Synthetic Light Chain VL CD33 (Myelotarg) polypeptide

<400> SEQUENCE: 151

```
Asp Ile Gln Leu Thr Gln Ser Pro Ser Thr Leu Ser Ala Ser Val Gly
  1               5                  10                  15

Asp Arg Val Thr Ile Thr Cys Arg Ala Ser Glu Ser Leu Asp Asn Tyr
             20                  25                  30

Gly Ile Arg Phe Leu Thr Trp Phe Gln Gln Lys Pro Gly Lys Ala Pro
```

```
            35                  40                  45
Lys Leu Leu Met Tyr Ala Ala Ser Asn Gln Gly Ser Gly Val Pro Ser
 50                  55                  60

Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln Gln Thr Lys
                     85                  90                  95

Glu Val Pro Trp Ser Phe Gly Gln Gly Thr Lys Val Glu Val Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 152
<211> LENGTH: 212
<212> TYPE: PRT
<213> ORGANISM: Artificial Sequence
<220> FEATURE:
<223> OTHER INFORMATION: Description of Artificial Sequence: Synthetic
      Light Chain V9 (VL-CH1) polypeptide

<400> SEQUENCE: 152

Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Asp Ile Arg Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys Ser Ser Ala Ser Thr
                100                 105                 110

Lys Gly Pro Ser Val Phe Pro Leu Ala Pro Ser Ser Lys Ser Thr Ser
                115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175
```

```
Val Val Thr Val Pro Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 153
<211> LENGTH: 459
<212> TYPE: PRT
<213> ORGANISM: Artificial Sequence
<220> FEATURE:
<223> OTHER INFORMATION: Description of Artificial Sequence: Synthetic
      Fab-Crossfab (VH-CH1(CD33 Myelotarg)-VH-CL [V9]) polypeptide

<400> SEQUENCE: 153

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Gly Gly Gly Gly
    210                 215                 220

Ser Gly Gly Gly Gly Ser Glu Val Gln Leu Val Glu Ser Gly Gly Gly
225                 230                 235                 240

Leu Val Gln Pro Gly Gly Ser Leu Arg Leu Ser Cys Ala Ala Ser Gly
                245                 250                 255

Tyr Ser Phe Thr Gly Tyr Thr Met Asn Trp Val Arg Gln Ala Pro Gly
            260                 265                 270

Lys Gly Leu Glu Trp Val Ala Leu Ile Asn Pro Tyr Lys Gly Val Ser
        275                 280                 285

Thr Tyr Asn Gln Lys Phe Lys Asp Arg Phe Thr Ile Ser Val Asp Lys
    290                 295                 300

Ser Lys Asn Thr Ala Tyr Leu Gln Met Asn Ser Leu Arg Ala Glu Asp
305                 310                 315                 320
```

```
Thr Ala Val Tyr Tyr Cys Ala Arg Ser Gly Tyr Tyr Gly Asp Ser Asp
                325                 330                 335

Trp Tyr Phe Asp Val Trp Gly Gln Gly Thr Leu Val Thr Val Ser Ser
            340                 345                 350

Ala Ser Val Ala Ala Pro Ser Val Phe Ile Phe Pro Pro Ser Asp Glu
        355                 360                 365

Gln Leu Lys Ser Gly Thr Ala Ser Val Val Cys Leu Leu Asn Asn Phe
    370                 375                 380

Tyr Pro Arg Glu Ala Lys Val Gln Trp Lys Val Asp Asn Ala Leu Gln
385                 390                 395                 400

Ser Gly Asn Ser Gln Glu Ser Val Thr Glu Gln Asp Ser Lys Asp Ser
                405                 410                 415

Thr Tyr Ser Leu Ser Ser Thr Leu Thr Leu Ser Lys Ala Asp Tyr Glu
            420                 425                 430

Lys His Lys Val Tyr Ala Cys Glu Val Thr His Gln Gly Leu Ser Ser
        435                 440                 445

Pro Val Thr Lys Ser Phe Asn Arg Gly Glu Cys
    450                 455

<210> SEQ ID NO 154
<211> LENGTH: 714
<212> TYPE: DNA
<213> ORGANISM: Artificial Sequence
<220> FEATURE:
<223> OTHER INFORMATION: Description of Artificial Sequence: Synthetic
      Light Chain VL(Myelotarg) DNA polynucleotide

<400> SEQUENCE: 154
atgggatgga gctgtatcat cctcttcttg gtagcaacag ctaccggtgt gcattccgac      60
atccagctga cccagagccc ctccacactc tctgcctcag tgggcgatag ggtcaccatt     120
acttgcagag ctagcgagtc cctggacaac tacggaatcc gcttccttac atggtttcag     180
cagaagcctg gaaaagcacc aaagctgctc atgtatgccg cttctaatca aggcagtggt     240
gtgcccagcc ggttctccgg gtctggctca ggaaccgaat ttactctgac cattagctcc     300
ttgcagcctg atgacttcgc aacatactat tgtcagcaga ccaaggaggt cccatggtct     360
tttggtcaag gcacaaaagt ggaggttaag cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttag     714

<210> SEQ ID NO 155
<211> LENGTH: 696
<212> TYPE: DNA
<213> ORGANISM: Artificial Sequence
<220> FEATURE:
<223> OTHER INFORMATION: Description of Artificial Sequence: Synthetic
      Light Chain V9 (VL-CH1)  DNA polynucleotide

<400> SEQUENCE: 155
atgggatgga gctgtatcat cctcttcttg gtagcaacag ctaccggtgt gcattccgat      60
attcagatga cccagagccc cagctctctg agcgccagcg tgggcgacag agtgaccatc     120
acctgtcggg ccagccagga catcagaaac tacctgaact ggtatcagca gaagcccggc     180
```

```
aaggccccca agctgctgat ctactacacc agcagactgg aaagcggcgt gccctccaga      240
ttttccggca gcggctccgg caccgactac accctgacca tcagcagcct gcagcccgag      300
gatttcgcca catattactg ccagcagggc aataccctgc cctggacctt cggacagggc      360
acaaaagtgg aaatcaagag cagcgcttcc accaaaggcc cttccgtgtt tcctctggct      420
cctagctcca agtccacctc tggaggcacc gctgctctcg gatgcctcgt gaaggattat      480
tttcctgagc ctgtgacagt gtcctggaat agcggagcac tgacctctgg agtgcatact      540
ttccccgctg tgctgcagtc ctctggactg tacagcctga gcagcgtggt gacagtgccc      600
agcagcagcc tgggcaccca gacctacatc tgcaacgtga accacaagcc cagcaacacc      660
aaggtggaca agaaggtgga acccaagtct tgttga                                696

<210> SEQ ID NO 156
<211> LENGTH: 1437
<212> TYPE: DNA
<213> ORGANISM: Artificial Sequence
<220> FEATURE:
<223> OTHER INFORMATION: Description of Artificial Sequence: Synthetic
      Fab-Crossfab (VH-CH1(CD33 Myelotarg)-VH-CL [V9]) polynucleotide

<400> SEQUENCE: 156
atgggatgga gctgtatcat cctcttcttg gtagcaacag ctaccggtgt gcattccgag       60
gtgcagctgg tgcagtctgg cgccgaagtg aagaaacccg gcagcagcgt gaaggtgtcc      120
tgcaaggcca gcggctacac catcaccgac agcaacatcc actgggtgcg ccaggcccct      180
ggccagtctc tggaatggat cggctacatc taccccctaca acggcggcac cgactacaac      240
cagaagttca agaaccgggc caccctgacc gtggacaacc caccaatac gcctacatg       300 gaactgagca gcctgcggag cgaggacacc gccttctact actgcgtgaa cggcaacccc      360
tggctggcct attggggcca gggaacactc gtgaccgtgt ccagcgctag caccaagggc      420
cctagcgtgt tccctctggc ccctagcagc aagagcacct ctggcggaac agccgccctg      480
ggctgcctcg tgaaggacta cttttcccgag cccgtgacag tgtcctggaa ctctggcgcc      540
ctgacaagcg gcgtgcacac ctttccagcc gtgctgcagt ctagcggcct gtacagcctg      600
agcagcgtcg tgactgtgcc cagcagcagc ctgggaaccc agacctacat ctgcaacgtg      660
aaccacaagc ccagcaacac caaggtggac aagaaggtgg aacccaagag ctgcgacggc      720
ggaggcggat ccggggggagg gggatctgaa gtgcagctgg tggaaagcgg cggaggcctg      780
gtgcagcctg gggatctct gagactgagc tgtgccgcct ccggctacag cttcaccggc      840
tacacaatga attgggtgcg gcaggctccc ggcaagggcc tggaatgggt ggccctgatc      900
aacccttaca agggcgtgtc cacctataat cagaagtttta aggaccgctt caccatcagc      960
gtggacaagt ccaagaacac cgcctacctg cagatgaact ccctgcgggc cgaggataca     1020
gccgtgtact actgtgccag aagcggctac tacggcgaca cgactggta cttcgacgtg     1080 tggggacagg gcaccctggt gaccgtgtct agtgcctctg tggccgctcc cagcgtgttc     1140
atcttcccac ctagcgacga gcagctgaag tccggcaccg cttctgtcgt gtgcctgctg     1200
aacaacttct accccgcga ggccaaggtg cagtggaaag tggacaatgc cctgcagagc     1260
ggcaacagcc aggaaagcgt gaccgagcag gacagcaagg actccaccta cagcctgtcc     1320 agcacccctga cactgagcaa ggccgactac gagaagcaca aggtgtacgc ctgcgaagtg     1380
acccaccagg gcctgtctag ccccgtgacc aagagcttca accggggcga gtgctga       1437
```

```
<210> SEQ ID NO 157
<211> LENGTH: 109
<212> TYPE: PRT
<213> ORGANISM: Artificial Sequence
<220> FEATURE:
<223> OTHER INFORMATION: Description of Artificial Sequence: Synthetic
      CD3 VL polypeptide

<400> SEQUENCE: 157

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 158
<211> LENGTH: 125
<212> TYPE: PRT
<213> ORGANISM: Artificial Sequence
<220> FEATURE:
<223> OTHER INFORMATION: Description of Artificial Sequence: Synthetic
      CD3 VH polypeptide

<400> SEQUENCE: 158

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 159
<211> LENGTH: 121
<212> TYPE: PRT
<213> ORGANISM: Artificial Sequence
<220> FEATURE:
<223> OTHER INFORMATION: Description of Artificial Sequence: Synthetic
      Anti-CEA VH polypeptide

<400> SEQUENCE: 159

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Glu Phe
         20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
 50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
             100                 105                 110

Gln Gly Thr Thr Val Thr Val Ser Ser
         115                 120
```

<210> SEQ ID NO 160
<211> LENGTH: 108
<212> TYPE: PRT
<213> ORGANISM: Artificial Sequence
<220> FEATURE:
<223> OTHER INFORMATION: Description of Artificial Sequence: Synthetic Anti-CEA VL polypeptide

<400> SEQUENCE: 160

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Ala Ala Val Gly Thr Tyr
             20                  25                  30

Val Ala Trp Tyr Gln Gln Lys Pro Gly Lys Ala Pro Lys Leu Leu Ile
         35                  40                  45

Tyr Ser Ala Ser Tyr Arg Lys Arg Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys
             100                 105
```

<210> SEQ ID NO 161
<211> LENGTH: 112
<212> TYPE: PRT
<213> ORGANISM: Artificial Sequence
<220> FEATURE:
<223> OTHER INFORMATION: Description of Artificial Sequence: Synthetic Anti-MCSP VH polypeptide

<400> SEQUENCE: 161

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Gly
             20                  25                  30

Tyr Tyr Trp Asn Trp Ile Arg Gln His Pro Gly Lys Gly Leu Glu Trp
         35                  40                  45

Ile Gly Tyr Ile Thr Tyr Asp Gly Ser Asn Asn Tyr Asn Pro Ser Leu
     50                  55                  60

Lys Ser Arg Val Thr Ile Ser Arg Asp Thr Ser Lys Asn Gln Phe Ser
 65                  70                  75                  80
```

```
Leu Lys Leu Ser Ser Val Thr Ala Ala Asp Thr Ala Val Tyr Tyr Cys
            85                  90                  95

Ala Asp Phe Asp Tyr Trp Gly Gln Gly Thr Leu Val Thr Val Ser Ser
        100                 105                 110
```

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic
      Anti-MCSP VL polypeptide

<400> SEQUENCE: 162

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
            100                 105
```

<210> SEQ ID NO 163
<211> LENGTH: 454
<212> TYPE: PRT
<213> ORGANISM: Artificial Sequence
<220> FEATURE:
<223> OTHER INFORMATION: Description of Artificial Sequence: Synthetic
      VLCL(MCSP) - (G4S)2-VHCL(CD3V9) polypeptide

<400> SEQUENCE: 163

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160
```

Val Gln Trp Lys Val Asp Asn Ala Leu Gln Ser Gly Asn Ser Gln Glu
             165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys Asp Gly Gly Gly Ser Gly Gly Gly Gly Ser
225                 230                 235                 240

Asp Ile Val Leu Thr Gln Ser Pro Ser Ser Leu Ser Ala Ser Leu Gly
                245                 250                 255

Asp Arg Val Thr Ile Ser Cys Ser Ala Ser Gln Gly Ile Arg Asn Tyr
            260                 265                 270

Leu Asn Trp Tyr Gln Gln Arg Pro Asp Gly Thr Val Lys Leu Leu Ile
        275                 280                 285

Tyr Tyr Thr Ser Ser Leu His Ser Gly Val Pro Ser Arg Phe Ser Gly
    290                 295                 300

Ser Gly Ser Gly Thr Asp Tyr Ser Leu Thr Ile Ser Asn Leu Glu Pro
305                 310                 315                 320

Glu Asp Ile Ala Thr Tyr Tyr Cys Gln Gln Tyr Ser Lys Leu Pro Trp
                325                 330                 335

Thr Phe Gly Gly Gly Thr Lys Leu Glu Ile Lys Arg Thr Val Ala Ala
            340                 345                 350

Pro Ser Val Phe Ile Phe Pro Pro Ser Asp Glu Gln Leu Lys Ser Gly
        355                 360                 365

Thr Ala Ser Val Val Cys Leu Leu Asn Asn Phe Tyr Pro Arg Glu Ala
    370                 375                 380

Lys Val Gln Trp Lys Val Asp Asn Ala Leu Gln Ser Gly Asn Ser Gln
385                 390                 395                 400

Glu Ser Val Thr Glu Gln Asp Ser Lys Asp Ser Thr Tyr Ser Leu Ser
                405                 410                 415

Ser Thr Leu Thr Leu Ser Lys Ala Asp Tyr Glu Lys His Lys Val Tyr
            420                 425                 430

Ala Cys Glu Val Thr His Gln Gly Leu Ser Ser Pro Val Thr Lys Ser
        435                 440                 445

Phe Asn Arg Gly Glu Cys
    450

<210> SEQ ID NO 164
<211> LENGTH: 438
<212> TYPE: PRT
<213> ORGANISM: Artificial Sequence
<220> FEATURE:
<223> OTHER INFORMATION: Description of Artificial Sequence: Synthetic
      VHCH1(MCSP)-(G4S)2-VLCH1(CD3V9 ) polypeptide

<400> SEQUENCE: 164

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu

```
            50                  55                  60
Lys Asn Arg Ile Ser Ile Thr Arg Asp Thr Ser Lys Asn Gln Phe Phe
 65                  70                  75                  80

Leu Lys Leu Asn Ser Val Thr Glu Asp Thr Ala Thr Tyr Tyr Cys
                 85                  90                  95

Ala Asp Phe Asp Tyr Trp Gly Gln Gly Thr Thr Leu Thr Val Ser Ser
                100                 105                 110

Ala Ser Thr Lys Gly Pro Ser Val Phe Pro Leu Ala Pro Ser Ser Lys
                115                 120                 125

Ser Thr Ser Gly Gly Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Gly Gly Gly Ser Gly Gly Gly
210                 215                 220

Gly Ser Asp Ile Gln Met Thr Gln Ser Pro Ser Ser Leu Ser Ala Ser
225                 230                 235                 240

Val Gly Asp Arg Val Thr Ile Thr Cys Arg Ala Ser Gln Asp Ile Arg
                245                 250                 255

Asn Tyr Leu Asn Trp Tyr Gln Gln Lys Pro Gly Lys Ala Pro Lys Leu
                260                 265                 270

Leu Ile Tyr Tyr Thr Ser Arg Leu Glu Ser Gly Val Pro Ser Arg Phe
                275                 280                 285

Ser Gly Ser Gly Ser Gly Thr Asp Tyr Thr Leu Thr Ile Ser Ser Leu
                290                 295                 300

Gln Pro Glu Asp Phe Ala Thr Tyr Tyr Cys Gln Gln Gly Asn Thr Leu
305                 310                 315                 320

Pro Trp Thr Phe Gly Gln Gly Thr Lys Val Glu Ile Lys Ser Ser Ala
                325                 330                 335

Ser Thr Lys Gly Pro Ser Val Phe Pro Leu Ala Pro Ser Ser Lys Ser
                340                 345                 350

Thr Ser Gly Gly Thr Ala Ala Leu Gly Cys Leu Val Lys Asp Tyr Phe
                355                 360                 365

Pro Glu Pro Val Thr Val Ser Trp Asn Ser Gly Ala Leu Thr Ser Gly
                370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
                420                 425                 430

Val Glu Pro Lys Ser Cys
                435

<210> SEQ ID NO 165
<211> LENGTH: 1375
<212> TYPE: DNA
<213> ORGANISM: Artificial Sequence
```

<220> FEATURE:
<223> OTHER INFORMATION: Description of Artificial Sequence: Synthetic
      DNA - VLCL(MCSP) - (G4S)2-VHCL(CD3V9) polynucleotide

<400> SEQUENCE: 165

| | | |
|---|---|---|
| cattccgagg tgcagctggt ggaatctggc ggcggactgg tgcagcctgg cggatctctg | 60 |
| agactgagct gtgccgccag cggctacagc ttcaccggct acaccatgaa ctgggtgcgc | 120 |
| caggcccctg gcaagggact ggaatgggtg gccctgatca accccctacaa gggcgtgtcc | 180 |
| acctacaacc agaagttcaa ggaccggttc accatcagcg tggacaagag caagaacacc | 240 |
| gcctacctgc agatgaacag cctgcgggcc gaggacaccg ccgtgtacta ttgtgccaga | 300 |
| agcggctact acggcgacag cgactggtac ttcgacgtgt ggggccaggg cacactcgtg | 360 |
| accgtgtcaa gcgctagcgt ggccgctccc agcgtgttca tcttcccacc tagcgacgag | 420 |
| cagctgaagt ccggcacagc ctctgtcgtg tgcctgctga caacttctca ccccgcgag | 480 |
| gccaaggtgc agtggaaggt ggacaatgcc ctgcagagcg gcaacagcca ggaaagcgtg | 540 |
| accgagcagg acagcaagga tagcacctac agcctgagca gcaccctgac cctgagcaag | 600 |
| gccgactacg agaagcacaa ggtgtacgcc tgcgaagtga cccaccaggg cctgtctagc | 660 |
| cccgtgacca gagcttcaa ccggggcgag tgtgatggcg gaggcggatc cggggaggc | 720 |
| ggctctgata ttgtgctgac ccagagcccc agcagcctgt ctgcctctct gggcgacaga | 780 |
| gtgaccatca gctgtagcgc ctctcagggc atccggaact acctgaactg gtatcagcag | 840 |
| cggcccgacg gcaccgtgaa gctgctgatc tactacacca gctccctgca ctccggcgtg | 900 |
| cccagcagat ttctggcag cggctccggc accgactact ccctgaccat ctccaacctg | 960 |
| gaacccgagg atatcgccac ctactactgc cagcagtact ccaagctgcc ctggaccttt | 1020 |
| ggaggcggca ccaagctgga aatcaagcgt acggtggctg ccccctccgt gtttatcttt | 1080 |
| cccccatccg atgaacagct gaaaagcggc accgccagcg tcgtgtgtct gctgaacaat | 1140 |
| ttttacccta gggaagctaa agtgcagtgg aaagtggata acgcactgca gtccggcaac | 1200 |
| tcccaggaat ctgtgacaga acaggactct aaggacagca catactccct gtcctccacc | 1260 |
| ctgacactgt ctaaggctga ttatgagaaa cacaaagtgt atgcttgtga agtgacacat | 1320 |
| cagggactga gcagccctgt gacaaagtcc ttcaacagag cgagtgctg atgaa | 1375 |

<210> SEQ ID NO 166
<211> LENGTH: 1374
<212> TYPE: DNA
<213> ORGANISM: Artificial Sequence
<220> FEATURE:
<223> OTHER INFORMATION: Description of Artificial Sequence: Synthetic
      DNA - VHCH1(MCSP)-(G4S)2-VLCH1(CD3V9 ) polynucleotide

<400> SEQUENCE: 166

| | | |
|---|---|---|
| atgggatgga gctgtatcat cctcttcttg gtagcaacag ctaccggtgt gcattcggag | 60 |
| gtgcagctgc aggaatctgg ccctggcctg gtcaagccaa gccagagtct gagcctgacc | 120 |
| tgcagcgtga ccggctacag cattaccagc ggctactact ggaactggat tcggcagttc | 180 |
| cccggcaata gctggaatg gatgggctac atcacctacg acggcagcaa caactacaac | 240 |
| cccagcctga agaaccggat cagcatcacc cgggacacca gcaagaacca gttcttcctg | 300 |
| aagctgaaca gcgtgaccac cgaggacacc gccacatact attgcgccga cttcgactac | 360 |
| tggggccagg gcaccaccct gaccgtgtcc agcgccagca aagggccc tagcgtgttc | 420 |
| cctctggccc ccagcagcaa gagcacaagc ggcggaacag ccgccctggg ctgcctcgtg | 480 |

```
aaggactact tccccgagcc cgtgacagtg tcttggaaca gcggagccct gacaagcggc    540
gtgcacacct tccctgccgt gctgcagagc agcggcctgt actccctgag cagcgtggtc    600
accgtgccta gcagcagcct gggcacccag acctacatct gcaacgtgaa ccacaagccc    660
agcaacacca aagtggacaa gaaggtggag cccaagagct gtgatggcgg aggagggtcc    720
ggaggcggtg gatccgacat ccagatgacc cagagcccct ctagcctgag cgccagcgtg    780
ggcgacagag tgaccatcac ctgtcgggcc agccaggaca tcagaaacta cctgaactgg    840
tatcagcaga gcccggcaa ggcccccaag ctgctgatct actacacctc tagactggaa    900
agcggcgtgc ccagccggtt tagcggcagc ggctccggca ccgactacac cctgaccatc    960
agcagcctgc agcccgagga cttcgccacc tactactgcc agcagggcaa cacactcccc   1020
tggaccttcg gccagggcac caaggtggag atcaagtcca gcgctagcac caagggcccc   1080
tccgtgttcc ccctggcccc cagcagcaag agcaccagcg gcggcacagc cgccctcggc   1140
tgcctggtca aggactactt ccccgagccc gtgaccgtgt cctggaacag cggagccctg   1200
acctccggcg tgcacacctt ccccgccgtg ctgcagagca gcggcctgta cagcctgtcc   1260
agcgtggtca ccgtgccctc agcagcctg ggcacccaga cctacatctg caacgtgaac   1320
cacaagccca gcaataccaa ggtggacaag aaggtggagc ccaagagctg ctga         1374
```

<210> SEQ ID NO 167
<211> LENGTH: 455
<212> TYPE: PRT
<213> ORGANISM: Artificial Sequence
<220> FEATURE:
<223> OTHER INFORMATION: Description of Artificial Sequence: Synthetic
      Heavy chain humanized CD3 binder polypeptide

<400> SEQUENCE: 167

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

-continued

Asn Val Asn His Lys Pro Ser Asn Thr Lys Val Asp Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 168
<211> LENGTH: 215
<212> TYPE: PRT
<213> ORGANISM: Artificial Sequence
<220> FEATURE:
<223> OTHER INFORMATION: Description of Artificial Sequence: Synthetic
      Light chain humanized CD3 binder "CD3 CH2527
      (VL_7-46(13))" polypeptide

<400> SEQUENCE: 168

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

```
Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 169
<211> LENGTH: 125
<212> TYPE: PRT
<213> ORGANISM: Artificial Sequence
<220> FEATURE:
<223> OTHER INFORMATION: Description of Artificial Sequence: Synthetic
      VH humanized CD3 binder polypeptide

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      VH CDR H1 humanized CD3 peptide

<400> SEQUENCE: 170

Thr Tyr Ala Met Asn
1               5

<210> SEQ ID NO 171
<211> LENGTH: 19
<212> TYPE: PRT
<213> ORGANISM: Artificial Sequence
<220> FEATURE:
```

<223> OTHER INFORMATION: Description of Artificial Sequence: Synthetic
      VH CDR H2 humanized CD3 peptide

<400> SEQUENCE: 171

Arg Ile Arg Ser Lys Tyr Asn Asn Tyr Ala Thr Tyr Tyr Ala Asp Ser
1               5                   10                  15

Val Lys Gly

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      VH CDR H3 humanized CD3 peptide

<400> SEQUENCE: 172

His Gly Asn Phe Gly Asn Ser Tyr Val Ser Trp Phe Ala Tyr
1               5                   10

<210> SEQ ID NO 173
<211> LENGTH: 109
<212> TYPE: PRT
<213> ORGANISM: Artificial Sequence
<220> FEATURE:
<223> OTHER INFORMATION: Description of Artificial Sequence: Synthetic
      VL CD3 humanized polypeptide

<400> SEQUENCE: 173

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      VH CDR L1 humanized CD3 peptide

<400> SEQUENCE: 174

Gly Ser Ser Thr Gly Ala Val Thr Thr Ser Asn Tyr Ala Asn
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR L2 humanized CD3 peptide

```
<400> SEQUENCE: 175

Gly Thr Asn Lys Arg Ala Pro
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR L3 humanized CD3 peptide

<400> SEQUENCE: 176

Ala Leu Trp Tyr Ser Asn Leu Trp Val
1               5

<210> SEQ ID NO 177
<211> LENGTH: 442
<212> TYPE: PRT
<213> ORGANISM: Artificial Sequence
<220> FEATURE:
<223> OTHER INFORMATION: Description of Artificial Sequence: Synthetic
      Heavy chain  MCSP clone M4-3 (C1) polypeptide

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
```

```
                260                 265                 270
Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 178
<211> LENGTH: 214
<212> TYPE: PRT
<213> ORGANISM: Artificial Sequence
<220> FEATURE:
<223> OTHER INFORMATION: Description of Artificial Sequence: Synthetic
      Light chain MCSP clone ML2 (G3) polypeptide

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 179
<211> LENGTH: 112
<212> TYPE: PRT
<213> ORGANISM: Artificial Sequence
<220> FEATURE:
<223> OTHER INFORMATION: Description of Artificial Sequence: Synthetic
      VH MCSP clone M4-3 (C1) polypeptide

<400> SEQUENCE: 179

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      VH CDR H1 MCSP clone M4-3 (C1) peptide

<400> SEQUENCE: 180

Ser Gly Tyr Tyr Trp Asn
1               5

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      VH CDR H2 MCSP clone M4-3 (C1) peptide

<400> SEQUENCE: 181

Tyr Ile Thr Phe Asp Gly Ser Asn Asn Tyr Asn Pro Ser Leu Lys Ser
1               5                   10                  15

<210> SEQ ID NO 182
<211> LENGTH: 107
<212> TYPE: PRT
<213> ORGANISM: Artificial Sequence
<220> FEATURE:
<223> OTHER INFORMATION: Description of Artificial Sequence: Synthetic
      VL MCSP clone  ML2 (G3) polypeptide

<400> SEQUENCE: 182
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys
            100                 105

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR L1 MCSP clone ML2 (G3) peptide

<400> SEQUENCE: 183

Arg Ala Ser Gln Gly Ile Arg Asn Tyr Leu Asn
1               5                   10

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR L3 MCSP clone ML2 (G3) peptide

<400> SEQUENCE: 184

Gln Gln Tyr Ser Ala Leu Pro Trp Thr
1               5

<210> SEQ ID NO 185
<211> LENGTH: 111
<212> TYPE: PRT
<213> ORGANISM: Artificial Sequence
<220> FEATURE:
<223> OTHER INFORMATION: Description of Artificial Sequence: Synthetic
      VL CD3 clone 7-43(11) polypeptide

<400> SEQUENCE: 185

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95
```

Leu Trp Val Phe Gly Gly Gly Thr Lys Leu Thr Val Leu Ser Ser
            100                 105                 110

<210> SEQ ID NO 186
<211> LENGTH: 125
<212> TYPE: PRT
<213> ORGANISM: Artificial Sequence
<220> FEATURE:
<223> OTHER INFORMATION: Description of Artificial Sequence: Synthetic
      VH CD3 clone VHcomboA49SV93A polypeptide

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 187
<211> LENGTH: 125
<212> TYPE: PRT
<213> ORGANISM: Artificial Sequence
<220> FEATURE:
<223> OTHER INFORMATION: Description of Artificial Sequence: Synthetic
      VH CD3 clone VHcomboA49SV93AR94K polypeptide

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 188
<211> LENGTH: 112
<212> TYPE: PRT
<213> ORGANISM: Artificial Sequence
<220> FEATURE:

<223> OTHER INFORMATION: Description of Artificial Sequence: Synthetic
VH MCSP clone M4-3 (D6) polypeptide

<400> SEQUENCE: 188

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Lys Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
VH CDR H2 MCSP clone M4-3 (D6) peptide

<400> SEQUENCE: 189

Ile Thr Phe Asp Gly Lys Asn Asn Tyr Asn Pro Ser Leu Lys Ser
1               5                   10                  15

<210> SEQ ID NO 190
<211> LENGTH: 112
<212> TYPE: PRT
<213> ORGANISM: Artificial Sequence
<220> FEATURE:
<223> OTHER INFORMATION: Description of Artificial Sequence: Synthetic
VH MCSP clone M4-3 (A7) polypeptide

<400> SEQUENCE: 190

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Asp Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Arg Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic VH CDR H1 MCSP clone M4-3 (A7) peptide

<400> SEQUENCE: 191

Asp Gly Tyr Tyr Trp Asn
1               5

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      H CDR H2 MCSP clone M4-3 (A7) peptide

<400> SEQUENCE: 192

Ile Thr Phe Asp Gly Arg Asn Asn Tyr Asn Pro Ser Leu Lys Ser
1               5                   10                  15

<210> SEQ ID NO 193
<211> LENGTH: 112
<212> TYPE: PRT
<213> ORGANISM: Artificial Sequence
<220> FEATURE:
<223> OTHER INFORMATION: Description of Artificial Sequence: Synthetic
      VH MCSP clone M4-3 (B7) polypeptide

<400> SEQUENCE: 193

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ile Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
                100                 105                 110

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR H2 MCSP clone M4-3 (B7) peptide

<400> SEQUENCE: 194

Ile Thr Phe Asp Gly Ile Asn Asn Tyr Asn Pro Ser Leu Lys Ser
1               5                   10                  15

<210> SEQ ID NO 195
<211> LENGTH: 112
<212> TYPE: PRT
<213> ORGANISM: Artificial Sequence
<220> FEATURE:
<223> OTHER INFORMATION: Description of Artificial Sequence: Synthetic
      VH MCSP clone M4-3 (B8) polypeptide

<400> SEQUENCE: 195

Gln Val Gln Leu Gln Glu Ser Gly Pro Gly Leu Val Lys Pro Ser Gln

```
                1               5                  10                 15
Thr Leu Ser Leu Thr Cys Thr Val Gly Gly Ser Ile Thr Ser Gly
            20                  25                 30

Tyr Tyr Trp Asn Trp Ile Arg Gln His Pro Gly Lys Gly Leu Glu Trp
            35                  40                 45

Ile Gly Tyr Ile Thr Phe Asp Gly Arg Asn Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
            85                  90                 95

Ala Asp Phe Asp Tyr Trp Gly Gln Gly Thr Leu Val Thr Val Ser Ser
            100                 105                110

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      VL MCSP clone ML2 (E10) polypeptide

<400> SEQUENCE: 196

Asp Ile Gln Met Thr Gln Ser Pro Ser Ser Leu Ser Ala Ser Val Gly
 1               5                  10                 15

Asp Arg Val Thr Ile Thr Cys Arg Ala Ser Tyr Gly Ile Arg Gly Tyr
            20                  25                 30

Leu Asn Trp Tyr Gln Gln Lys Pro Gly Lys Ala Pro Lys Leu Leu Ile
            35                  40                 45

Tyr Tyr Thr Ser Ser Leu His Ser Gly Val Pro Ser Arg Phe Ser Gly
            50                  55                 60

Ser Gly Ser Gly Thr Asp Phe Thr Leu Thr Ile Ser Ser Leu Gln Pro
 65                  70                  75                  80

Glu Asp Phe Ala Thr Tyr His Cys Gln Gln Tyr Ser Lys Leu Pro Trp
            85                  90                 95

Thr Phe Gly Gln Gly Thr Lys Val Glu Ile Lys
            100                 105

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR L1 MCSP clone ML2 (E10) peptide

<400> SEQUENCE: 197

Arg Ala Ser Tyr Gly Ile Arg Gly Tyr Leu Asn
 1               5                  10

<210> SEQ ID NO 198
<211> LENGTH: 107
<212> TYPE: PRT
<213> ORGANISM: Artificial Sequence
<220> FEATURE:
<223> OTHER INFORMATION: Description of Artificial Sequence: Synthetic
      VL MCSP clone ML2 (E10-G3) polypeptide

<400> SEQUENCE: 198

Asp Ile Gln Met Thr Gln Ser Pro Ser Ser Leu Ser Ala Ser Val Gly
 1               5                  10                 15
```

```
Asp Arg Val Thr Ile Thr Cys Arg Ala Ser Tyr Gly Ile Arg Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Tyr Ser Ala Leu Pro Trp
                85                  90                  95

Thr Phe Gly Gln Gly Thr Lys Val Glu Ile Lys
            100                 105
```

<210> SEQ ID NO 199
<211> LENGTH: 107
<212> TYPE: PRT
<213> ORGANISM: Artificial Sequence
<220> FEATURE:
<223> OTHER INFORMATION: Description of Artificial Sequence: Synthetic
      VL MCSP clone ML2 (C5) polypeptide

<400> SEQUENCE: 199

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Glu Tyr
            20                  25                  30

Leu Asn Trp Tyr Gln Gln Lys Pro Gly Lys Ala Pro Lys Leu Leu Ile
        35                  40                  45

Tyr Tyr Thr Gly Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105
```

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR L1 MCSP clone ML2 (C5) peptide

<400> SEQUENCE: 200

```
Arg Ala Ser Arg Gly Ile Arg Glu Tyr Leu Asn
1               5                   10
```

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR L2 MCSP clone ML2 (C5) peptide

<400> SEQUENCE: 201

```
Tyr Thr Gly Ser Leu His Ser
1               5
```

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR L3 MCSP clone ML2 (C5) peptide

<400> SEQUENCE: 202

Gln Gln Tyr Ser Glu Leu Pro Trp Thr
1               5

<210> SEQ ID NO 203
<211> LENGTH: 107
<212> TYPE: PRT
<213> ORGANISM: Artificial Sequence
<220> FEATURE:
<223> OTHER INFORMATION: Description of Artificial Sequence: Synthetic
      VL MCSP clone ML2 (C5-G3) polypeptide

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Glu Tyr
            20                  25                  30

Leu Asn Trp Tyr Gln Gln Lys Pro Gly Lys Ala Pro Lys Leu Leu Ile
        35                  40                  45

Tyr Tyr Thr Gly Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys
            100                 105

<210> SEQ ID NO 204
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This sequence may encompass 3-6
      'Gly-Gly-Gly-Ser' repeating units

<400> SEQUENCE: 204

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 205
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)

```
<223> OTHER INFORMATION: This region may encompass 3-6 'Gly-Gly-Gly-Ser'
      repeating units
<220> FEATURE:
<221> NAME/KEY: misc_feature
<222> LOCATION: (25)..(27)
<223> OTHER INFORMATION: May or may not be present

<400> SEQUENCE: 205

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly
            20                  25

<210> SEQ ID NO 206
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(25)
<223> OTHER INFORMATION: This sequence may encompass 2-5
      'Gly-Gly-Gly-Gly-Ser' repeating units

<400> SEQUENCE: 206

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 207
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(25)
<223> OTHER INFORMATION: This region may encompass 2-5
      'Gly-Gly-Gly-Gly-Ser' repeating units
<220> FEATURE:
<221> NAME/KEY: misc_feature
<222> LOCATION: (26)..(28)
<223> OTHER INFORMATION: May or may not be present

<400> SEQUENCE: 207

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly
            20                  25

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

His His His His His
1               5

<210> SEQ ID NO 209
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Gly Gly Ser
1               5
```